(12) United States Patent
Tello-Aburto et al.

(10) Patent No.: US 11,396,497 B2
(45) Date of Patent: Jul. 26, 2022

(54) PROTEASOME INHIBITORS

(71) Applicant: New Mexico Tech University Research Park Corporation, Socorro, NM (US)

(72) Inventors: Rodolfo Tello-Aburto, Albuquerque, NM (US); Snezna Rogelj, Socorro, NM (US); Liam Hallada, Albuquerque, NM (US); Doleshwar Niroula, Socorro, NM (US)

(73) Assignee: NEW MEXICO TECH UNIVERSITY RESEARCH PARK CORPORATION, Socorro, NM (US)

( * ) Notice: Subject to any disclaimer, the term of this patent is extended or adjusted under 35 U.S.C. 154(b) by 0 days.

(21) Appl. No.: 17/052,580

(22) PCT Filed: May 2, 2019

(86) PCT No.: PCT/US2019/030386
§ 371 (c)(1),
(2) Date: Nov. 3, 2020

(87) PCT Pub. No.: WO2019/213386
PCT Pub. Date: Nov. 7, 2019

(65) Prior Publication Data
US 2021/0363119 A1 Nov. 25, 2021

Related U.S. Application Data

(60) Provisional application No. 62/666,856, filed on May 4, 2018.

(51) Int. Cl.
*C07D 305/12* (2006.01)
(52) U.S. Cl.
CPC .................... *C07D 305/12* (2013.01)
(58) Field of Classification Search
CPC .................................... C07D 305/12
See application file for complete search history.

(56) References Cited

U.S. PATENT DOCUMENTS

| | | | |
|---|---|---|---|
| 8,119,653 B2 * | 2/2012 | Romo | C07D 305/12 514/279 |
| 10,662,221 B2 * | 5/2020 | Gill | A61P 35/00 |
| 2004/0048327 A1 | 3/2004 | Powers et al. | |
| 2005/0049257 A1 | 3/2005 | Verhoest et al. | |
| 2006/0058242 A1 | 3/2006 | Fink | |
| 2009/0042922 A1 | 2/2009 | Romo et al. | |
| 2009/0324621 A1 | 12/2009 | Senter et al. | |
| 2012/0101026 A1 | 4/2012 | Smyth et al. | |
| 2016/0017015 A1 | 1/2016 | Iwamoto et al. | |

FOREIGN PATENT DOCUMENTS

WO WO-2016123699 A1 8/2016

OTHER PUBLICATIONS

Gill KA, et al., Cystargolides, 20S Proteasome Inhibitors Isolated from Kitasatospora cystarginea, J Nat Prod.Apr. 24, 2015;78(4):822-6. doi: 10.1021/np501060k. Epub Mar. 13, 2015. PMID:25769015.
Ma, Yuheng et al. "Synthesis and SAR study of novel peptide aldehydes as inhibitors of 20S proteasome." Molecules(Basel, Switzerland) vol. 16,9 7551-64. Sep. 5, 2011,doi:10.3390/molecules16097551.
Tello-Aburto, Rodolfo et al. "Total synthesis and absolute stereochemistry of the proteasome inhibitors cystargolides A and B." Organic & biomolecular chemistry vol. 13,40 (2015):10127-30. doi:10.1039/c5ob01821h.

* cited by examiner

*Primary Examiner* — Golam M Shameem
(74) *Attorney, Agent, or Firm* — Wilson Sonsini Goodrich & Rosati

(57) ABSTRACT

The disclosure provides proteasome inhibitors that can be used to halt cell division of rapidly dividing cells by preventing the degradation of cell cycle-regulating proteins, such as cyclins, cyclin-dependent kinase inhibitors, and p53. The proteasome inhibitor compounds can be used to inhibit the proliferation of cancer cells.

20 Claims, 68 Drawing Sheets

PROTEASOME INHIBITORS

CROSS REFERENCE

This application claims the benefit of U.S. Provisional Application No. 62/666,856 filed on May 4, 2018, which is incorporated herein by reference in its entirety.

GOVERNMENT RIGHTS

This invention was made with the support of the United States government under Contract number P20GM103451 by the National Institutes of Health. The government has certain rights in the invention.

BACKGROUND

Proteasome inhibitors halt cell division of rapidly dividing cells by preventing the degradation of cell cycle-regulating proteins, such as cyclins, cyclin-dependent kinase (CDK) inhibitors, and p53. Proteasome inhibition can prevent degradation of pro-apoptotic factors, permitting the activation or programmed cell death in neoplastic cells that are dependent upon suppression of pro-apoptotic pathways. Proteasome inhibitors can also selectively inhibit non-human proteasomes, such as parasites that cause malaria.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the disclosure provides a compound of the formula:

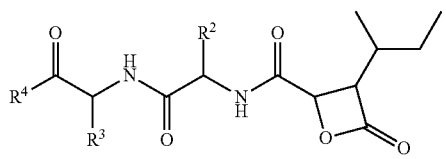

or a pharmaceutically-acceptable salt thereof, wherein:
  $R^2$ is alkyl or branched alkyl, each of which is independently substituted or unsubstituted, or hydrogen;
  $R^3$ is alkyl or branched alkyl, each of which is independently substituted or unsubstituted; and
  $R^4$ is alkoxy, which is substituted or unsubstituted, or $NR^5R^6$, wherein each $R^5$ and $R^6$ is independently alkyl, which is substituted or unsubstituted, or hydrogen.

In some embodiments, the disclosure provides a pharmaceutical composition comprising a compound of the formula:

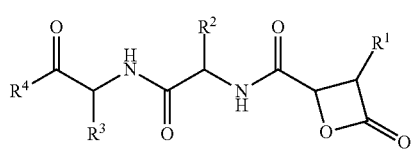

or a pharmaceutically-acceptable salt thereof, wherein:
  $R^1$ is alkyl, which is substituted or unsubstituted.
  $R^2$ is alkyl or branched alkyl, each of which is independently substituted or unsubstituted, or hydrogen;
  $R^3$ is alkyl or branched alkyl, each of which is independently substituted or unsubstituted; and
  $R^4$ is alkoxy, which is substituted or unsubstituted, or $NR^5R^6$, wherein each $R^5$ and $R^6$ is independently alkyl, which is substituted or unsubstituted, or hydrogen.

In some embodiments, the disclosure provides a method of treating a condition, the method comprising administering to a subject in need thereof a therapeutically-effective amount of a compound of the formula:

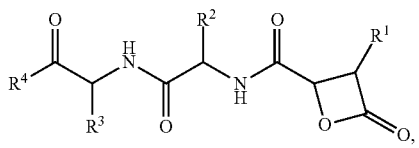

or a pharmaceutically-acceptable salt thereof.

In some embodiments, the disclosure provides a method of inhibiting a proteasome, the method comprising administering to a subject in need thereof a therapeutically-effective amount of a compound of the formula:

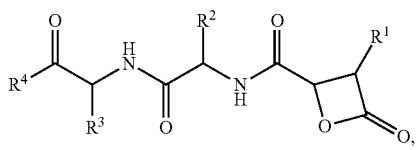

or a pharmaceutically-acceptable salt thereof.

BRIEF DESCRIPTION OF THE DRAWINGS

FIG. 18 shows the $^1$H NMR and $^{13}$C NMR spectra of compound 7a.

FIG. 35 shows the $^1$H NMR and $^{13}$C NMR spectra of compound 9a.

FIG. 39 shows the $^1$H NMR and $^{13}$C NMR spectra of compound 10a.

FIG. 50 shows the $^1$H NMR and $^{13}$C NMR spectra of compound 11a.

FIG. 64 PANEL A compares proteasome inhibitory effects of compounds 8, 10k, and 12a. FIG. 64 PANEL B compares the effects of compounds 8, 10k, and 12a on multiple myeloma toxicity.

FIG. 66 PANEL B shows dose response curves for the cytotoxicity of compound 12a towards the MCF-7 breast cancer cell line.

DETAILED DESCRIPTION OF THE INVENTION

Proteasome Inhibitors

Figure 1:
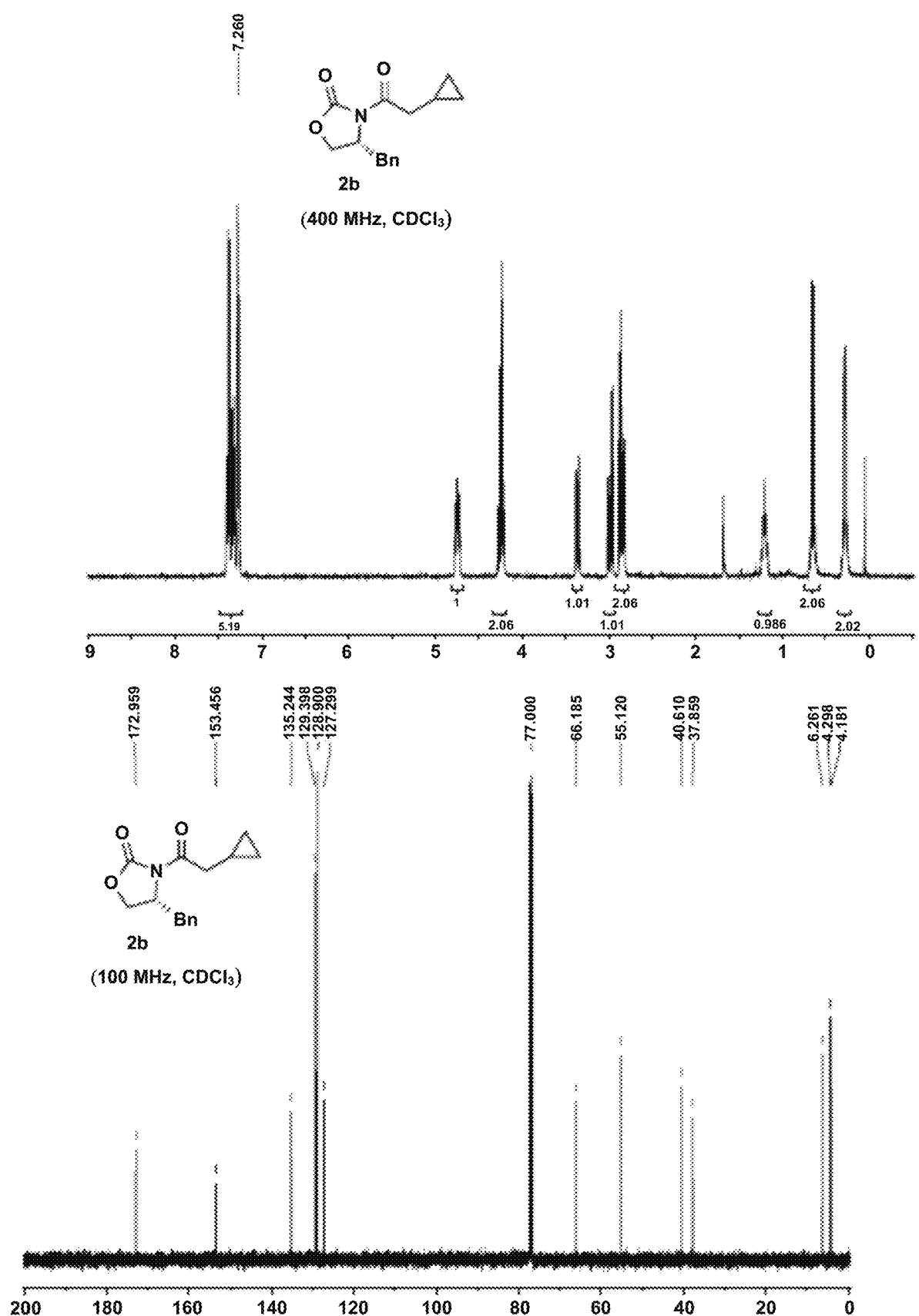
FIG. 1 shows the $^1$H NMR and $^{13}$C NMR spectra of compound 2b.

Proteasomes are cellular complexes that break down proteins. Proteasome inhibitors (PIs) halt cell division of rapidly dividing cells by preventing the degradation of cell cycle-regulating proteins, such as cyclins, cyclin-dependent kinase (CDK) inhibitors, and p53. Proteasome inhibition can prevent degradation of pro-apoptotic factors, permitting the activation or programmed cell death in neoplastic cells that are dependent upon suppression of pro-apoptotic pathways. Inhibition of the proteasome can impact the regulation of the NF-κB pathway, which is an essential mechanism of homeostasis involved in the control of inflammatory responses. Proteasome inhibitors can also selectively inhibit non-human proteasomes, such as parasites that cause malaria.

Proteasome inhibitors can achieve cell toxicity via induction of apoptosis caused by GM2/M cell cycle arrest due to the accumulation of ubiquitinated proteins.

Examples of different classes of proteasome inhibitors include boronic acids (e.g., borteazomib), epoxyketones (e.g., epoxomicin), and β-lactones (e.g., belactosins A and C, salinosporamide A). The β-lactone-containing natural products cystargolide A and cystargolide B are proteasome inhibitors that exhibit activity as 20S proteasome inhibitors with potencies comparable to that of the betalactosins A and C.

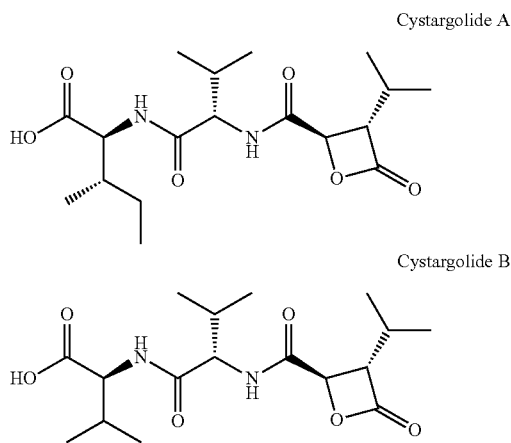

Cystargolide A

Cystargolide B

Compounds of the Invention

The disclosed compounds can inhibit proteasomes to halt cell division by reducing the degradation of pro-apoptotic factors. In some embodiments, the disclosed compounds can reduce the degradation of cyclins, CDK inhibitors, and p53. In some embodiments, the compounds are deactivated by paraoxonase proteases, which are involved in the degradation of organophosphate insecticides.

In some embodiments, the compounds of the disclosure kill human breast cancer cells at nanomolar concentrations. In some embodiments, the compounds of the invention have a higher efficacy of killing cancer cells than carfilzomib exhibits in the same assay. In some embodiments, the compounds of the invention can infiltrate solid or liquid tumors.

Non-limiting examples of compounds of the disclosure include compounds of the formula:

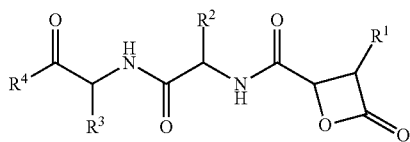

or a pharmaceutically-acceptable salt thereof, wherein:
each $R^1$, $R^2$, $R^3$, and $R^4$ is independently alkyl, branched alkyl, cycloalkyl, alkenyl, aryl, heteroaryl, heterocyclyl, alkoxy, or $NR^5R^6$, each of which is independently substituted or unsubstituted, or hydrogen; and
wherein each $R^5$ and $R^6$ is independently alkyl, alkylene, alkenyl, alkenylene, aryl, heteroaryl, heterocyclyl, or alkoxy, each of which is independently substituted or unsubstituted; $R^5$ and $R^6$ together with the atoms to which $R^5$ and $R^6$ are bound form a ring; or hydrogen.

In some embodiments, $R^1$ is alkyl. In some embodiments, $R^1$ is cycloalkyl. In some embodiments, $R^1$ is cycloproyl. In some embodiments, $R^1$ is cyclobutyl. In some embodiments, $R^1$ is cyclopentyl. In some embodiments, $R^1$ is cyclohexyl. In some embodiments, $R^1$ is branched alkyl. In some embodiments, $R^1$ is isopropyl. In some embodiments, $R^1$ is isobutyl. In some embodiments, $R^1$ is tert-butyl. In some embodiments, $R^1$ is sec-butyl.

In some embodiments, $R^2$ is alkyl. In some embodiments, $R^2$ is branched alkyl. In some embodiments, $R^2$ is isopropyl. In some embodiments, $R^2$ is isobutyl. In some embodiments, $R^2$ is tert-butyl. In some embodiments, $R^2$ is substituted alkyl. In some embodiments, $R^2$ is alkyl substituted with aryl. In some embodiments, $R^2$ is alkyl substituted with phenyl. In some embodiments, $R^2$ is alkyl substituted with alkoxy. In some embodiments, $R^2$ is alkyl substituted with O-benzyl.

In some embodiments, $R^3$ is alkyl. In some embodiments, $R^3$ is branched alkyl. In some embodiments, $R^3$ is isopropyl. In some embodiments, $R^3$ is isobutyl. In some embodiments, $R^3$ is tert-butyl. In some embodiments, $R^3$ is substituted alkyl. In some embodiments, $R^3$ is alkyl substituted with aryl. In some embodiments, $R^3$ is alkyl substituted with alkoxy. In some embodiments, $R^3$ is alkyl substituted with O-benzyl.

In some embodiments, $R^4$ is alkoxy substituted with aryl. In some embodiments, $R^4$ is alkoxy substituted with aryl, wherein the aryl is substituted with halo or alkoxy. In some embodiments, $R^4$ is alkoxy substituted with branched alkyl. In some embodiments, $R^4$ is alkoxy substituted with cycloalkyl. In some embodiments, $R^4$ is methoxy. In some embodiments, $R^4$ is alkoxy substituted with alkyl. In some embodiments, $R^4$ is $NR^5R^6$, wherein $R^5$ is hydrogen and $R^6$ is alkyl. In some embodiments, $R^4$ is $NR^5R^6$, wherein $R^5$ is hydrogen and $R^6$ is substituted alkyl. In some embodiments, $R^4$ is $NR^5R^6$, wherein $R^5$ is hydrogen and $R^6$ is benzyl.

In some embodiments, each $R^1$, $R^2$, and $R^3$ is independently alkyl, and $R^4$ is alkoxy. In some embodiments, each $R^1$, $R^2$, and $R^3$ is independently alkyl, and $R^4$ is $NR^5R^6$, wherein each $R^5$ and $R^6$ is independently alkyl, alkylene, alkenyl, alkenylene, aryl, heteroaryl, heterocyclyl, or alkoxy, each of which is independently substituted or unsubstituted. In some embodiments, each $R^1$, $R^2$, and $R^3$ is independently branched alkyl, and $R^4$ is alkoxy. In some embodiments, $R^1$ is cycloalkyl, each $R^2$ and $R^3$ is independently branched alkyl, and $R^4$ is alkoxy. In some embodiments, $R^1$ is cycloalkyl, each $R^2$ and $R^3$ is independently isopropyl, and $R^4$ is alkoxy. In some embodiments, $R^1$ is cycloalkyl, each $R^2$ and $R^3$ is independently isopropyl, and $R^4$ is O-benzyl. In some embodiments, $R^1$ is sec-butyl, each $R^2$ and $R^3$ is independently isopropyl, and $R^4$ is alkoxy. In some embodiments, $R^1$ is tert-butyl, each $R^2$ and $R^3$ is independently isopropyl, and $R^4$ is alkoxy.

In some embodiments, the disclosure includes compounds of the formula:

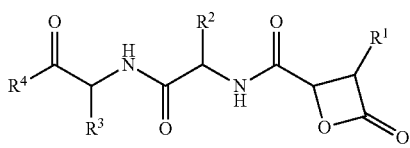

or a pharmaceutically acceptable salt thereof, wherein:
R$^1$ is branched alkyl or cycloalkyl;
R$^2$ is alkyl or branched alkyl, each of which is independently substituted or unsubstituted, or hydrogen;
R$^3$ is alkyl or branched alkyl, each of which is independently substituted or unsubstituted; and
R$^4$ is alkoxy, which is substituted or unsubstituted, or NR$^5$R$^6$, wherein each R$^5$ and R$^6$ is independently alkyl, which is substituted or unsubstituted, or hydrogen.

In some embodiments, R$^1$ is branched alkyl. In some embodiments, R$^1$ is sec-butyl or iso-butyl. In some embodiments, R$^1$ is cycloalkyl. In some embodiments, R$^1$ is cyclopropyl, cyclobutyl, cyclopentyl, or cyclohexyl. In some embodiments, R$^1$ is cyclopropyl. In some embodiments, R$^1$ is cyclobutyl. In some embodiments, R$^1$ is cyclopentyl.

In some embodiments, R$^2$ is branched alkyl. In some embodiments, R$^2$ is iso-propyl, tert-butyl, or iso-butyl. In some embodiments, R$^2$ is benzyl. In some embodiments, R$^2$ is hydrogen.

In some embodiments, R$^3$ is branched alkyl. In some embodiments, R$^3$ is iso-propyl, tert-butyl, or iso-butyl. In some embodiments, R$^3$ is substituted alkyl. In some embodiments, R$^3$ is benzyl. In some embodiments, R$^3$ is alkyl substituted with alkoxy. In some embodiments, R$^3$ is alkyl substituted with O-benzyl.

In some embodiments, R$^4$ is alkoxy. In some embodiments, R$^4$ is O-benzyl. In some embodiments, R$^4$ is substituted O-benzyl. In some embodiments, R$^4$ is O-benzyl substituted with halo or alkoxy. In some embodiments, R$^4$ is methoxy. In some embodiments, R$^4$ is cyclohexylmethoxy. In some embodiments, R$^4$ is but-3-en-1-oxy. In some embodiments, R$^4$ is NR$^5$R$^6$, wherein R$^5$ is hydrogen and R$^6$ is substituted alkyl. In some embodiments, R$^4$ is NR$^5$R$^6$, wherein R$^5$ is hydrogen and R$^6$ is benzyl.

In some embodiments, each R$^1$, R$^2$, and R$^3$ is independently alkyl, and R$^4$ is alkoxy. In some embodiments, each R$^1$, R$^2$, and R$^3$ is independently alkyl, and R$^4$ is NR$^5$R$^6$, wherein each R$^5$ and R$^6$ is independently alkyl, alkylene, alkenyl, alkenylene, aryl, heteroaryl, heterocyclyl, or alkoxy, each of which is independently substituted or unsubstituted, or hydrogen. In some embodiments, each R$^1$, R$^2$, and R$^3$ is independently branched alkyl, and R$^4$ is alkoxy. In some embodiments, R$^1$ is cycloalkyl, each R$^2$ and R$^3$ is independently branched alkyl, and R$^4$ is alkoxy. In some embodiments, R$^1$ is cycloalkyl, each R$^2$ and R$^3$ is independently isopropyl, and R$^4$ is alkoxy. In some embodiments, R$^1$ is cycloalkyl, each R$^2$ and R$^3$ is independently isopropyl, and R$^4$ is O-benzyl. In some embodiments, R$^1$ is sec-butyl, each R$^2$ and R$^3$ is independently isopropyl, and R$^4$ is alkoxy. In some embodiments, R$^1$ is tert-butyl, each R$^2$ and R$^3$ is independently isopropyl, and R$^4$ is alkoxy.

In some embodiments, the disclosure includes compounds of the formula:

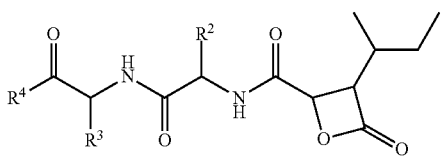

or a pharmaceutically acceptable salt thereof, wherein:
R$^2$ is alkyl or branched alkyl, each of which is independently substituted or unsubstituted, or hydrogen;
R$^3$ is alkyl or branched alkyl, each of which is independently substituted or unsubstituted; and
R$^4$ is alkoxy, which is substituted or unsubstituted, or NR$^5$R$^6$, wherein each R$^5$ and R$^6$ is independently alkyl, which is substituted or unsubstituted, or hydrogen.

In some embodiments, R$^2$ is branched alkyl. In some embodiments, R$^2$ is iso-propyl, tert-butyl, or iso-butyl. In some embodiments, R$^2$ is benzyl. In some embodiments, R$^2$ is hydrogen. In some embodiments, R$^3$ is branched alkyl. In some embodiments, R$^3$ is iso-propyl, tert-butyl, or iso-butyl. In some embodiments, R$^3$ is substituted alkyl. In some embodiments, R$^3$ is benzyl. In some embodiments, R$^3$ is alkyl substituted with alkoxy. In some embodiments, R$^3$ is alkyl substituted with O-benzyl. In some embodiments, R$^4$ is alkoxy. In some embodiments, R$^4$ is O-benzyl. In some embodiments, R$^4$ is substituted O-benzyl. In some embodiments, R$^4$ is O-benzyl substituted with halo or alkoxy. In some embodiments, R$^4$ is methoxy. In some embodiments, R$^4$ is cyclohexylmethoxy. In some embodiments, R$^4$ is but-3-en-1-oxy. In some embodiments, R$^4$ is NR$^5$R$^6$, wherein R$^5$ is hydrogen and R$^6$ is substituted alkyl. In some embodiments, R$^4$ is NR$^5$R$^6$, wherein R$^5$ is hydrogen and R$^6$ is benzyl.

In some embodiments, each R$^2$ and R$^3$ is independently branched alkyl, and R$^4$ is alkoxy. In some embodiments, each R$^2$ and R$^3$ is independently iso-propyl, and R$^4$ is alkoxy. In some embodiments, each R$^2$ and R$^3$ is independently tert-butyl, and R$^4$ is alkoxy. In some embodiments, each R$^2$ and R$^3$ is independently benzyl, and R$^4$ is alkoxy. In some embodiments, each R$^2$ and R$^3$ is independently branched alkyl, and R$^4$ is O-benzyl. In some embodiments, each R$^2$ and R$^3$ is independently iso-propyl, and R$^4$ is NR$^5$R$^6$, wherein each R$^5$ is hydrogen, and R$^6$ is substituted alkyl. In some embodiments, each R$^2$ and R$^3$ is independently branched alkyl, and R$^4$ is NR$^5$R$^6$, wherein each R$^5$ is hydrogen, and R$^6$ is benzyl.

In some embodiments, the disclosure includes compounds of the formula:

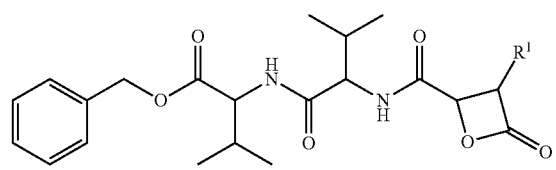

or a pharmaceutically acceptable salt thereof,
wherein R$^1$ is alkyl, branched alkyl, or cycloalkyl, each of which is independently substituted or unsubstituted.

In some embodiments, R$^1$ is branched alkyl. In some embodiments, R$^1$ is iso-butyl. In some embodiments, R$^1$ is sec-butyl. In some embodiments, R$^1$ is cycloalkyl. In some embodiments, R$^1$ is cyclopropyl. In some embodiments, R$^1$ is cyclobutyl. In some embodiments, R$^1$ is cyclopentyl.

In some embodiments, the disclosure includes compounds of the formula:

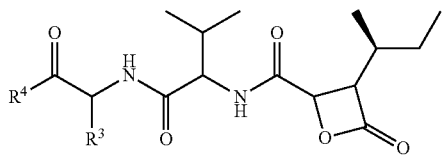

or a pharmaceutically acceptable salt thereof, wherein:
R³ is alkyl or branched alkyl, each of which is independently substituted or unsubstituted; and
R⁴ is alkoxy, which is substituted or unsubstituted, or NR⁵R⁶, wherein each R⁵ and R⁶ is independently alkyl, which is substituted or unsubstituted, or hydrogen.

In some embodiments, R³ is branched alkyl. In some embodiments, R³ is iso-propyl. In some embodiments, R³ is tert-butyl. In some embodiments, R³ is iso-butyl. In some embodiments, R³ is sec-butyl. In some embodiments, R³ is benzyl. In some embodiments, R³ is substituted alkyl. In some embodiments, R³ is alkyl substituted with alkoxy. In some embodiments, R³ is alkyl substituted with O-benzyl.

In some embodiments, R⁴ is alkoxy. In some embodiments, R⁴ is O-benzyl. In some embodiments, R⁴ is substituted O-benzyl. In some embodiments, R⁴ is O-benzyl substituted with halo or alkoxy. In some embodiments, R⁴ is methoxy. In some embodiments, R⁴ is cyclohexylmethyl. In some embodiments, R⁴ is but-3-en-1-oxy. In some embodiments, R⁴ is NR⁵R⁶, wherein R⁵ is hydrogen and R⁶ is substituted alkylene. In some embodiments, R⁴ is NR⁵R⁶, wherein R⁵ is hydrogen and R⁶ is benzyl.

In some embodiments, R³ is alkyl, and R⁴ is alkoxy. In some embodiments, R³ is alkyl, and R⁴ is NR⁵R⁶, wherein each R⁵ and R⁶ is independently alkyl, which is substituted or unsubstituted, or hydrogen. In some embodiments, R³ is branched alkyl, and R⁴ is alkoxy. In some embodiments, R³ is iso-propyl, and R⁴ is alkoxy. In some embodiments, R³ is tert-butyl, and R⁴ is alkoxy. In some embodiments, R³ is iso-butyl, and R⁴ is alkoxy. In some embodiments, R³ is branched alkyl, and R⁴ is O-benzyl. In some embodiments, R³ is branched alkyl, and R⁴ is NR⁵R⁶, wherein each R⁵ and R⁶ is independently alkyl, which is substituted or unsubstituted, or hydrogen. In some embodiments, R³ is branched alkyl, and R⁴ is NR⁵R⁶, wherein each R⁵ and R⁶ is independently substituted alkyl or hydrogen.

In some embodiments, the disclosure includes compounds of the formula:

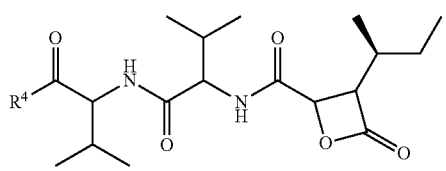

or a pharmaceutically acceptable salt thereof, wherein R⁴ is alkoxy, which is substituted or unsubstituted, or NR⁵R⁶, wherein each R⁵ and R⁶ is independently alkylene, which is substituted or unsubstituted.

In some embodiments, R⁴ is alkoxy. In some embodiments, R⁴ is O-benzyl. In some embodiments, R⁴ is substituted O-benzyl. In some embodiments, R⁴ is O-benzyl substituted with halo or alkoxy. In some embodiments, R⁴ is methoxy. In some embodiments, R⁴ is cyclohexylmethoxy. In some embodiments, R⁴ is but-3-en-1-oxy. In some embodiments, R⁴ is NR⁵R⁶, wherein R⁵ is hydrogen and R⁶ is substituted alkyl. In some embodiments, R⁴ is NR⁵R⁶, wherein R⁵ is hydrogen and R⁶ is benzyl.

In some embodiments, the disclosure includes compounds of the formula:

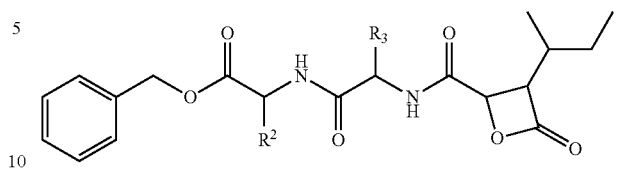

or a pharmaceutically-acceptable salt thereof, wherein R² is alkyl or branched alkyl, each of which is independently substituted or unsubstituted, or hydrogen, and R³ is alkyl or branched alkyl, each of which is independently substituted or unsubstituted, or hydrogen.

In some embodiments, R² is branched alkyl. In some embodiments, R² is iso-propyl, tert-butyl, or iso-butyl. In some embodiments, R² is benzyl. In some embodiments, R² is hydrogen. In some embodiments, R³ is branched alkyl. In some embodiments, R³ is iso-propyl, tert-butyl, or iso-butyl. In some embodiments, R³ is substituted alkyl. In some embodiments, R³ is benzyl. In some embodiments, R³ is alkyl substituted with alkoxy. In some embodiments, R³ is alkyl substituted with O-benzyl.

In some embodiments, R² is branched alkyl, and R³ is branched alkyl. In some embodiments, R² is iso-propyl, and R³ is iso-propyl. In some embodiments, R² is benzyl, and R³ is iso-propyl. In some embodiments, R² is iso-propyl, and R³ is tert-butyl. In some embodiments, R² is tert-butyl, and R³ is iso-propyl. In some embodiments, R² is iso-propyl, and R³ is hydrogen. In some embodiments, R² is benzyl, and R³ is benzyl.

In some embodiments, the disclosure includes compounds of the formula:

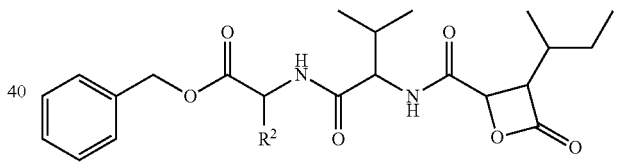

or a pharmaceutically-acceptable salt thereof, wherein R² is alkyl or branched alkyl, each of which is independently substituted or unsubstituted, or hydrogen.

In some embodiments, R² is branched alkyl. In some embodiments, R² is iso-propyl, tert-butyl, or sec-butyl. In some embodiments, R² is benzyl. In some embodiments, R² is alkyl substituted with O-benzyl.

Non-limiting examples of compounds of the invention include:

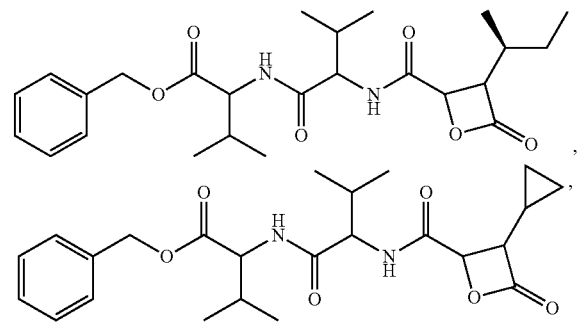

-continued

13
-continued
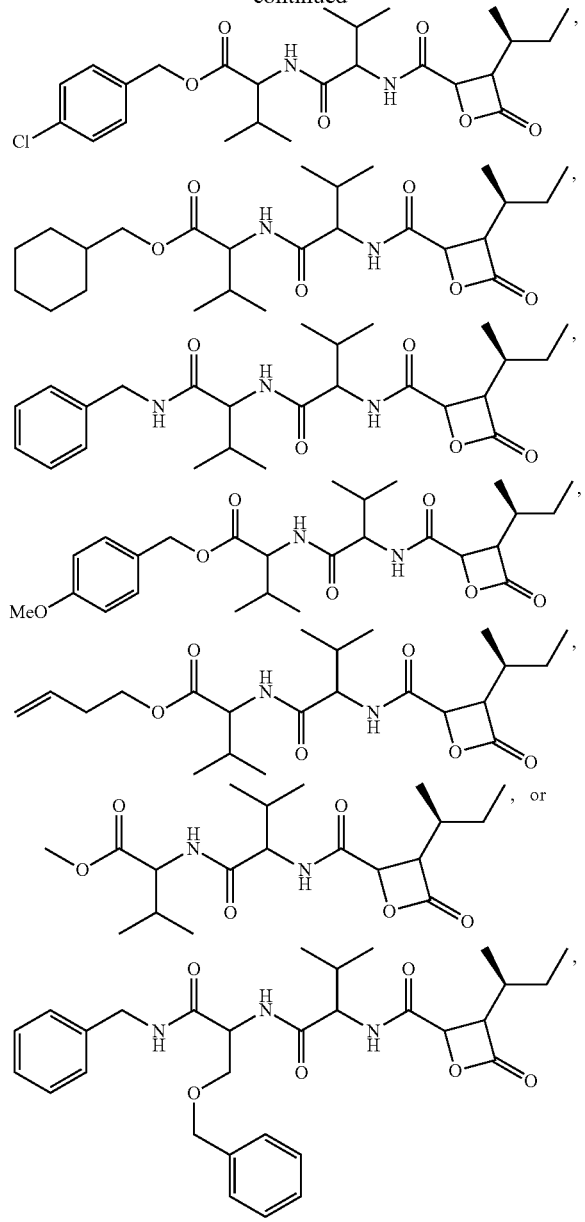
or a pharmaceutically acceptable salt thereof.
Non-limiting examples of compounds of the invention include:
14
-continued
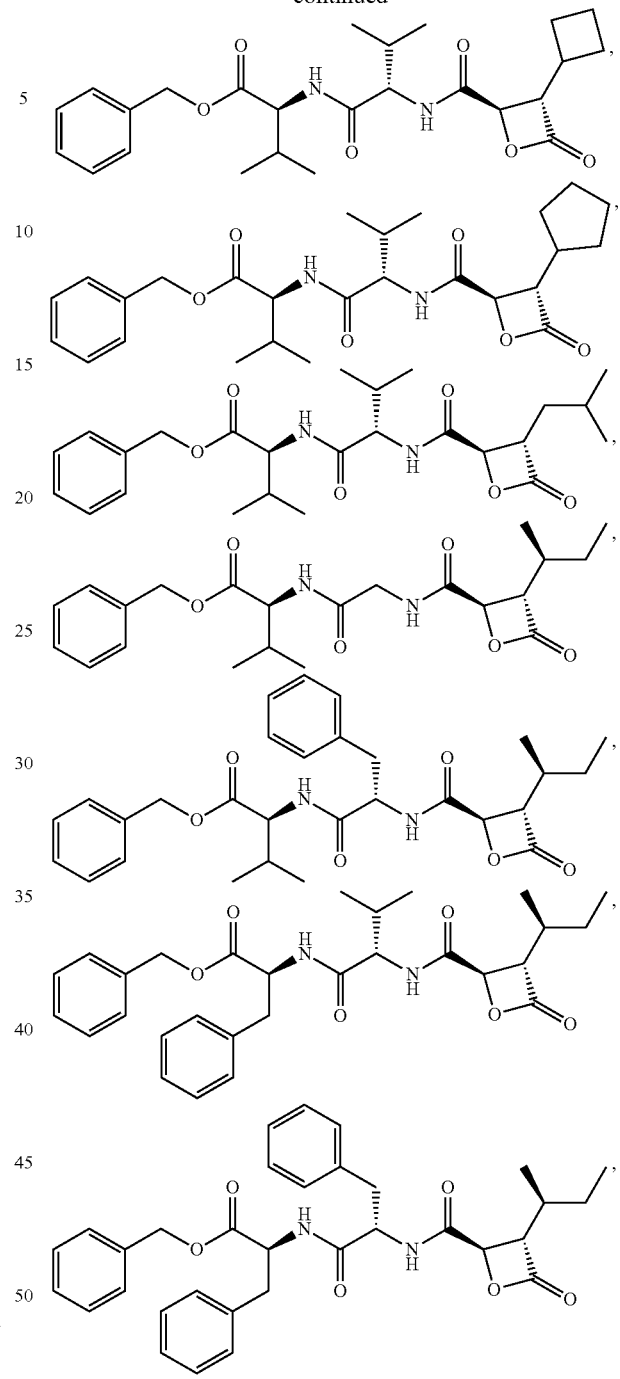
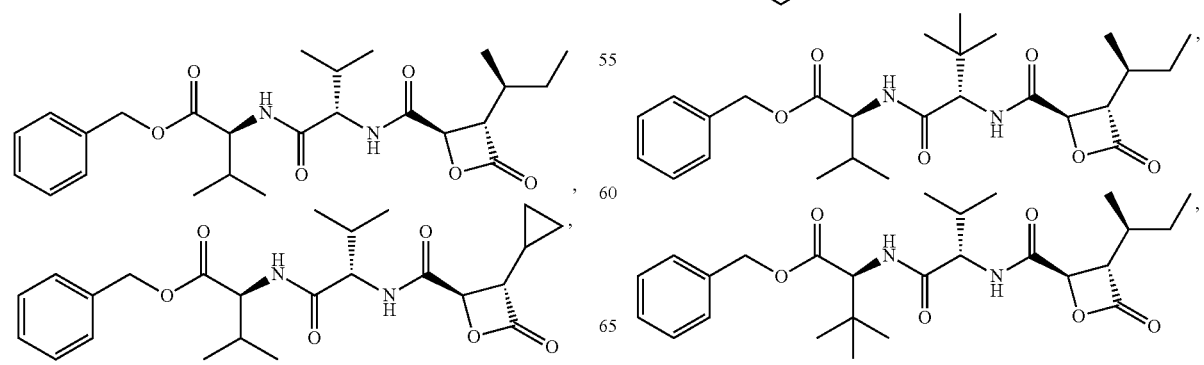

-continued

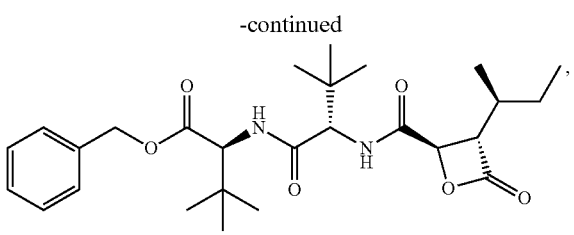

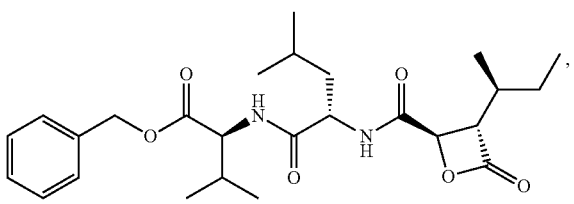

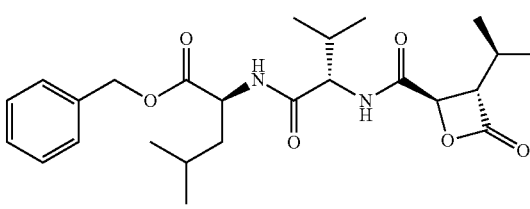

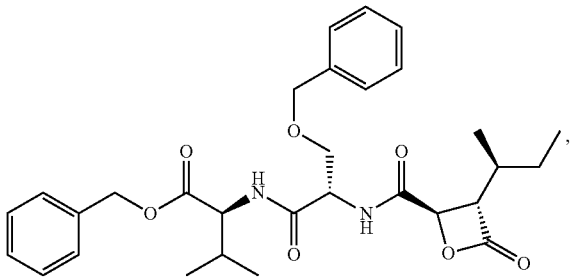

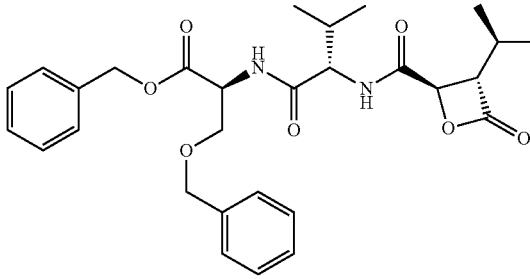

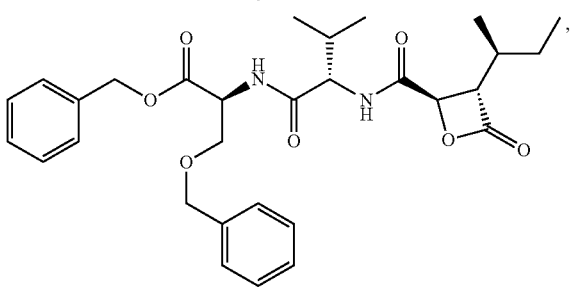

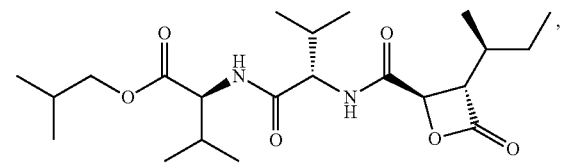

-continued

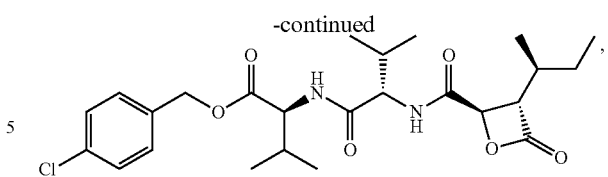

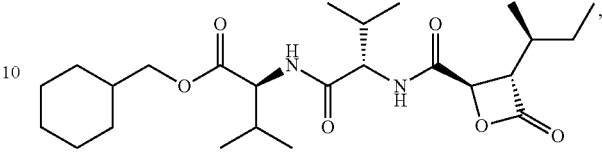

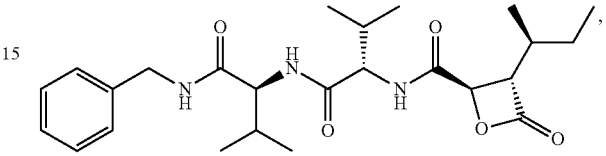

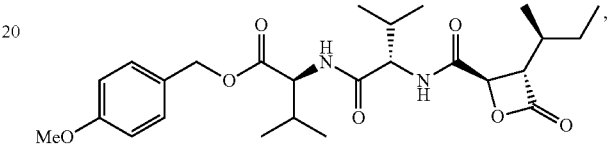

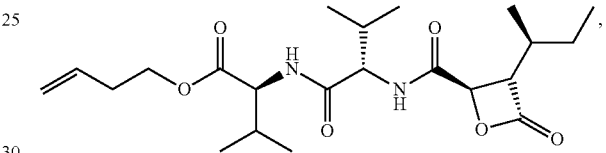

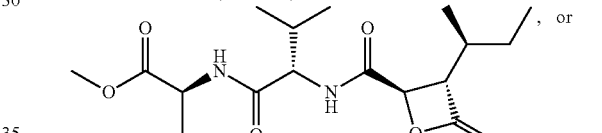

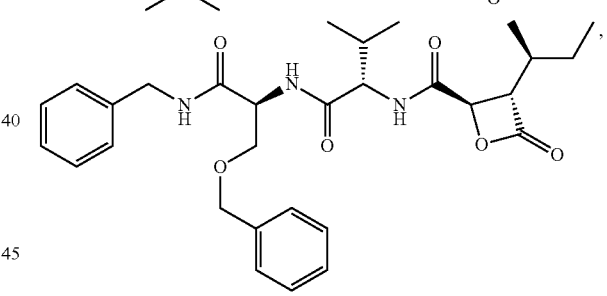

or a pharmaceutically acceptable salt thereof.

Optional Substituents for Chemical Groups

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxyethyl, 1,2-difluoroethyl, and 3-carboxypropyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Pharmaceutically Acceptable Salts

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Purity of Compounds

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Pharmaceutical Compositions of the Invention

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after an antibiotic. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

Applications

In some embodiments, compounds of the invention can be used to treat cancer in a subject. A compound of the invention can, for example, slow the proliferation of cancer cell lines, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, compounds of the invention can be used to treat non-solid tumors. In some embodiments compounds of the invention can be used to treat cancer cells that are present in body fluids, such as blood, lymph, and bone marrow. In some embodiments, the compounds of the invention can be used to treat leukemia, myeloma, myelodysplastic syndrome (MDS), and liquid lymphomas. In some embodiments, the compounds of the invention can be used to treat acute myeloid leukemia. In some embodiments the compounds of the invention can be used to treat liquid lymphomas, such as lymphomas that contain cysts or liquid areas.

In some embodiments, the compounds of the invention can be used to treat solid tumors. In some embodiments, the compounds of the invention can be used to treat pancreatic cancer, bladder cancer, colon cancer, liver cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, central nervous system cancers, brain tumors, bone cancer, skin cancer, ocular tumors, rectal cancer, choriocarcinoma, sarcoma, soft tissue cancer, testicular cancer, gall bladder cancer, and biliary cancer. The ocular tumor can be choroidal nevus, choroidal melanoma, choroidal metastasis, choroidal hemangioma, choroidal osteoma, iris melanoma, uveal melanoma, melanocytoma, metastasis retinal capillary hemangioma, congenital hypertrophy of the retinal pigment epithelium (RPE), RPE adenoma, or retinoblastoma.

The compounds of the invention can inhibit one or more proteasomes. In some embodiments, the compounds of the invention can inhibit each of the three proteolytic β-subunits for the human 20S constitutive proteasome, the human 20S proteasome, yeast 20S constitutive proteasome, plasmodium 20S proteasome, and the trypanosome 20S proteasome.

EXAMPLES

Example 1: Synthetic Methods

All moisture sensitive reactions were conducted in oven-dried glassware under an atmosphere of dry nitrogen or argon. Reaction solvents ($CH_2Cl_2$, $Et_2O$, THF) were dried and degassed by passing through a column of activated alumina in a solvent purification system. N-methyl morpholine was distilled from $CaH_2$. Dimethyl formamide (DMF) was dried over activated 4 Å molecular sieves and distilled under high vacuum. All other solvents and reagents were purchased from commercial suppliers and used as received, unless otherwise specified. Thin layer chromatography (TLC) was performed with glass plates pre-coated with silica 60 Å F-254 (250 µm) and visualized by UV light, $KMnO_4$, phosphomolybdic acid, anisaldehyde or Cerium Ammonium Molybdate stains. $^1H$ and $^{13}C$ NMR spectra were recorded using a 400 MHz Bruker instrument working at a frequency of 400 MHz for $^1H$ and at 100 MHz for $^{13}C$. Chemical shifts are reported in ppm using residual solvent resonances as internal reference (δ 7.26 and δ 77.0 for $^1H$ and $^{13}C$ in $CDCl_3$, δ 2.50 and δ 39.51 for $^1H$ and $^{13}C$ in DMSO-d6). $^1H$ NMR data are reported as follows: b=broad, s=singlet, d=doublet, t=triplet, q=quartet, m=multiplet. Coupling constants are given in Hertz. IR measurements were performed in a Nicolet FTIR as thin films. Optical rotations were measured on a Rudolph Autopol III polarimeter. High-resolution mass spectrometry analyses were conducted at the Montana State University Mass Spectrometry facility.

Example 2: Synthesis of β-Lactones

The cystargolide analogues were synthesized by coupling $P_1$ substituted β-lactones with dipeptide moieties. The dipeptide fragments were designed to be differentially substituted at the $P_2$, $P_3$, and $P_4$ positions. The β-lactone warheads 5a-5e were synthesized by acylation of (R)-4-benzyl-2-oxazolidinone with $P_1$-containing carboxylic acids to afford imides 2a-2e (SCHEME 1).

SCHEME 1

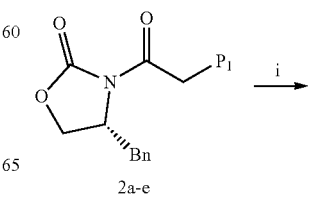

2a-e

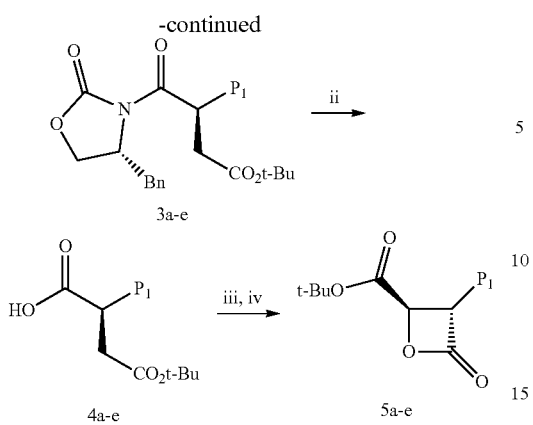

3a-e 4a-e → 5a-e

P₁ = a = sec-butyl, b = cyclopropyl, c = cyclobutyl, d = cyclopentyl, e = iso-butyl Reagents and conditions: (i) NaHMDS, THF, -78° C. then t-Bu bromoacetate (ii) LiOH/H₂O₂, THF:H₂O (3:2), 0° C to rt (iii) LHMDS, CCl₄, THF, -78° C. (iv) aq. 5% NaHCO₃, ether, rt.

Example 3: Synthesis of Compounds 2a-2e

Synthesis of compound 2b: Cyclopropyl acetic acid (1.00 g, 9.98 mmol) was dissolved in 35.0 mL of dry CH₂Cl₂ at 0° C., and a catalytic amount of DMF (1 drop) was added. The resulting solution was stirred, and oxalyl chloride (0.9 mL, 10.40 mmol) was added dropwise. The mixture was stirred overnight, and the reaction was slowly warmed to room temperature. After 12 hours, the solvent was evaporated in vacuo with minimum exposure to air to yield the crude acid chloride. The crude product was immediately used for the next step without further purification.

A solution of (R)-4-benzyloxazolidin-2-one (1.32 g, 7.50 mmol) dissolved in 30.0 mL of dry THF was cooled to −78° C. under an argon atmosphere. n-BuLi (4.46 mL, 1.68 M in Hexanes, 7.50 mmol) was added dropwise to the solution. The resulting mixture was stirred for 20 minutes at the same temperature, and a solution of acid chloride dissolved in 45.0 mL of dry THF was slowly added via cannula. The reaction was stirred at −78° C. for 30 minutes and at 0° C. for 1.5 hours. Analysis using thin layer chromatography (TLC) revealed complete conversion of the starting material. The mixture was then quenched with saturated solution of NH₄Cl and extracted with ethyl acetate (2×20 mL). The aqueous layer was further extracted with ethyl acetate, and the combined organic layer was washed with brine, dried over MgSO₄, filtered, and concentrated in vacuo. The crude product was purified by flash column chromatography using hexanes:ethyl acetate (8:2) to afford the title compound.

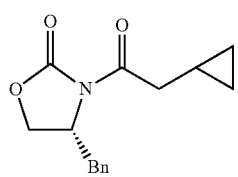

2b (R)-4-benzyl-3-(2-cyclopropylacetyl)oxazolidin-2-one (2b)

Pale yellow oil; Yield: 71%; Rf: 0.7 (Hexanes:ethyl acetate=7:3); $[\alpha]^{21}_D$−59.2 (c 0.5, CHCl₃); ¹H NMR (400 MHz, CDCl₃): δ 7.38-7.24 (m, 5H), 4.75-4.70 (m, 1H), 4.27-4.21 (m, 2H), 3.37 (dd, J=13.2, 12.6 Hz, 1H), 2.99 (dd, J=9.9, 6.9 Hz, 1H), 2.86 (m, 2H), 1.19 (m, 1H), 0.64 (m, 2H), 0.27 (m, 2H); ¹³C NMR (100 MHz, CDCl₃): δ 173.0, 153.5, 135.2, 129.4, 128.9, 121.3, 66.2, 55.1, 40.6, 37.8, 6.2; HRMS (ESI+) m/z: [M+Na]⁺ Calc'd for C₁₅H₁₇NNaO₃ 282.1101; Found 282.1118. FIG. 1 shows the ¹H NMR and ¹³C NMR spectra of compound 2b.

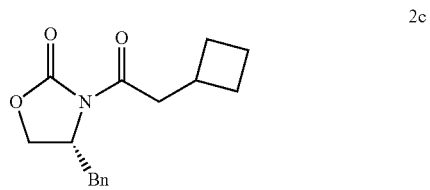 [SMILES: O=C(CC1CCC1)N1C(=O)OC[C@H]1Cc1ccccc1]

2c (R)-4-benzyl-3-(2-cyclobutylacetyl)oxazolidin-2-one (2c)

Figure 2:
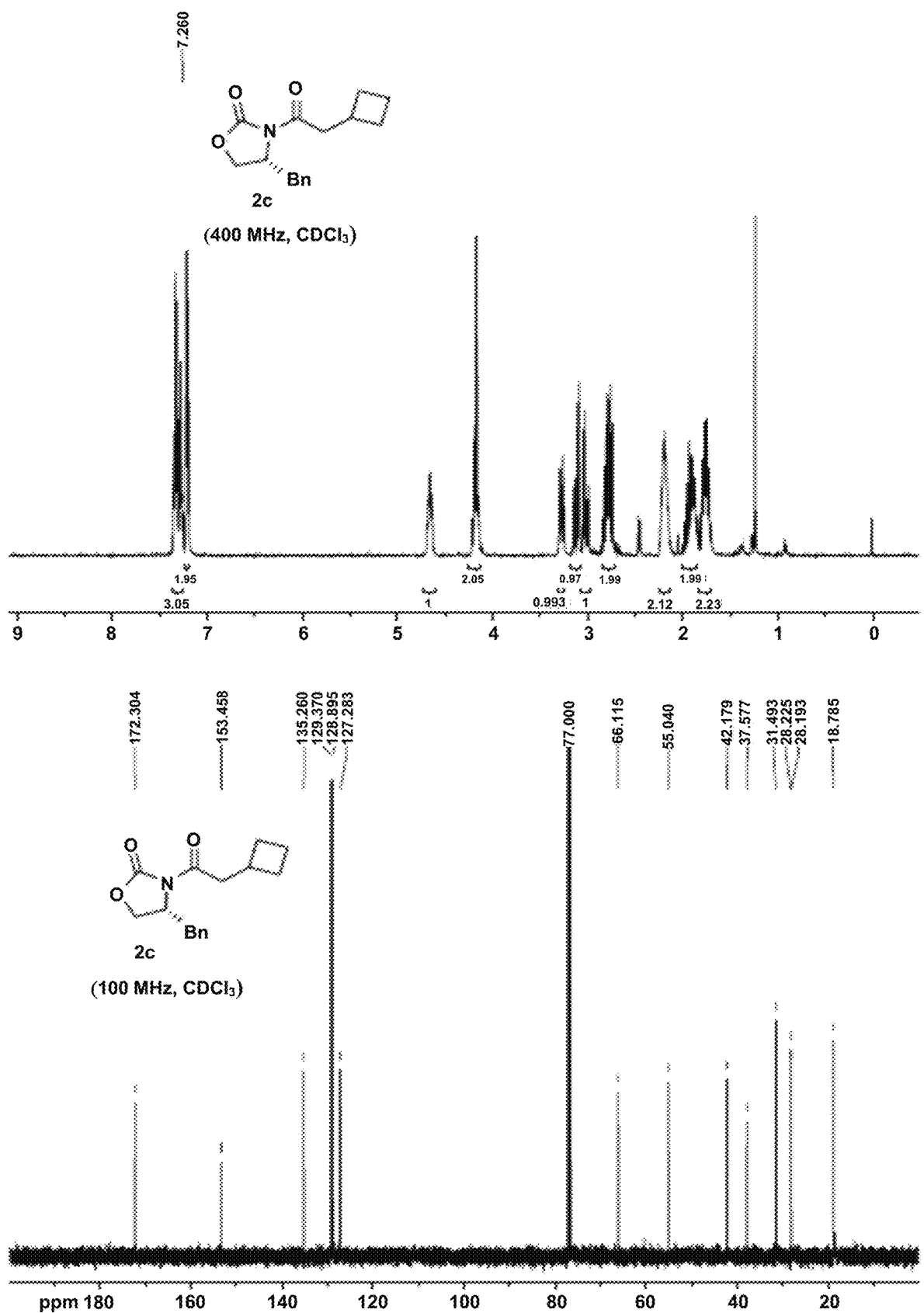
FIG. 2 shows the $^1$H NMR and $^{13}$C NMR spectra of compound 2c.

White solid; Yield: 68%; Rf: 0.7 (Hexanes:ethyl acetate=9:1); $[\alpha]^{22}_D$=−47.6 (c 0.6, CHCl₃); ¹H NMR (400 MHz, CDCl₃): δ 7.42-7.26 (m, 5H), 4.75-4.69 (m, 1H), 4.28 (m, 2H), 3.37 (dd, J=9.83, 3.21 Hz, 2H), 3.21-3.05 (m, 2H), 2.92-2.79 (m, 2H), 2.29-2.21 (m, 1H), 2.06-1.9 (m, 2H), 1.87-1.76 (m, 2H); ¹³C NMR (100 MHz, CDCl₃): δ 172.3, 153.5, 135.3, 129.4, 128.9, 127.3, 66.1, 55.0, 42.2, 37.9, 31.5, 28.2, 18.8; HRMS (ESI+) m/z: [M+Na]⁺ Calc'd for C₁₆H₁₉NNaO₃ 296.1257; Found 296.1269. FIG. 2 shows the ¹H NMR and ¹³C NMR spectra of compound 2c.

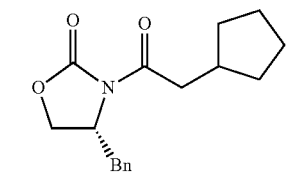

2d (R)-4-benzyl-3-(2-cyclopentylacetyl)oxazolidin-2-one (2d)

Figure 3:
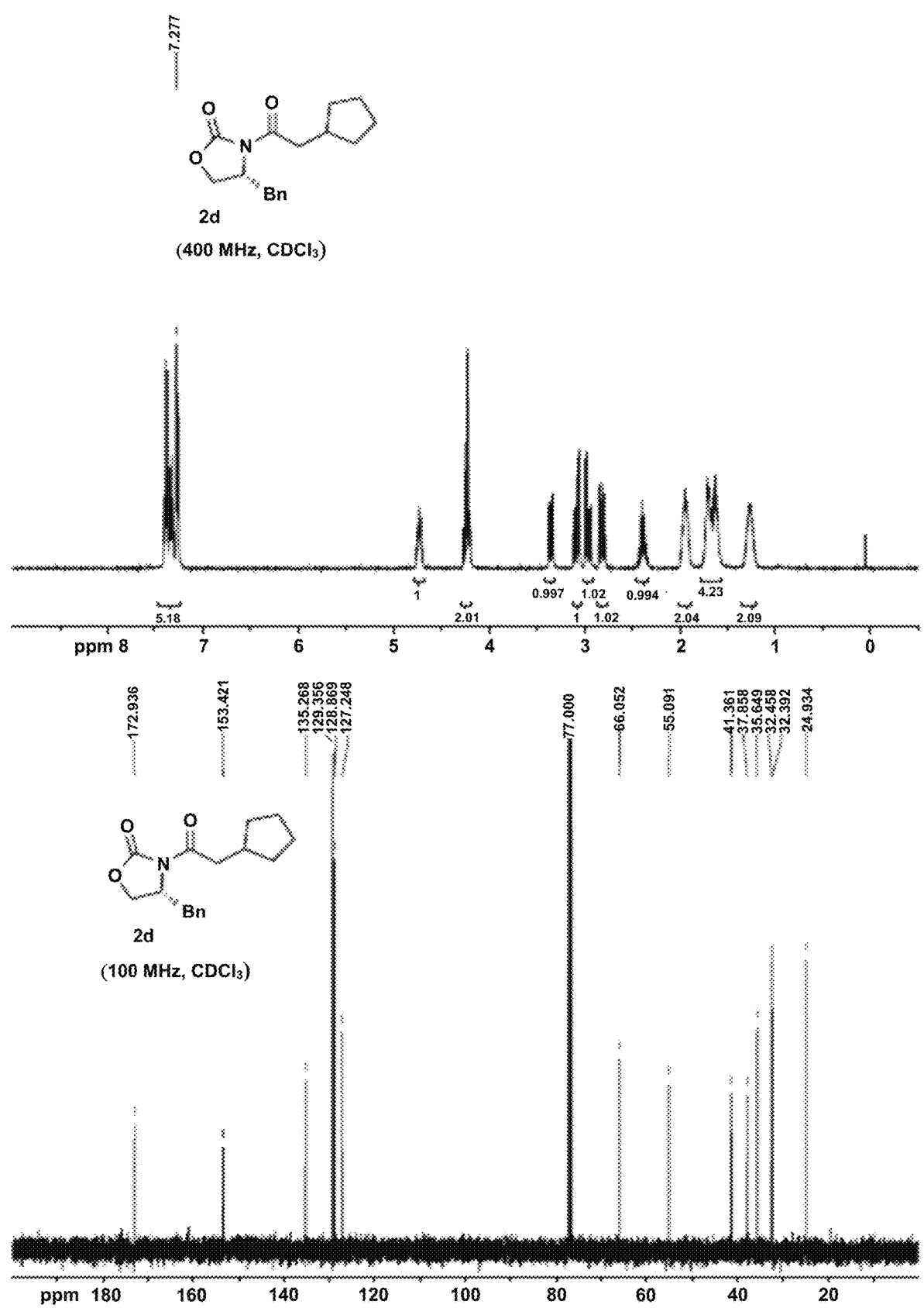
FIG. 3 shows the $^1$H NMR and $^{13}$C NMR spectra of compound 2d.

White solid; Yield: 82%; Rf: 0.6 (Hexanes:ethyl acetate=9:1); $[\alpha]^{21}_D$=−50.6 (c 0.6, CHCl₃); ¹H NMR (400 MHz, CDCl₃): δ 7.35-7.21 (m, 5H), 4.71-4.65 (m, 1H), 4.22-4.14 (m, 2H), 3.32 (dd, J=13.1, 3.4 Hz, 1H), 3.06 (dd, J=16.3, 6.6 Hz, 1H), 2.94 (dd, J=16.5, 7.6 Hz, 1H), 2.79 (dd, J=13.4, 9.4 Hz, 1H), 2.39-2.28 (m, 1H), 1.94-1.85 (m, 2H), 1.69-1.53 (m, 4H), 1.26-1.17 (m, 2H); ¹³C NMR (100 MHz, CDCl₃): δ 173.0, 153.4, 135.3, 129.4, 128.9, 127.3, 66.1, 55.1, 41.4, 37.9, 35.6, 32.5, 32.4, 24.9, 24.9; HRMS (ESI+) m/z: [M+Na]⁺ Calc'd for C₁₇H₂₁NNaO₃ 310.1414; Found 310.1412. FIG. 3 shows the ¹H NMR and ¹³C NMR spectra of compound 2d.

Example 4: Synthesis of Compound 3a-3e

Diastereoselective alkylation of 2a-2e with t-butyl bromoacetate under Evans conditions afforded intermediates 3a-3e.

Synthesis of compound 3b: A solution of imide 2b (2.24 g, 8.67 mmol) in 80.0 mL of dry THF was cooled to −78°

C. and treated by adding NaHMDS dropwise (6.5 mL, 2M solution in THF, 13.0 mmol). The enolate formation was allowed for 1 hour at the same temperature before t-Butyl bromoacetate (2.56 mL, 17.34 mmol) was slowly added using a syringe. The reaction was stirred overnight slowly warming to room temperature. After 12 hours, the reaction was quenched with a saturated solution of NH$_4$Cl and extracted with EtOAc (2×50 mL). The organic phase separated and remaining aqueous phase was further extracted with 25 mL of EtOAc. The combined organic phase was washed with brine, dried over MgSO$_4$, and filtered, and solvent was evaporated in vacuo. The crude product was purified by flash column chromatography using hexanes:ethyl acetate (1:9) to afford the title compounds.

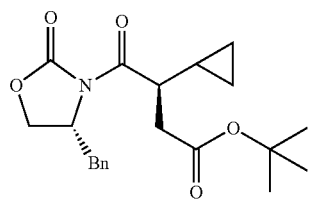

3b tert-butyl(R)-4-((R)-4-benzyl-2-oxooxazolidin-3-yl)-3-cyclopropyl-4-oxobutanoate (3b)

Figure 4:
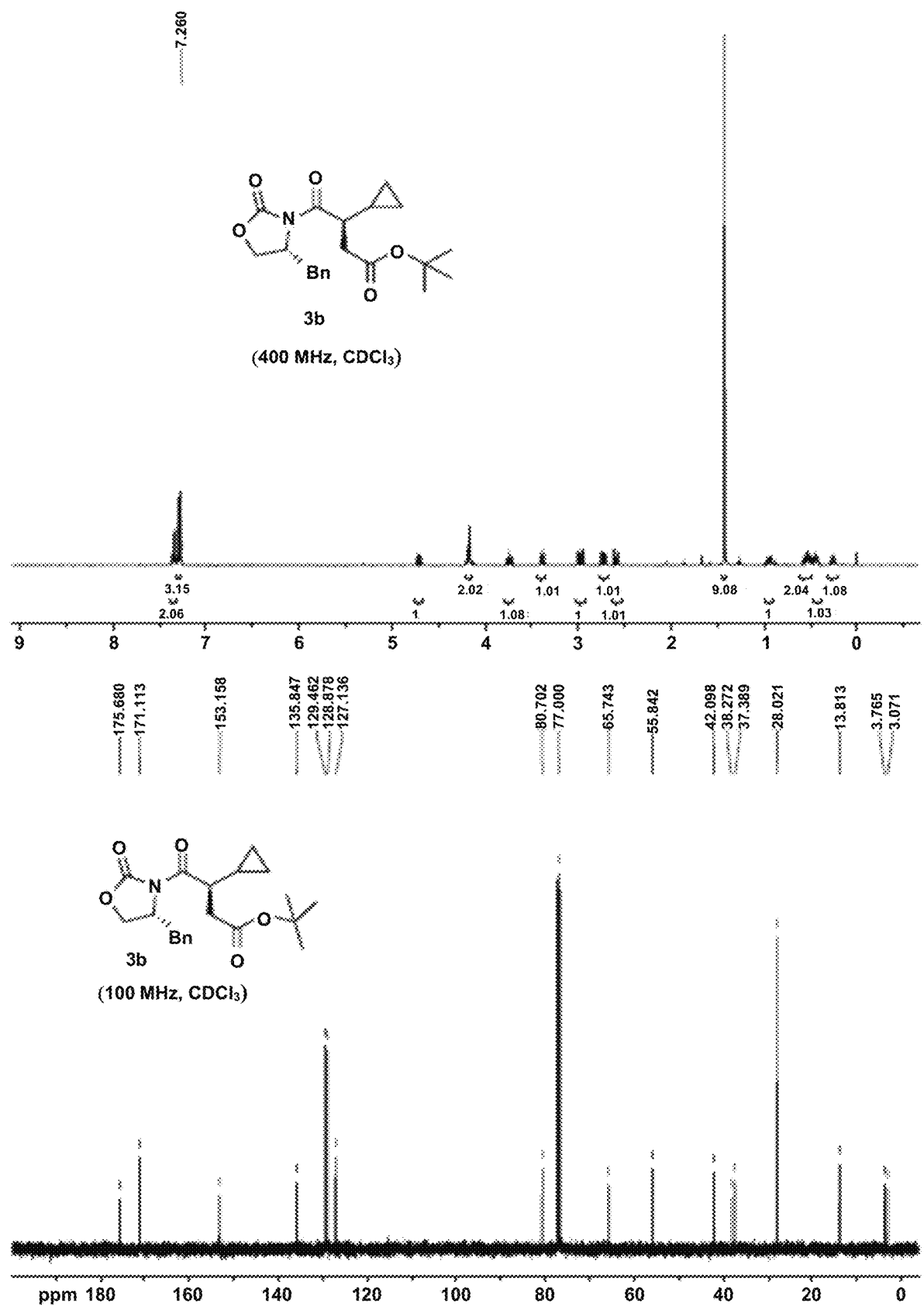
FIG. 4 shows the $^1$H NMR and $^{13}$C NMR spectra of compound 3b.

White solid; Yield: 82%; Rf: 0.5 (Hexanes:EtOAc=8:2); $[\alpha]^{21}_D$=−28.0 (c 0.5, CHCl$_3$); $^1$H NMR (400 MHz, CDCl$_3$): δ 7.37-7.27 (m, 5H), 4.73-4.68 (m, 1H), 4.21-4.15 (m, 2H), 3.77 (td, J=6.45, 3.52 Hz, 1H), 3.41 (dd, J=10.2, 8.0 Hz, 1H), 3.01 (dd, J=11.01, 6.26 Hz, 1H), 2.76 (dd, J=13.23, 10.1 Hz, 1H), 2.62 (dd, J=12.2, 4.3 Hz, 1H), 1.43 (s, 9H), 1.0-0.89 (m, 1H), 0.59-0.48 (m, 2H), 0.47-0.4 (m, 1H), 0.29-0.23 (m, 1H); $^{13}$C NMR (100 MHz, CDCl$_3$): δ 171.1, 153.1, 135.9, 129.5, 128.9, 127.1, 171.1, 153.1, 135.9, 129.5, 128.9, 127.1, 80.7, 65.7, 55.9, 42.1, 38.3, 37.4, 28.0, 13.8, 3.8, 3.0; HRMS (ESI+) m/z: [M+Na]$^+$ Calc'd for C$_{21}$H$_{27}$NNaO$_5$ 396.1781; Found 396.1775. FIG. 4 shows the $^1$H NMR and $^{13}$C NMR spectra of compound 3b.

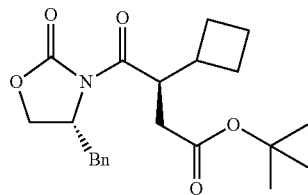

3c tert-butyl(R)-4-((R)-4-benzyl-2-oxooxazolidin-3-yl)-3-cyclobutyl-4-oxobutanoate (3c)

Figure 5:
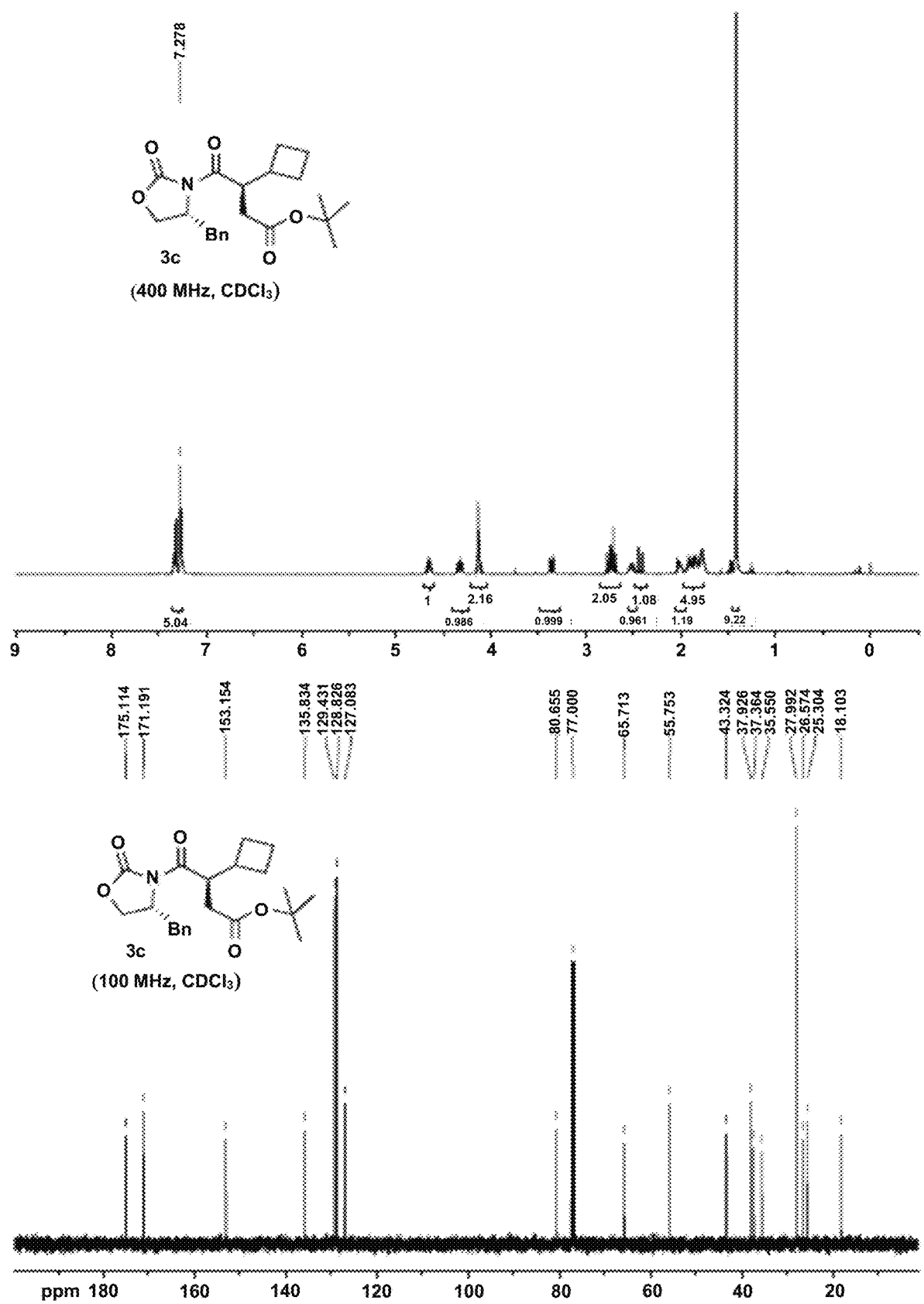
FIG. 5 shows the $^1$H NMR and $^{13}$C NMR spectra of compound 3c.

White solid; Yield: 80%; Rf: 0.4 (Hexanes:EtOAc=9:1); $[\alpha]^{22}_D$=−35.7 (c 3.0, CHCl$_3$); $^1$H NMR (400 MHz, CDCl$_3$): 7.37-7.26 (m, 5H), 4.70-4.64 (m, 1H), 4.38-4.32 (m, 1H), 4.17 (m, 2H), 3.40 (dd, J=10.69, 3.51 Hz, 1H), 2.80-2.70 (m, 2H), 2.47 (dd, J=16.7, 4.17 Hz), 1.94-1.85 (m, 3H), 1.82-1.75 (m, 3H), 1.44 (s, 9H); $^{13}$C NMR (100 MHz, CDCl$_3$): δ 175.1, 171.2, 153.2, 129.5, 128.9, 127.1, 55.8, 38.0, 34.6, 31.5, 26.6, 26.5, 22.6; HRMS (ESI+) m/z: [M+Na]$^+$ Calc'd for C$_{22}$H$_{29}$NNaO$_5$ 410.1938; Found 410.1944. FIG. 5 shows the $^1$H NMR and $^{13}$C NMR spectra of compound 3c.

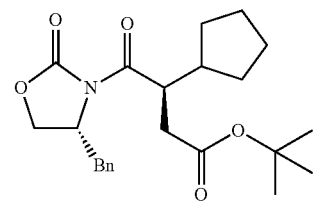

3d tert-butyl(R)-4-((R)-4-benzyl-2-oxooxazolidin-3-yl)-3-cyclopentyl-4-oxobutanoate (3d)

Figure 6:
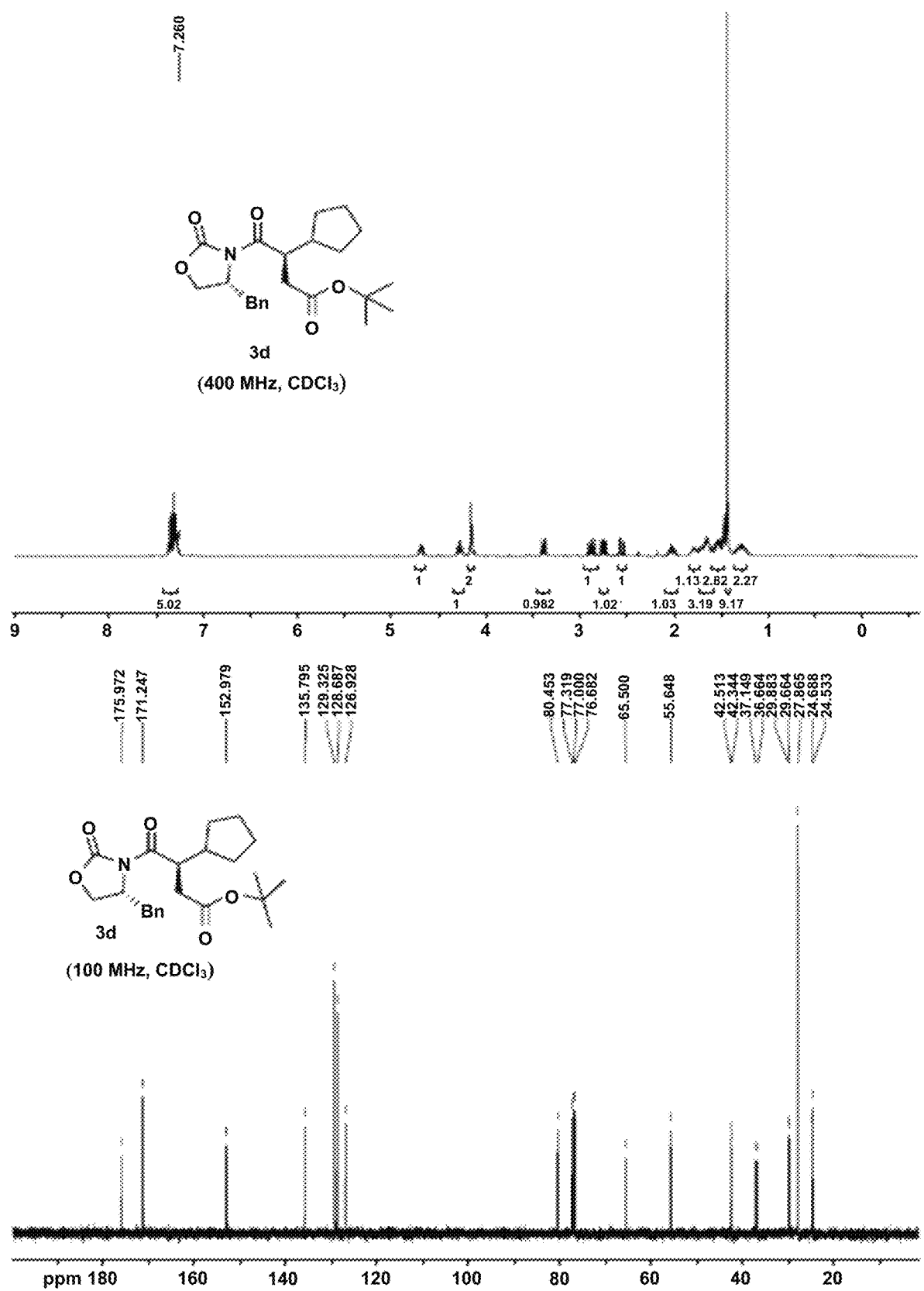
FIG. 6 shows the $^1$H NMR and $^{13}$C NMR spectra of compound 3d.

White solid; Yield: 93%; Rf: 0.6 (Hexanes:EtOAc=9:1); $[\alpha]^{23}_D$=−40.0 (c 0.5, CHCl$_3$); $^1$H NMR (400 MHz, CDCl$_3$): δ 7.35-7.24 (m, 5H), 4.70-4.64 (m, 1H), 4.29-4.23 (m, 1H), 4.15-4.12 (m, 2H), 3.39 (dd, J=13.8, 3.0 Hz, 1H), 2.89 (dd, J=16.7, 11.3 Hz, 1H), 2.76 (dd, J=13.3, 10.3 Hz, 1H), 2.56 (dd, J=13.0, 3.6 Hz, 1H), 2.06-1.95 (m, 1H), 1.80-1.44 (m, 6H), 1.42 (s, 9H), 1.33-1.21 (m, 2H); $^{13}$C NMR (100 MHz, CDCl$_3$): δ 176.0, 171.3, 153.0, 135.8, 129.3, 128.7, 126.9, 80.5, 65.5, 55.7, 42.5, 42.3, 37.2, 36.7, 29.9, 29.7, 27.9, 27.8, 24.7, 24.5; HRMS (ESI+) m/z: [M+Na]$^+$ Calc'd for C$_{23}$H$_{31}$NNaO$_5$ 424.2094; Found 424.2102. FIG. 6 shows the $^1$H NMR and $^{13}$C NMR of compound 3d.

Example 5: Synthesis of Compounds 4a-4e

Cleavage of the chiral auxiliary using LiOH/H$_2$O$_2$ yielded acid derivatives 4a-4e.

Synthesis of compound 4b: A solution of imide 3b (0.565 g, 1.51 mmol) in 7.0 mL of THF and 3.0 mL of deionized water was cooled to 0° C. and treated with 1.10 mL of a 30% wt. H$_2$O$_2$ solution. The mixture was stirred, and a freshly prepared solution of LiOH (0.14 g, 3.48 mmol) in 3.0 mL of deionized water was added to the mixture. The reaction mixture was stirred for 12 hours slowly warming to room temperature. Next, the mixture was cooled to 0° C. and quenched with 0.4 mL of 2N Na$_2$S$_2$O$_3$ solution with continuous stirring. The THF was evaporated in vacuo and the aqueous residue was diluted with 2N NaOH solution until the pH reached 12. The solution was then diluted with CH$_2$Cl$_2$ (25 mL). The first organic layer (CH$_2$Cl$_2$) containing chiral auxiliary was set aside. The remaining aqueous layer was then acidified with 10% HCl solution until the pH reached to 2; and extracted with CH$_2$Cl$_2$ (3×30 mL). This second CH$_2$Cl$_2$ layer containing required acid product was then dried over MgSO$_4$, filtered and the solvent was evaporated under reduced pressure to yield the title compound.

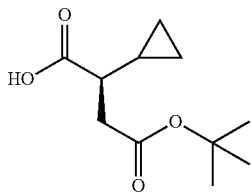

4b

(R)-4-(tert-butoxy)-2-cyclopropyl-4-oxobutanoic acid (4b)

Figure 7:
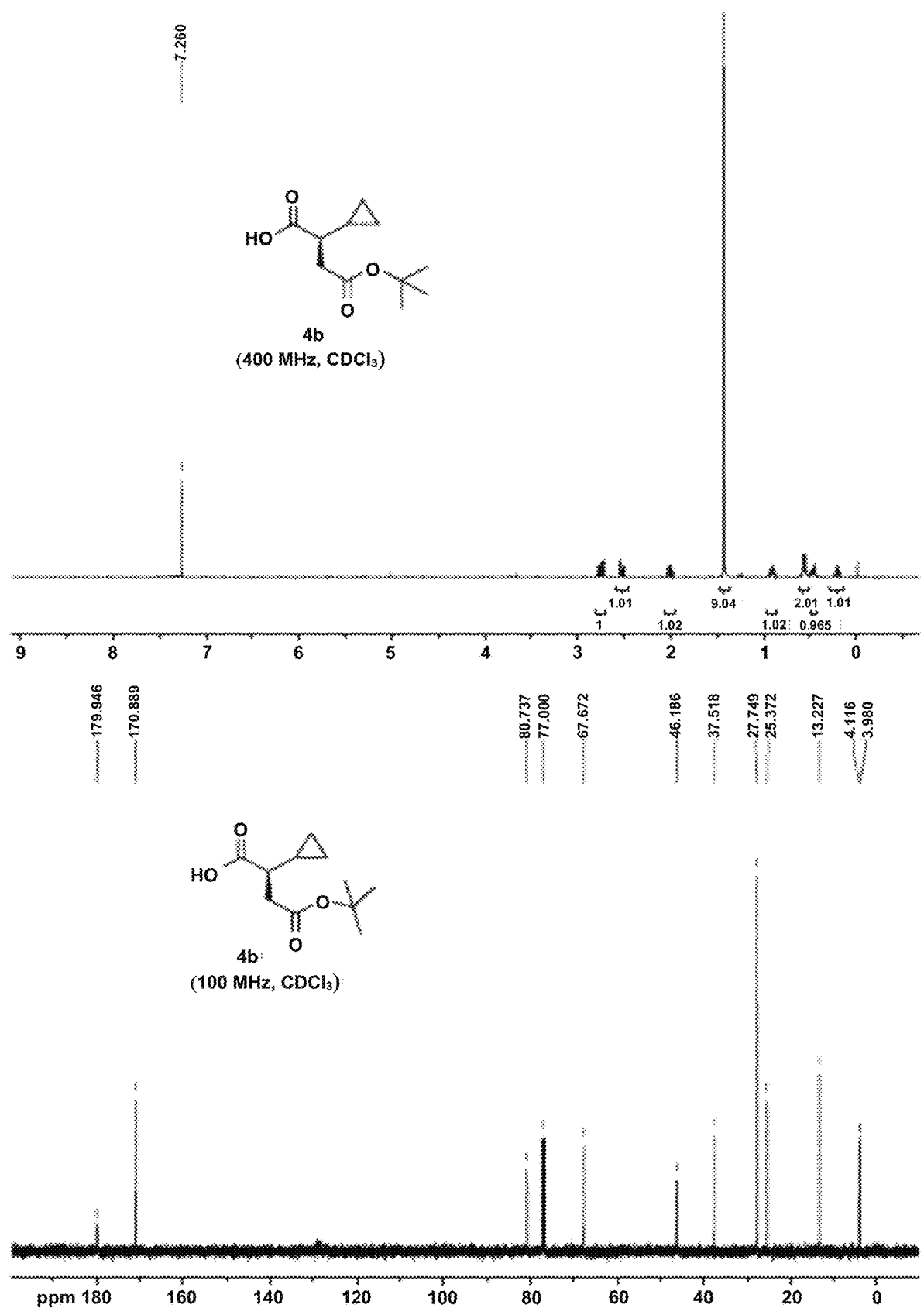
FIG. 7 shows the $^1$H NMR and $^{13}$C NMR spectra of compound 4b.

Colorless oil; Yield: 99%; Rf: 0.15 (Acetone:EtOAc=3:2); $[\alpha]^{20}{}_D$=−39.4 (c 0.5, CHCl3); $^1$H NMR (400 MHz, CDCl$_3$): δ 2.78 (dd, J=10.2, 6.02 Hz, 1H), 2.55 (dd, J=12.2, 4.71 Hz, 1H), 2.04 (m, 1H), 1.43 (m, 9H), 0.96-0.87 (m, 1H), 0.59-0.54 (m, 2H), 0.49-0.45 (m, 1H), 0.22-0.18 (m, 1H); $^{13}$C NMR (100 MHz, CDCl$_3$): δ 180.8, 170.9, 80.9, 46.3, 37.6, 27.8, 13.3, 4.2, 4.1; HRMS (ESI+) m/z: [M+Na]+ Calc'd for $C_{11}H_{18}NaO_4$ 237.1097; Found 237.1102. FIG. 7 shows the $^1$H NMR and $^{13}$C NMR spectra of compound 4b.

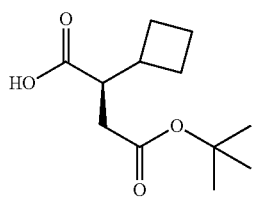

4c (R)-4-(tert-butoxy)-2-cyclobutyl-4-oxobutanoic acid (4c)

Figure 8:
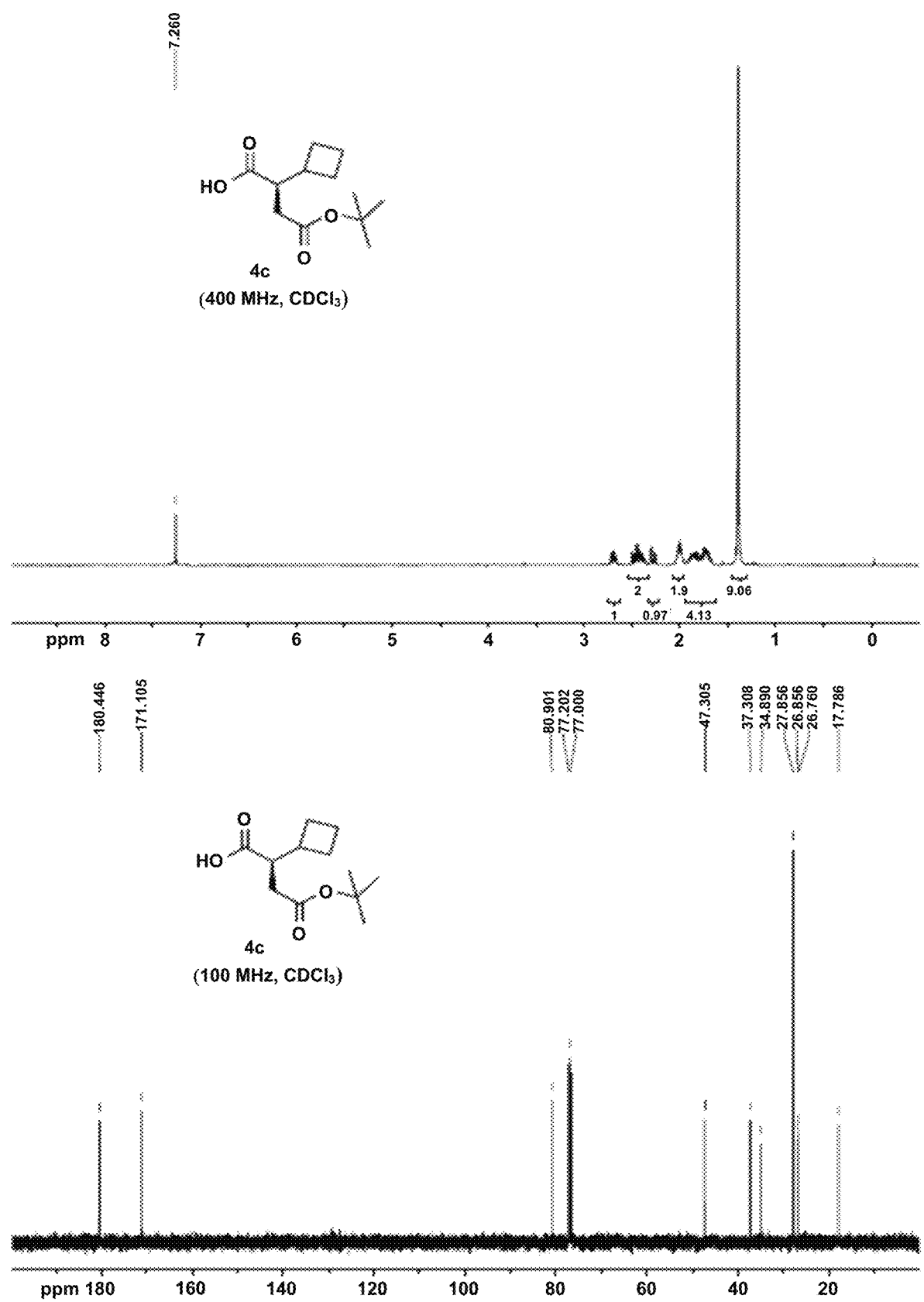
FIG. 8 shows the $^1$H NMR and $^{13}$C NMR spectra of compound 4c.

Colorless oil; Yield: 89%; Rf: 0.1 (Acetone:EtOAc=3:1); $[\alpha]^{22}{}_D$=−20.0 (c 3.3, CHCl$_3$); $^1$H NMR (400 MHz, CDCl$_3$): δ 12.1 (bs, 1H), 4.71-4.64 (m, 1H), 4.48-4.36 (m, 2H), 4.29-4.24 (m, 1H), 4.0 (m, 1H), 3.87-3.78 (m, 3H), 3.74-3.67 (m, 3H), 3.38 (s, 9H); $^{13}$C NMR (100 MHz, CDCl$_3$): δ 180.1, 171.2, 80.9, 53.4, 47.3, 37.3, 34.9, 26.8, 26.7, 17.8; HRMS (ESI+) m/z: [M+Na]+ Calc'd for $C_{12}H_{20}NaO_4$ 251.1254; Found 251.1257. FIG. 8 shows the $^1$H NMR and $^{13}$C NMR spectra of compound 4c.

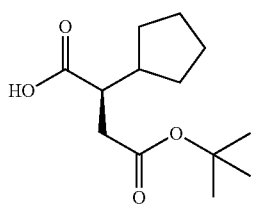

4d (R)-4-(tert-butoxy)-2-cyclopentyl-4-oxobutanoic acid (4d)

Figure 9:
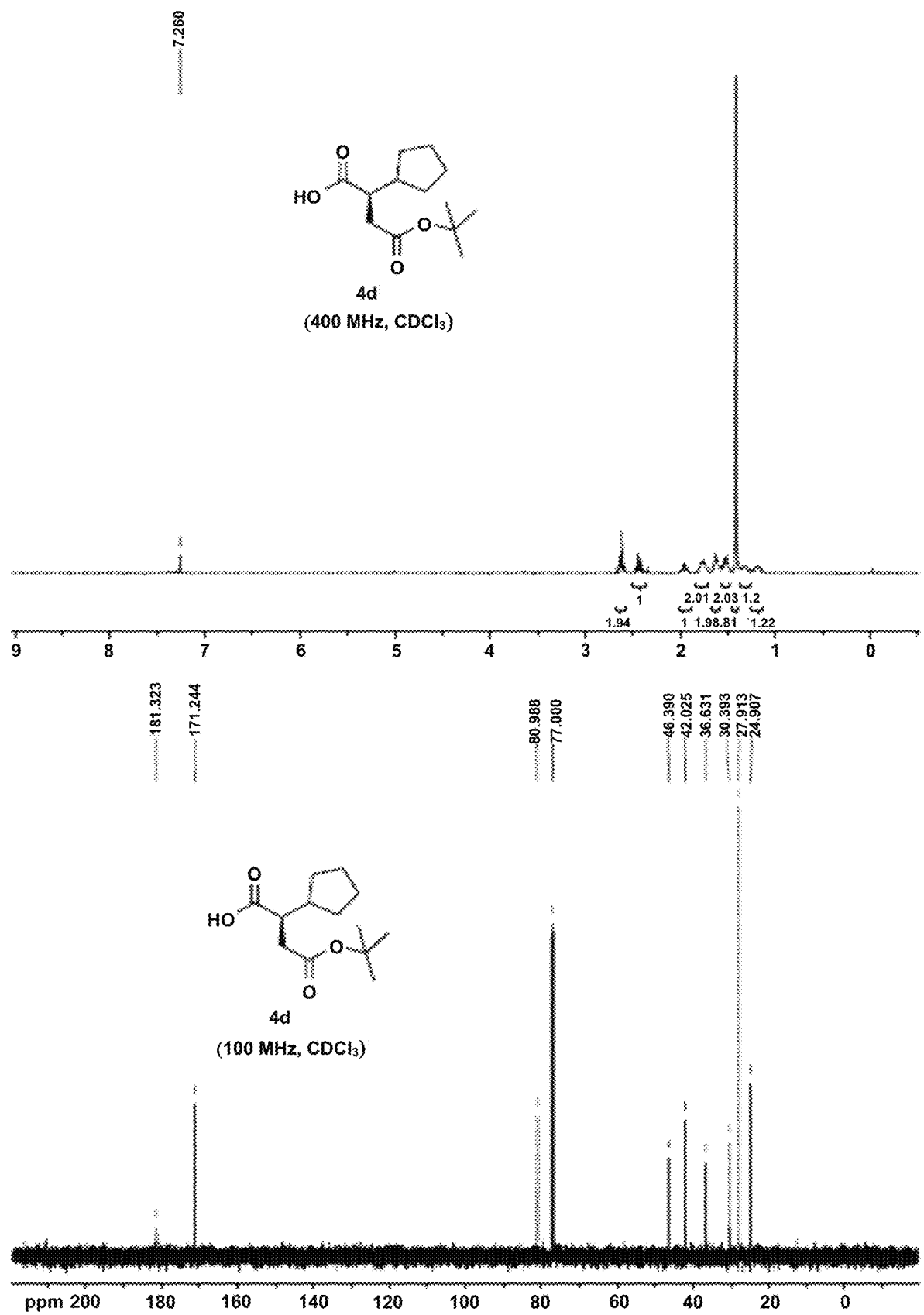
FIG. 9 shows the $^1$H NMR and $^{13}$C NMR spectra of compound 4d.

Colorless oil; Yield: 62%; Rf: 0.2 (Acetone:EtOAc=3:1); $[\alpha]^{21}{}_D$=−5.4 (c 2.2, CHCl$_3$); $^1$H NMR (400 MHz, CDCl$_3$): δ 2.67-2.58 (m, 2H), 2.46-2.39 (m, 1H), 1.99-1.91 (m, 1H), 1.81-1.73 (m, 2H), 1.67-1.60 (m, 2H), 1.57-1.47 (m, 2H), 1.41 (s, 9H), 1.37-1.27 (m, 1H), 1.25-1.14 (m, 1H); $^{13}$C NMR (100 MHz, CDCl$_3$): δ 171.3, 81.0, 46.4, 42.0, 36.6, 30.4, 30.4, 27.9, 24.9, 24.8; HRMS (ESI+) m/z: [M+Na]+ Calc'd for $C_{13}H_{22}NaO_4$ 265.1410; Found 265.1402. FIG. 9 shows the $^1$H NMR and $^{13}$C NMR spectra of compound 4d.

Example 6: Synthesis of Compounds 5a-5e

Compounds 4a-4e were subjected to one-pot chlorination-lactonization sequences to afford trans-β-lactones 5a-5e. A decrease in the yield for β-lactone formation was observed as P1 became progressively more strained.

Synthesis of compound 5d: A solution of HMDS (0.47 mL, 2.30 mmol) in 3.5 mL of dry THF was cooled to 0° C. and treated with n-BuLi (1.16 mL of a 1.97 M solution in hexanes, 2.30 mmol) dropwise. The reaction mixture was stirred for 20 minutes at the same temperature before cooling to −78° C. To the solution of LHMDS thus obtained was added a solution of acid 4d (0.223 g, 0.92 mmol) in 3.5 mL of dry THF via cannula at −78° C. The reaction was stirred for 1 hour at the same temperature to form the required enolate before freshly distilled CCl$_4$ (0.10 mL, 1.10 mmol) was added. The reaction mixture was stirred for 12 hours slowly warming to room temperature. After 12 hours, solvent was evaporated in rotavapor and the residue thus obtained was suspended in 22.0 mL of diethyl ether. With continuous stirring, the suspension was treated with 18.0 mL of 5% NaHCO$_3$ solution. The flask was capped and the mixture was vigorously stirred at room temperature overnight and then diluted with Et$_2$O, washed with saturated solutions of NaHCO$_3$ and brine, dried over MgSO$_4$, and filtered, and the solvent was evaporated under reduced pressure. The crude product was purified by flash column chromatography using hexane-EtOAc (9:1) to obtain 0.110 g of title compound.

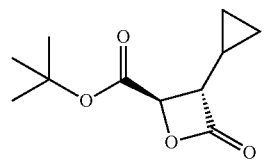

5b tert-butyl(2R,3S)-3-cyclopropyl-4-oxooxetane-2-carboxylate (5b)

Figure 10:
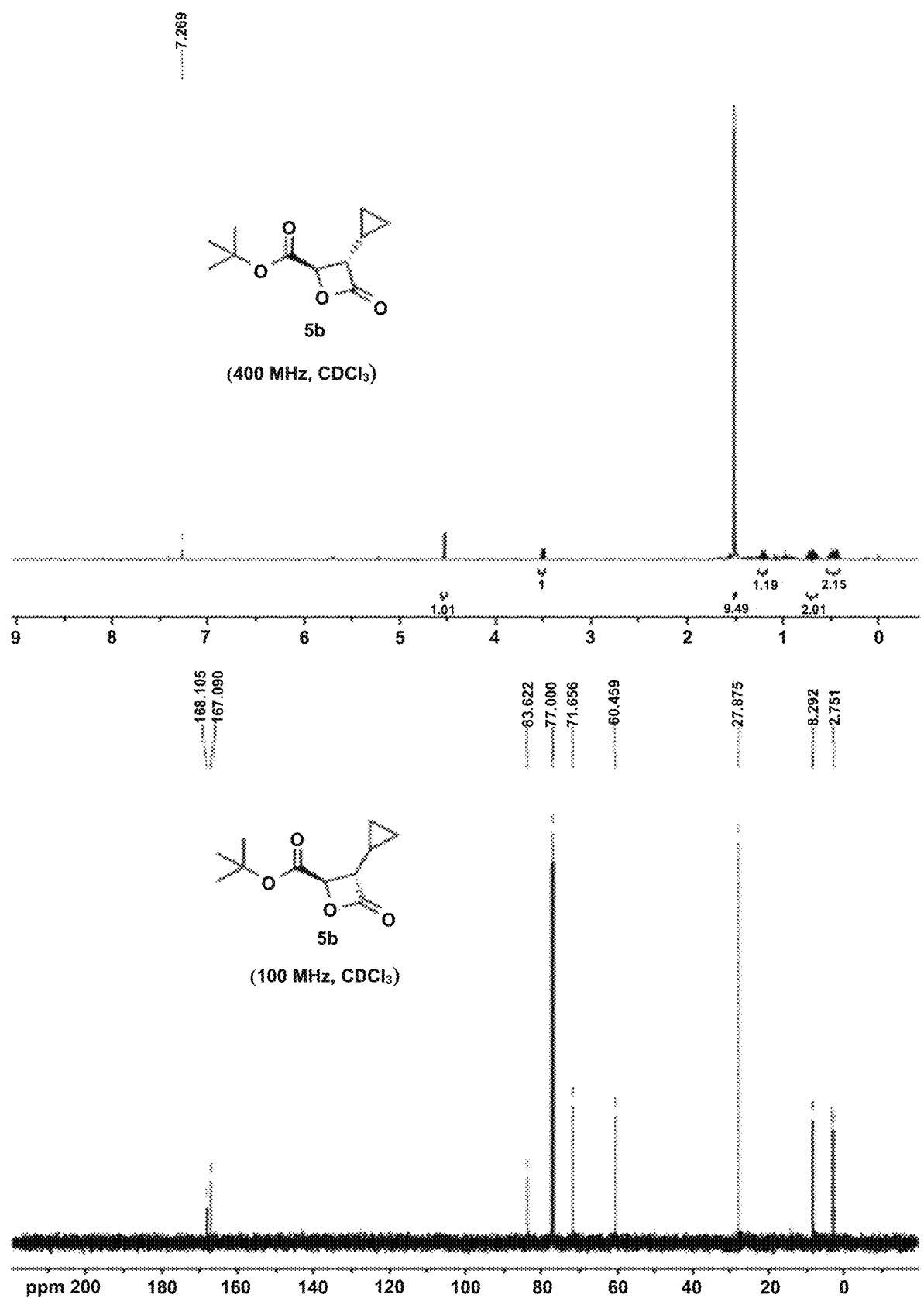
FIG. 10 shows the $^1$H NMR and $^{13}$C NMR spectra of compound 5b.

Colorless oil; Yield: 11%; Rf: 0.5 (Hexanes:EtOAc=8:2); $[\alpha]^{22}{}_D$=−19.3 (c 0.3, CHCl$_3$); $^1$H NMR (400 MHz, CDCl$_3$): δ 4.53 (d, J=4.49 Hz, 1H), 3.51 (dd, J=7.47, 4.4 Hz, 1H), 1.5 (s, 9H), 1.22-1.15 (m, 1H), 0.75-0.63 (m, 2H), 0.5-0.39 (m, 2H); $^{13}$C NMR (100 MHz, CDCl$_3$): δ 168.1, 167.0, 83.6, 71.7, 60.5, 27.9, 8.3, 3.2, 2.8. FIG. 10 shows the $^1$H NMR and $^{13}$C NMR spectra of compound 5b.

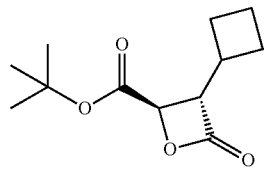

5c tert-butyl (2R,3S)-3-cyclobutyl-4-oxooxetane-2-carboxylate (5c)

Figure 11:
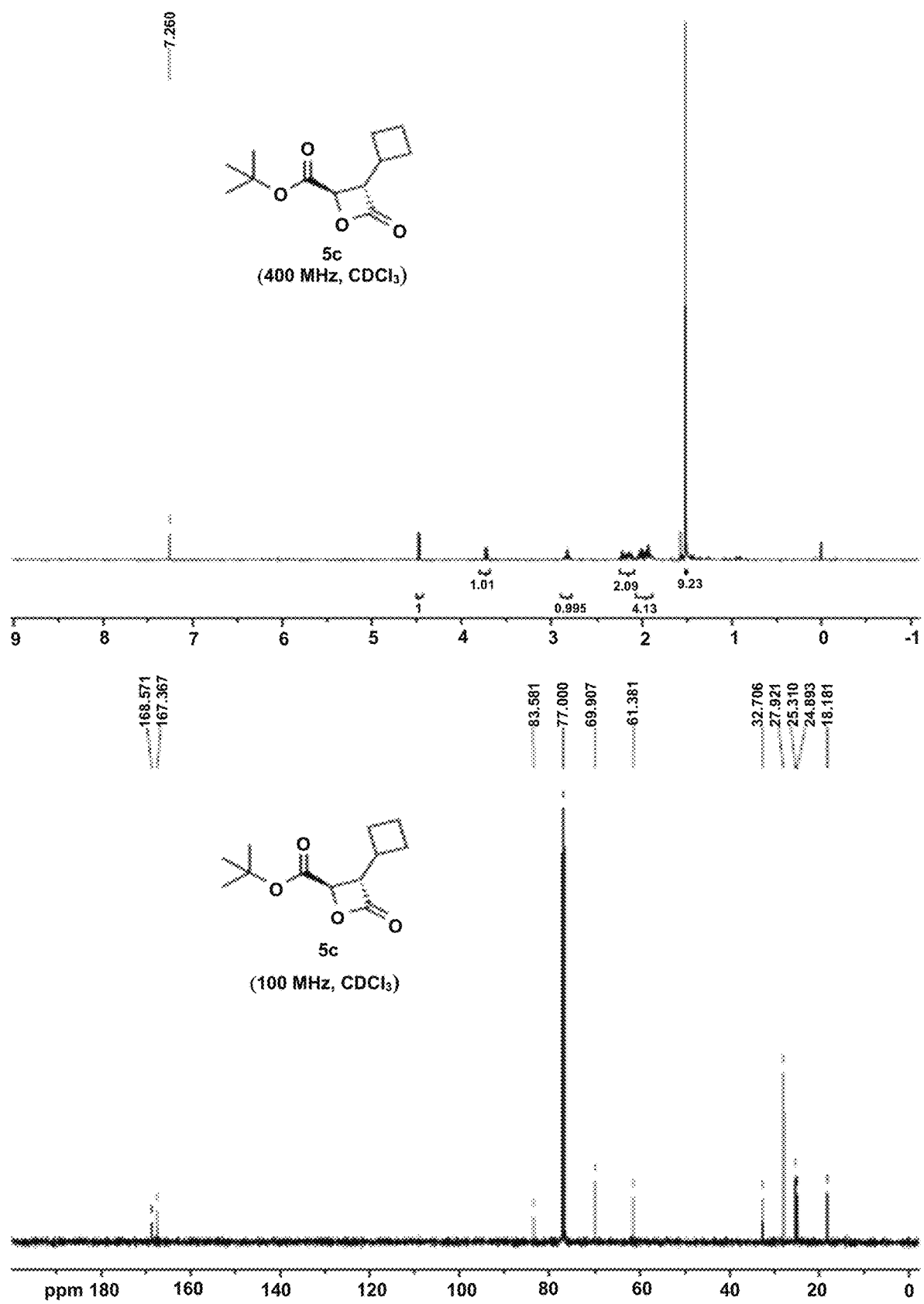
FIG. 11 shows the $^1$H NMR and $^{13}$C NMR spectra of compound 5c.

Colorless oil; Yield: 20%; Rf: 0.4 (Hexanes:Et$_2$O=9:1); $[\alpha]^{22}{}_D$=−2.3 (c 1.7, CHCl$_3$); $^1$H NMR (400 MHz, CDCl$_3$): δ 4.49 (d, J=4.36 Hz), 3.75 (dd, J=4.55, 4.28 Hz, 1H), 2.85-2.81 (m, 1H), 2.21-2.10 (m, 3H), 1.93-1.89 (m, 2H), 1.51 (s, 9H); $^{13}$C NMR (100 MHz, CDCl$_3$): δ 168.6, 167.4, 83.6, 69.9, 61.3, 32.6, 27.9, 25.3, 24.8, 18.1; HRMS (ESI+)

m/z: [M+Na]+ Calc'd for $C_{12}H_{18}NaO_4$ 249.1097; Found 249.1103. FIG. 11 shows the $^1$H NMR and $^{13}$C NMR spectra of compound 5c.

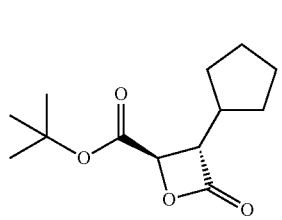

tert-butyl (2S,3S)-3-cyclopentyl-4-oxooxetane-2-carboxylate (5d)

Figure 12:
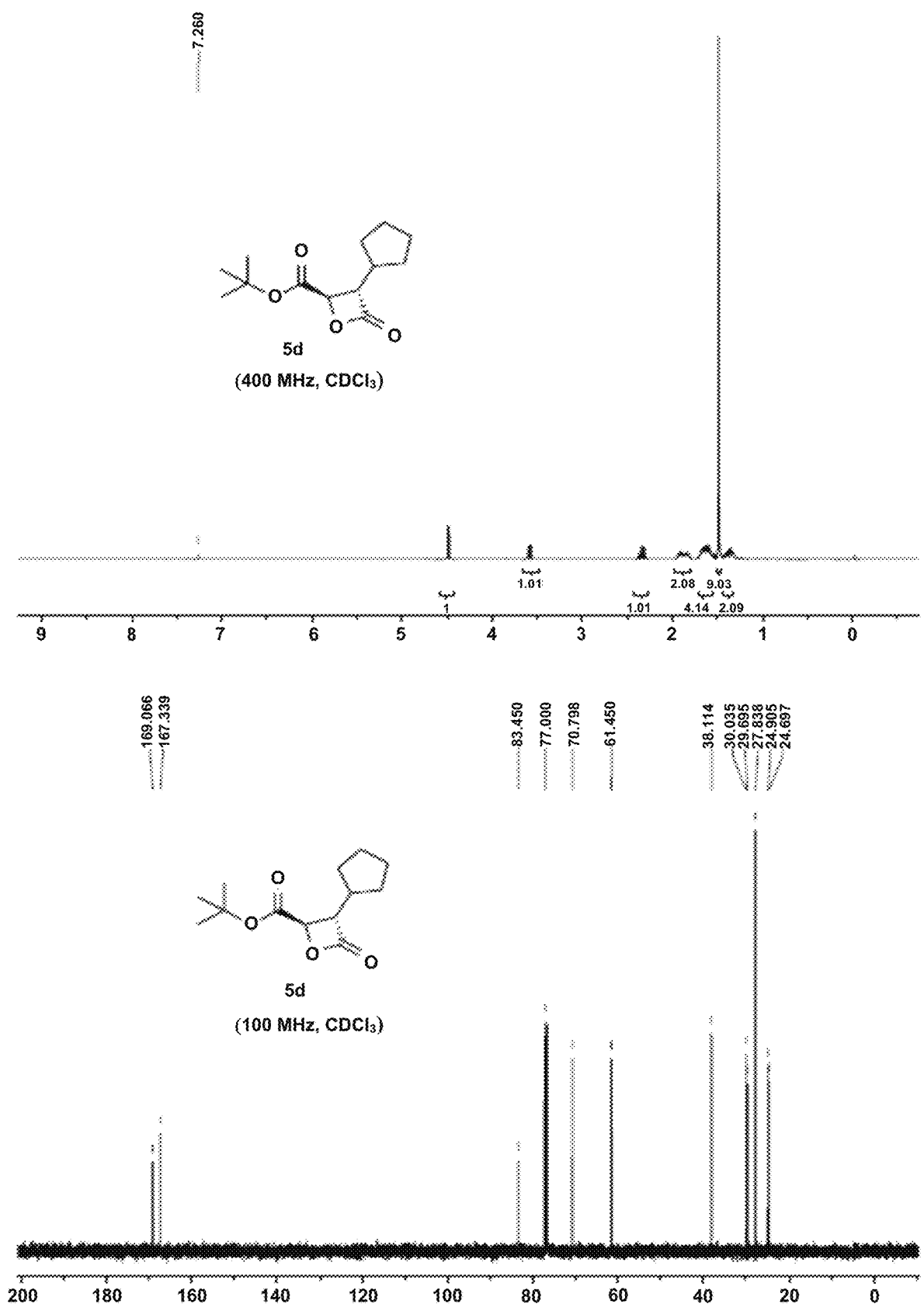
FIG. 12 shows the $^1$H NMR and $^{13}$C NMR spectra of compound 5d.

White solid; Yield: 50%; Rf: 0.4 (Hexanes:EtOAc=9:1); $[\alpha]^{22}_D = -27.4$ (c 0.5, CHCl$_3$); $^1$H NMR (400 MHz, CDCl$_3$): δ 4.49 (d, J=4.4 Hz, 1H), 3.60 (dd, J=8.5, 4.6 Hz, 1H), 2.38-2.28 (m, 1H), 1.94-1.82 (m, 2H), 1.70-1.56 (m, 4H), 1.49 (s, 9H), 1.43-1.31 (m, 2H); $^{13}$C NMR (100 MHz, CDCl$_3$): δ 169.0, 167.4, 83.5, 70.8, 61.5, 38.1, 30.0, 29.7, 27.8, 24.9, 24.7; HRMS (ESI+) m/z: [M+Na]+ Calc'd for $C_{13}H_{20}NaO_4$ 263.1254; Found 263.1258. FIG. 12 shows the $^1$H NMR and $^{13}$C NMR spectra of compound 5d.

Example 7: Synthesis of Dipeptide Fragments 7a-7s

Dipeptide fragments 7a-7s were assembled by esterification of L-amino acids with aliphatic or aromatic alcohols, followed by coupling with either N-Boc of Fmoc protected amino acids (SCHEME 2).

SCHEME 2

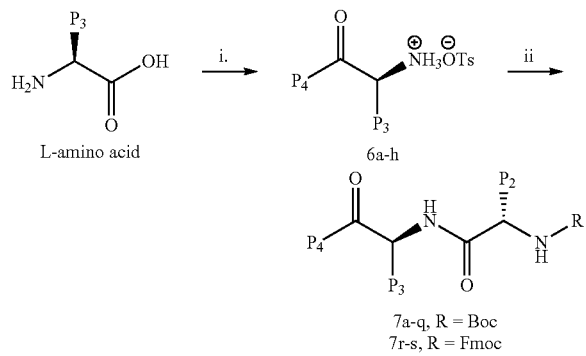

7a-q, R = Boc
7r-s, R = Fmoc

Reagents and conditions: (i) P$_4$—OH, p-TSA • H$_2$O, toluene, reflux (ii) N-Boc/Fmoc amino acid, EDCI, HOBt, THF 0° C. to rt.

Example 8: Synthesis of Compounds 6a-6h

Synthesis of compound 6b: A mixture of L-valine (1.00 g, 8.53 mmol), cyclohexylmethanol (3.67 mL, 29.87 mmol) and p-TsOH.H$_2$O (1.948 g, 10.24 mmol) in 15.0 mL of toluene were heated to reflux using a Dean-Stark apparatus for 24 hours. Next, the reaction mixture was allowed to cool to room temperature and the solvent was evaporated. The viscous oil thus obtained was placed under high vacuum pump for several hours and recrystallized using 5% hexane in EtOAc to afford 2.985 g (7.74 mmol) of creamy white solid as a product. The crude product thus obtained was used directly for the next step without further purification or characterization.

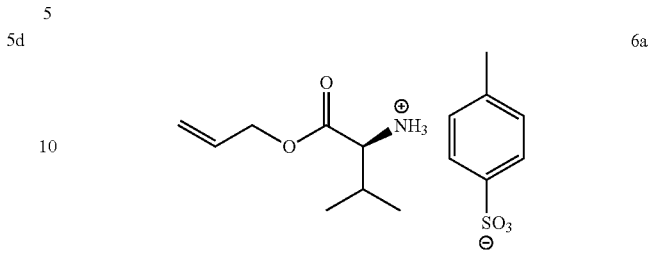

(S)-1-(allyloxy)-3-methyl-1-oxobutan-2-aminium 4-methylbenzenesulfonate (6a)

Compound 6a was synthesized following the general procedure.

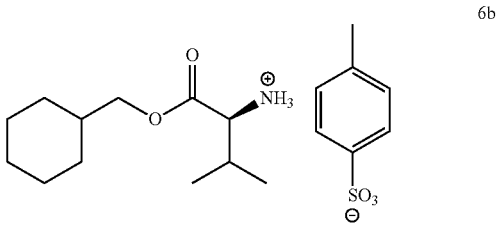

(S)-1-(cyclohexylmethoxy)-3-methyl-1-oxobutan-2-aminium-4-methylbenzenesulfonate (6b)

Figure 13:
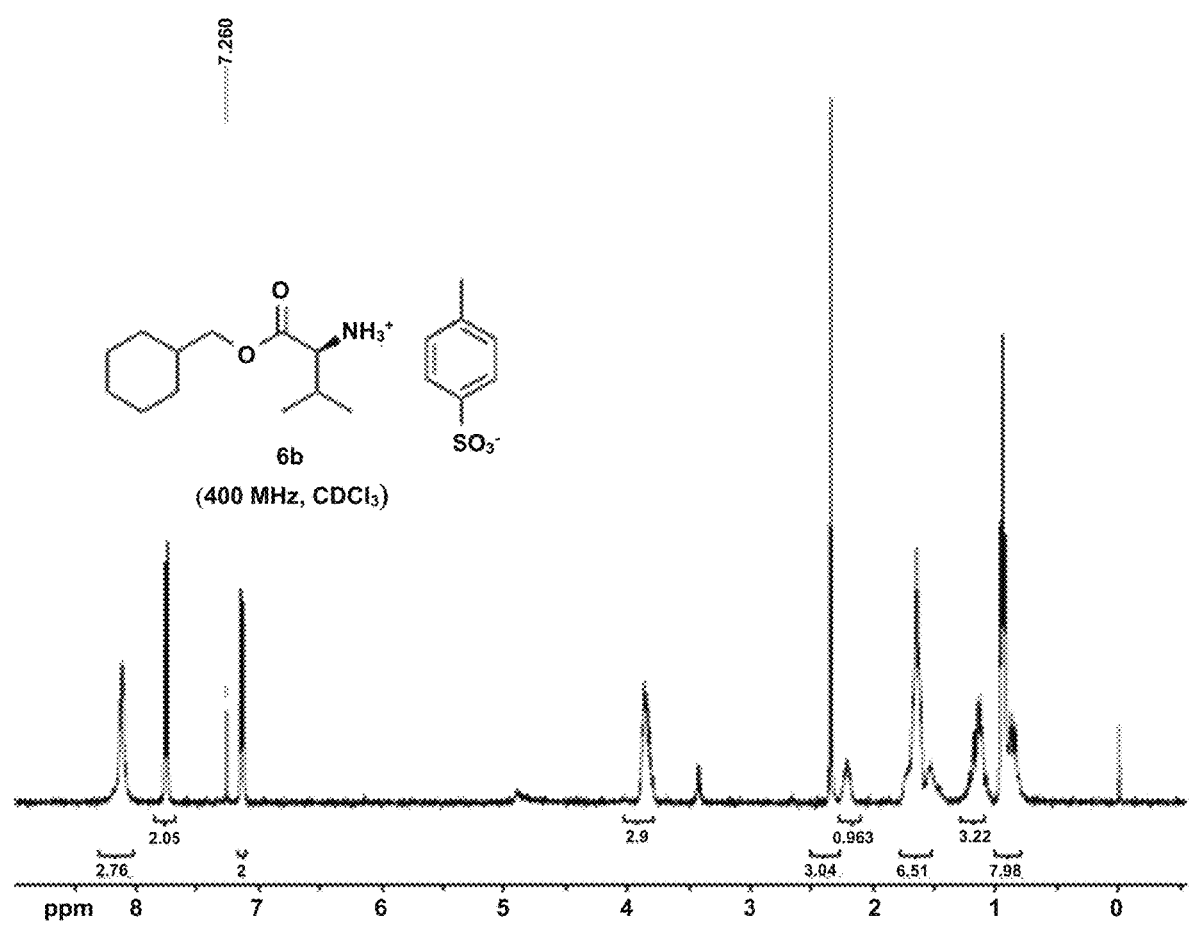
FIG. 13 shows the $^1$H NMR spectrum of compound 6b.

White solid; Yield: 90%; $^1$H NMR (400 MHz, CDCl3): δ 8.11 (bs, 3H), 7.77 (d, J=8.0 Hz, 2H), 7.14 (d, J=8.0 Hz, 2H), 3.79-3.88 (m, 3H), 2.34 (s, 3H), 2.25-2.17 (1H), 1.74-1.58 (m, 6H), 1.25-1.05 (m, 3H), 0.96-0.81 (m, 8H);); 13C NMR (100 MHz, CDCl3): δ 68.9, 141.2, 140.3, 128.8, 126.1, 71.2, 58.3, 36.6, 29.6, 29.5, 29.5, 29.4, 26.5, 26.2, 25.8, 25.5, 25.4. FIG. 13 shows the $^1$H NMR spectrum of compound 6b.

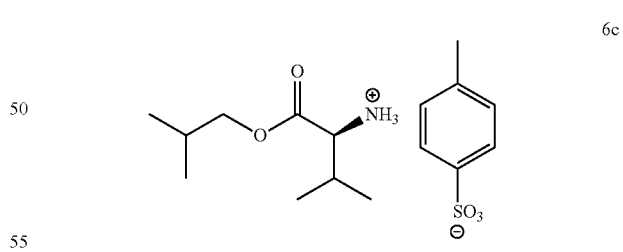

(S)-1-isobutoxy-3-methyl-1-oxobutan-2-aminium 4-methylbenzenesulfonate (6c)

Figure 14:
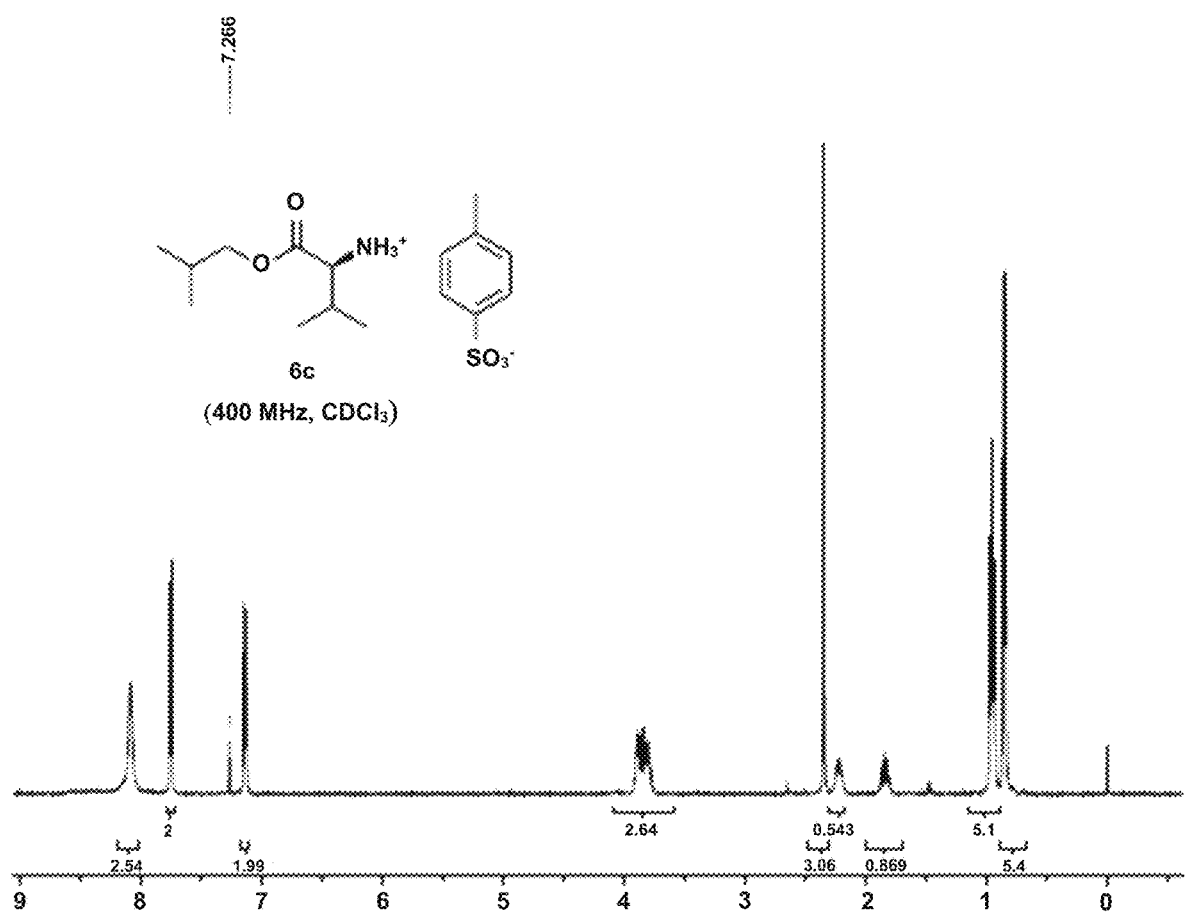
FIG. 14 shows the $^1$H NMR spectrum of compound 6c.

White solid; Yield: quant.; $^1$H NMR (400 MHz, CDCl$_3$): δ 8.08 (bs, 3H), 7.77 (d, J=8.0 Hz, 2H), 7.14 7.77 (d, J=8.0 Hz, 2H), 3.91-3.77 (m, 3H), 2.34 (s, 3H), 2.25-2.20 (m, 1H), 1.89-1.79 (m, 1H), 0.97-0.93 (m, 5H), 0.86 (d, J=6.8 Hz, 5H); $^{13}$C NMR (100 MHz, CDCl$_3$): δ 168.7, 140.8, 140.5, 128.8, 126.2, 72.1, 58.4, 29.6, 27.4, 21.3, 19.0, 18.9, 18.2, 17.4. FIG. 14 shows the $^1$H NMR spectrum of compound 6c.

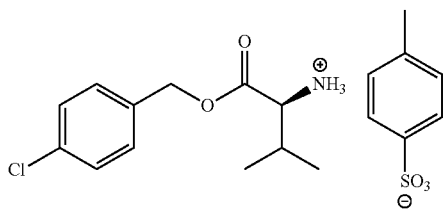

(S)-1-((4-chlorobenzyl)oxy)-3-methyl-1-oxobutan-2-aminium-4-methylbenzenesulfonate (6d)

White solid; Yield: quant.; $^1$H NMR (400 MHz, CDCl$_3$): δ 8.23 (bs, 2H), 7.78 (d, J=8.0 Hz, 2H), 7.41-7.33 (m, 8H), 5.13 (dd, J=12.4, 12.6 Hz, 2H), 3.97 (m, 1H), 2.41 (s, 3H), 0.97 (m, 6H).

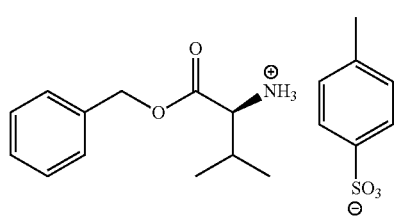

(S)-1-(benzyloxy)-3-methyl-1-oxobutan-2-aminium 4-methylbenzenesulfonate (6e)

Compound 6e was synthesized following the general procedure.

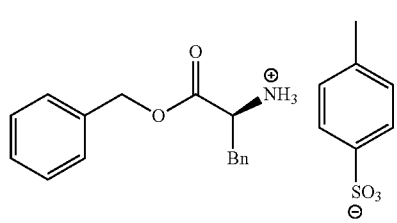

(S)-1-(benzyloxy)-1-oxo-3-phenylpropan-2-aminium 4-methylbenzenesulfonate (6f)

Compound 6f was synthesized following the general procedure.

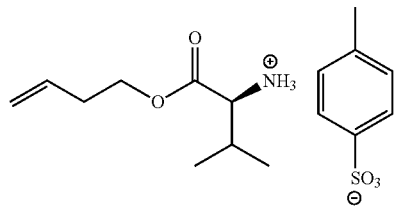

(S)-1-(but-3-en-1-yloxy)-3-methyl-1-oxobutan-2-aminium 4-methylbenzenesulfonate (6g)

Figure 15:
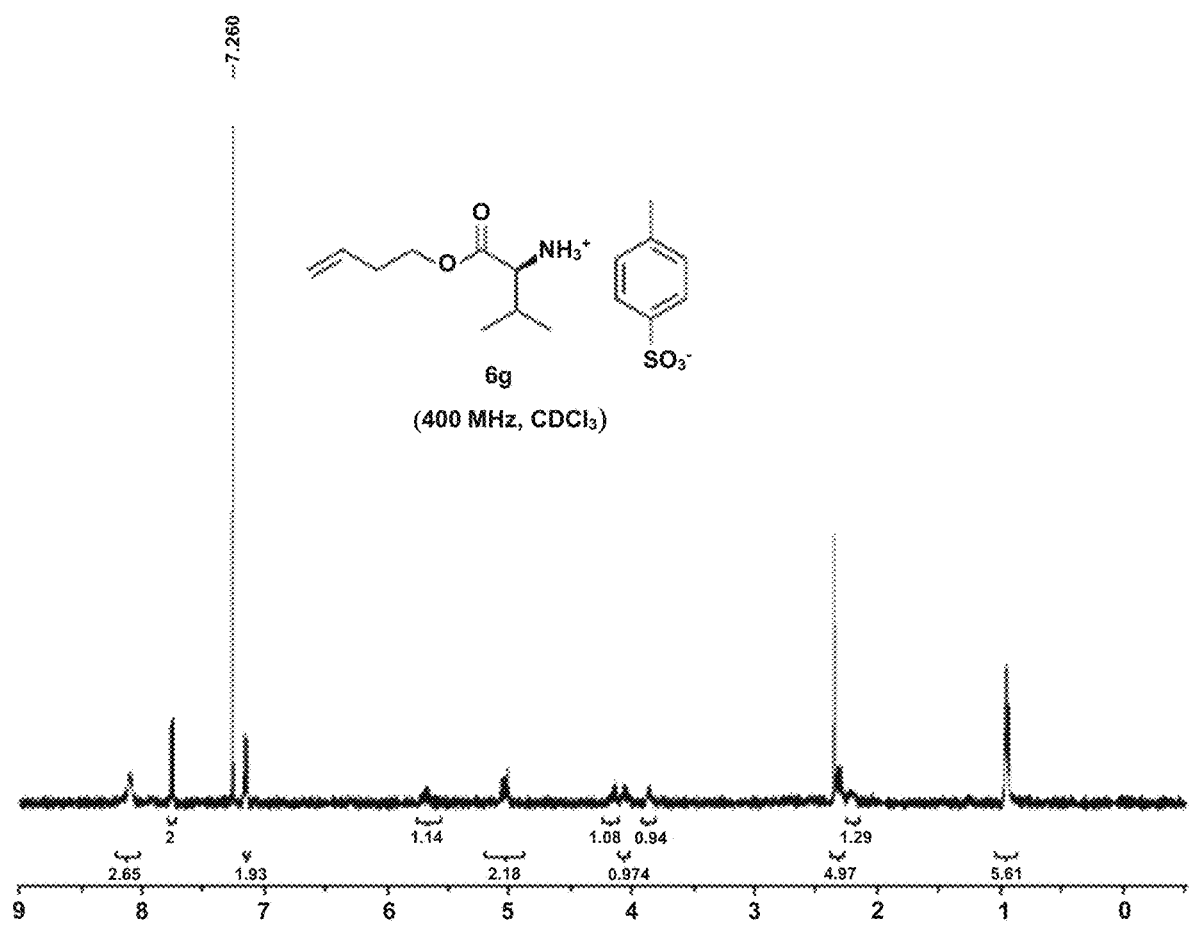
FIG. 15 shows the $^1$H NMR spectrum of compound 6g.

White solid; Yield: quant.; $^1$H NMR (400 MHz, CDCl$_3$): δ 8.10 (bs, 2H), 7.76 (d, J=8.0 Hz, 2H), 7.16 (d, J=8.0 Hz, 2H), 5.73-5.63 (m, 1H), 5.07-5.02 (m, 2H), 4.19-4.11 (m, 1H), 4.09-4.03 (m, 1H), 3.89-3.84 (m, 1H), 2.35 (s, 3H), 2.33-2.28 (m, 2H), 2.26-2.17 (m, 1H), 0.96 (dd, J=6.3, 5.8 Hz, 6H); $^{13}$C NMR (100 MHz, CDCl$_3$): δ 168.6, 140.5, 133.4, 128.8, 126.1, 117.5, 65.0, 58.4, 32.6, 29.5, 21.3, 18.3, 17.4. FIG. 15 shows the $^1$H NMR spectrum of compound 6g.

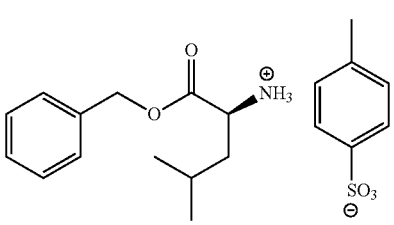

(S)-1-(benzyloxy)-4-methyl-1-oxopentan-2-aminium 4-methylbenzenesulfonate (6h)

Compound 6h was synthesized following the general procedure.

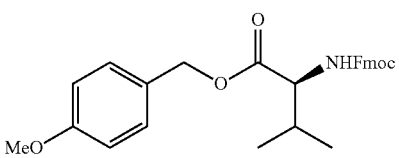

4-methoxybenzyl (((9H-fluoren-9-yl)methoxy)carbonyl)-L-valinate (6i)

Compound 6i was synthesized following the general procedure.

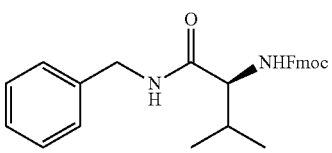

(9H-fluoren-9-yl)methyl(S)-(1-(benzylamino)-3-methyl-1-oxobutan-2-yl)carbamate (6j)

Compound 6j was synthesized following the general procedure.

Example 9: Deprotection of Fmoc Groups

Synthesis of compound 6i (a): A solution of—Fmoc compound 6i (1.82 g, 3.96 mmol) in 14.0 mL of dry CH$_2$Cl$_2$ at 0° C. under nitrogen atmosphere was treated with Et$_2$NH (14.0 mL). The reaction mixture was stirred at 0° C. for 1 hour and at room temperature for 4 hours. TLC examination indicated complete conversion of starting material. The excess solvent/reagents were then removed under reduced pressure and the residue was directly loaded into a SiO₂ column. Compound 6i (a) was purified using hexanes: EtOAc (5:1) followed by 1% Et₃N in EtOAc afforded the free amine.

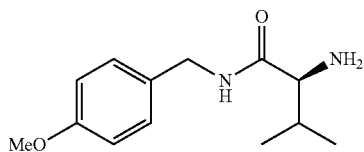

4-methoxybenzyl L-valinate 6i (a)

Figure 16:
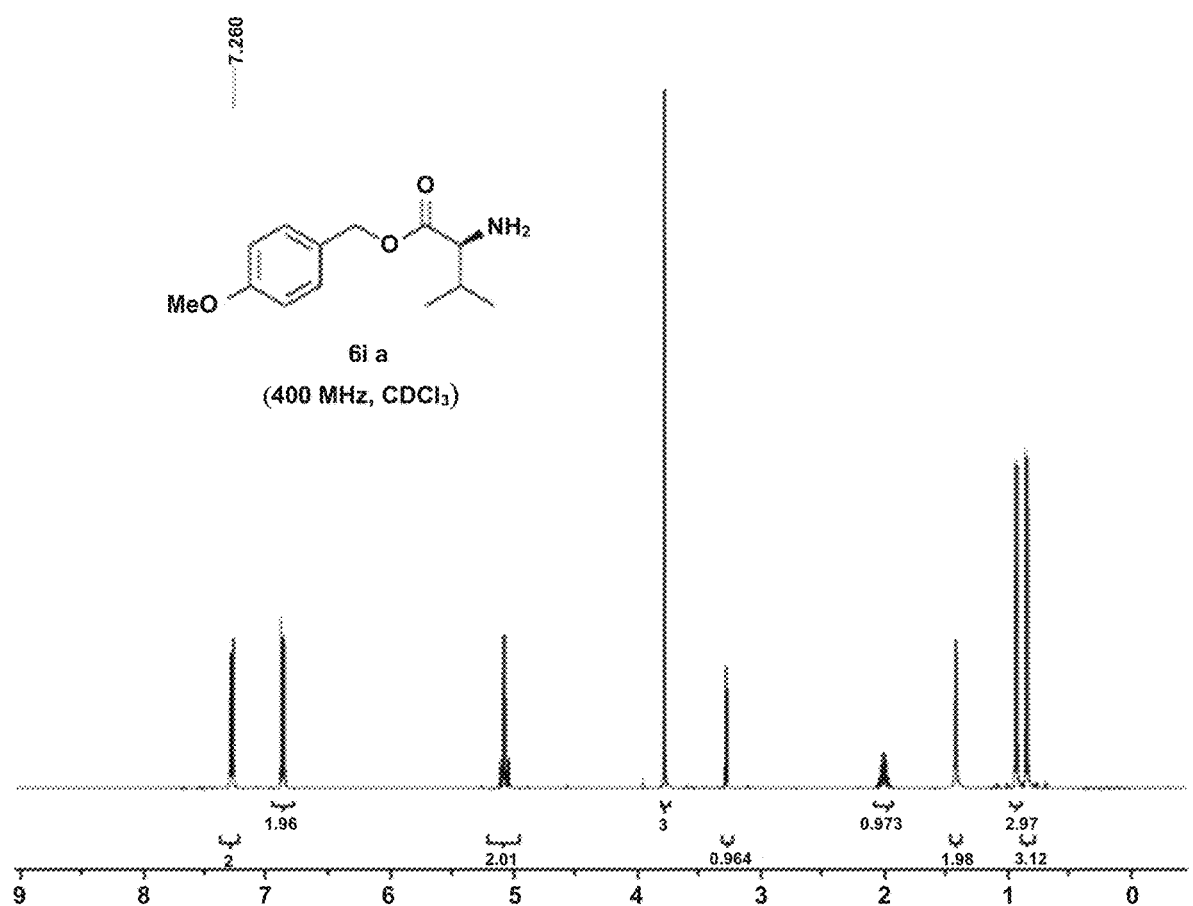
FIG. 16 shows the $^1$H NMR spectrum of compound 6i (a).

Pale yellow oil; Yield: 53%; ¹H NMR (400 MHz, CDCl₃): δ 7.29 (d, J=8.7 Hz, 2H), 6.88 (d, J=8.7 Hz, 2H), 5.11 (d, J=11.8 Hz, 1H), 5.06 (d, J=11.8 Hz, 1H), 3.78 (s, 3H), 3.28 (d, J=4.9 Hz, 1H), 2.05-1.96 (m, 1H), 1.41 (s, 2H), 0.93 (d, J=7.0 Hz, 3H), 0.85 (d, J=6.8 Hz, 3H); ¹³C NMR (100 MHz, CDCl₃): δ 175.3, 159.5, 130.0, 127.8, 113.7, 66.1, 59.7, 55.1, 31.9, 19.1, 16.9. FIG. 16 shows the ¹H NMR spectrum of compound 6i (a).

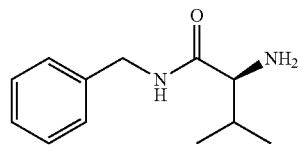

(S)-2-amino-N-benzyl-3-methylbutanamide 6j (a)

Figure 17:
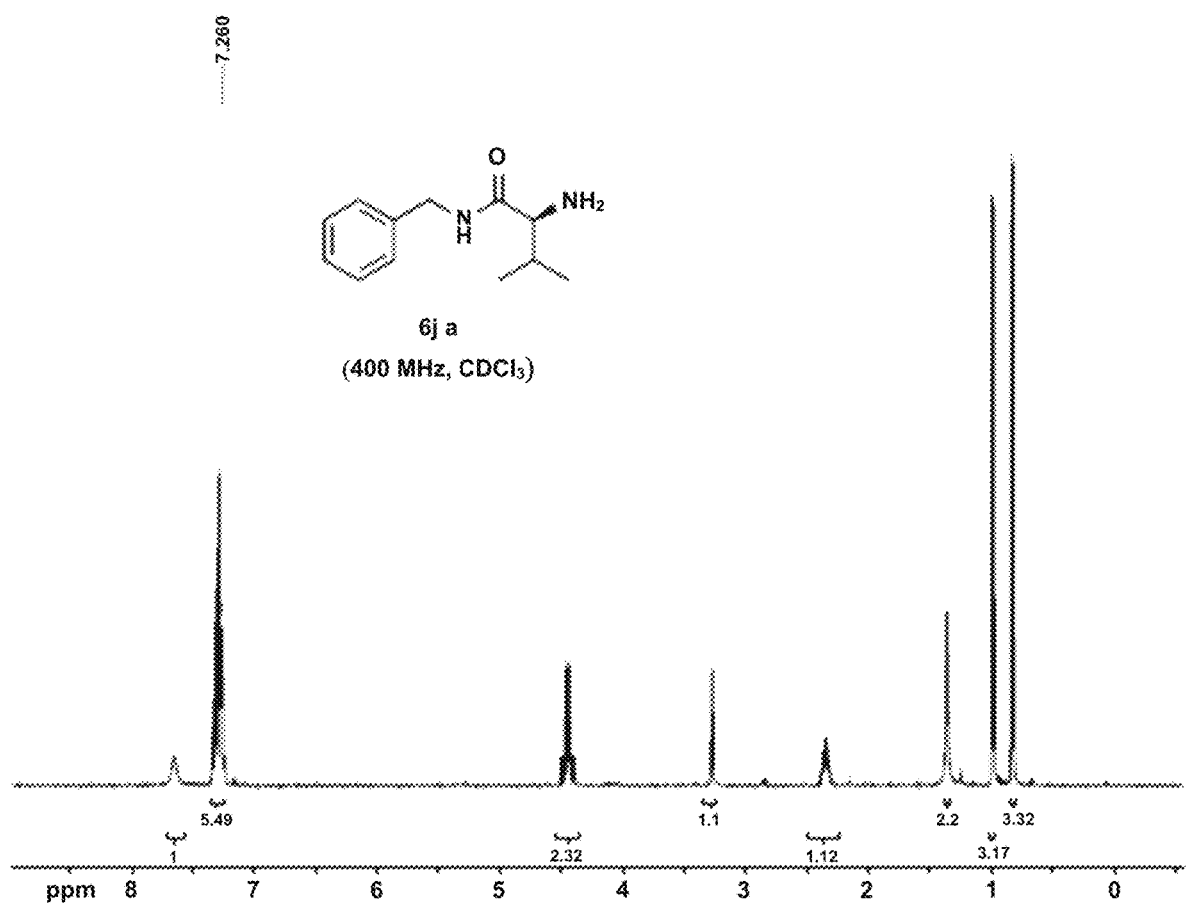
FIG. 17 shows the $^1$H NMR spectrum of compound 6j (a).

Pale yellow oil; Yield: quant.; ¹H NMR (400 MHz, CDCl₃): δ 7.69 (bs, 1H), 7.36-7.29 (m, 5H), 4.52-4.41 (m, 2H), 3.29 (bs, 1H), 2.40-2.32 (m, 1H), 1.35 (s, 2H), 1.01 (d, J=7.0 Hz, 3H), 0.86 (d, J=7.0 Hz. 3H). FIG. 17 shows the ¹H NMR spectrum of compound 6j (a).

Example 10: Synthesis of Compounds 6k-6l

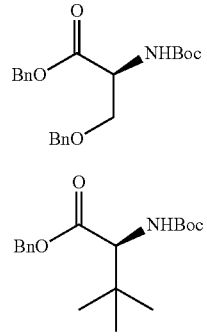

The Boc group was cleaved using 0.3 M solution of TFA in CH₂Cl₂ for 30 minutes at room temperature. The excess solvent and reagent were removed under high vacuum for 1 hour, and the crude TFA salt thus obtained was directly used for the next coupling step without characterization.

Example 11: Synthesis of Dipeptides 7a-7t

Synthesis of compound 7a: A mixture of L-valine p-TsOH salt 6a (100 mg, 0.30 mmol) and N-Boc valine (87.12 mg, 0.30 mmol) was taken in 2.5 mL of dry THF and cooled to 0° C. under nitrogen atmosphere. After stirring, freshly distilled NMM (0.16 mL, 1.51 mmol) was added via syringe followed by HOBt (46.61 mg, 0.34 mmol) and EDCI (65.18 mg, 0.34 mmol) in a single portion. The mixture was stirred overnight slowly warming to room temperature. After 12 hours, the mixture was concentrated by a rotavapor and the residue was taken in EtOAc (20.0 mL), and washed with saturated NaHCO₃ solution followed by brine. The organic layer was dried over MgSO₄, filtered, and then the solvent was evaporated under reduced pressure. The residue was purified by flash column chromatography using hexane-EtOAc (8:2) to afford the title compound.

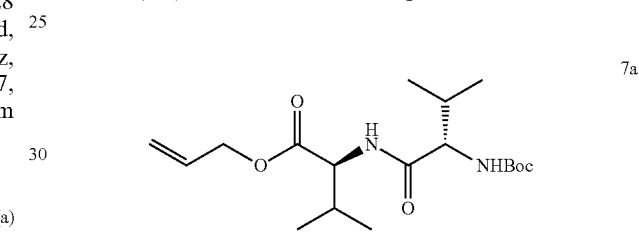

Allyl(2S,5S)-5-((tert-butoxycarbonyl)amino)-2-isopropyl-6-methyl-4-oxoheptanoate (7a)

Figure 18:
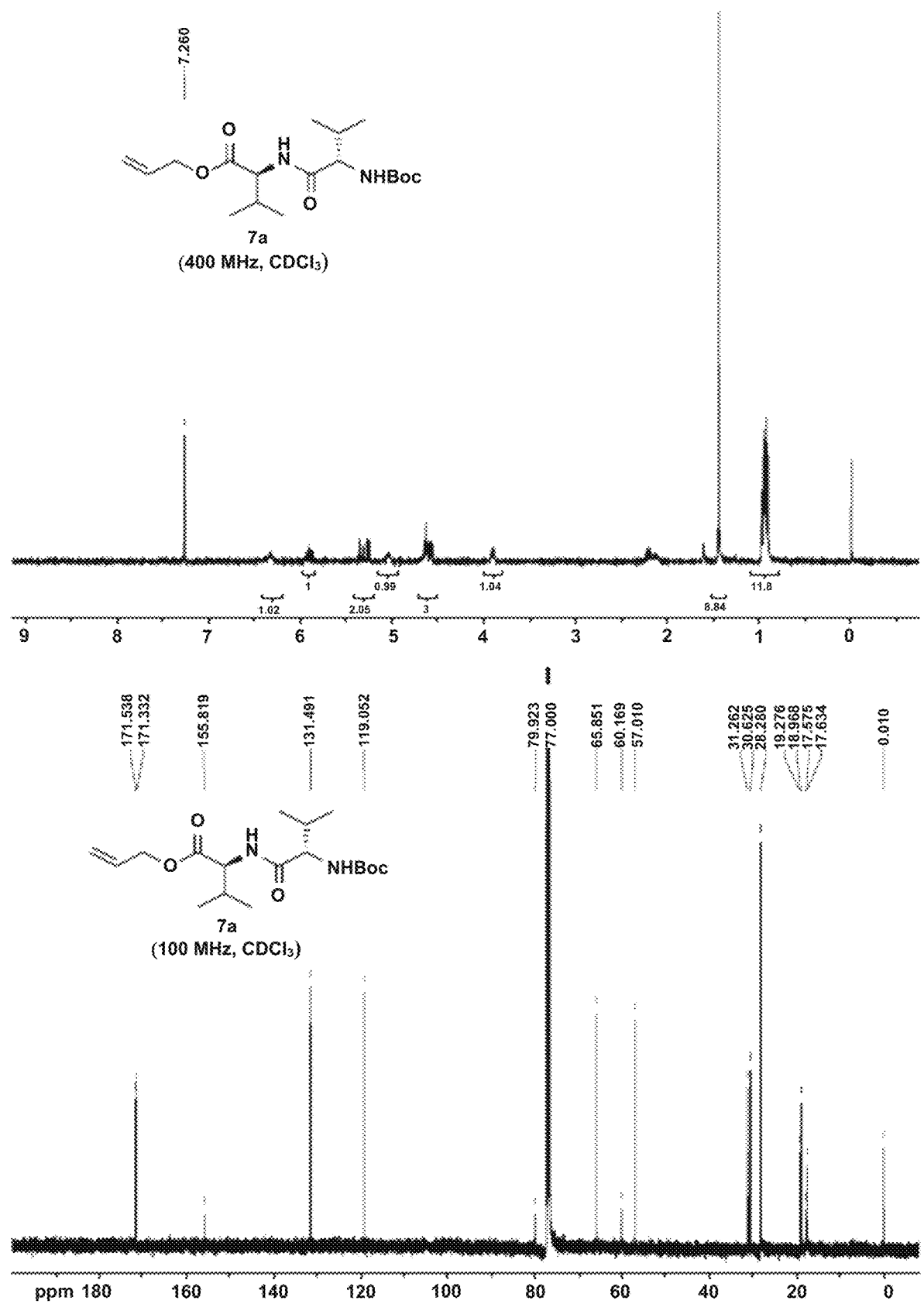

Colorless liquid; Yield: 99%; Rf: 0.3 (Hexanes:EtOAc=8:2); $[\alpha]^{22}_D$=−17.7 (c 0.5, CHCl₃); IR (γ, cm-1): 2977, 2894, 2882, 2357, 2313, 1776, 1691, 1552, 1502; ¹H NMR (400 MHz, CDCl₃): δ 6.46 (bs, 1H), 5.93-5.83 (m, 1H), 5.34 (d, J=17.2 Hz, 1H), 5.25 (d, J=10.3 Hz, 1H), 5.15 (bs, 1H), 4.65 (m, 2H), 4.57 (m, 1H), 3.93 (t, J=15.2, 7.6 Hz, 1H), 2.21 (m, 2H), 1.42 (s, 9H), 0.95 (m, 12H); ¹³C NMR (100 MHz, CDCl₃): δ 171.6, 171.3, 131.5, 120.9, 118.9, 65.8, 57.0, 31.2, 30.6, 28.2, 19.2, 18.9, 17.6. FIG. 18 shows the ¹H NMR and ¹³C NMR spectra of compound 7a.

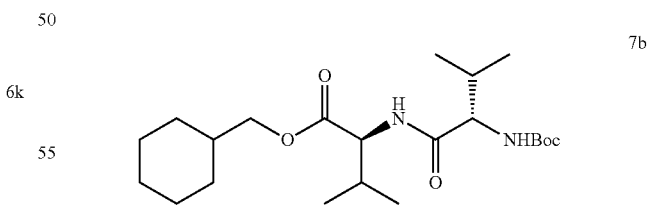

Cyclohexylmethyl (tert-butoxycarbonyl)-L-valyl-L-valinate (7b)

Figure 19:
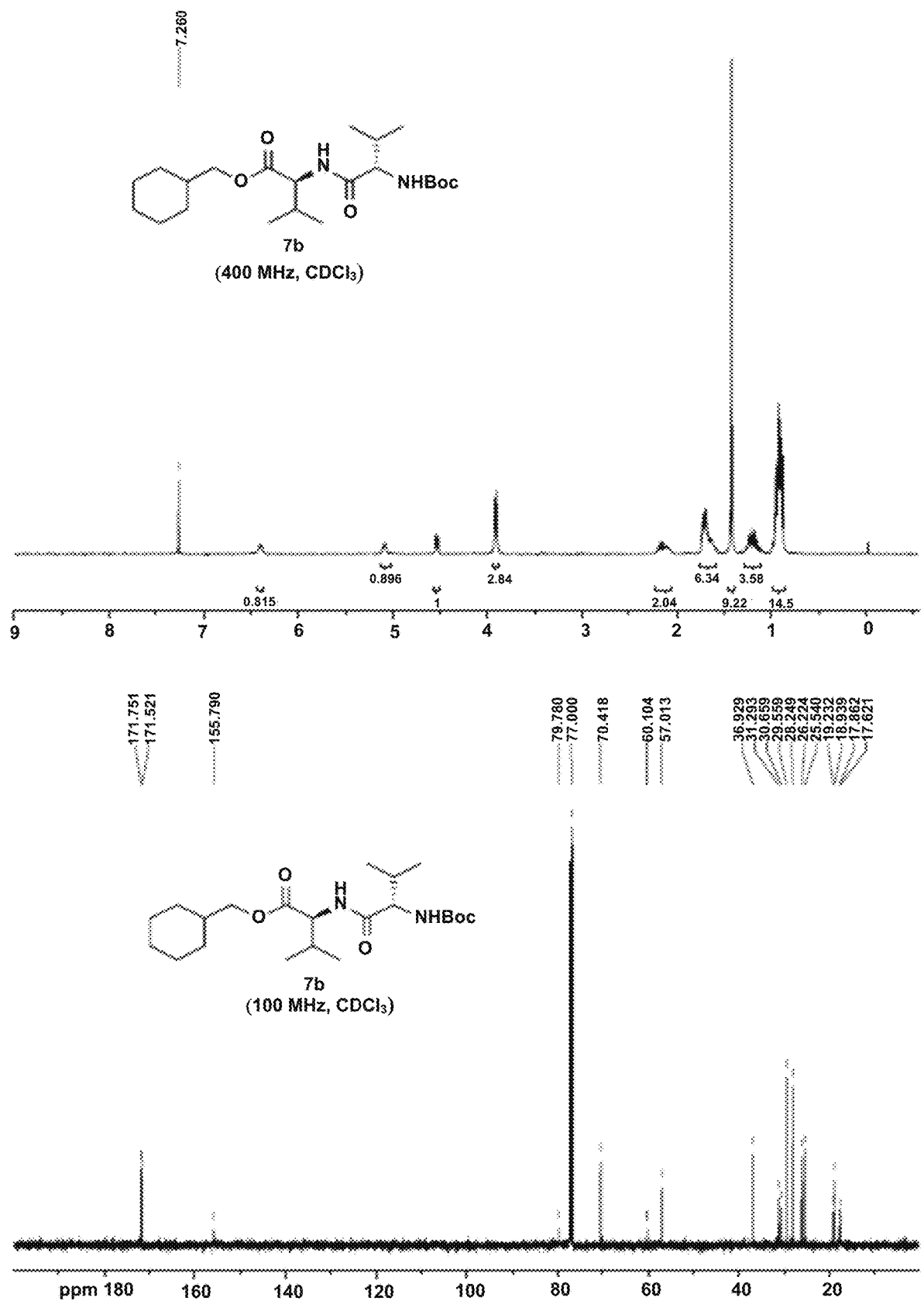
FIG. 19 shows the $^1$H NMR and $^{13}$C NMR spectra of compound 7b.

Pale yellow liquid; Yield: 89%; Rf: 0.3 (Hexanes:EtOAc=7:3); $[\alpha]^{21}_D$=−9.2 (c 0.5, CHCl₃); IR (γ, cm-1): 3316, 2929, 1738, 1688, 1657, 1529; ¹H NMR (400 MHz, CDCl₃): δ 6.47 (bs, 1H), 5.15 (d, J=8.6 Hz, 1H), 4.53 (m, 1H), 3.91 (d, J=6.5 Hz, 3H), 2.19-2.01 (m, 2H), 1.70-1.61 (m, 6H), 1.40 (s, 9H), 1.22-1.10 (m, 3H), 0.97 (m, 14H); $^{13}$C NMR (100 MHz, CDCl$_3$): δ 171.7, 171.6, 155.8, 79.7, 70.4, 60.0, 57.0, 40.4, 36.9, 31.2, 30.6, 29.5, 28.2, 26.2, 25.5, 25.5, 19.2, 18.9, 17.6. FIG. 19 shows the $^1$H NMR and $^{13}$C NMR spectra of compound 7b.

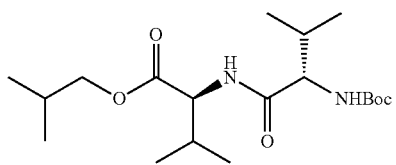

Isobutyl (tert-butoxycarbonyl)-L-valyl-L-valinate (7c)

Figure 20:
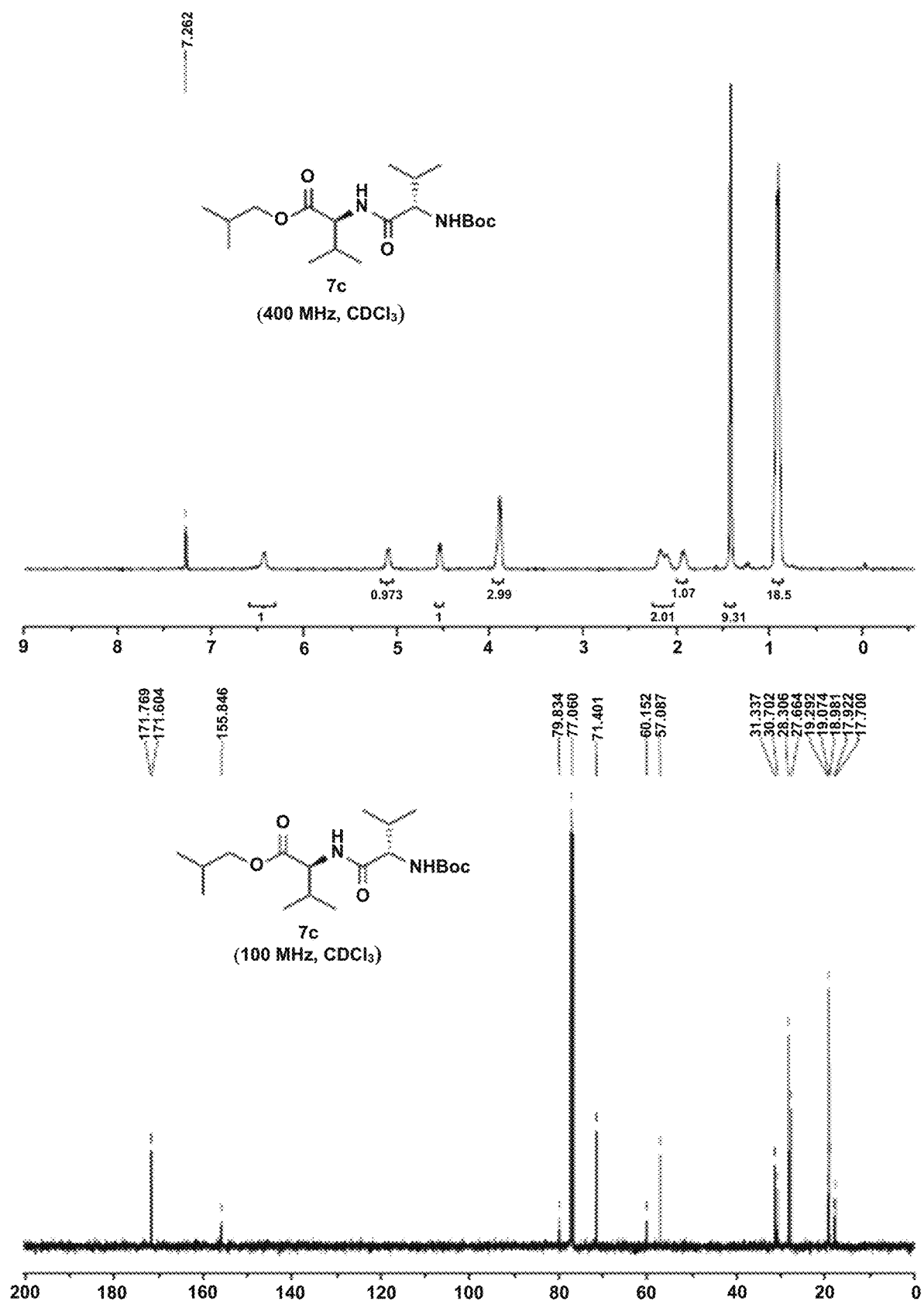
FIG. 20 shows the $^1$H NMR and $^{13}$C NMR spectra of compound 7c.

Colorless liquid; Yield: 87%; Rf: 0.3 (Hexanes:EtOAc=7: 3); $[\alpha]^{22}_D$=−8.2 (c 0.5, CHCl$_3$); IR (γ, cm-1): 3313, 3060, 1748, 1707, 1679, 1646, 1523, 1368; $^1$H NMR (400 MHz, CDCl$_3$): δ 6.49 (bs, 1H), 5.15 (bs, 1H), 4.54 (m, 1H), 3.93 (m, 3H), 2.19-2.07 (m, 2H), 1.94-1.87 (m, 1H), 1.40 (s, 9H), 0.93 (m, 18H); $^{13}$C NMR (400 MHz, CDCl$_3$): δ 171.7, 171.6, 155.8, 79.8, 71.3, 60.1, 57.0, 31.3, 30.6, 28.2, 27.6, 19.2, 19.0, 18.9, 17.9, 17.6. FIG. 20 shows the $^1$H NMR and $^{13}$C NMR spectra of compound 7c.

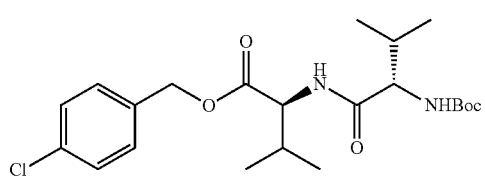

4-chlorobenzyl (tert-butoxycarbonyl)-L-valyl-L-valinate (7d)

Figure 21:
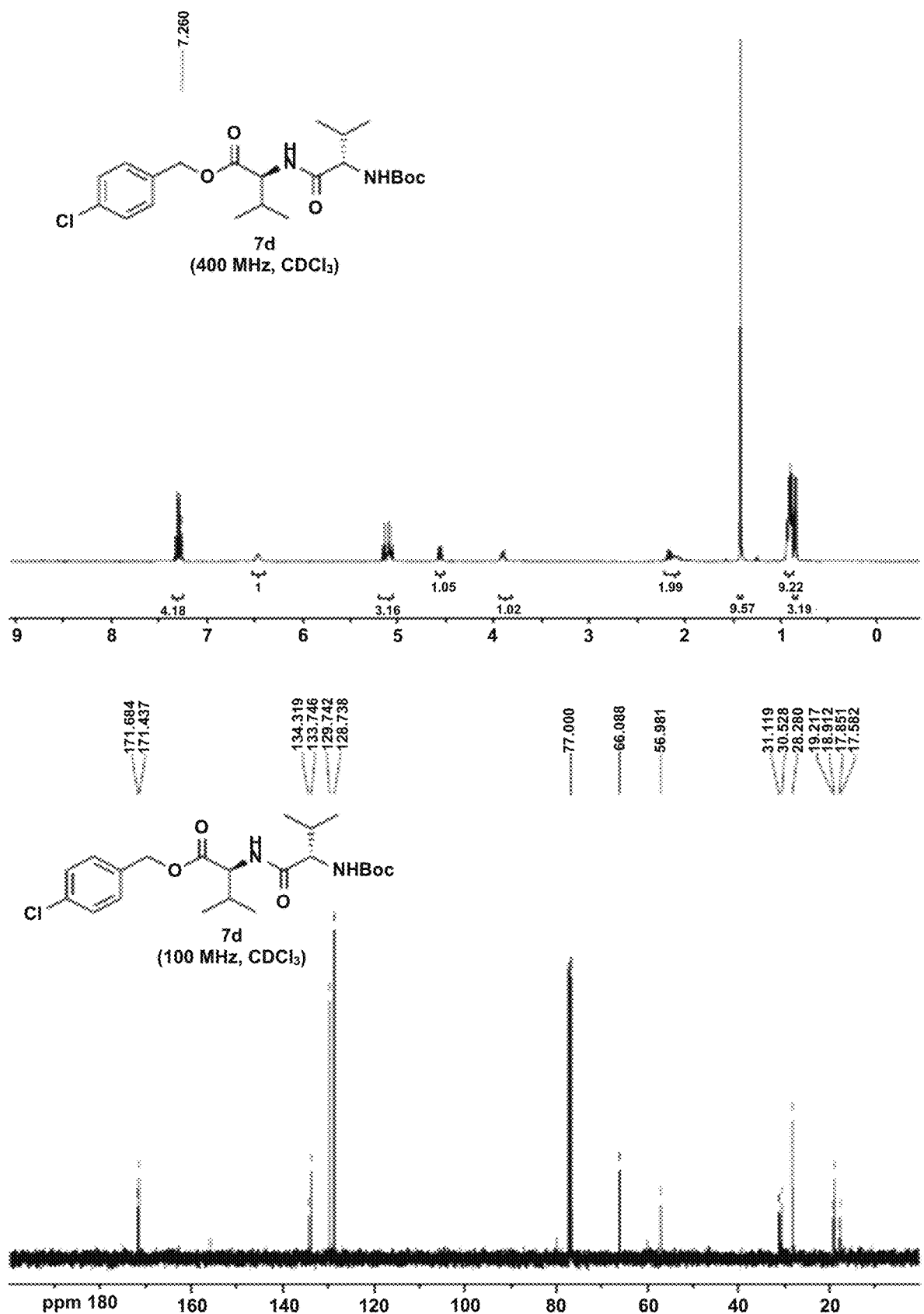
FIG. 21 shows the $^1$H NMR and $^{13}$C NMR spectra of compound 7d.

Colorless liquid; Yield: 66%; Rf: 0.3 (Hexanes:EtOAc=7: 3); $[\alpha]^{22}_D$=−15.0 (c 0.25, CHCl$_3$); IR (γ, cm-1): 3305, 3060, 1753, 1738, 1726, 1657, 1650, 1366; $^1$H NMR (400 MHz, CDCl$_3$): δ 7.33 (d, J=8.3 Hz, 2H), 7.28 (d, J=6.8 Hz, 2H), 6.46 (s, 1H), 5.16 (m, 3H), 4.58 (dd, J=4.9, 4.8 Hz, 1H), 3.93 (m, 1H), 2.20 (m, 2H), 1.42 (s, 9H), 0.94 (m, 9H), 0.86 (d, J=7.0 Hz, 3H); $^{13}$C NMR (100 MHz, CDCl$_3$): δ 171.7, 171.4, 134.3, 133.8, 129.8, 128.7, 66.1, 57.0, 31.1, 30.5, 28.2, 19.2, 18.9, 17.6. FIG. 21 shows the $^1$H NMR and $^{13}$C NMR spectra of compound 7d.

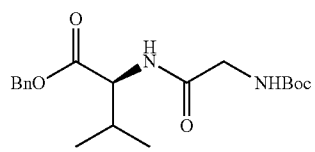

Benzyl (tert-butoxycarbonyl)glycyl-L-valinate (7e)

Figure 22:
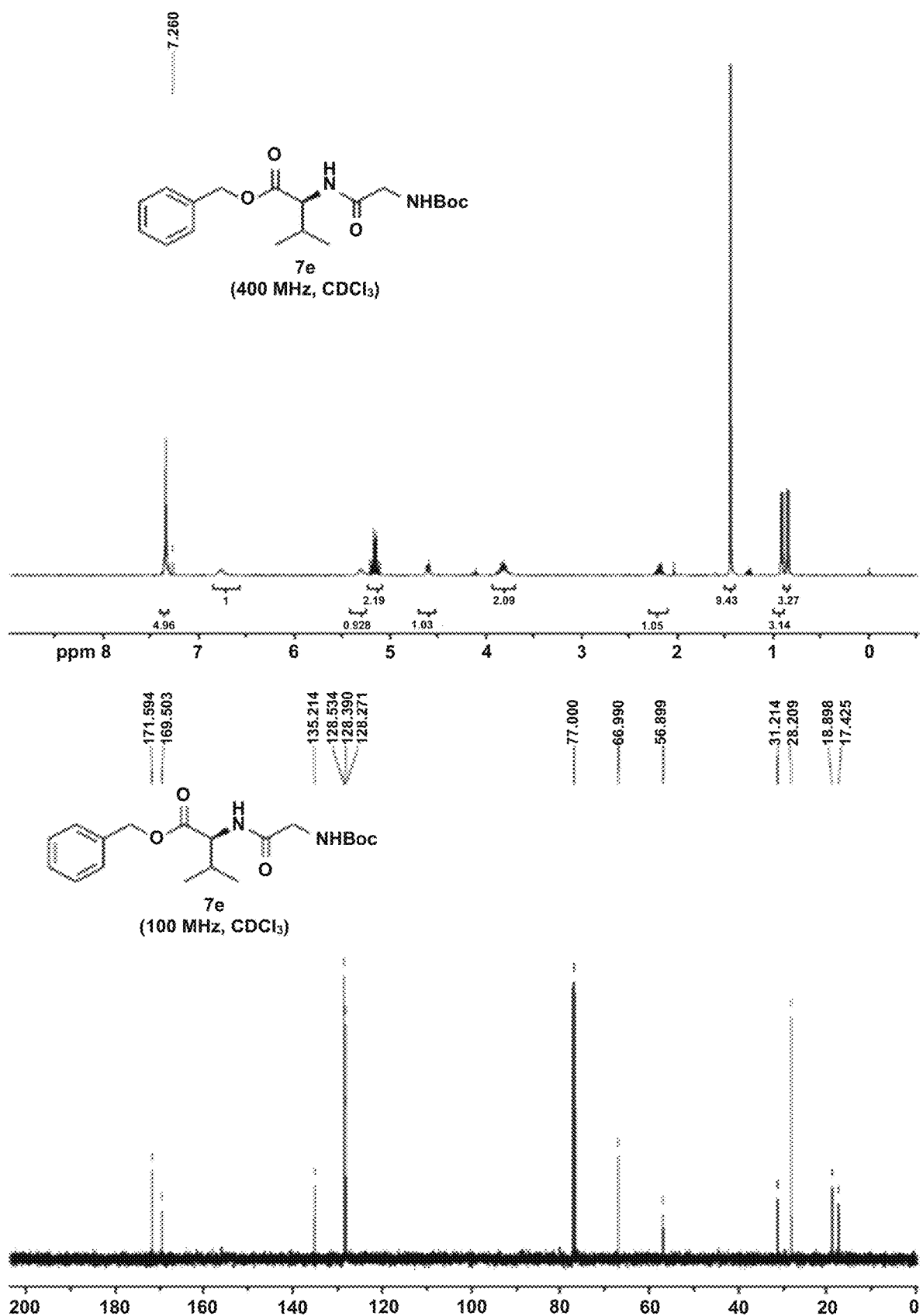
FIG. 22 shows the $^1$H NMR and $^{13}$C NMR spectra of compound 7e.

Colorless liquid; Yield: 94%; Rf: 0.5 (Hexanes:EtOAc=1: 1); $[\alpha]^{25}_D$=+15.3 (c 0.1, CHCl$_3$); IR (γ, cm-1): 2969, 2926, 1736, 1691, 1664, 1554; $^1$H NMR (400 MHz, CDCl$_3$): δ 7.37-7.30 (m, 5H), 6.76 (bs, 1H), 5.30 (bs, 1H), 5.20 (d, J=12.1 Hz, 1H), 5.14 (d, J=12.2 Hz, 1H), 4.61 (dd, J=8.7, 4.9 Hz, 1H), 3.88-3.75 (m, 2H), 2.24-2.13 (m, 1H), 1.44 (s, 9H), 0.92 (d, J=6.9 Hz, 3H), 0.85 (d, J=6.9 Hz, 3H); $^{13}$C NMR (100 MHz, CDCl$_3$): δ 171.6, 169.5, 135.2, 128.5, 128.4, 128.3, 67.0, 56.9, 31.2, 28.2, 18.9, 17.4. FIG. 22 shows the $^1$H NMR and $^{13}$C NMR spectra of compound 7e.

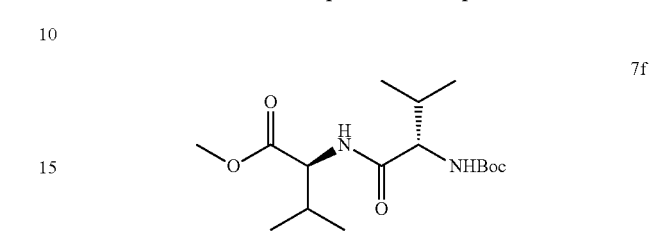

Methyl (tert-butoxycarbonyl)-L-valyl-L-valinate (7f)

Figure 23:
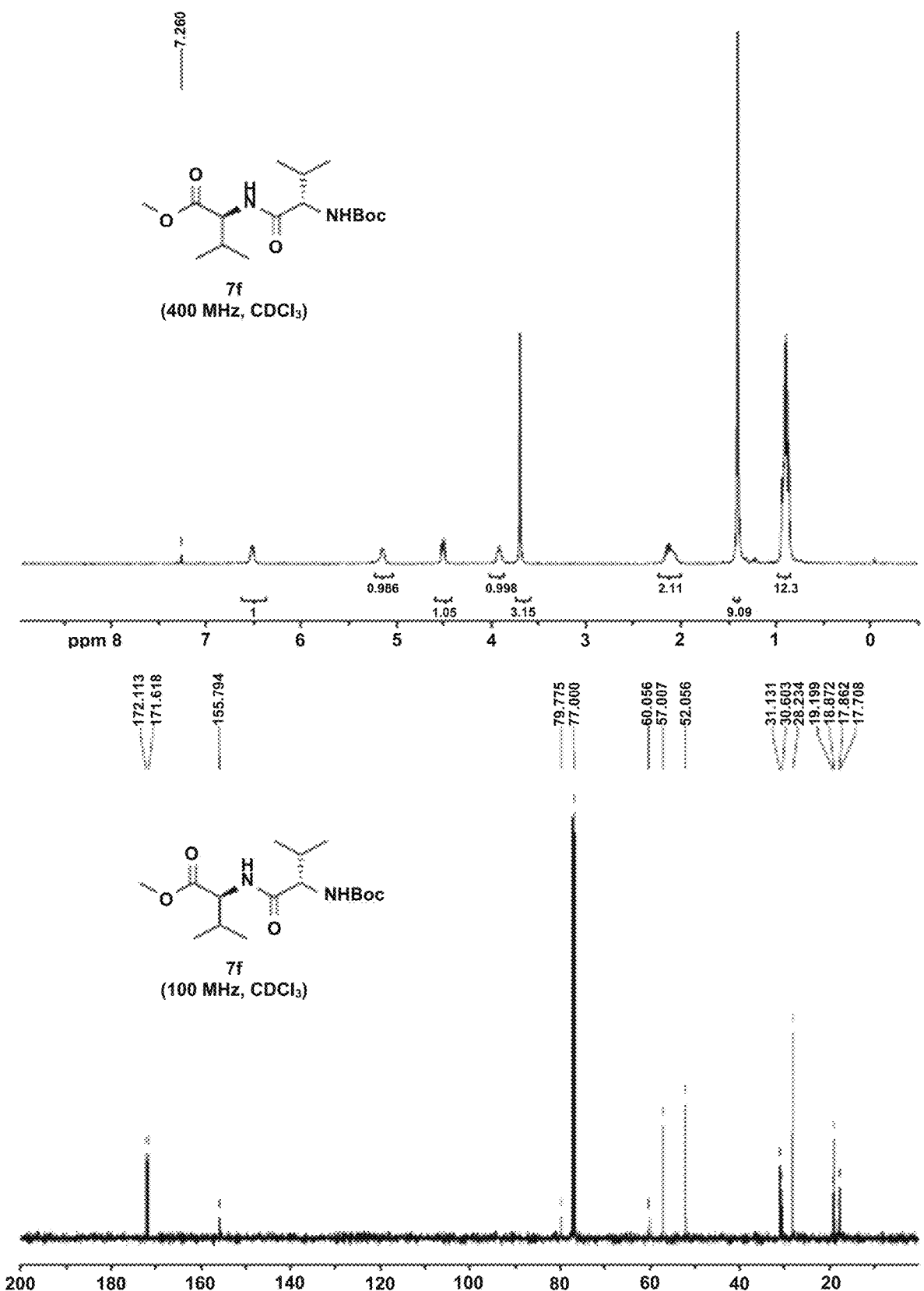
FIG. 23 shows the $^1$H NMR and $^{13}$C NMR spectra of compound 7f.

Colorless liquid; Yield: 36%; Rf: 0.4 (Hexanes:EtOAc=7: 3); $[\alpha]^{25}_D$=−8.5 (c 0.9, CHCl$_3$); IR (γ, cm-1): 2969, 2371, 1685, 1654, 1528; $^1$H NMR (400 MHz, CDCl$_3$): δ 6.52 (d, J=8.4 Hz, 1H), 6.15 (d, J=7.8 Hz, 1H), 4.52 (m, 1H), 3.93 (m, 1H), 3.69 (s, 3H), 2.17-2.06 (m, 2H), 1.40 (s, 9H), 0.94-0.86 (m, 12H); $^{13}$C NMR (100 MHz, CDCl$_3$): δ 172.1, 171.6, 155.8, 79.8, 60.1, 57.0, 52.1, 31.1, 30.6, 28.2, 19.2, 18.9, 17.9, 17.7. FIG. 23 shows the $^1$H NMR and $^{13}$C NMR spectra of compound 7f.

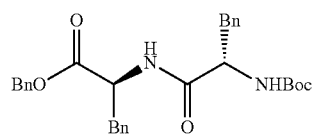

tert-butyl((S)-1-oxo-1-(((S)-3-oxo-1,4-diphenylbutan-2-yl)amino)-3-phenylpropan-2-yl)carbamate (7g)

Figure 24:
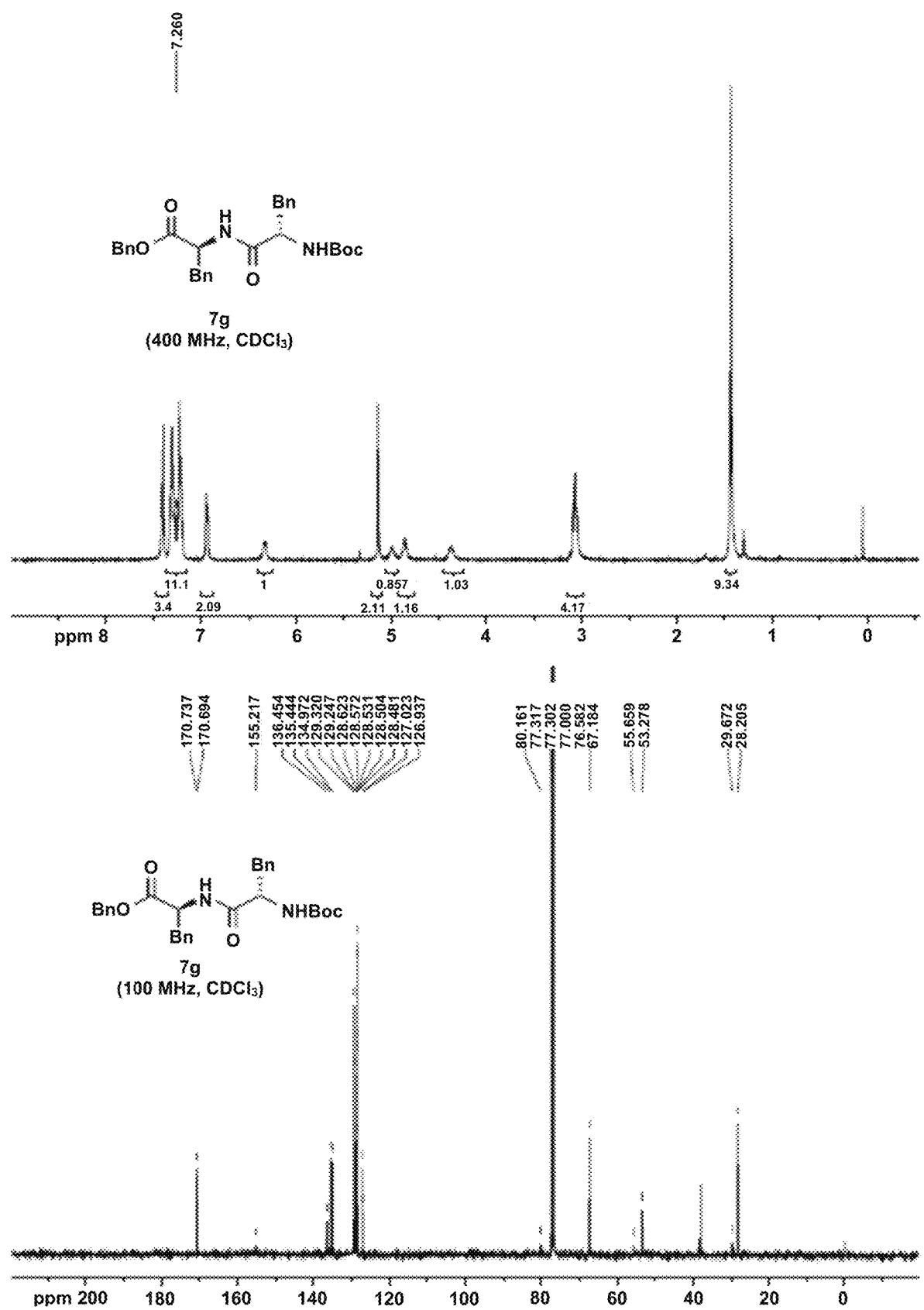
FIG. 24 shows the $^1$H NMR and $^{13}$C NMR spectra of compound 7g.

Colorless liquid; Yield: 88%; Rf: 0.7 (Hexanes:EtOAc=5: 1); $[\alpha]^{25}_D$=−8.4 (c 0.3, CHCl$_3$); IR (γ, cm-1): 2912, 2355, 1693, 1652, 1560; $^1$H NMR (400 MHz, CDCl$_3$): δ 7.38-7.35 (m, 3H), 7.27-7.21 (m, 5H), 7.19-7.16 (m, 5H), 6.90-6.88 (m, 2H), 6.29 (d, J=6.4 Hz, 1H), 5.09 (s, 2H), 4.94 (bs, 1H), 4.83-4.79 (m, 1H), 4.32 (bs, 1H), 3.08-3.01 (m, 4H), 1.39 (s, 9H); $^{13}$C NMR (100 MHz, CDCl$_3$): δ 170.7, 170.7, 155.2, 136.5, 135.5, 135.0, 129.3, 129.3, 128.6, 128.6, 128.5, 128.5, 128.5, 127.0, 127.0, 80.2, 67.2, 55.7, 53.3, 38.3, 37.9, 29.7, 28.2. FIG. 24 shows the $^1$H NMR and $^{13}$C NMR spectra of compound 7g.

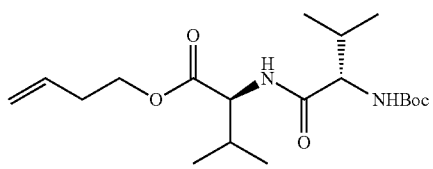

But-3-en-1-yl (tert-butoxycarbonyl)-L-valyl-L-valinate (7h)

Figure 25:
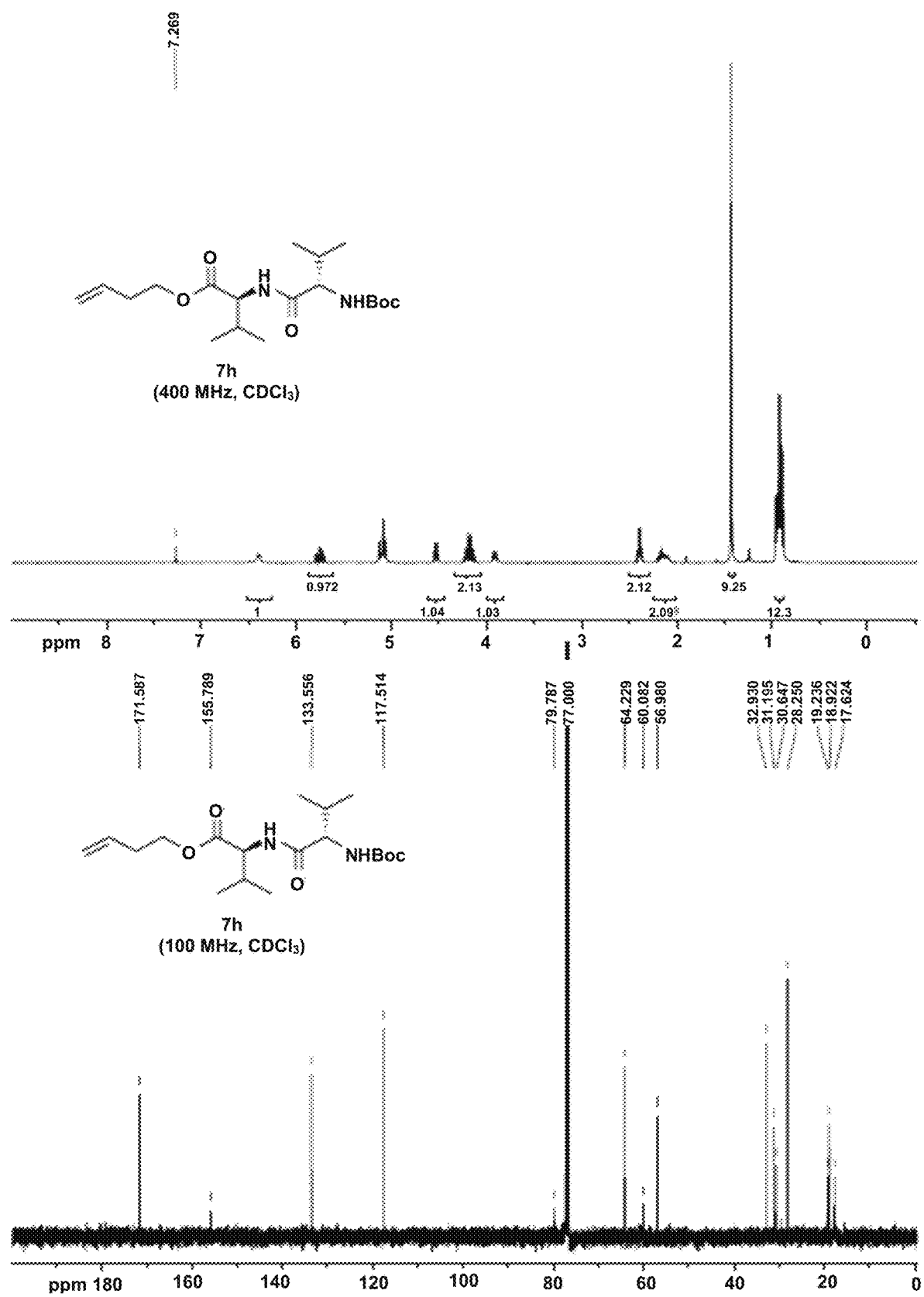
FIG. 25 shows the $^1$H NMR and $^{13}$C NMR spectra of compound 7h.

Colorless solid; Yield: 45%; Rf: 0.7 (Hexanes:EtOAc=7:3); $[\alpha]^{24}_D$=−12.6 (c 0.7, CHCl$_3$); IR (γ, cm-1): 2969, 2371, 1746, 1685, 1654; $^1$H NMR (400 MHz, CDCl$_3$): δ 6.40 (d, J=8.5 Hz, 1H), 5.80-5.70 (m, 1H), 5.12-5.05 (m, 3H), 4.54 (dd, J=8.6, 4.8 Hz, 1H), 4.23-4.11 (m, 2H), 3.93 (m, 1H), 2.41-2.36 (m, 2H), 2.20-2.07 (m, 2H), 1.42 (s, 9H), 0.96-0.88 (m, 12H); $^{13}$C NMR (100 MHz, CDCl$_3$): δ 171.6, 171.6, 133.6, 117.5, 64.2, 57.0, 32.9, 31.2, 30.6, 28.2, 19.2, 18.9, 17.6. FIG. 25 shows the $^1$H NMR and $^{13}$C NMR spectra of compound 7h.

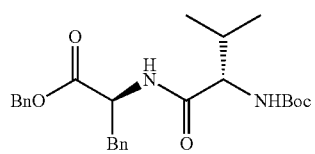

Benzyl (tert-butoxycarbonyl)-L-valyl-L-phenylalaninate (7i)

Figure 26:
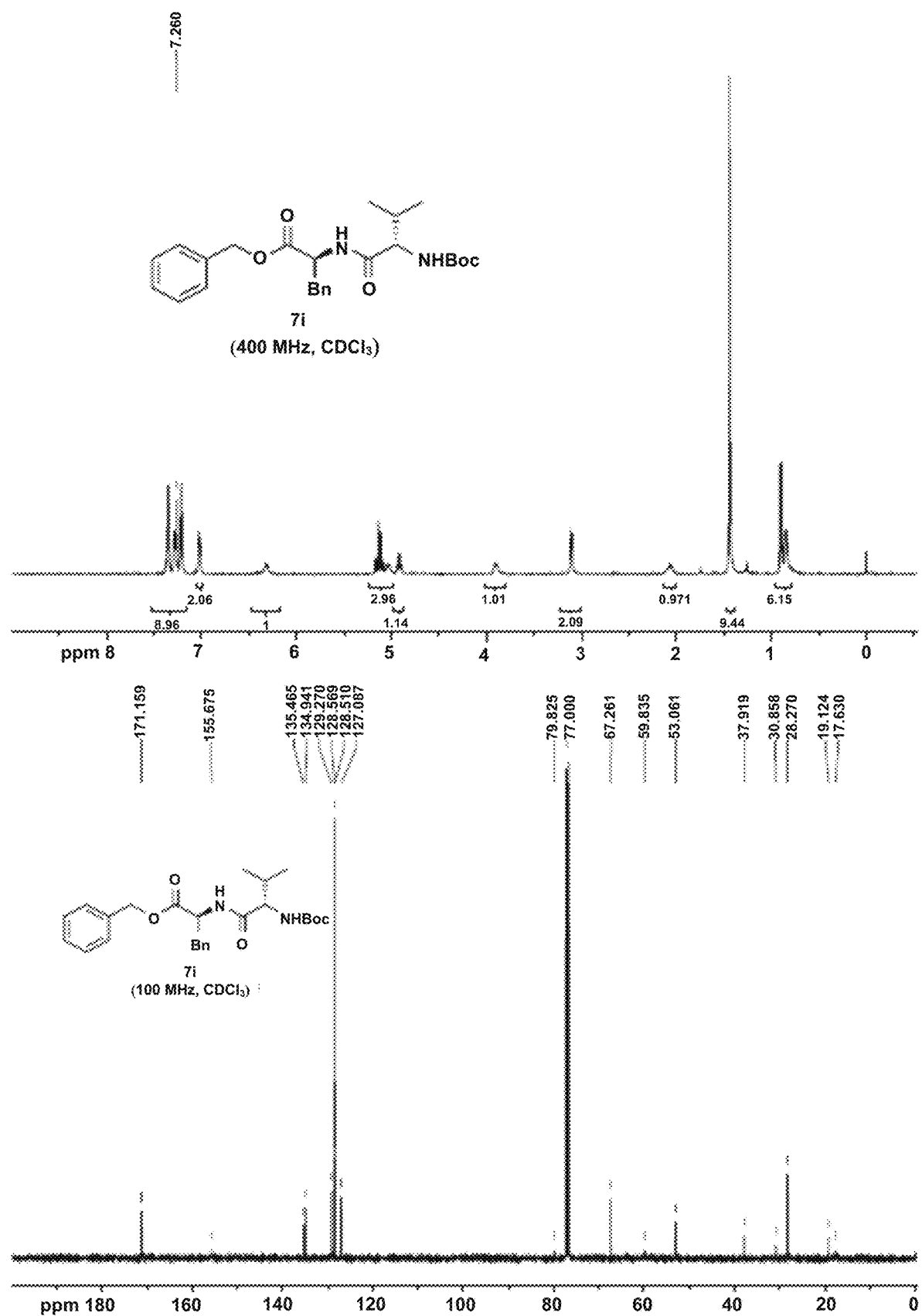
FIG. 26 shows the $^1$H NMR and $^{13}$C NMR spectra of compound 7i.

Colorless liquid; Yield: 83%; Rf: 0.5 (Hexanes:EtOAc=3:1); $[\alpha]^{25}_D$=+2.6 (c 0.4, CHCl$_3$); IR (γ, cm-1): 2969, 2371, 1746, 1685, 1654; $^1$H NMR (400 MHz, CDCl$_3$): δ 7.37-7.21 (m, 8H), 7.03-7.01 (m, 2H), 6.33 (d, J=7.3 Hz, 1H), 5.17 (d, J=11.6 Hz, 1H), 5.11 (m, J=11.5 Hz, 1H), 5.09 (d, J=8.7 Hz, 1H), 4.94 (m, 1H), 3.92-3.87 (m, 1H), 3.11 (d, J=6.0 Hz, 2H), 2.09-2.03 (m, 1H), 1.44 (s, 9H), 0.91 (d, J=3.1 Hz, 3H), 0.85 (d, J=6.7 Hz, 3H); $^{13}$C NMR (100 MHz, CDCl$_3$): δ 171.2, 171.0, 155.7, 135.5, 134.9, 129.3, 128.6, 128.5, 127.1, 79.8, 77.2, 67.3, 59.8, 53.1, 37.9, 30.9, 28.3, 19.1, 17.6. FIG. 26 shows the $^1$H NMR and $^{13}$C NMR spectra of compound 7i.

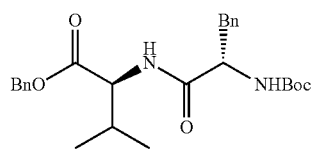

Benzyl (tert-butoxycarbonyl)-L-phenylalanyl-L-valinate (7j)

Figure 27:
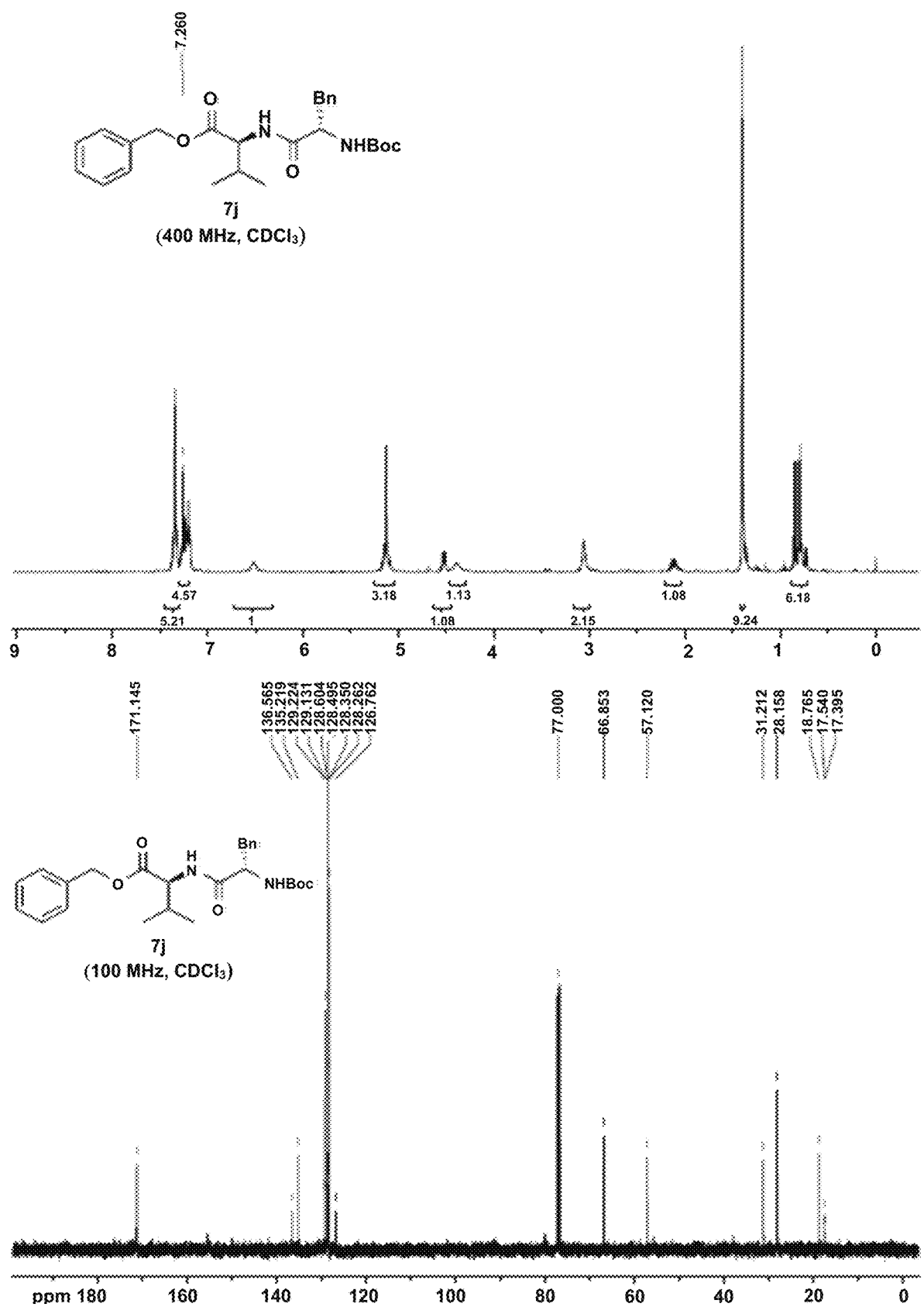
FIG. 27 shows the $^1$H NMR and $^{13}$C NMR spectra of compound 7j.

Colorless liquid; Yield: 90%; Rf: 0.5 (Hexanes:EtOAc=3:1); $[\alpha]^{25}_D$=−10.7 (c 2.3, CHCl$_3$); IR (γ, cm-1): 2966, 2349, 1736, 1675, 1657; $^1$H NMR (400 MHz, CDCl$_3$): δ 7.38-7.31 (m, 5H), 7.27-7.18 (m, 5H), 6.52 (bs, 1H), 5.18-5.08 (m, 3H), 4.54 (dd, J=8.3, 4.9 Hz, 1H), 4.39-4.37 (m, 1H), 3.11-2.98 (m, 2H), 2.16-2.04 (m, 1H), 1.40 (s, 9H), 0.86 (d, J=6.9 Hz, 3H), 0.81 (d, J=6.9 Hz, 3H); $^{13}$C NMR (100 MHz, CDCl$_3$): δ 171.2, 136.6, 135.2, 129.2, 129.1, 128.6, 128.5, 128.4, 128.3, 128.2, 126.8, 66.9, 66.6, 57.1, 31.2, 28.2, 18.8, 17.5. FIG. 27 shows the $^1$H NMR and $^{13}$C NMR spectra of compound 7j.

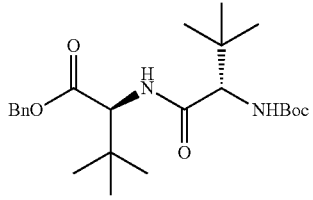

Benzyl(S)-2-((S)-2-((tert-butoxycarbonyl)amino)-3,3-dimethylbutanamido)-3,3-dimethylbutanoate (7k)

Figure 28:
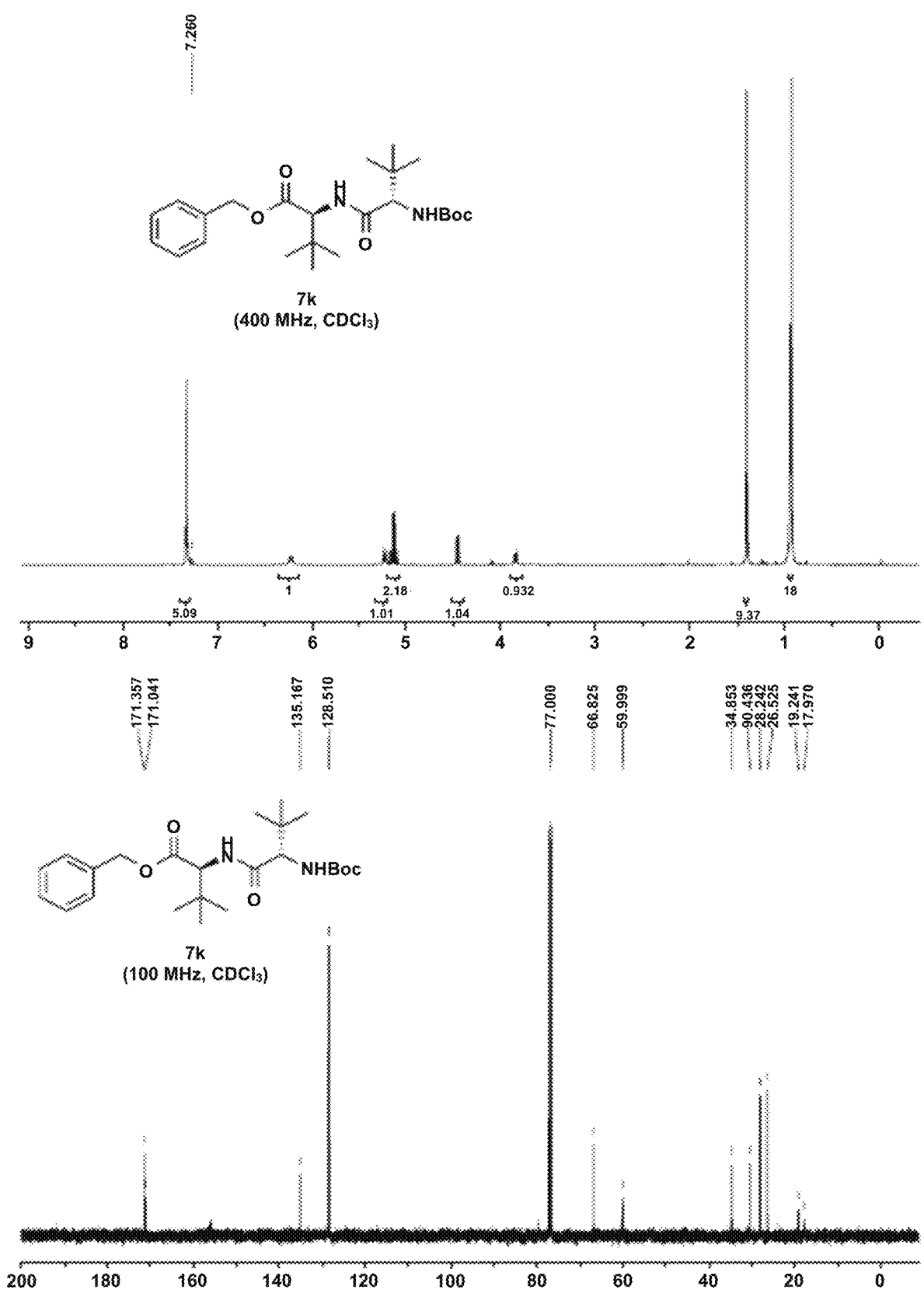
FIG. 28 shows the $^1$H NMR and $^{13}$C NMR spectra of compound 7k.

Colorless solid; Yield: 43%; Rf: 0.4 (Hexanes:EtOAc=9:1); $[\alpha]^{26}_D$=−3.3 (c 0.05, CHCl$_3$); $^1$H NMR (400 MHz, CDCl$_3$): δ 7.35-7.31 (m, 5H), 6.31 (d, J=9.0 Hz, 1H), 5.28 (d, J=9.2 Hz, 1H), 5.19 (d, J=12.1 Hz, 1H), 5.14 (d, J=9.1 Hz, 1H), 4.5 (d, J=9.1 Hz, 1H), 3.9 (d, J=9.1 Hz, 1H), 1.42 (s, 9H), 0.97-0.95 (m, 18H); $^{13}$C NMR (100 MHz, CDCl$_3$): δ 171.4, 171.0, 135.2, 128.5, 128.5, 66.8, 60.0, 34.9, 30.4, 28.2, 26.5, 19.2, 18.0. FIG. 28 shows the $^1$H NMR and $^{13}$C NMR spectra of compound 7k.

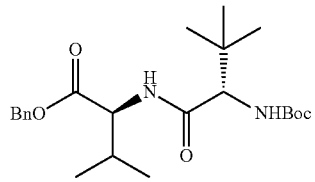

Benzyl ((S)-2-((tert-butoxycarbonyl)amino)-3,3-dimethylbutanoyl)-L-valinate (7l)

Figure 29:
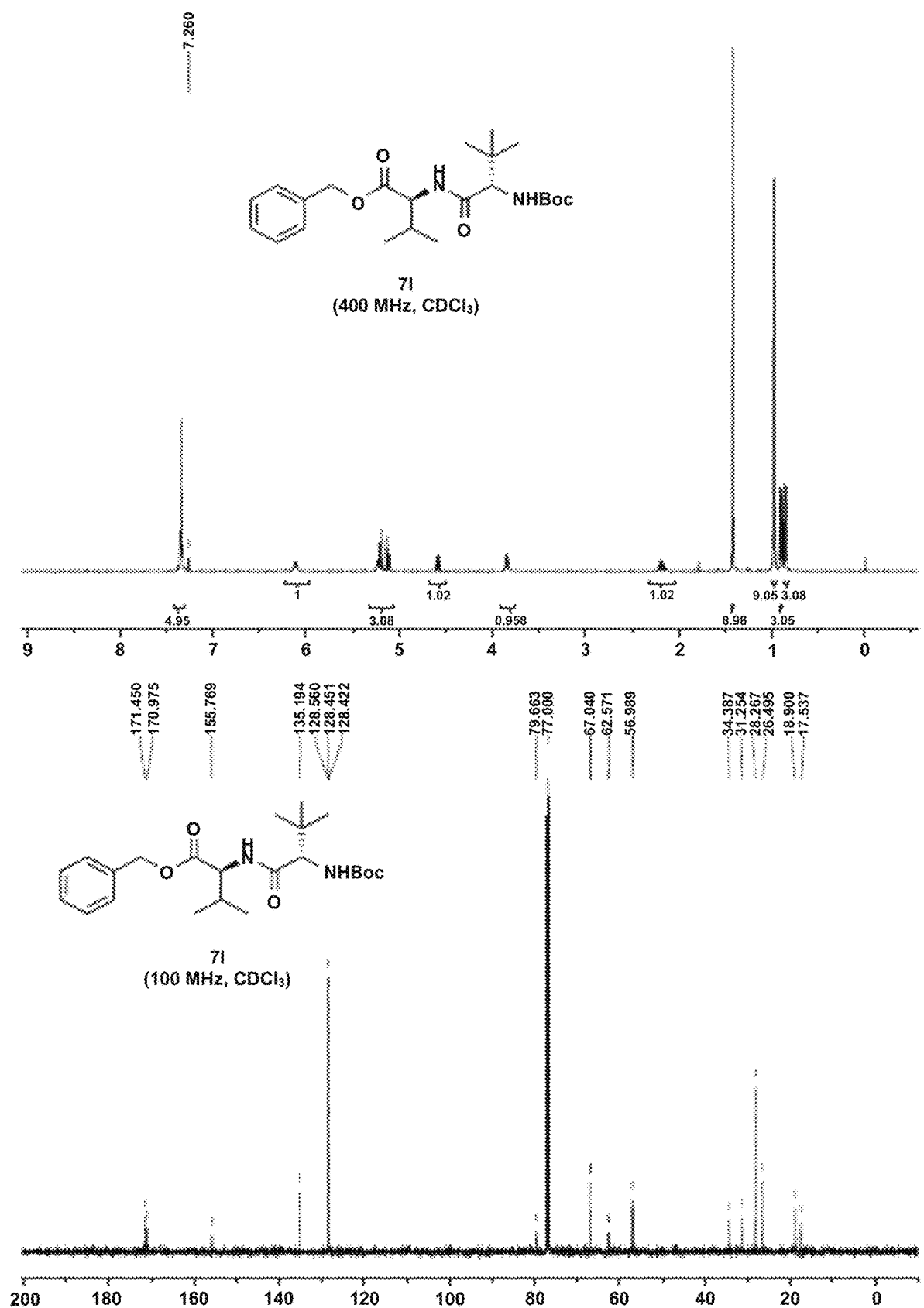
FIG. 29 shows the $^1$H NMR and $^{13}$C NMR spectra of compound 7l.

Colorless solid; Yield: 89%; Rf: 0.5 (Hexanes:EtOAc=3:2); $[\alpha]^{26}_D$=−24.2 (c 0.4, CHCl$_3$); $^1$H NMR (400 MHz, CDCl$_3$): δ 7.38-7.31 (m, 5H), 6.13 (d, J=8.6 Hz, 1H), 5.24-5.10 (m, 3H), 4.60 (dd, J=8.7, 4.9 Hz, 1H), 3.86 (dd, J=9.2 Hz, 1H), 2.24-2.14 (m, 1H), 1.42 (s, 9H), 0.98 (s, 9H), 0.91 (d, J=6.7 Hz, 3H), 0.86 (d, J=6.7 Hz, 3H); $^{13}$C NMR (100 MHz, CDCl$_3$): δ 171.5, 171.0, 155.8, 135.2, 128.6, 128.5, 128.4, 79.7, 67.0, 62.6, 57.0, 34.4, 31.2, 28.3, 26.5, 18.9, 17.5. FIG. 29 shows the $^1$H NMR and $^{13}$C NMR spectra of compound 7l.

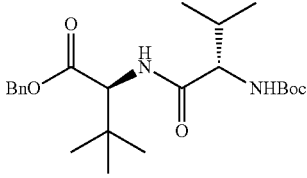

Benzyl(S)-2-((S)-2-((tert-butoxycarbonyl)amino)-3-methylbutanamido)-3,3-methylbutanoate (7m)

Colorless solid; Yield: 77%; Rf: 0.4 (Hexanes:EtOAc=9:1); $[\alpha]^{26}_D$=−1.05 (c 0.02, CHCl$_3$); $^1$H NMR (400 MHz, CDCl$_3$): δ 7.37-7.32 (m, 5H), 6.41 (d, J=9.2 Hz, 1H), 5.19

Figure 30:
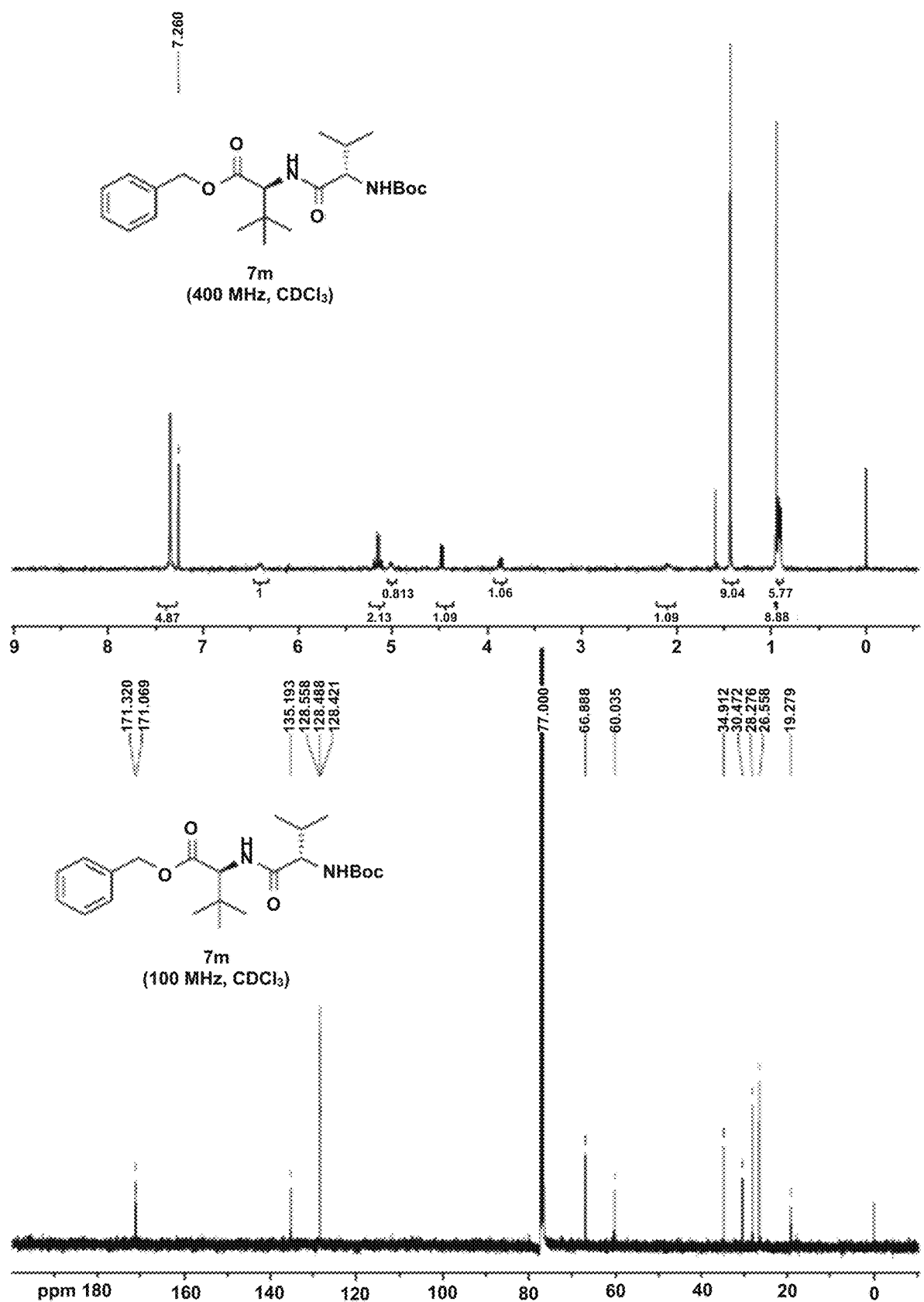
FIG. 30 shows the $^1$H NMR and $^{13}$C NMR spectra of compound 7m.

(d, J=12.2 Hz, 1H), 5.14 (d, J=12.1 Hz, 1H), 5.03 (d, J=8.2 Hz, 1H), 4.49 (d, J=9.2 Hz, 1H), 3.88 (dd, J=8.6, 6.7 Hz, 1H), 2.13-2.04 (m, 1H), 1.43 (s, 9H), 0.95 (s, 9H), 0.93-0.90 (m, 6H); $^{13}$C NMR (100 MHz, CDCl$_3$): δ 171.3, 171.1, 135.2, 128.6, 128.5, 128.4, 77.2, 66.9, 60.0, 34.9, 30.5, 28.3, 26.6, 19.3. FIG. 30 shows the $^1$H NMR and $^{13}$C NMR spectra of compound 7m.

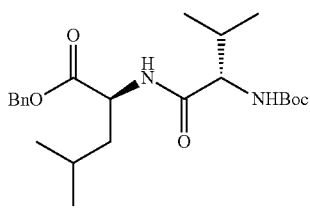

Benzyl (tert-butoxycarbonyl)-L-valyl-L-leucinate (7n)

Dipeptide 7n was prepared following the general method described above.

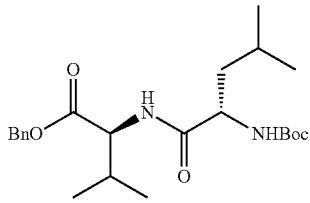

Benzyl (S)-2-((S)-2-((tert-butoxycarbonyl)amino)-3-methylbutanamido)-3,3-dimethylbutanoate (7o)

Dipeptide 7o was prepared following the general method described above.

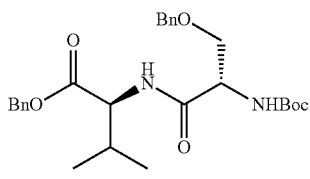

Benzyl O-benzyl-N-(tert-butoxycarbonyl)-L-seryl-L-valinate (7p)

Dipeptide 7p was prepared following the general method described above.

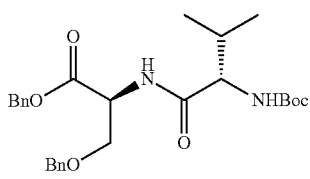

Benzyl O-benzyl-N-((tert-butoxycarbonyl)-L-valyl)-L-serinate (7q)

Figure 31:
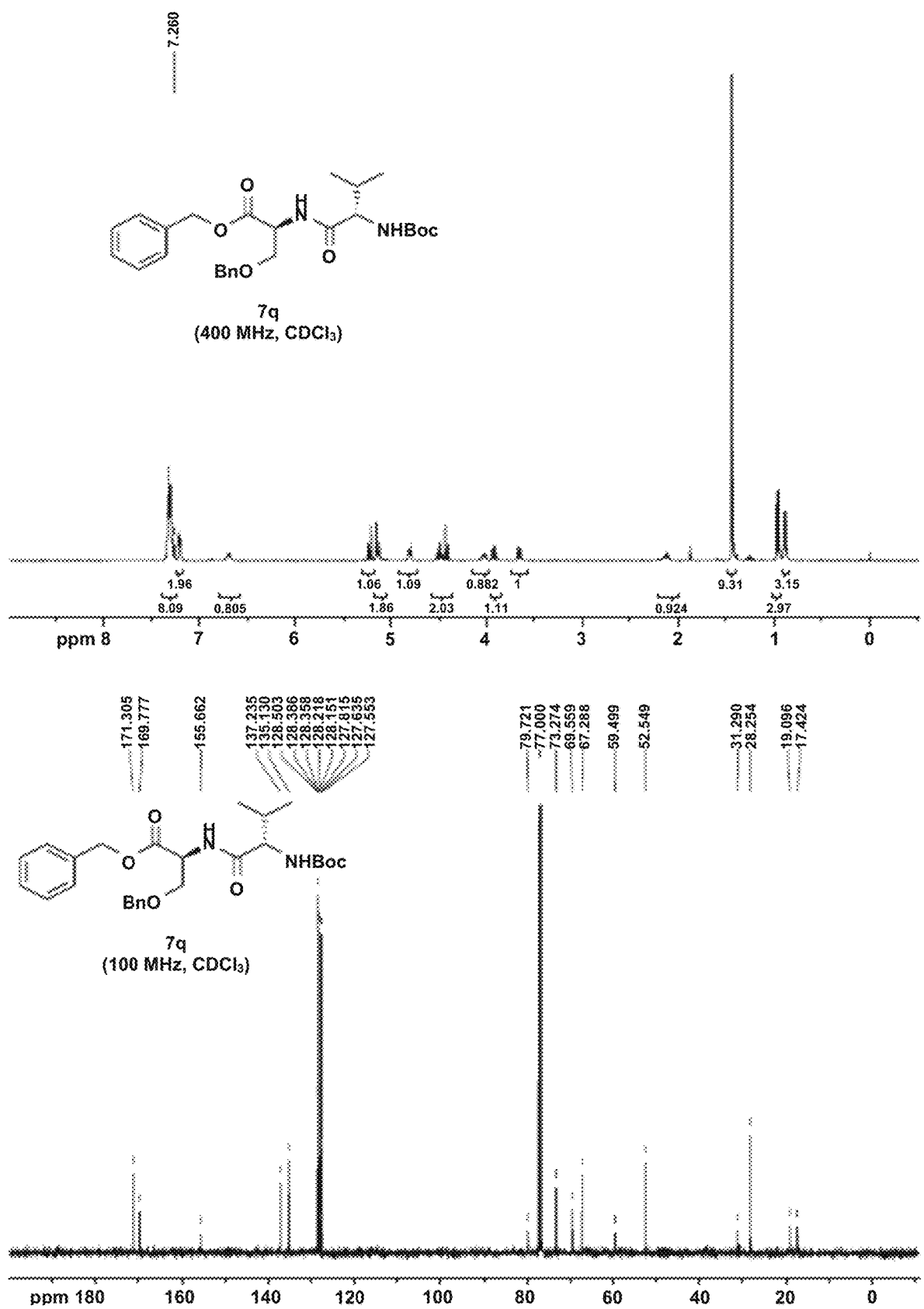
FIG. 31 shows the $^1$H NMR and $^{13}$C NMR spectra of compound 7q.

Colorless oil; Yield: 65%; Rf: 0.5 (Hexanes:EtOAc=7:3); [α]$^{26}_D$=−16.1 (c 0.5, CHCl$_3$); $^1$H NMR (400 MHz, CDCl$_3$): δ 7.34-7.28 (m, 8H), 7.21-7.20 (m, 2H), 6.70 (d, J=7.7 Hz, 1H), 5.23 (d, J=12.3 Hz, 1H), 5.15 (d, J=12.3 Hz, 2H), 4.82-4.78 (m, 1H), 4.51-4.40 (m, 2H), 4.05-4.01 (m, 1H), 3.94-3.90 (m, 1H), 3.67 (dd, J=9.4, 3.2 Hz, 1H), 2.21-2.08 (m, 1H), 1.44 (s, 9H), 0.97 (d, J=6.8 Hz, 3H), 0.90 (d, J=7.2 Hz, 3H); $^{13}$C NMR (100 MHz, CDCl$_3$): δ 171.3, 169.8, 169.8, 155.6, 137.2, 135.1, 128.4, 128.3, 128.3, 128.2, 127.8, 127.6, 79.6, 73.2, 69.5, 67.2, 59.4, 52.5, 31.3, 28.2, 19.1, 17.4. FIG. 31 shows the $^1$H NMR and $^{13}$C NMR spectra of compound 7q.

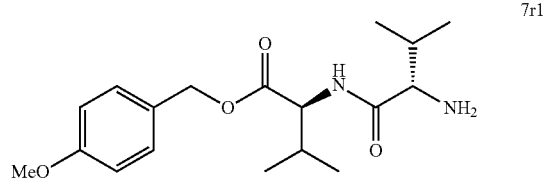 [SMILES: COc1ccc(COC(=O)[C@@H](NC(=O)[C@@H](N)C(C)C)C(C)C)cc1]

4-Methoxybenzyl L-valyl-L-valinate (7r1)

Figure 32:
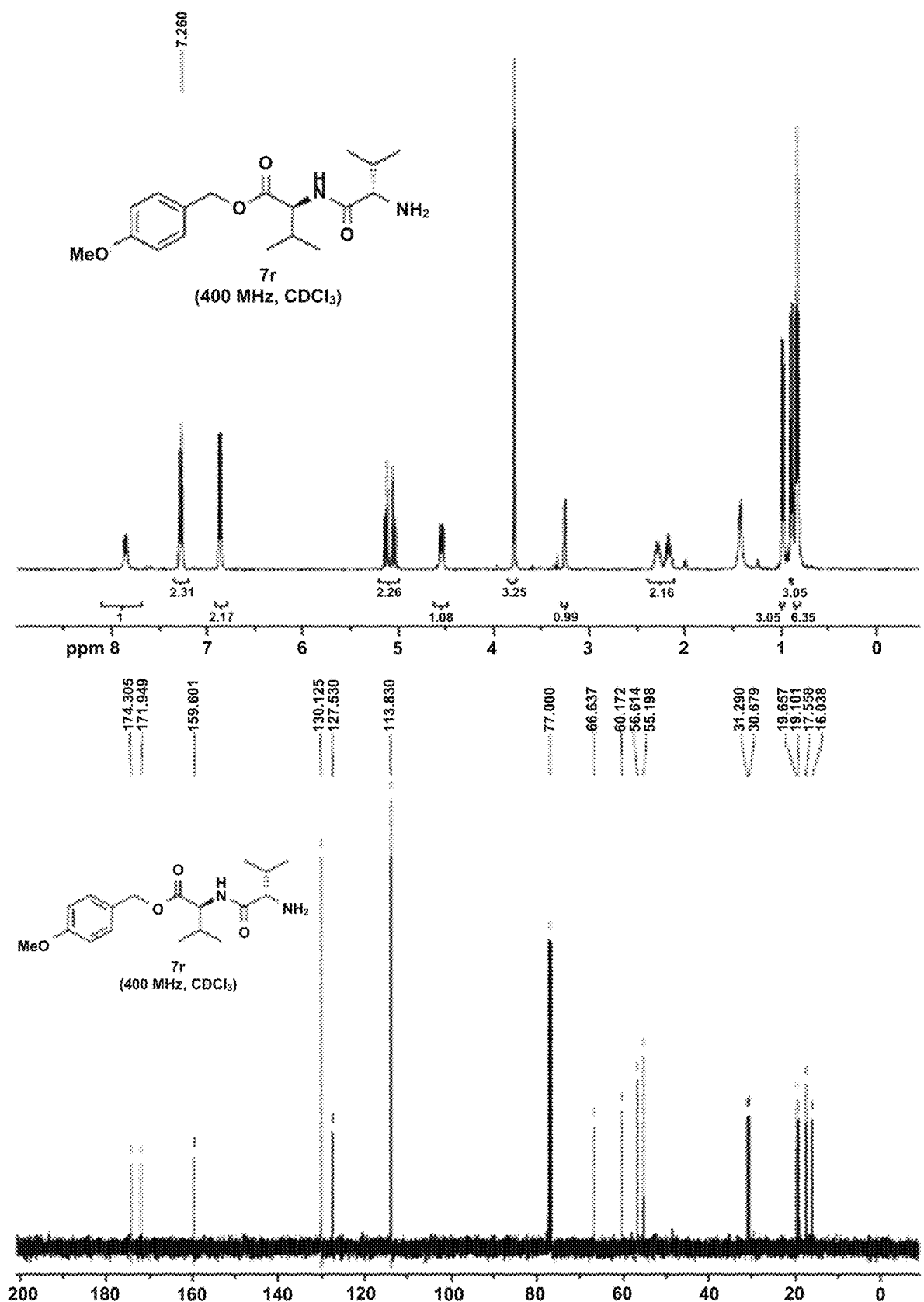
FIG. 32 shows the $^1$H NMR and $^{13}$C NMR spectra of compound 7r1.

Colorless liquid; Yield: 89%; Rf: 0.1 (Hexanes:EtOAc=1:4); [α]$^{26}_D$=−11.6 (c 0.25, CHCl$_3$); IR (γ, cm-1): 3320, 2405, 1737, 1665, 1612, 1514; $^1$H NMR (400 MHz, CDCl$_3$): δ 7.87 (d, J=8.8 Hz, 1H), 7.29 (d, J=8.4 Hz, 2H), 6.88 (d, J=8.7 Hz, 2H), 5.14 (d, J=11.6 Hz, 1H), 5.06 (d, J=11.6 Hz, 1H), 4.56 (m, 1H), 3.79 (s, 3H), 3.27 (m, 1H), 2.34 (m, 1H), 2.23 (m, 1H), 1.42 (bs, 2H), 0.99 (d, J=7.0 Hz, 3H), 0.90 (d, J=6.8 Hz, 3H), 0.85 (dd, J=6.4, 6.4 Hz, 6H); $^{13}$C NMR (100 MHz, CDCl$_3$): δ 174.3, 172.0, 159.6, 130.1, 127.5, 113.8, 66.6, 60.2, 56.6, 55.2, 31.1, 30.7, 19.7, 19.1, 17.6, 16.0. FIG. 32 shows the $^1$H NMR and $^{13}$C NMR spectra of compound 7r1.

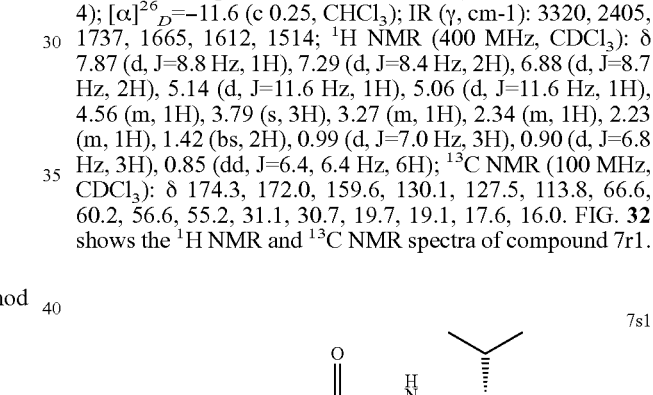

(S)-2-amino-N—((S)-1-(benzylamino)-3-methyl-1-oxobutan-2-yl)-3-methylbutanamide (7s1)

Figure 33:
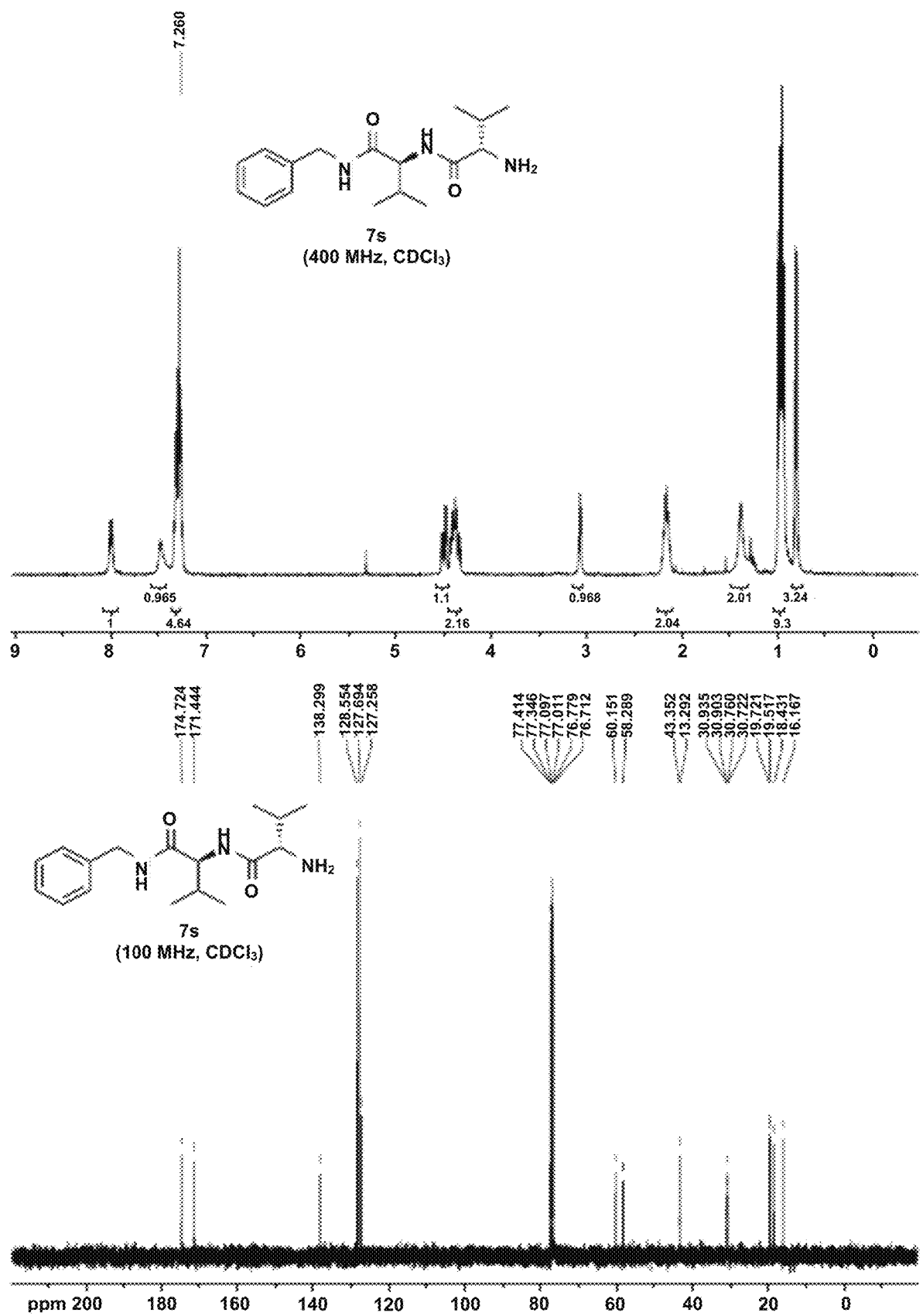
FIG. 33 shows the $^1$H NMR and $^{13}$C NMR spectra of compound 7s1.

Colorless liquid; Yield: 88%; Rf: 0.1 (Hexanes:EtOAc=1:4); [α]$^{26}_D$=−56.3 (c 0.05, CHCl$_3$); IR (γ, cm-1): 3386, 3051, 1724, 1637, 1655, 1514; $^1$H NMR (400 MHz, CDCl$_3$): δ 7.48 (bs, 1H), 7.33-7.27 (m, 5H), 4.53 (d, J=6.5 Hz, 1H), 4.49 (d, J=5.7 Hz, 1H), 4.43 (m, 2H), 3.07 (bs, 1H), 2.21-2.13 (m, 2H), 1.38 (bs, 2H), 0.99-0.93 (m, 9H), 0.81 (d, J=6.9 Hz, 3H); $^{13}$C NMR (100 MHz, CDCl$_3$): δ 174.6, 171.4, 138.2, 128.5, 127.6, 121.2, 60.0, 58.2, 43.3, 30.8, 30.7, 19.6, 19.4, 18.3, 16.1. FIG. 33 shows the $^1$H NMR and $^{13}$C NMR spectra of compound 7s1.

Example 12: Assembly of Compounds 8-11h

Assembly of compounds 8-11h were carried out by cleavage of the protecting groups on dipeptides 7a-7s and the β-lactones 5a-5e, followed by coupling using EDCl/HOBt (SCHEME 3).

SCHEME 3

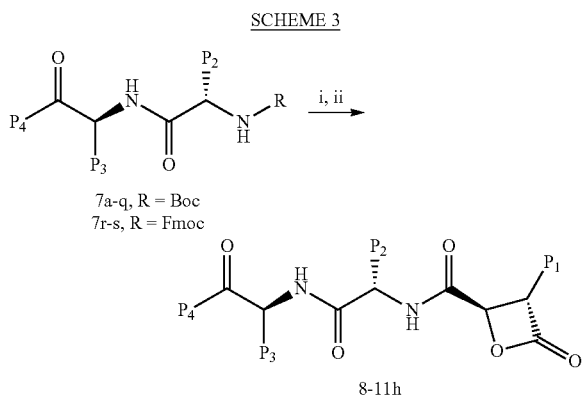

7a-q, R = Boc
7r-s, R = Fmoc 8-11h

Representative synthesis of final compounds. Reagents and conditions: (i) TFA, CH$_2$Cl$_2$, rt, for 7a-q, Et$_2$NH, CH$_2$Cl$_2$, 0° C., for 7r-7s (ii) 5a-e, TFA, CH$_2$Cl$_2$, then TFA salt of 7a-q or free amine of 7r-s, then EDCI, HOBt, NMM, THF, 0° C. to rt.

Benzyl ((2R,3S)-3-((S)-sec-butyl)-4-oxooxetane-2-carbonyl)-L-valyl-L-valinate (8)

Figure 34:
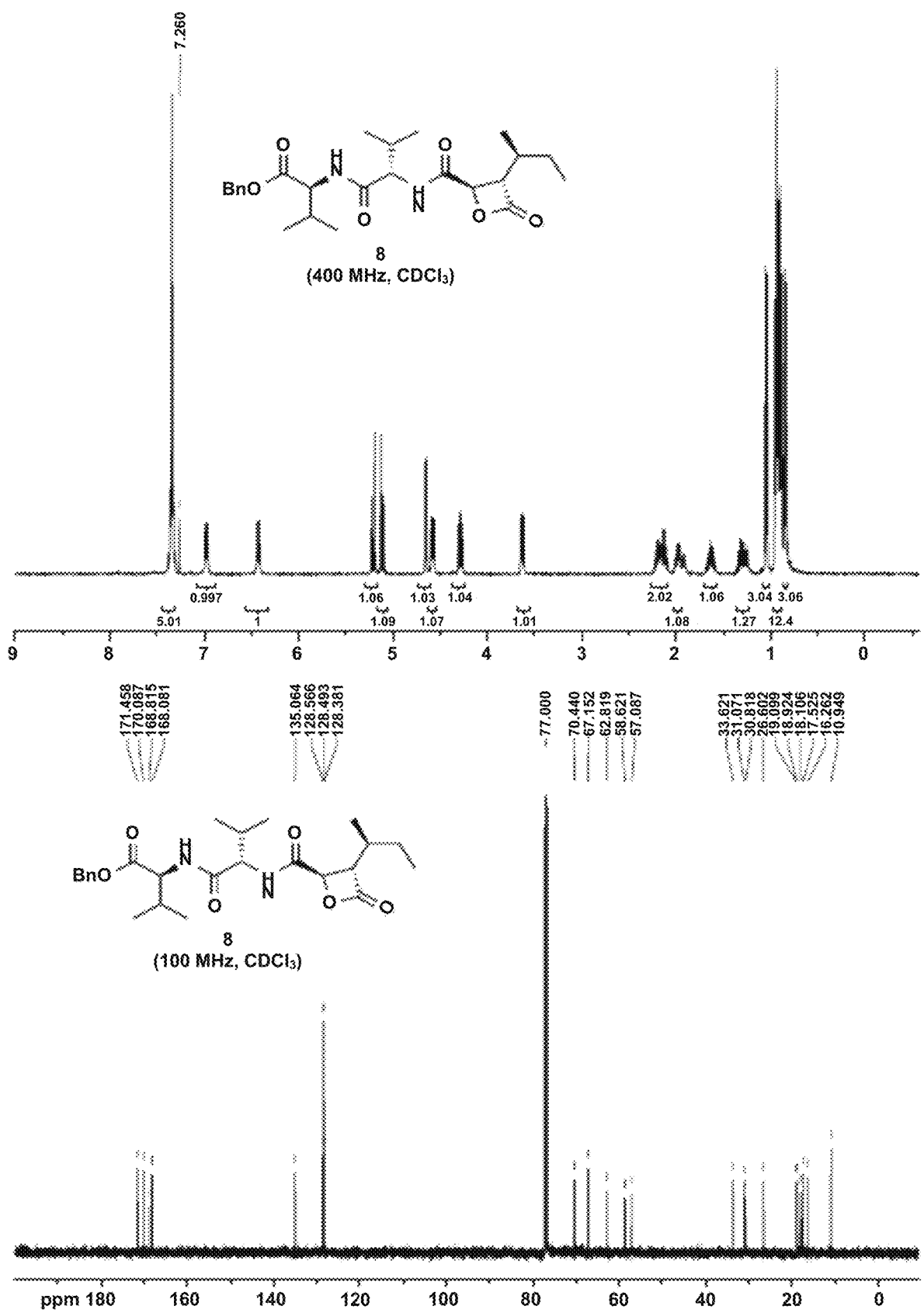
FIG. 34 shows the $^1$H NMR and $^{13}$C NMR spectra of compound 8.

White solid; Yield: 41%; R$_f$: 0.4 (Hexanes:EtOAc=7:3); $[\alpha]_D^{25}$=−16.4 (c 0.2, CHCl$_3$); IR ($\gamma$, cm$^{-1}$): 2948, 2387, 1914, 1762, 1713, 1614, 1518, 1416; $^1$H NMR (400 MHz, CDCl$_3$): δ 7.35-7.32 (m, 5H), 6.99 (d, J=8.3 Hz, 1H), 6.44 (d, J=8.9 Hz, 1H), 5.22 (d, J=12.2 Hz, 1H), 5.13 (d, J=12.0 Hz, 1H), 4.66 (d, J=4.5 Hz, 1H), 4.60 (dd, J=8.7, 4.7 Hz, 1H), 4.30 (m, 1H), 3.65 (dd, J=7.9, 4.7 Hz, 1H), 2.22-2.10 (m, 2H), 2.01-1.91 (m, 1H), 1.68-1.60 (m, 1H), 1.35-1.24 (m, 1H), 1.05 (d, J=6.7 Hz, 3H), 0.95-0.88 (m, 12H), 0.85 (d, J=6.7 Hz, 3H); $^{13}$C NMR (100 MHz, CDCl$_3$): δ 171.5, 170.1, 168.8, 168.1, 135.1, 128.6, 128.5, 128.4, 70.4, 67.2, 62.8, 58.6, 57.1, 33.6, 31.1, 30.8, 26.6, 19.1, 18.9, 18.1, 17.5, 16.3, 10.9; HRMS (ESI+) m/z: [M+H]$^+$ Calc'd for C$_{25}$H$_{37}$N$_2$O$_6$; 461.2646; Found 461.2668. FIG. 34 shows the $^1$H NMR and $^{13}$C NMR spectra of compound 8.

Benzyl ((2R,3S)-3-cyclopropyl-4-oxooxetane-2-carbonyl)-L-valyl-L-valinate (9a)

Figure 35:
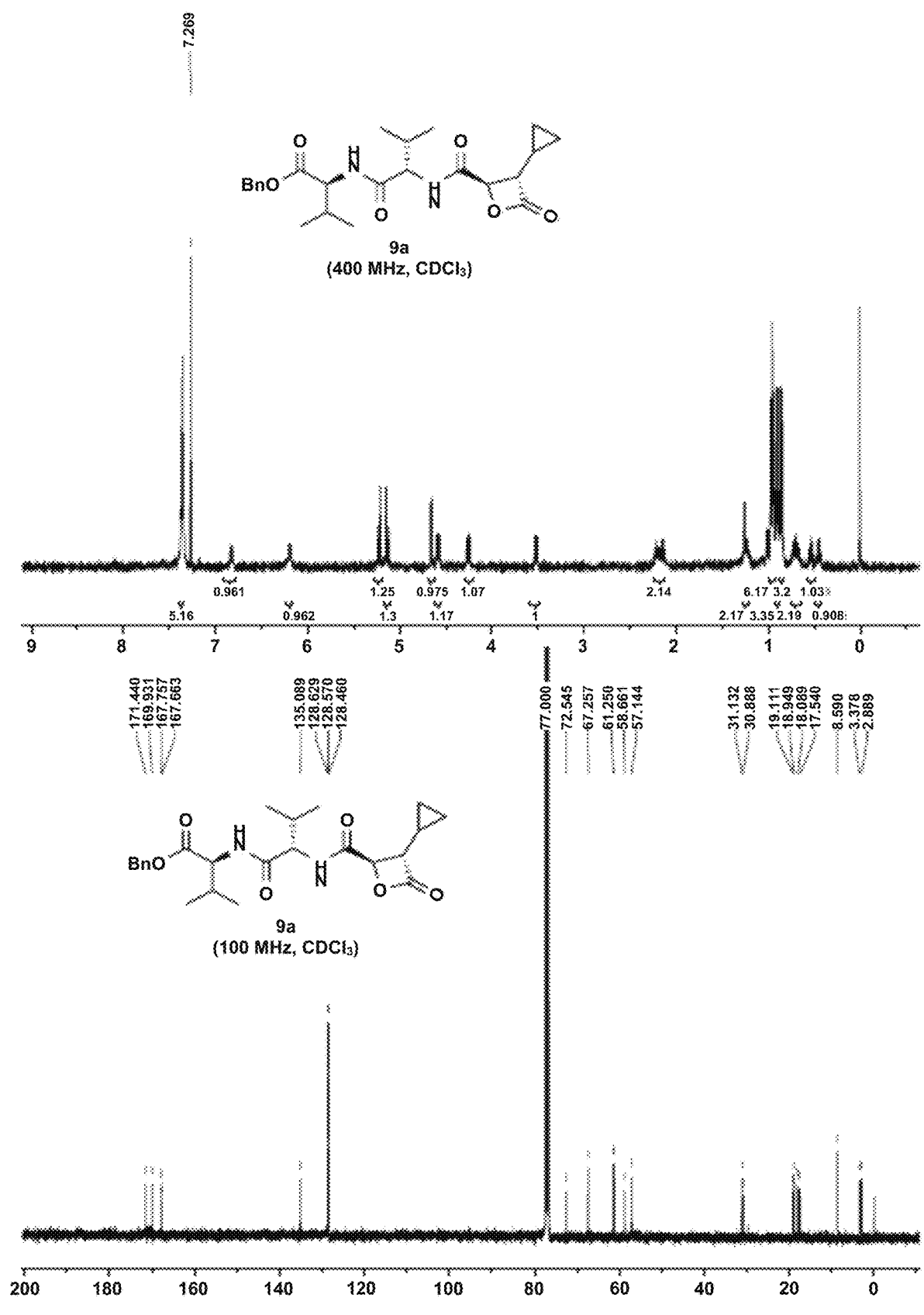

Pale yellow oil; Yield: 53%; R$_f$: 0.5 (Hexanes:EtOAc=2:1); $[\alpha]_D^{21}$=−5.2 (c 0.23, CHCl$_3$); IR ($\gamma$, cm$^{-1}$): 3270, 2360, 1843, 1740, 1646, 1558, 1457, 1205; $^1$H NMR (400 MHz, CDCl$_3$): δ 7.37-7.32 (m, 5H), 6.83 (d, J=8.5 Hz, 1H), 6.2 (d, J=8.4 Hz, 1H), 5.23-5.11 (m, 2H), 4.65 (d, J=4.6 Hz, 1H), 4.59-4.55 (m, 1H), 4.26 (dd, J=8.42, 8.25 Hz, 1H), 3.53 (dd, J=4.9, 4.5 Hz, 1H), 2.22-2.11 (m, 2H), 1.25-1.20 (m, 2H), 0.97-0.84 (m, 12H), 0.74-0.65 (m, 2H), 0.54-0.51 (m, 1H), 0.46-0.42 (m, 1H); $^{13}$C NMR (100 MHz, CDCl$_3$): δ 171.5, 169.9, 167.8, 167.7, 135.1, 128.6, 128.5, 77.2, 67.3, 61.3, 58.7, 57.2, 31.1, 30.9, 19.1, 18.9, 18.1, 17.5, 8.6, 3.4, 2.9; HRMS (ESI+) m/z: [M+H]$^+$ Calc'd for C$_{24}$H$_{33}$N$_2$O$_6$ 445.2333; Found 445.2323. FIG. 35 shows the $^1$H NMR and $^{13}$C NMR spectra of compound 9a.

Benzyl ((2R,3S)-3-cyclobutyl-4-oxooxetane-2-carbonyl)-L-valyl-L-valinate (9b)

Figure 36:
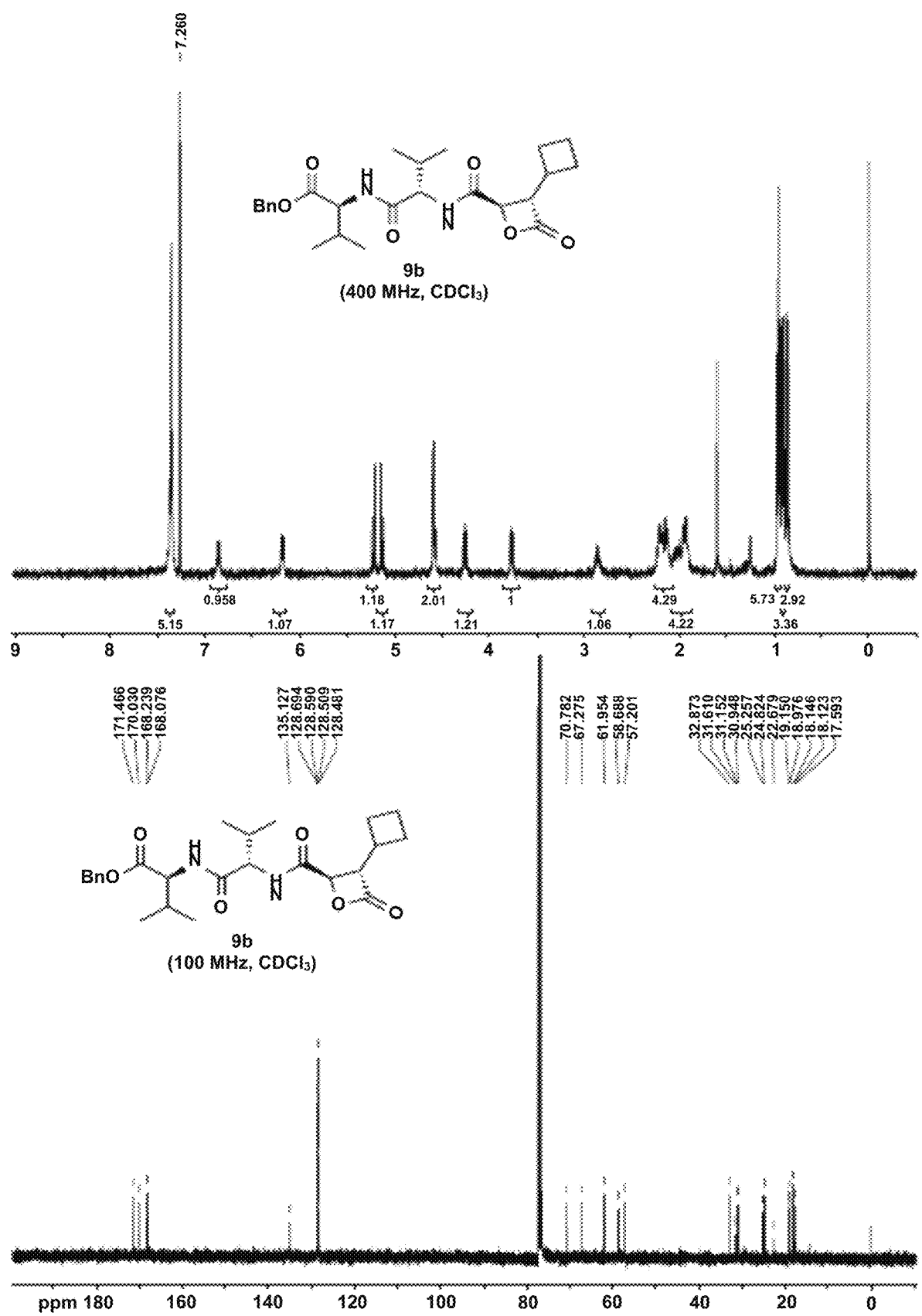
FIG. 36 shows the $^1$H NMR and $^{13}$C NMR spectra of compound 9b.

Pale yellow oil; Yield: 54%; R$_f$: 0.3 (Hexanes:EtOAc: 2:1); $[\alpha]_D^{21}$=−8.0 (c 0.26, CHCl$_3$); IR ($\gamma$, cm$^{-1}$): 3011, 2994, 2369, 1739, 1725, 1691; $^1$H NMR (400 MHz, CDCl$_3$): δ 7.39-7.32 (m, 5H), 6.86 (d, J=8.3 Hz, 1H), 6.19 (d, J=8.7 Hz, 1H), 5.23 (d, J=12.1 Hz, 1H), 5.14 (d, J=12.2 Hz, 1H), 4.60 (d, J=4.6 Hz, 2H), 4.27 (dd, J=8.3, 6.8 Hz, 1H), 3.78 (dd, J=7.0, 4.6 Hz, 1H), 2.90-2.81 (m, 1H), 2.24-2.09 (m, 4H), 2.06-1.89 (m, 4H), 0.97-0.94 (m, 6H), 0.92 (d, J=6.7 Hz, 3H), 0.87 (d, J=6.9 Hz, 3H); $^{13}$C NMR (100 MHz, CDCl$_3$): δ 171.4, 170.0, 168.2, 168.0, 135.1, 128.6, 128.5, 128.4, 70.8, 67.2, 61.9, 58.7, 51.2, 32.8, 31.6, 31.1, 30.9, 25.2, 24.8, 22.6, 19.1, 18.9, 18.1, 18.1, 17.6; HRMS (ESI+) m/z: [M+H]$^+$ Calc'd for C$_{25}$H$_{35}$N$_2$O$_6$ 459.2490; Found 459.2439. FIG. 36 shows the $^1$H NMR and $^{13}$C NMR spectra of compound 9b.

Benzyl ((2R,3S)-3-cyclopentyl-4-oxooxetane-2-carbonyl)-L-valyl-L-valinate (9c)

Figure 37:
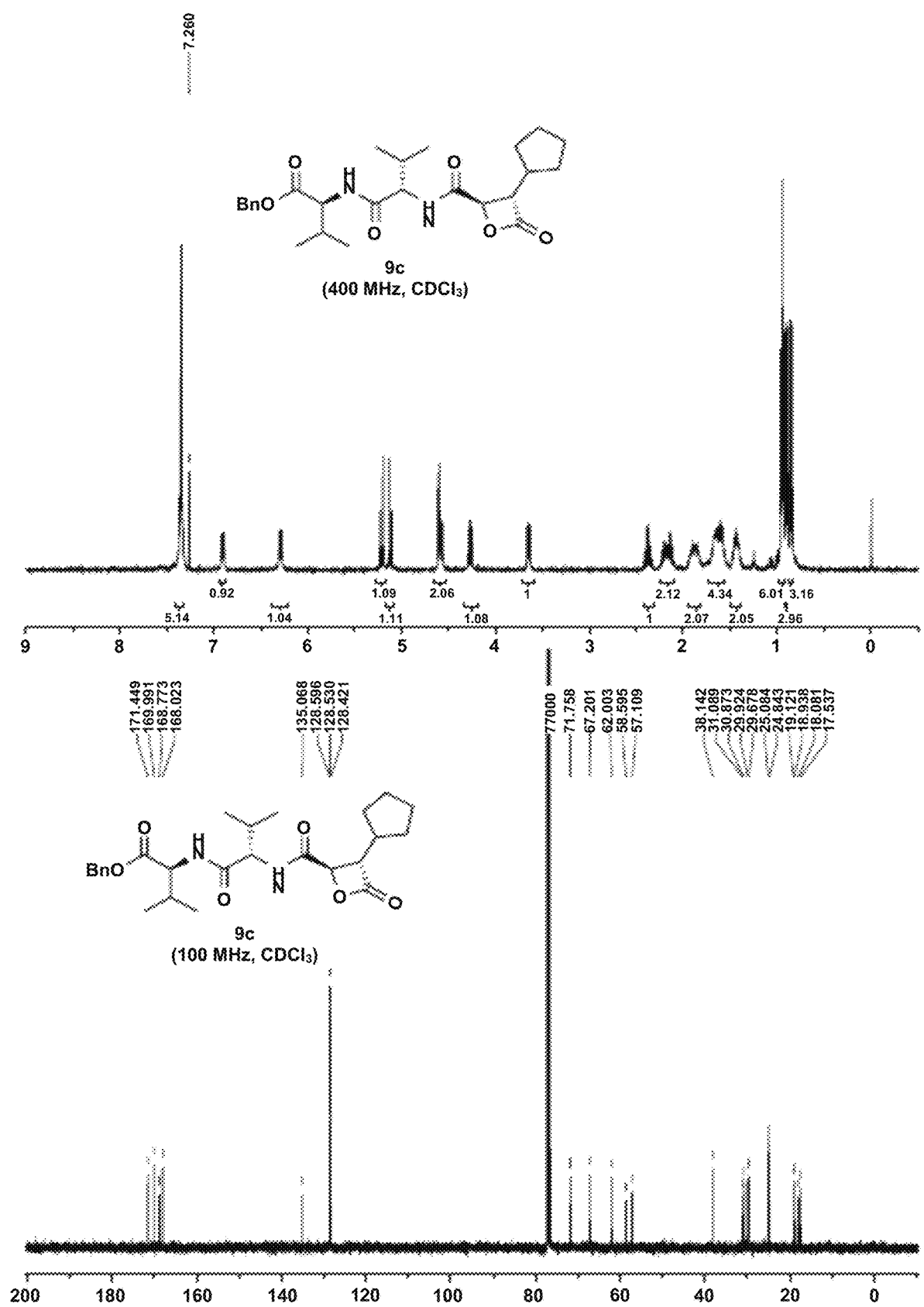
FIG. 37 shows the $^1$H NMR and $^{13}$C NMR spectra of compound 9c.

Colorless oil; Yield: 67%; R$_f$: 0.6 (Hexanes:EtOAc=3:1); $[\alpha]_D^{22}$=−10.6 (c 0.4, CHCl$_3$); IR ($\gamma$, cm$^{-1}$): 3175, 2323, 1642, 1599, 1471; $^1$H NMR (400 MHz, CDCl$_3$): δ 7.38-7.31 (m, 5H), 6.91 (d, J=8.3 Hz, 1H), 6.30 (d, J=8.7 Hz, 1H), 5.23 (d, J=11.9 Hz, 1H), 5.13 (d, J=11.9 Hz, 1H), 4.61-4.56 (m, 2H), 4.29 (dd, J=8.4, 6.7 Hz, 1H), 3.67 (dd, J=8.4, 4.5 Hz, 1H), 2.42-2.33 (m, 1H), 2.24-2.09 (m, 2H), 1.95-1.82 (m, 2H), 1.70-1.58 (m, 4H), 1.47-1.39 (m, 2H), 0.96 (dd, J=6.5, 6.0 Hz, 6H), 0.91 (d, J=6.9 Hz, 3H), 0.86 (d, J=7.0 Hz, 3H); $^{13}$C NMR (100 MHz, CDCl$_3$): δ 171.5, 170.0, 168.8, 168.0, 135.1, 128.6, 128.5, 128.4, 71.8, 67.2, 62.0, 58.6, 57.1, 38.1, 31.1, 30.9, 29.9, 29.7, 25.1, 24.8, 19.1, 18.9, 18.1, 17.5; HRMS (ESI+) m/z: [M+H]$^+$ Calc'd for C$_{26}$H$_{37}$N$_2$O$_6$ 473.2646; Found 473.2636. FIG. 37 shows the $^1$H NMR and $^{13}$C NMR spectra of compound 9c.

Benzyl ((2R,3S)-3-isobutyl-4-oxooxetane-2-carbonyl)-L-valyl-L-valinate (9d)

Figure 38:
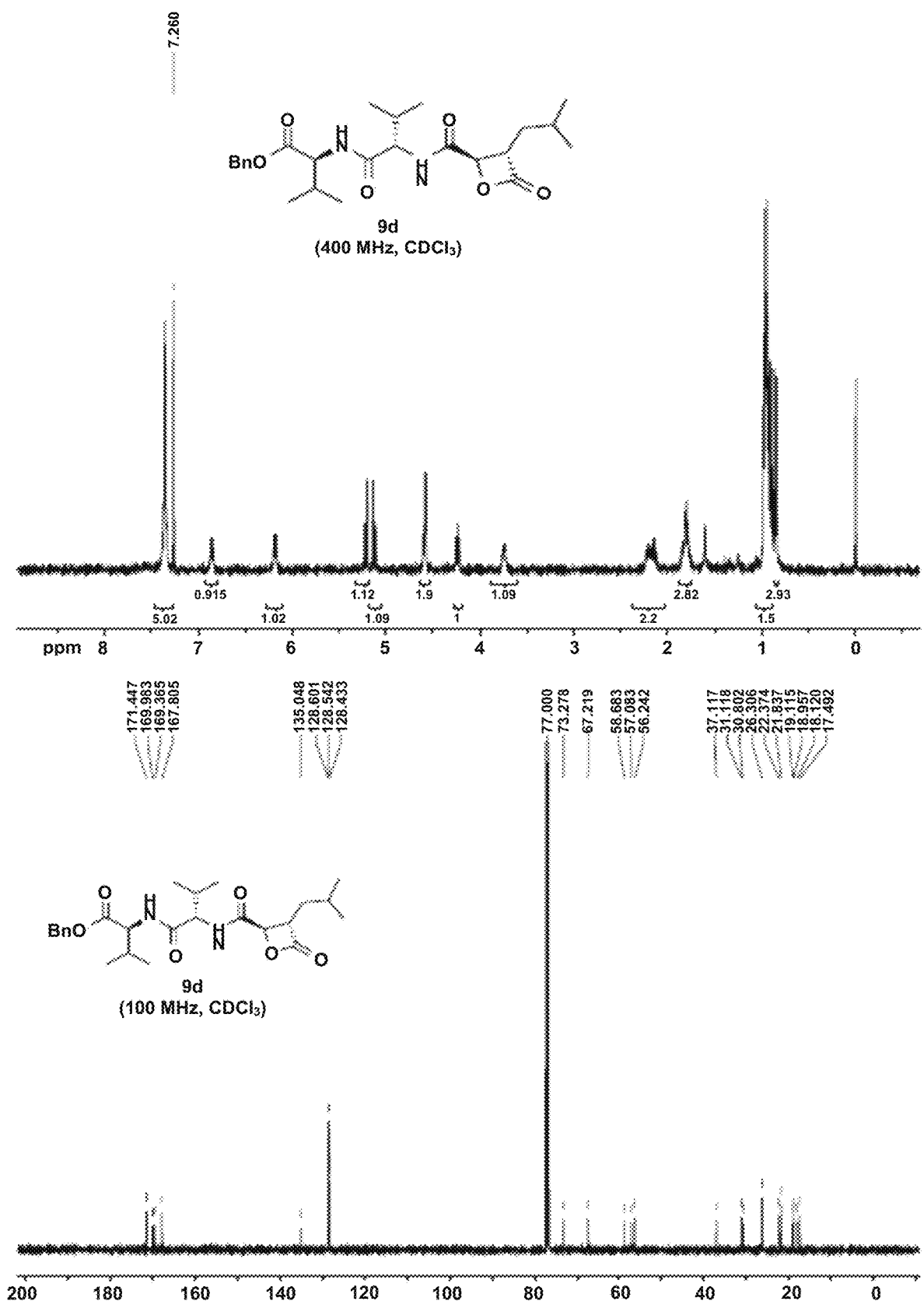
FIG. 38 shows the $^1$H NMR and $^{13}$C NMR spectra of compound 9d.

White solid; Yield: 31%; R$_f$: 0.6 (Hexanes:EtOAc=2:1); $[\alpha]_D^{21}$=−12.0 (c 0.1, CHCl$_3$); IR ($\gamma$, cm$^{-1}$): 3027, 2353, 1744, 1739, 1764, 1454, 1376; $^1$H NMR (400 MHz, CDCl$_3$): δ 7.37-7.35 (m, 5H), 6.87 (d, J=8.8 Hz, 1H), 6.19 (d, J=8.8 Hz, 1H), 5.23 (d, J=12.0 Hz, 1H), 5.14 (d, J=12.2 Hz, 1H), 4.60-4.57 (m, 2H), 4.26 (m, 1H), 3.77-3.72 (m, 1H), 2.23-2.11 (m, 2H), 1.86-1.76 (m, 3H), 0.98 (m, 15H), 0.86 (d, J=6.9 Hz, 3H); $^{13}$C NMR (100 MHz, CDCl$_3$): δ 171.4, 170.0, 169.4, 167.8, 135.1, 128.6, 128.5, 128.4, 73.3, 67.2, 58.7, 57.1, 56.2, 37.1, 31.1, 30.8, 26.3, 22.4, 21.8, 19.1, 18.9, 18.1, 17.5; HRMS (ESI+) m/z: [M+H]$^+$ Calc'd for C$_{25}$H$_{37}$N$_2$O$_6$ 461.2646; Found 461.2644. FIG. 38 shows the $^1$H NMR and $^{13}$C NMR spectra of compound 9d.

Benzyl ((2R,3S)-3-((S)-sec-butyl)-4-oxooxetane-2-carbonyl)glycyl-L-valinate (10a)

Figure 39:
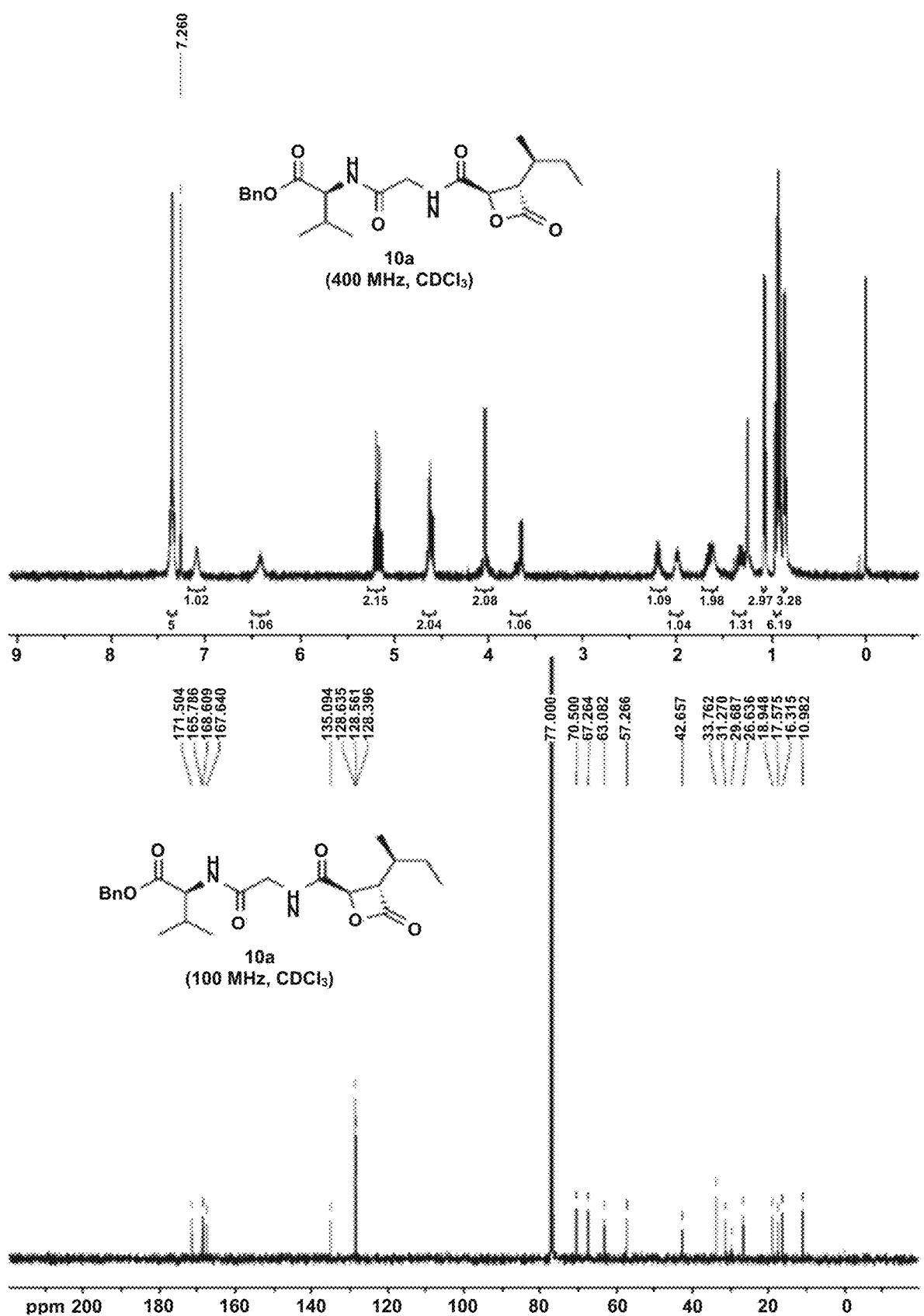

Colorless solid; Yield: 84%; R$_f$: 0.4 (Hexanes:EtOAc=7:3); $[\alpha]_D^{25}$=+18.3 (c 0.08, CHCl$_3$); IR ($\gamma$, cm$^{-1}$): 2956, 2806, 1692, 1646, 1536, 1425; $^1$H NMR (400 MHz, CDCl$_3$): δ 7.39-7.32 (m, 5H), 7.10 (bs, 1H), 6.46-6.42 (m, 1H), 5.22 (d, J=12.3 Hz, 1H), 5.16 (d, J=12.1 Hz, 1H), 4.65-4.57 (m, 2H), 4.04 (d, J=5.2 Hz, 1H), 3.67 (dd, J=7.8, 4.6 Hz, 1H), 2.24-2.16 (m, 1H), 2.03-1.96 (m, 1H), 1.71-1.61 (m, 2H), 1.39-1.29 (m, 1H), 1.08 (d, J=6.6 Hz, 3H), 0.96-0.91 (m, 6H), 0.87-0.84 (m, 3H); $^{13}$C NMR (100 MHz, CDCl$_3$): δ 171.5, 168.8, 168.6, 167.7, 135.1, 128.6, 128.6, 128.4, 70.5, 67.3, 63.1, 57.3, 42.7, 33.8, 31.3, 31.2, 29.7, 26.6, 18.9, 17.6, 16.3, 11.0; HRMS (ESI+) m/z: [M+H]$^+$ Calc'd for C$_{22}$H$_{31}$N$_2$O$_6$ 419.2177; Found 419.2162. FIG. 39 shows the $^1$H NMR and $^{13}$C NMR spectra of compound 10a.

Benzyl((2R,3S)-3-((S)-sec-butyl)-4-oxooxetane-2-carbonyl)-L-phenylalanyl-L-valinate (10b)

Figure 40:
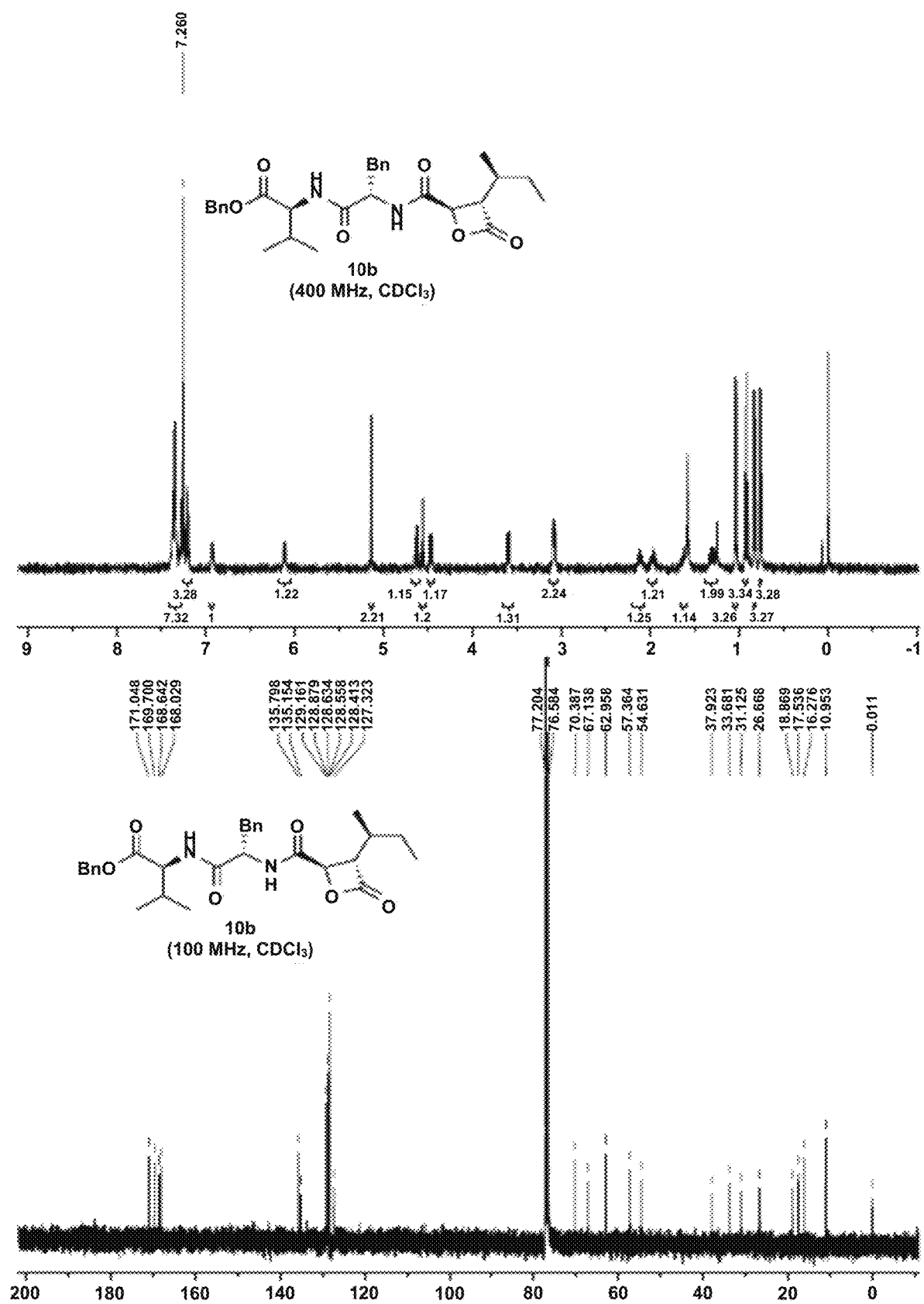
FIG. 40 shows the $^1$H NMR and $^{13}$C NMR spectra of compound 10b.

White solid; Yield: 46%; R$_f$: 0.3 (Hexanes:EtOAc=3:1); $[\alpha]_D^{21}$=−5.5 (c 0.18, CHCl$_3$); IR ($\gamma$, cm$^{-1}$): 3082, 2947, 1804, 1743, 1638, 1556; $^1$H NMR (400 MHz, CDCl$_3$): δ 7.39-7.33 (m, 5H), 7.30-7.26 (m, 2H), 7.24-7.20 (m, 3H), 6.93 (d, J=7.5 Hz, 1H), 6.11 (d, J=8.5 Hz, 1H), 5.14 (m, 2H), 4.65 (dd, J=14.4, 7.4 Hz, 1H), 4.57 (d, J=4.5 Hz, 1H), 4.49 (dd, J=8.34, 4.7 Hz, 1H), 3.62 (dd, J=7.5, 4.8 Hz, 1H), 3.10 (dd, J=7.1, 4.3 Hz, 2H), 2.16-2.08 (m, 1H), 2.01-1.92 (m, 1H), 1.68-1.60 (m, 1H), 1.35-1.27 (m, 2H), 1.05 (d, J=6.7 Hz, 3H), 0.95 (m, 3H), 0.84 (d, J=6.8 Hz, 3H), 0.78 (d, J=7.0 Hz, 3H); $^{13}$C NMR (100 MHz, CDCl$_3$): δ 171.1, 169.7, 168.6, 168.0, 135.8, 135.2, 129.2, 128.9, 128.6, 128.6, 128.4. 127.3, 70.4, 67.1, 63.0, 57.4, 54.6, 37.9, 33.7, 31.1, 26.7, 18.9, 17.5, 16.3, 10.9; HRMS (ESI+) m/z: [M+H]$^+$ Calc'd for C$_{29}$H$_{37}$N$_2$O$_6$ 509.2646; Found 509.2637. FIG. 40 shows the $^1$H NMR and $^{13}$C NMR spectra of compound 10b.

Benzyl((2R,3S)-3-((S)-sec-butyl)-4-oxooxetane-2-carbonyl)-L-valyl-phenylalaninate (10c)

Figure 41:
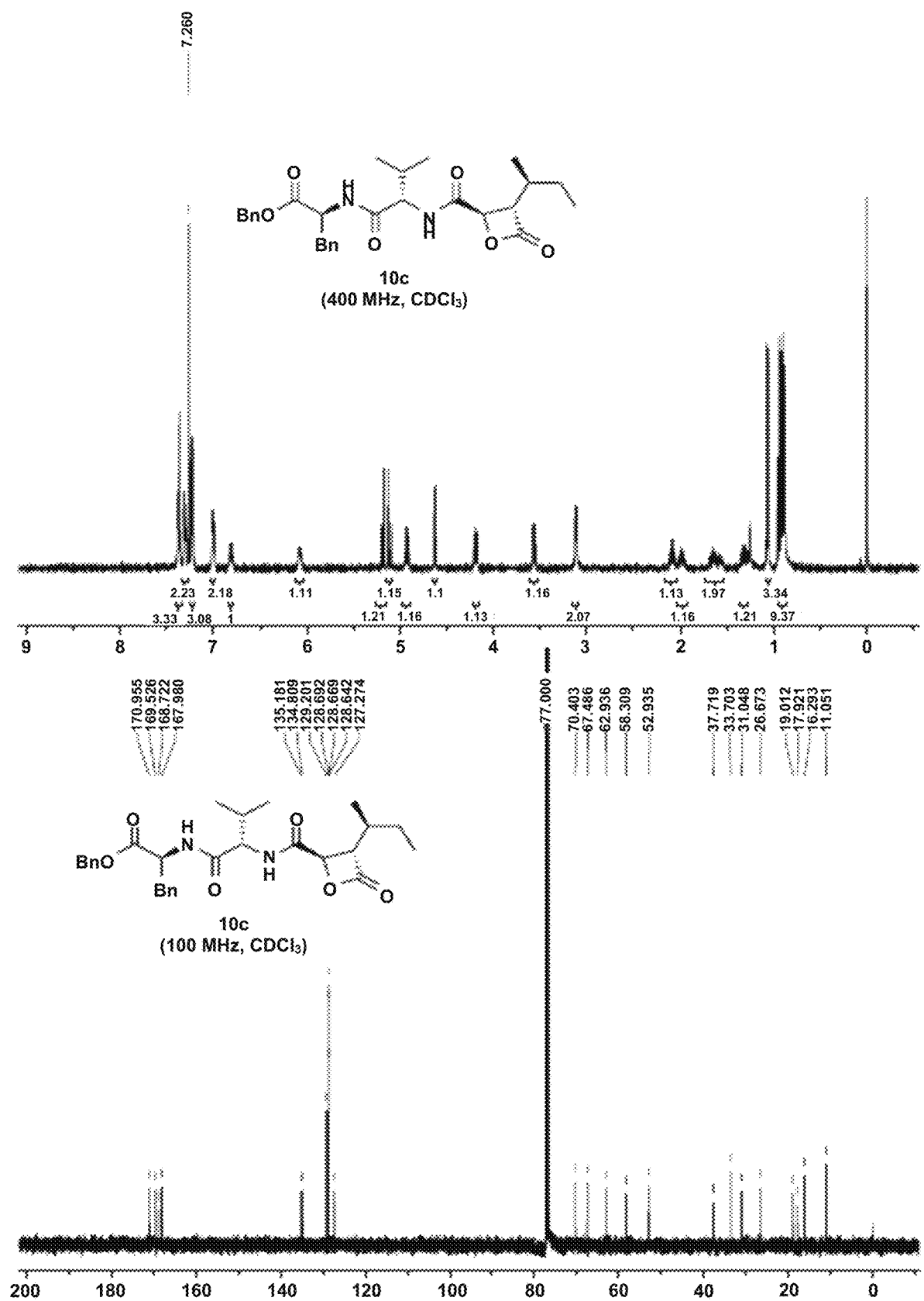
FIG. 41 shows the $^1$H NMR and $^{13}$C NMR spectra of compound 10c.

White solid; Yield: 63%; R$_f$: 0.3 (Hexanes:EtOAc=3:1); [α]$_D^{21}$=+2.5 (c 0.2, CHCl$_3$); IR (γ, cm$^{-1}$): 3282, 2965, 2360, 1838, 1739, 1645; $^1$H NMR (400 MHz, CDCl$_3$): δ 7.39-7.36 (m, 3H), 7.31-7.29 (m, 2H), 7.23-7.22 (m, 3H), 7.01-6.99 (m, 2H), 6.82 (d, J=8.5 Hz, 1H), 6.08 (d, J=7.5 Hz, 1H), 5.20 (d, J=12.2 Hz, 1H), 5.12 (d, J=12.1 Hz, 1H), 4.95-4.90 (m, 1H), 4.63 (d, J=4.8 Hz, 1H), 4.21 (dd, J=8.5, 6.3 Hz, 1H), 3.58 (dd, J=7.6, 4.6 Hz, 1H), 3.13 (dd, J=6.0, 2.3 Hz, 2H), 2.13-2.04 (m, 1H), 2.02-1.93 (m, 1H), 1.70-1.60 (m, 1H), 1.36-1.28 (m, 1H), 1.08 (d, J=6.7 Hz, 3H), 0.96 (m, 9H); $^{13}$C NMR (100 MHz, CDCl$_3$): δ 171.0, 169.5, 168.7, 168.0, 135.2, 134.8, 129.2, 128.7, 128.7, 128.6, 127.3, 70.4, 67.5, 62.9, 58.3, 52.9, 37.7, 33.7, 31.0, 26.7, 19.0, 17.9, 16.3, 11.0; HRMS (ESI+) m/z: [M+H]$^+$ Calc'd for C$_{29}$H$_{37}$N$_2$O$_6$ 509.2646; Found 509.2650. FIG. 41 shows the $^1$H NMR and $^{13}$C NMR spectra of compound 10c.

Benzyl((2R,3S)-3-((S)-sec-butyl)-4-oxooxetane-2-carbonyl)-L-phenylalanyl-L-phenylalaninate (10d)

Figure 42:
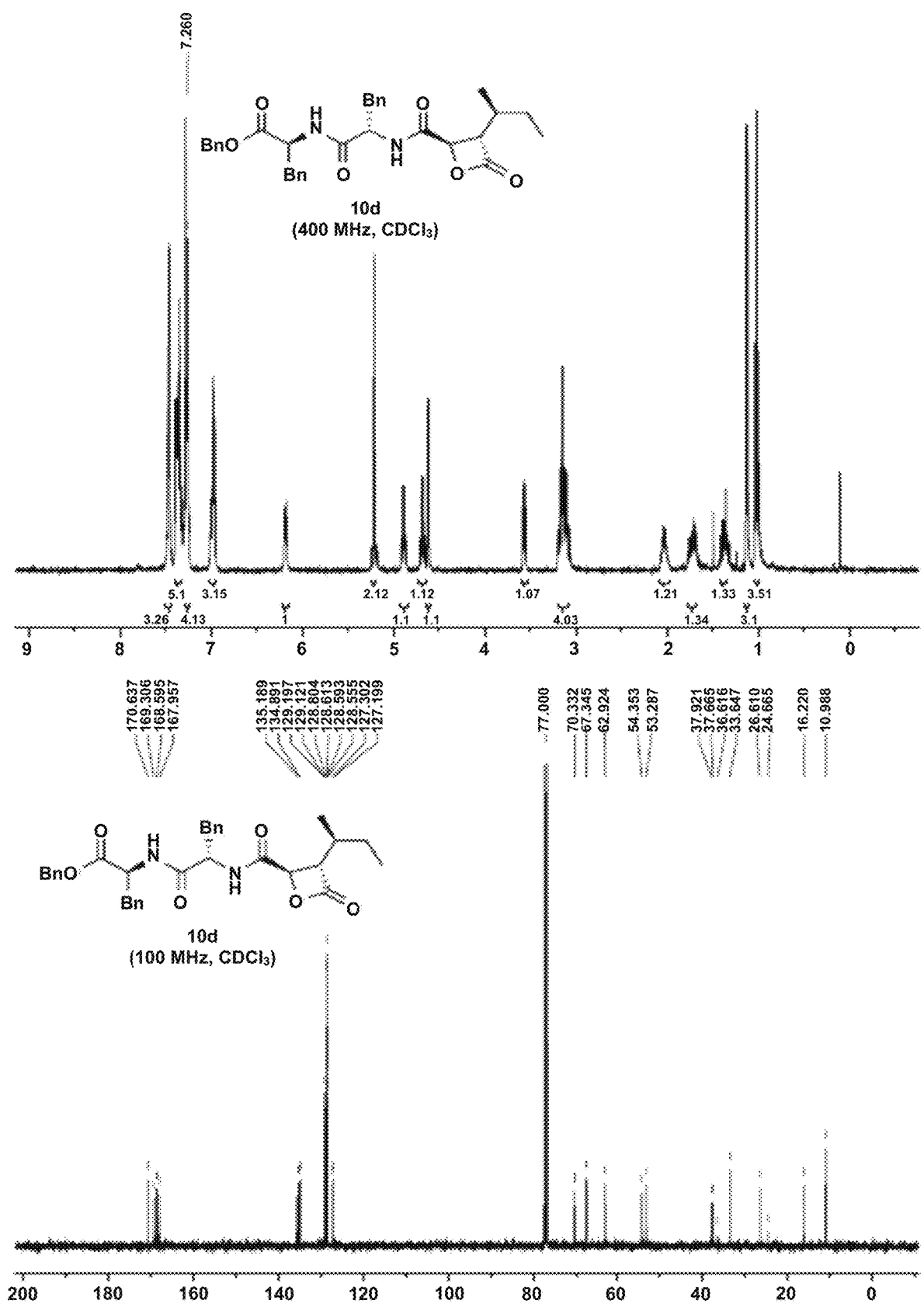
FIG. 42 shows the $^1$H NMR and $^{13}$C NMR spectra of compound 10d.

White solid; Yield: 51%; R$_f$: 0.3 (Hexanes:EtOAc=7:3); [α]$_D^{25}$=−1.8 (c 0.2, CHCl$_3$); IR (γ, cm$^{-1}$): 3082, 2947, 1840, 1743, 1638, 1556; $^1$H NMR (400 MHz, CDCl$_3$): δ 7.40-7.37 (m, 3H), 7.31-7.24 (m, 5H), 7.21-7.16 (m, 5H), 6.92-6.87 (m, 3H), 6.11 (d, J=7.6 Hz, 1H), 5.16-5.09 (m, 2H), 4.83 (dd, J=13.4, 5.9 Hz, 1H), 4.62 (dd, J=14.1, 7.2 Hz, 1H), 4.54 (d, J=4.8 Hz, 1H), 3.50 (dd, J=7.4, 4.4 Hz, 1H), 3.12-2.98 (m, 4H), 2.0-1.89 (m, 1H), 1.68-1.57 (m, 1H), 1.33-1.23 (m, 1H), 1.05 (d, J=6.8 Hz, 3H), 0.95-0.89 (m, 3H); $^{13}$C NMR (100 MHz, CDCl$_3$): δ 170.6, 169.3, 168.6, 168.0, 135.8, 135.2, 134.9, 129.2, 129.1, 128.8, 128.6, 128.6, 128.5, 127.3, 127.2, 70.3, 67.3, 62.9, 54.4, 53.3, 37.9, 37.7, 33.6, 26.6, 24.7, 16.2, 11.0; HRMS (ESI+) m/z: [M+H]$^+$ Calc'd for C$_{33}$H$_{37}$N$_2$O$_6$ 557.2646; Found 557.2642. FIG. 42 shows the $^1$H NMR and $^{13}$C NMR spectra of compound 10d.

Benzyl((S)-2-((2R,3S)-3-((S)-sec-butyl)-4-oxooxetane-2-carboxamido)-3,3-dimethylbutanoyl)-L-valinate (10e)

Figure 43:
FIG. 43 shows the $^1$H NMR and $^{13}$C NMR spectra of compound 10e.

White solid; Yield: 82%; R$_f$: 0.5 (Hexanes:EtOAc=4:1); [α]$_D^{25}$=−6.3 (c 0.4, CHCl$_3$); IR (γ, cm$^{-1}$): 2995, 2933, 1771, 1734, 1716, 1443, 1373, 1368; $^1$H NMR (400 MHz, CDCl$_3$): δ 7.38-7.31 (m, 5H), 6.98 (d, J=8.7 Hz, 1H), 6.22 (d, J=7.6 Hz, 1H), 5.22 (d, J=12.1 Hz, 1H), 5.13 (d, J=12.2 Hz, 1H), 4.66 (d, J=4.5 Hz, 1H), 4.58 (dd, J=8.5, 4.9 Hz, 1H), 4.29 (d, J=9.1 Hz, 1H), 3.63 (dd, J=7.8, 4.6 Hz, 1H), 2.22-2.14 (m, 1H), 2.01-1.93 (m, 1H), 1.69-1.58 (m, 1H), 1.36-1.21 (m, 1H), 1.06 (d, J=6.8 Hz, 3H), 0.99 (s, 9H), 0.93-0.88 (m, 6H), 0.86 (d, J=6.9 Hz, 3H); $^{13}$C NMR (100 MHz, CDCl$_3$): δ 171.4, 169.4, 168.8, 167.8, 135.0, 128.6, 128.5, 128.4, 70.4, 67.1, 62.7, 60.8, 57.2, 34.6, 33.6, 31.1, 26.6, 26.5, 18.9, 17.6, 16.3, 11.0; HRMS (ESI+) m/z: [M+H]$^+$ Calc'd for C$_{26}$H$_{39}$N$_2$O$_6$ 475.2803; Found 475.2814. FIG. 43 shows the $^1$H NMR and $^{13}$C NMR spectra of compound 10e.

Benzyl(S)-2-((S)-2-((2R,3S)-3-((S)-sec-butyl)-4-oxooxetane-2-carboxamido)-3-methylbutanamido)-3,3-dimethylbutanoate (10f)

Figure 44:
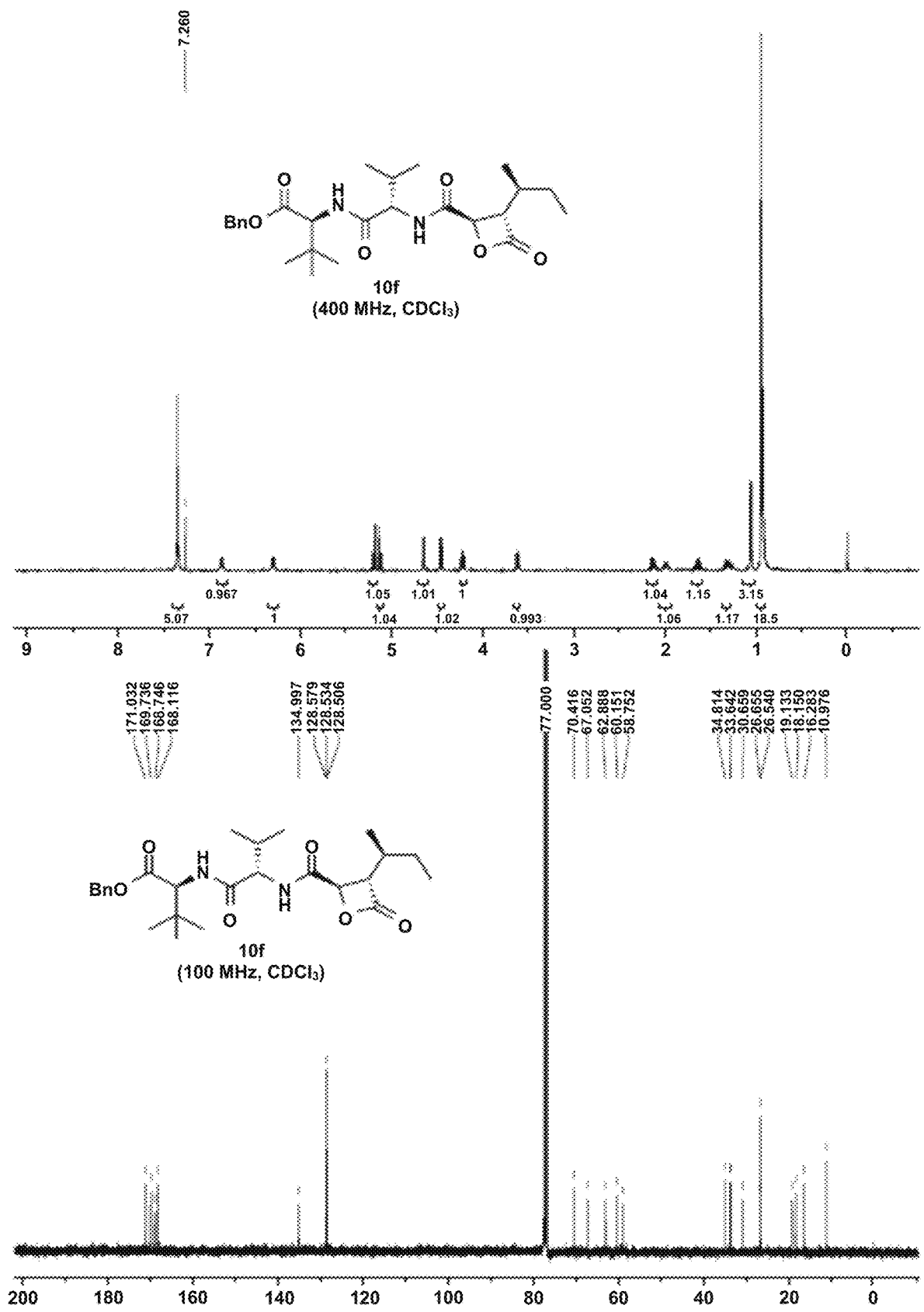
FIG. 44 shows the $^1$H NMR and $^{13}$C NMR spectra of compound 10f.

White solid; Yield: 42%; R$_f$: 0.4 (Hexanes/EtOAc=4:1); [α]$_D^{26}$=−2.4 (c 0.3, CHCl$_3$); IR (γ, cm$^{-1}$): 2957, 1740, 1706, 1476, 1436, 1266; $^1$H NMR (400 MHz, CDCl$_3$): δ 7.37-7.33 (m, 5H), 6.88 (d, J=8.2 Hz, 1H), 6.31 (d, J=9.1 Hz, 1H), 5.21 (d, J=12.1 Hz, 1H), 5.14 (d, J=12.2 Hz, 1H), 4.65 (d, J=4.5 Hz, 1H), 4.47 (d, J=9.1 Hz, 1H), 4.24 (dd, J=8.3, 7.3 Hz, 1H), 3.63 (dd, J=7.6, 4.5 Hz, 1H), 2.17-2.08 (m, 1H), 2.04-1.94 (m, 1H), 1.69-1.58 (m, 1H), 1.37-1.28 (m, 1H), 1.06 (d, J=6.7 Hz, 3H), 0.94-0.91 (m, 18H); $^{13}$C NMR (100 MHz, CDCl$_3$): δ 171.0, 169.8, 168.8, 168.1, 135.0, 128.6, 128.5, 128.5, 70.4, 67.1, 62.9, 60.2, 58.8, 34.8, 33.6, 30.7, 26.7, 26.5, 19.1, 18.1, 16.3, 11.0; HRMS (ESI+) m/z: [M+H]$^+$ Calc'd for C$_{26}$H$_{39}$N$_2$O$_6$ 475.2803; Found 475.2813. FIG. 44 shows the $^1$H NMR and $^{13}$C NMR spectra of compound 10f.

Benzyl(S)-2-((S)-2-((2R,3S)-3-((S)-sec-butyl)-4-oxooxetane-2-carboxamido)-3,3-dimethylbutanamido)-3,3-dimethylbutanoate (10g)

Figure 45:
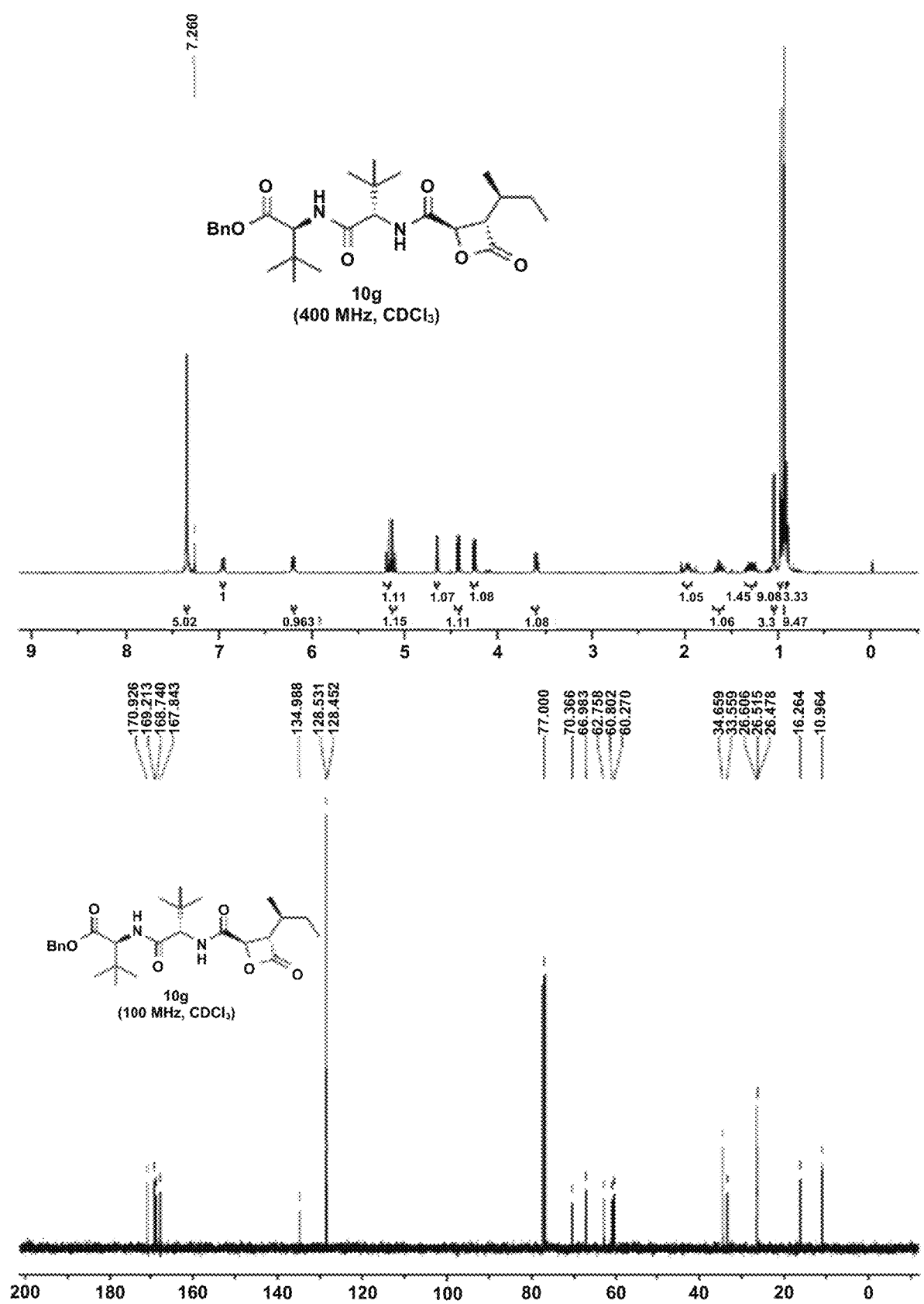
FIG. 45 shows the $^1$H NMR and $^{13}$C NMR spectra of compound 10g.

White solid; Yield: 94%; R$_f$: 0.6 (Hexanes:EtOAc=3:1); [α]$_D^{25}$=−9.7 (c 0.4, CHCl$_3$); IR (γ, cm$^{-1}$): 2954, 1837, 1738, 1640, 1527, 1443, 1323; $^1$H NMR (400 MHz, CDCl$_3$): δ 7.37-7.32 (m, 5H), 6.96 (d, J=9.1 Hz, 1H), 6.21 (d, J=9.1 Hz, 1H), 5.2 (d, J=12.2 Hz, 1H), 5.13 (d, J=12.1 Hz, 1H), 4.66 (d, J=4.7 Hz, 1H), 4.44 (d, J=8.7 Hz, 1H), 4.27 (d, J=8.8 Hz, 1H), 3.61 (dd, J=7.6, 4.6 Hz, 1H), 2.01-1.92 (m, 1H), 1.68-1.58 (m, 1H), 1.35-1.24 (m, 1H), 1.05 (d, J=6.8 Hz, 3H), 0.97 (s, 9H), 0.93 (s, 9H), 0.91-0.89 (m, 3H) $^{13}$C NMR (100 MHz, CDCl$_3$): δ 170.9, 169.2, 168.8, 167.9, 135.0, 128.5, 128.5, 70.4, 67.0, 62.8, 60.8, 60.3, 34.7, 34.7, 33.6, 26.6, 26.5, 16.3, 11.0; HRMS (ESI+) m/z: [M+H]$^+$ Calc'd for C$_{27}$H$_{41}$N$_2$O$_6$ 489.2959; Found 489.2954. FIG. 45 shows the $^1$H NMR and $^{13}$C NMR spectra of compound 10g.

Benzyl((2R,3S)-3-((S)-sec-butyl)-4-oxooxetane-2-carbonyl)-L-leucyl-L-valinate (10h)

Figure 46:
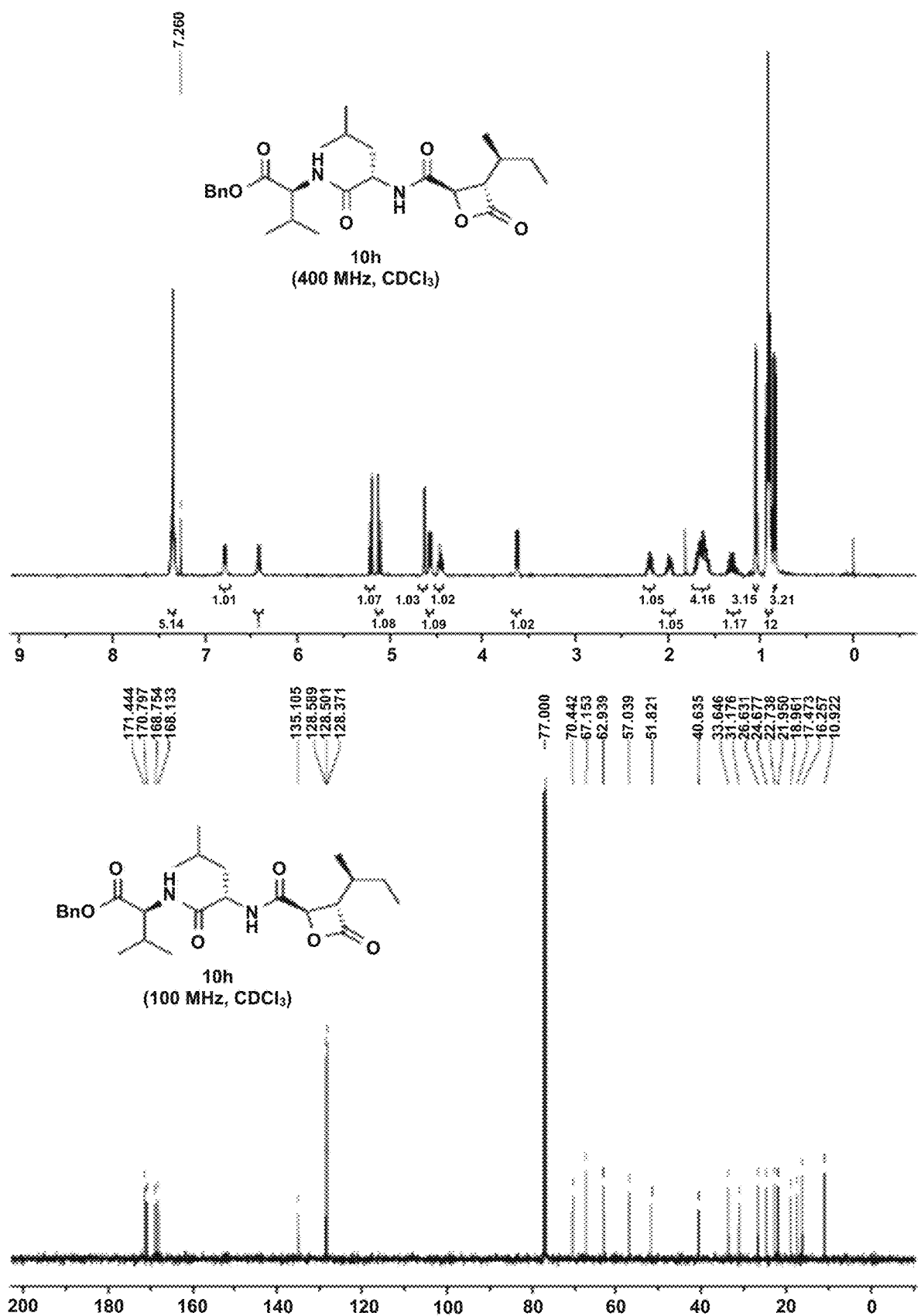
FIG. 46 shows the $^1$H NMR and $^{13}$C NMR spectra of compound 10h.

White solid; Yield: 77%; R$_f$: 0.4 (Hexanes:EtOAc=3:1); [α]$_D^{23}$=−97.0 (c 0.4, CHCl$_3$) IR (γ, cm$^{-1}$): 3018, 2941, 1764, 1735, 1719, 1433, 1392; $^1$H NMR (400 MHz, CDCl$_3$): δ 7.38-7.33 (m, 5H), 6.8 (d, J=8.1 Hz, 1H), 6.43 (d, J=8.9 Hz, 1H), 5.22 (d, J=12.1 Hz, 1H), 5.13 (d, J=12.1 Hz, 1H), 4.63 (d, J=4.6 Hz, 1H), 4.58 (dd, J=8.8, 4.8 Hz, 1H), 4.48-4.43 (m, 1H), 3.64 (dd, J=7.6, 4.6 Hz, 1H), 2.23-2.15 (m, 1H), 2.04-1.93 (m, 1H), 1.73-1.58 (m, 4H), 1.37-1.27 (m, 1H), 1.06 (d, J=6.8 Hz, 3H), 0.94-0.88 (m, 12H), 0.85 (d, J=6.9 Hz, 3H); $^{13}$C NMR (100 MHz, CDCl$_3$): δ 171.5, 170.8, 168.8, 168.1, 135.1, 128.6, 128.5, 128.4, 70.4, 67.2, 62.9, 57.0, 51.8, 40.6, 33.6, 31.2, 26.6, 24.7, 22.7, 21.9, 19.0, 17.5, 16.3, 11.0; HRMS (ESI+) m/z: [M+H]$^+$ Calc'd for C$_{26}$H$_{39}$N$_2$O$_6$ 475.2803; Found 475.2810. FIG. 46 shows the $^1$H NMR and $^{13}$C NMR spectra of compound 10h.

Benzyl((2R,3S)-3-((S)-sec-butyl)-4-oxooxetane-2-carbonyl)-L-valyl-L-leucinate (10i)

Figure 47:
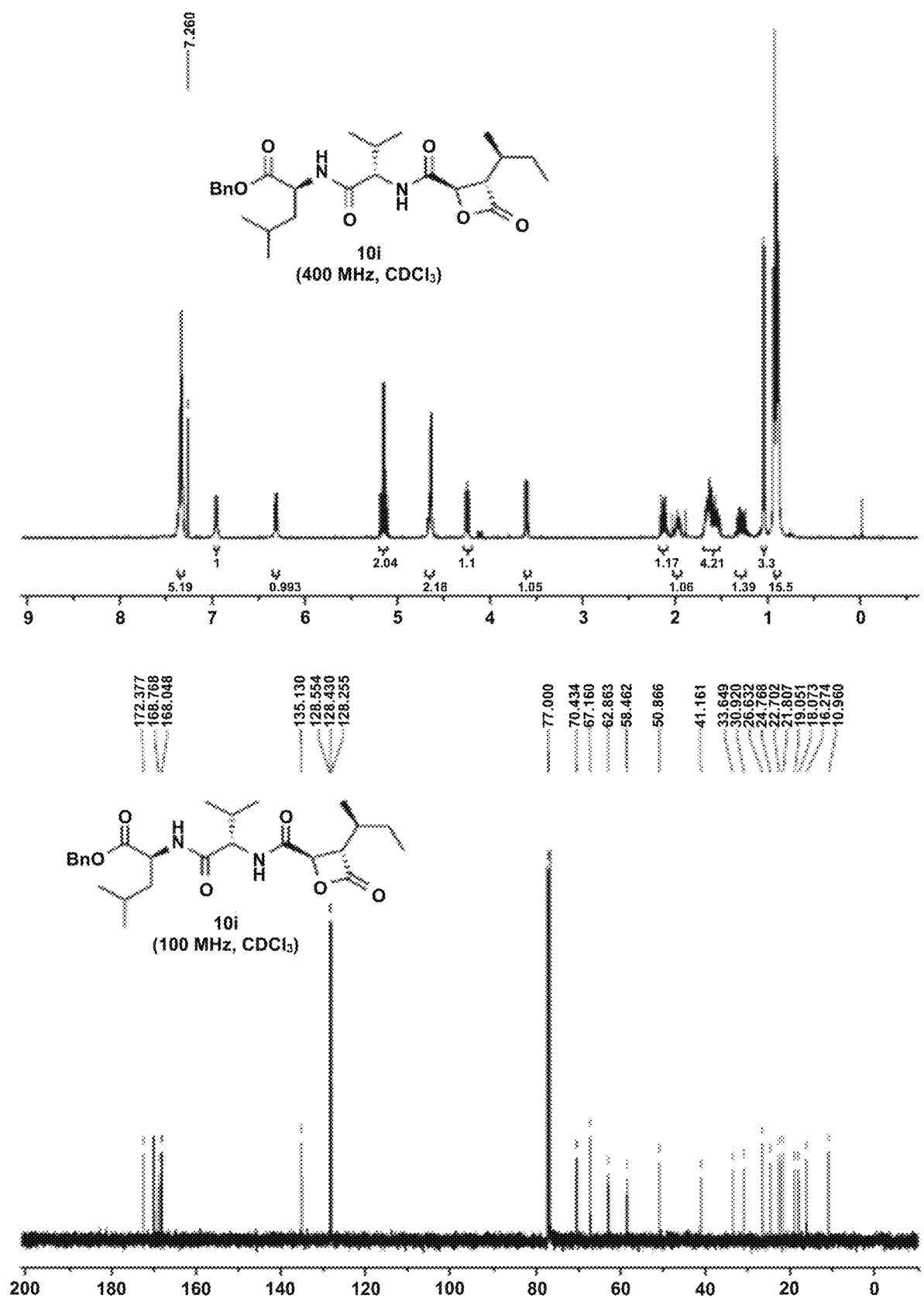
FIG. 47 shows the $^1$H NMR and $^{13}$C NMR spectra of compound 10i.

White solid; Yield: 98%; R$_f$: 0.5 (Hexanes/EtOAc=3:1); [α]$_D^{23}$=−9.6 (c 0.5, CHCl$_3$); IR (γ, cm$^{-1}$): 3015, 2932, 2350, 1836, 1769, 1736, 1704, 1452, 1369; $^1$H NMR (400 MHz, CDCl$_3$): δ 7.38-7.31 (m, 5H), 6.97 (d, J=8.5 Hz, 1H), 6.32 (d, J=8.3 Hz, 1H), 5.19 (d, J=12.3 Hz, 1H), 5.14 (d, J=12.1 Hz, 1H), 4.67-4.62 (m, 2H), 4.27 (dd, J=8.4, 7.0 Hz, 1H), 3.62 (dd, J=7.8, 4.5 Hz, 1H), 2.16-2.08 (m, 1H), 2.01-1.94 (m, 1H), 1.70-1.51 (m, 4H), 1.35-1.23 (m, 1H), 1.06 (d, J=6.7 Hz, 3H), 0.95-0.89 (m, 15H); $^{13}$C NMR (100 MHz, CDCl$_3$): δ 172.4, 169.9, 168.8, 168.1, 135.1, 128.6, 128.4, 128.3, 70.4, 67.2, 62.9, 58.5, 50.9, 41.2, 33.7, 30.9, 26.6, 24.8, 22.7, 21.8, 19.0, 18.1, 16.3, 11.0; HRMS (ESI+) m/z: [M+H]$^+$ Calc'd for C$_{26}$H$_{39}$N$_2$O$_6$ 475.2803; Found 475.2813. FIG. 47 shows the $^1$H NMR and $^{13}$C NMR spectra of compound 10i.

BenzylO-benzyl-N-((2R,3S)-3-((S)-sec-butyl)-4-oxooxetane-2-carbonyl)-L-seryl-L-valinate (10j)

Figure 48:
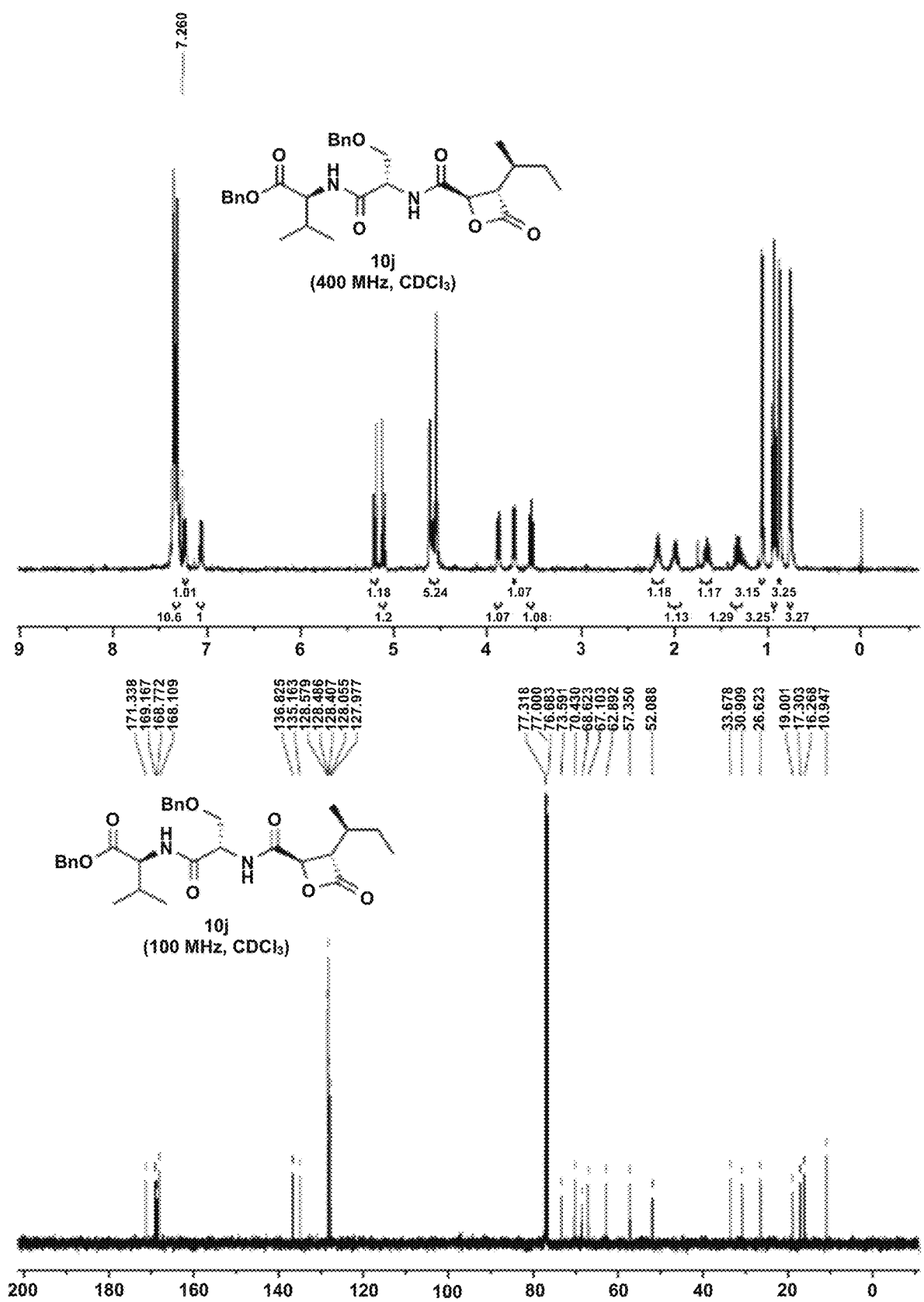
FIG. 48 shows the $^1$H NMR and $^{13}$C NMR spectra of compound 10j.

White solid; Yield: 67%; R$_f$: 0.6 (Hexanes/EtOAc=3:1); [α]$_D^{24}$=+5.1 (c 0.5, CHCl$_3$); IR (γ, cm$^{-1}$): 2960, 2925, 1839, 1734, 1667, 1640, 1533, 1454; $^1$H NMR (400 MHz, CDCl$_3$): δ 7.39-7.27 (m, 10H), 7.24 (d, J=7.2 Hz, 1H), 7.07 (d, J=8.8 Hz, 1H), 5.22 (d, J=12.2 Hz, 1H), 5.12 (d, J=12.2 Hz, 1H), 4.62-4.51 (m, 5H), 3.90 (dd, J=9.1, 4.3 Hz, 1H), 3.73 (dd, J=7.8, 4.8 Hz, 1H), 3.55 (dd, J=9.1, 7.9 Hz, 1H), 2.23-2.14 (m, 1H), 2.04-1.95 (m, 1H), 1.71-1.60 (m, 1H), 1.38-1.26 (m, 1H), 1.07 (d, J=6.8 Hz, 3H), 0.96-0.92 (m, 3H), 0.89 (d, J=6.8 Hz, 3H), 0.77 (d, J=6.9 Hz, 3H); $^{13}$C NMR (100 MHz, CDCl$_3$): δ 171.4, 169.2, 168.7, 168.1, 136.8, 135.2, 128.6, 128.5, 128.4, 128.1, 128.0, 73.6, 70.4, 68.6, 67.1, 62.9, 57.4, 52.1, 33.7, 30.9, 26.6, 19.0, 17.3, 16.3, 10.9; HRMS (ESI+) m/z: [M+H]$^+$ Calc'd for C$_{30}$H$_{39}$N$_2$O$_7$ 539.2752; Found 539.2731. FIG. 48 shows the $^1$H NMR and $^{13}$C NMR spectra of compound 10j.

Benzyl O-benzyl-N-(((2R,3S)-3-((S)-sec-butyl)-4-oxooxetane-2-carbonyl)-L-valyl)-L-serinate (10k)

Figure 49:
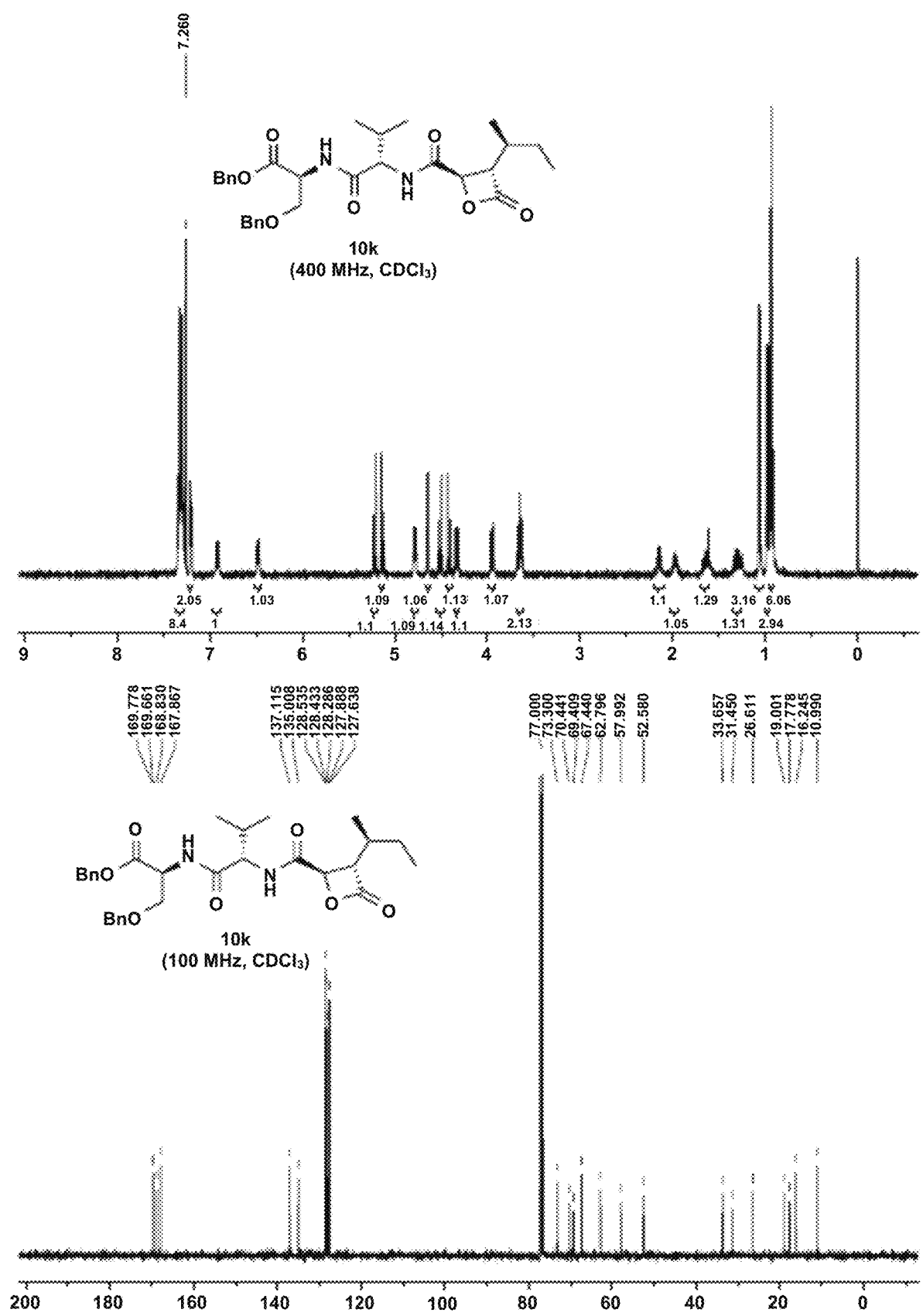
FIG. 49 shows the $^1$H NMR and $^{13}$C NMR spectra of compound 10k.

White solid; Yield: 69%; R$_f$: 0.5 (Hexanes/EtOAc=2:1); [α]$_D^{24}$=+21.1 (c 0.5, CHCl$_3$); IR (γ, cm$^{-1}$): 2958, 1857, 1848, 1743, 1637, 1197; $^1$H NMR (400 MHz, CDCl$_3$): δ 7.34-7.28 (m, 8H), 7.21-7.19 (m, 2H), 6.93 (d, J=8.6 Hz, 1H), 6.49 (d, J=8.0 Hz, 1H), 5.23 (d, J=12.1 Hz, 1H), 5.15 (d, J=12.1 Hz, 1H), 4.80-4.76 (m, 1H), 4.65 (d, J=4.7 Hz, 1H), 4.53 (d, J=12.0 Hz, 1H), 4.43 (d, J=12.1 Hz, 1H), 4.35 (dd, J=8.6, 5.8 Hz, 1H), 3.97 (dd, J=9.6, 3.1 Hz, 1H), 3.68-3.62 (m, 2H), 2.19-2.10 (m, 1H), 2.01-1.94 (m, 1H), 1.70-1.60 (m, 1H), 1.36-1.25 (m, 1H), 1.07 (d, J=6.7 Hz, 3H), 0.98 (d, J=6.8 Hz, 3H), 0.95-0.91 (m, 6H); $^{13}$C NMR (100 MHz, CDCl$_3$): δ 169.8, 169.7, 168.8, 167.9 137.1, 135.0, 128.5, 128.5, 128.4, 128.3, 127.9, 127.7, 73.3, 70.5, 69.4, 67.4, 62.8, 58.0, 52.6, 33.7, 31.5, 26.6, 19.0, 17.8, 16.2, 11.0; HRMS (ESI+) m/z: [M+H]$^+$ Calc'd for C$_{30}$H$_{39}$N$_2$O$_7$ 539.2752; Found 539.2762. FIG. 49 shows the $^1$H NMR and $^{13}$C NMR spectra of compound 10k.

Allyl((2R,3S)-3-((S)-sec-butyl)-4-oxooxetane-2-carbonyl)-L-valyl-L-valinate (11a)

Figure 50:
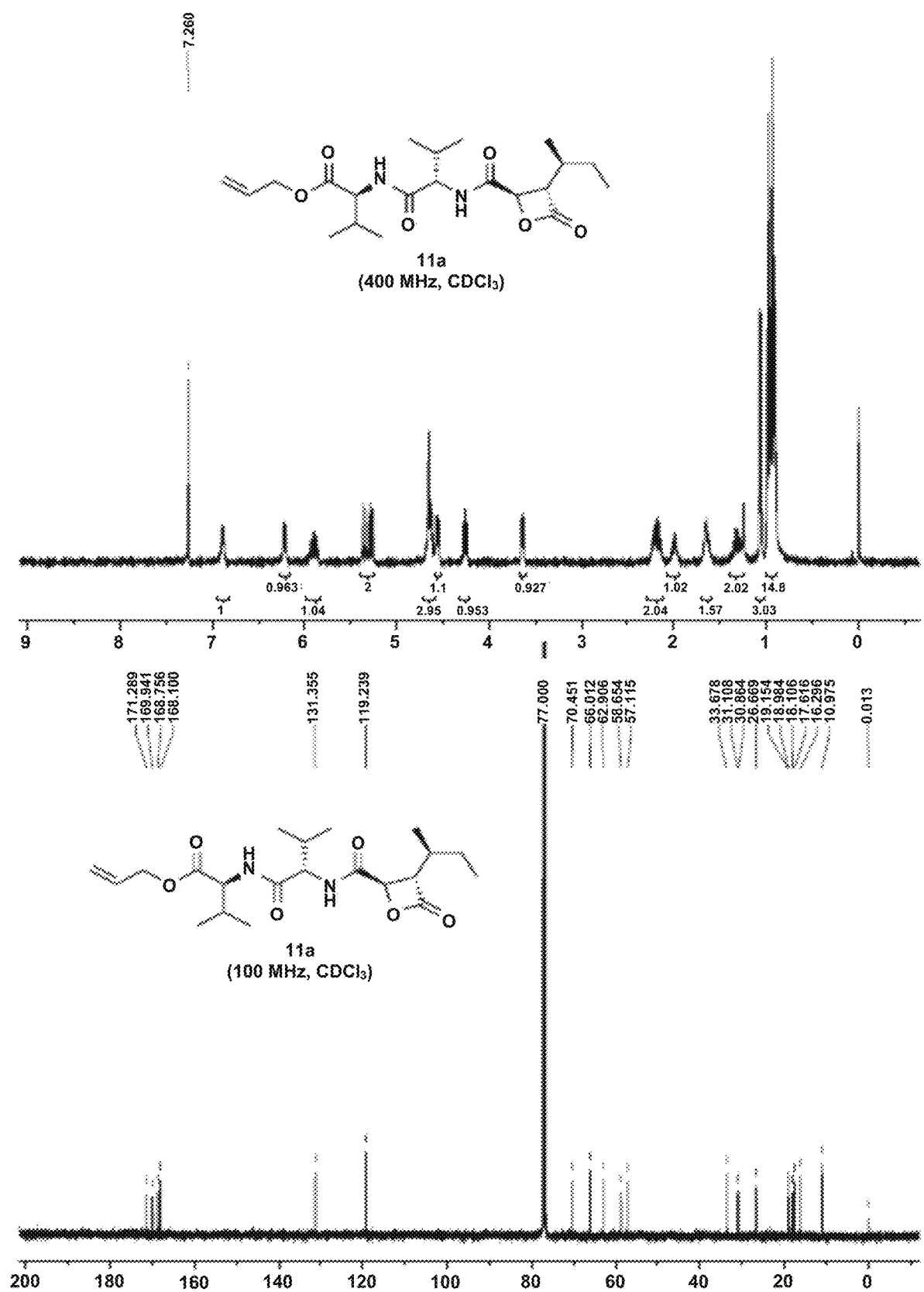

White solid; Yield: 58%; R$_f$: 0.6 (Hexanes:EtOAc=2:1); [α]$_D^{24}$=-3.6 (c 0.025, CHCl$_3$); IR (γ, cm$^{-1}$): 3276, 3075, 1841, 1743, 1614, 1550, 1465; $^1$H NMR (400 MHz, CDCl$_3$): δ 6.94 (d, J=8.3 Hz, 1H), 6.34 (d, J=8.5 Hz, 1H), 5.94-5.84 (m, 1H), 5.35 (d, J=17.1 Hz, 1H), 5.27 (d, J=10.3 Hz, 1H), 4.68 (m, 3H), 4.56 (dd, J=4.6, 4.6 Hz, 1H), 4.29 (dd, J=8.3, 8.3 Hz, 1H), 3.65 (dd, J=4.6, 4.6 Hz, 1H), 2.24 (m, 2H), 2.03 (m, 1H), 1.69 (m, 1H), 1.38 (m, 2H), 1.06 (d, J=6.8 Hz, 3H), 0.98 (m, 15H); $^{13}$C NMR (100 MHz, CDCl$_3$): δ 171.3, 170.0, 168.8, 168.1, 131.4, 119.2, 70.5, 66.0, 62.9, 58.7, 57.1, 33.7, 31.0, 30.8, 26.6, 19.1, 19.0, 18.1, 17.6, 16.3, 10.9; HRMS (ESI+) m/z: [M+H]$^+$ Calc'd for C$_{21}$H$_{35}$N$_2$P$_6$ 411.2490; Found 411.2502. FIG. 50 shows the $^1$H NMR and $^{13}$C NMR spectra of compound 11a.

4-chlorobenzyl((2R,3S)-3-((S)-sec-butyl)-4-oxooxetane-2-carbonyl)-L-valyl-L-valinate (11b)

Figure 51:
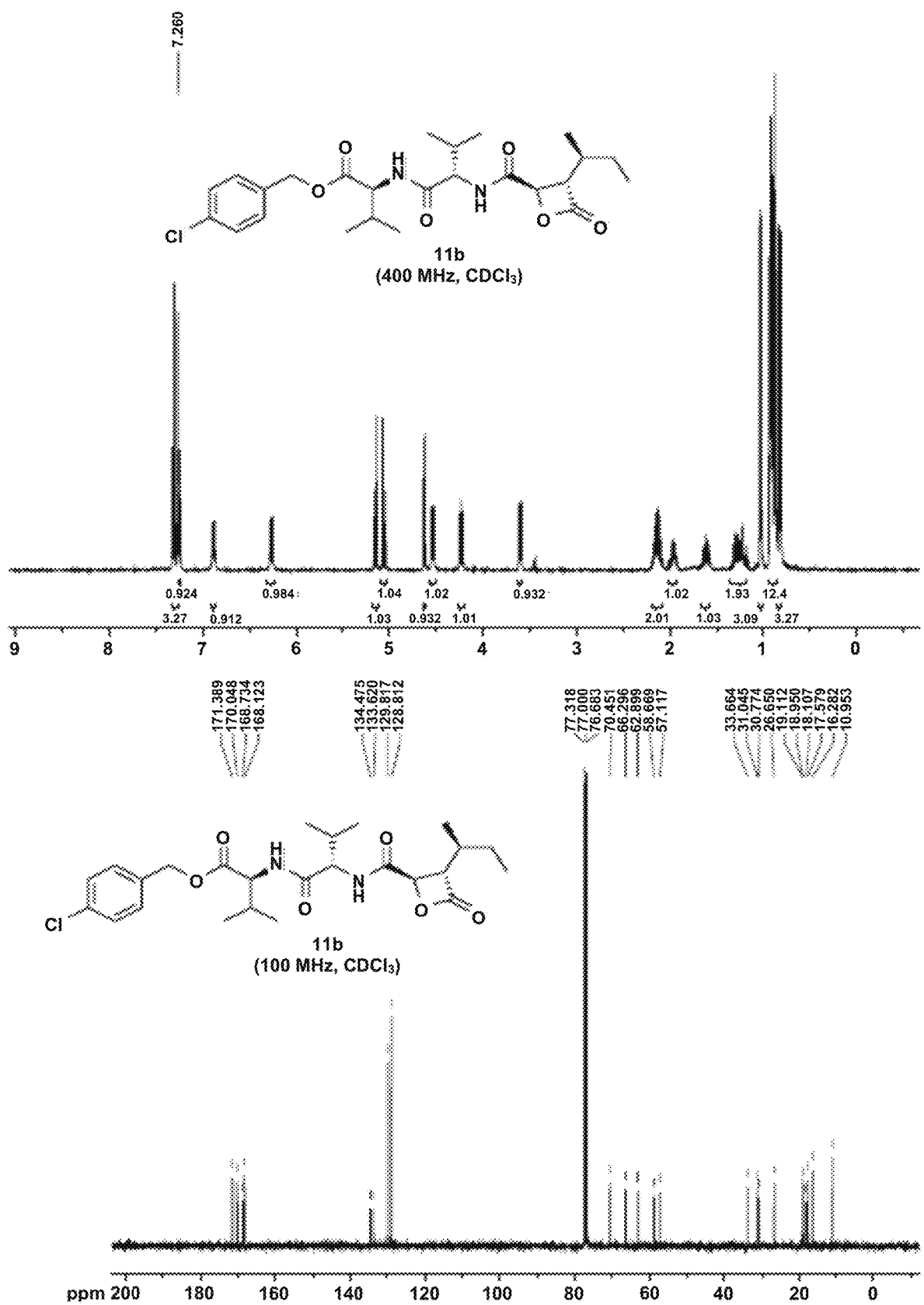
FIG. 51 shows the $^1$H NMR and $^{13}$C NMR spectra of compound 11b.

White solid; Yield: 45%; R$_f$: 0.5 (Hexanes:EtOAc=3:1); [α]$_D^{24}$=-12.5 (c 0.025, CHCl$_3$); IR (γ, cm$^{-1}$): 3272, 1840, 1744, 1644, 1553; $^1$H NMR (400 MHz, CDCl$_3$): δ 7.36-7.28 (m, 4H), 6.93 (d, J=8.9 Hz, 1H), 6.32 (d, J=8.9 Hz, 1H), 5.20 (d, J=12.4 Hz, 1H), 5.11 (d, J=12.2 Hz, 1H), 4.67 (d, J=4.5 Hz, 1H), 4.59 (dd, J=4.7, 4.7 Hz, 1H), 4.29 (dd, J=6.9, 6.8 Hz, 1H), 3.66 (dd, J=4.6, 4.5 Hz, 1H), 2.24-2.12 (m, 2H), 2.06-1.95 (m, 1H), 1.71-1.61 (m, 1H), 1.38-1.21 (m, 2H), 1.08 (d, J=6.9 Hz, 3H), 0.98 (m, 12H), 0.87 (d, J=7.0 Hz, 3H); $^{13}$C NMR (100 MHz, CDCl$_3$): δ 171.4, 170.1, 168.8, 168.1, 134.5, 133.6, 129.8, 128.8, 70.5, 66.3, 62.9, 58.7, 57.1, 33.7, 31.0, 30.8, 26.7, 19.1, 19.0, 18.1, 17.6, 16.3, 11.0; HRMS (ESI+) m/z: [M+H]$^+$ Calc'd for C$_{25}$H$_{36}$ClN$_2$O$_6$ 495.2256; Found 495.2260. FIG. 51 shows the $^1$H NMR and $^{13}$C NMR spectra of compound 11b.

Cyclohexylmethyl((2R,3S)-3-((S)-sec-butyl)-4-oxooxetane-2-carbonyl)-L-valyl-L-valinate (11c)

Figure 52:
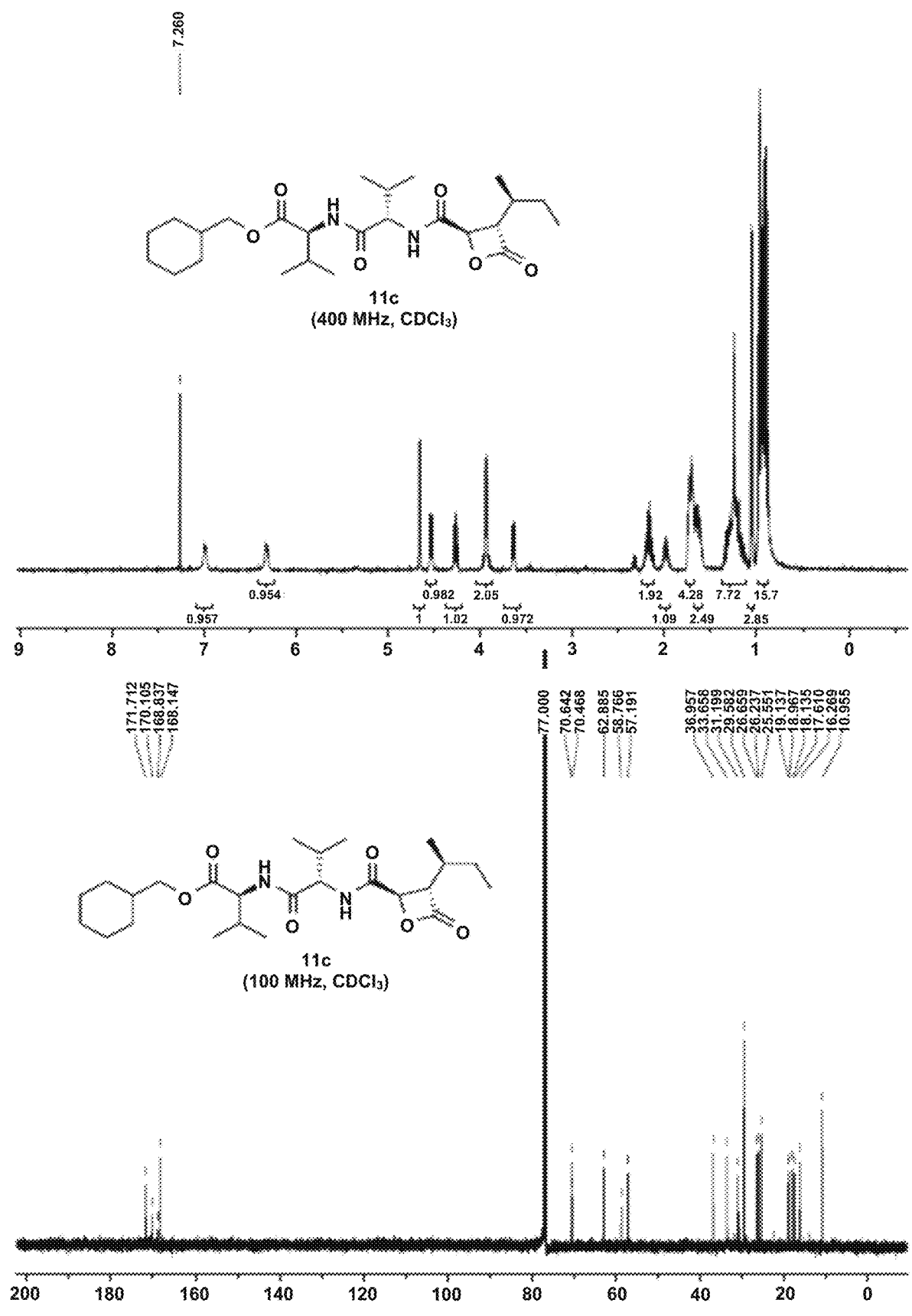
FIG. 52 shows the $^1$H NMR and $^{13}$C NMR spectra of compound 11c.

White solid; Yield: 31%; R$_f$: 0.4 (Hexanes:EtOAc=5:1); [α]$_D^{22}$=-4.4 (c 0.08, CHCl$_3$); IR (γ, cm$^{-1}$): 3276, 2360, 1843, 1740, 1646, 1558, 1457; $^1$H NMR (400 MHz, CDCl$_3$): δ 7.0 (d, J=8.2 Hz, 1H), 6.33 (d, J=8.2 Hz, 1H), 4.66 (d, J=4.6 Hz, 1H), 4.65 (dd, J=4.6, 4.6 Hz, 1H), 4.29 (dd, J=7.2, 6.9 Hz, 1H), 3.98-3.90 (m, 2H), 3.66 (dd, J=7.5, 7.4 Hz, 1H), 2.23-2.12 (m, 2H), 2.04-1.93 (m, 1H), 1.73-1.60 (m, 6H), 1.35-1.14 (m, 7H), 1.07 (d, J=6.9 Hz, 3H), 0.98 (m, 15H); $^{13}$C NMR (100 MHz, CDCl$_3$): δ 171.7, 170.2, 168.8, 168.2, 70.6, 70.4, 62.9, 58.7, 57.2, 36.9, 33.6, 31.9, 31.2, 30.9, 29.7, 29.6, 26.7, 26.2, 25.6, 25.5, 19.1, 19.0, 18.1, 17.6, 16.3, 11.0; HRMS (ESI+) m/z: [M+H]$^+$ Calc'd for C$_{25}$H$_{43}$N$_2$O$_6$ 467.3116; Found 467.3115. FIG. 52 shows the $^1$H NMR and $^{13}$C NMR spectra of compound 11c.

Isobutyl((2R,3S)-3-((S)-sec-butyl)-4-oxooxetane-2-carbonyl)-L-valyl-L-valinate (11d)

Figure 53:
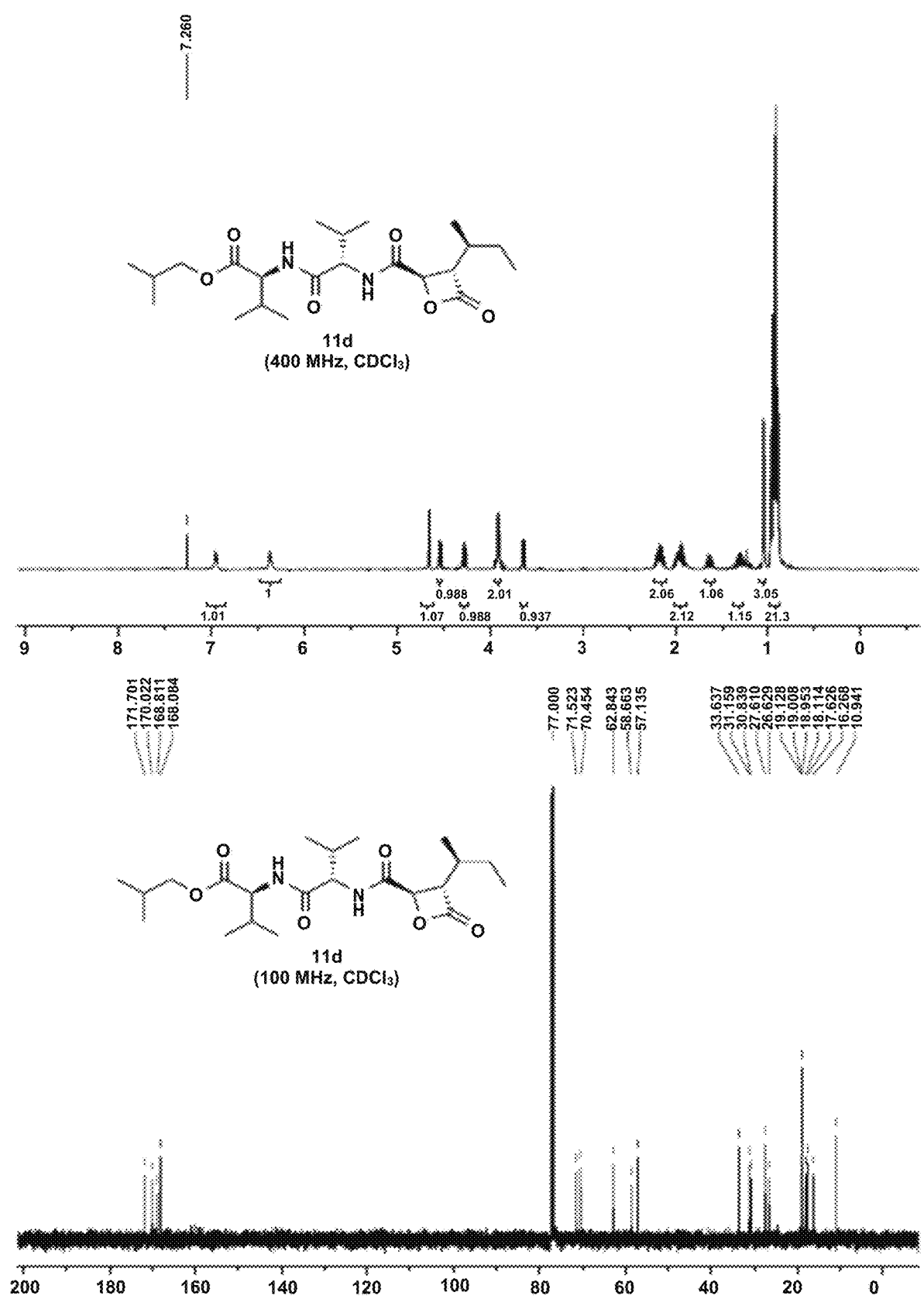
FIG. 53 shows the $^1$H NMR and $^{13}$C NMR spectra of compound 11d.

White solid; Yield: 70%; R$_f$: 0.5 (Hexanes:EtOAc=5:1); [α]$_D^{23}$=-2.8 (c 0.25, CHCl$_3$); IR (γ, cm$^{-1}$): 3290, 2351, 1843, 1645, 1557; $^1$H NMR (400 MHz, CDCl$_3$): δ 6.96 (d, J=8.5 Hz, 1H), 6.38 (d, J=8.5 Hz, 1H), 4.66 (d, J=4.77 Hz, 1H), 4.55 (dd, J=4.8, 4.8 Hz, 1H), 4.29 (dd, J=8.1, 6.9 Hz, 1H), 3.95 (m, 2H), 3.65 (dd, J=7.6, 7.6 Hz, 1H), 2.23-2.11 (m, 2H), 2.01-1.88 (m, 3H), 1.67-1.59 (m, 1H), 1.34-1.23 (m, 2H), 1.06 (d, J=6.8 Hz, 3H), 0.98 (m, 19H); $^{13}$C NMR (100 MHz, CDCl$_3$): δ 171.7, 170.0, 168.8, 168.0, 71.5, 70.5, 62.8, 58.7, 57.1, 33.6, 31.2, 30.8, 27.6, 26.6, 19.1, 19.0, 18.9, 18.1, 17.6, 16.3, 10.9; HRMS (ESI+) m/z: [M+H]$^+$ Calc'd for C$_{22}$H$_{39}$N$_2$O$_6$ 427.2803; Found 427.2823. FIG. 53 shows the $^1$H NMR and $^{13}$C NMR spectra of compound 11d.

(2R,3S)—N—((S)-1-(((S)-1-(benzylamino)-3-methyl-1-oxobutan-2-yl)amino)-3-methyl-1-oxobutan-2-yl)-3-((S)-sec-butyl)-4-oxooxetane-2-carboxamide (11e)

Figure 54:
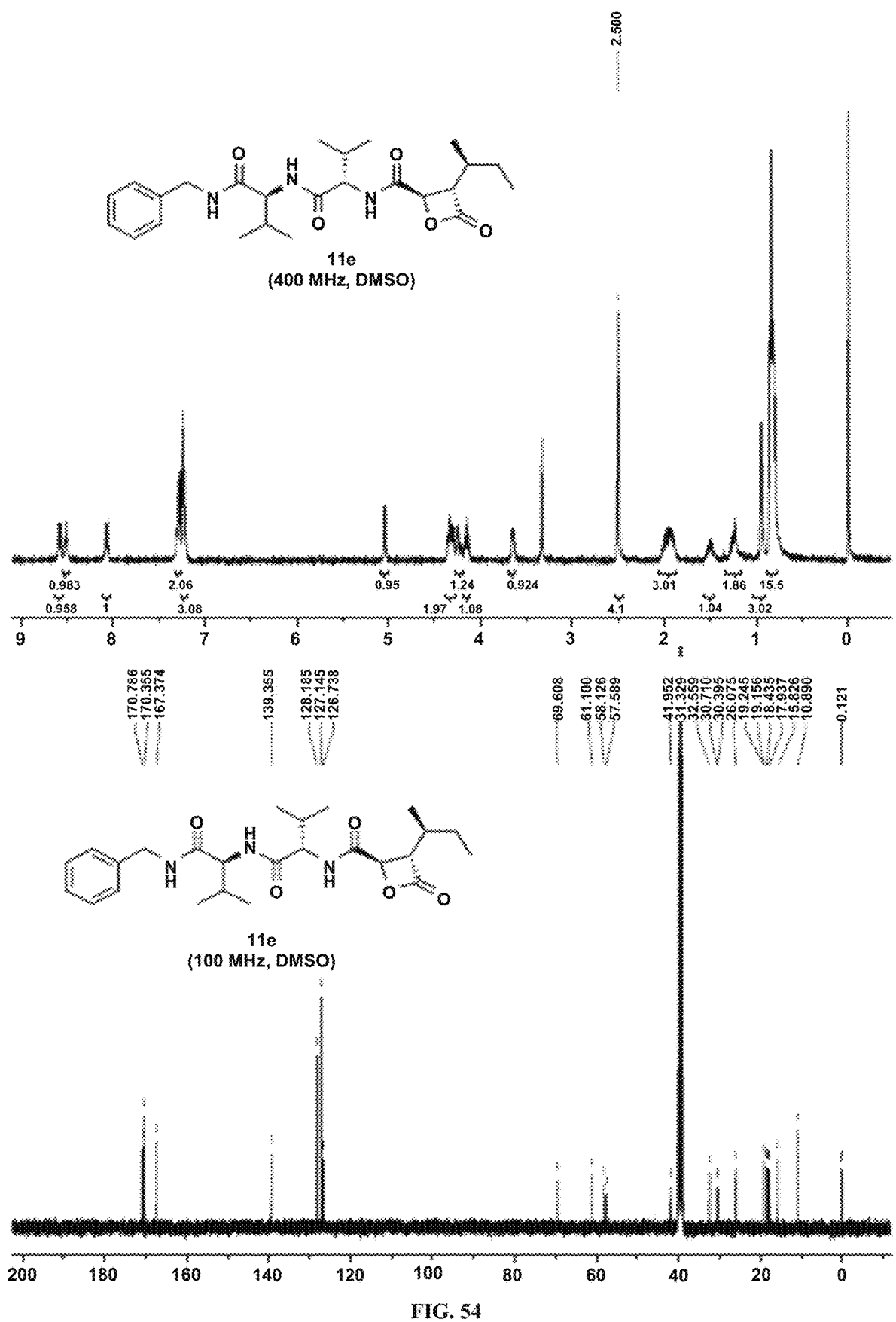
FIG. 54 shows the $^1$H NMR and $^{13}$C NMR spectra of compound 11e.

White solid; Yield: 52%; R$_f$: 0.3 (Hexanes:EtOAc=2:1); [α]$_D^{22}$=-74.0 (c 0.25, MeOH); IR (γ, cm$^{-1}$): 3269, 3085, 2324, 1842, 1635, 1551; $^1$H NMR (400 MHz, DMSO): δ 8.59 (d, J=8.8 Hz, 1H), 8.53 (m, 1H), 8.08 (d, J=8.7 Hz, 1H), 7.31-7.20 (m, 5H), 5.04 (d, J=4.0 Hz, 1H), 4.36-4.30 (m, 2H), 4.26-4.13 (m, 2H), 3.66 (dd, J=7.6, 7.6 Hz, 1H), 2.50 (m, 1H), 2.02-1.89 (m, 3H), 1.56-1.45 (m, 1H), 1.29-1.20 (m, 1H), 0.95 (d, J=6.7 Hz, 3H), 0.86-0.80 (m, 15H); $^{13}$C NMR (100 MHz, DMSO): δ 170.8, 170.4, 167.4, 139.4, 128.2, 127.1, 126.7, 69.6, 61.1, 58.1, 57.6, 42.0, 32.6, 30.7, 30.4, 26.0, 19.2, 19.2, 18.4, 17.9, 15.8, 10.9; HRMS analysis of 11e was not successful using ESI. FIG. 54 shows the $^1$H NMR and $^{13}$C NMR spectra of compound 11e.

4-methoxybenzyl((2R,3S)-3-((S)-sec-butyl)-4-oxooxetane-2-carbonyl)-L-valyl-L-valinate (11f)

Figure 55:
FIG. 55 shows the $^1$H NMR and $^{13}$C NMR spectra of compound 11f.

White solid; Yield: 39%; $R_f$: 0.3 (Hexanes:EtOAc=5:1); $[α]_D^{22}$=−11.2 (c 0.24, CHCl$_3$); IR (γ, cm$^{-1}$): 3278, 2964, 1837, 1739, 1646, 1614, 1515; $^1$H NMR (400 MHz, CDCl$_3$): δ 7.31 (d, J=9.0 Hz, 2H), 6.91 (d, J=8.7 Hz, 2H), 6.33 (d, J=8.9 Hz, 1H), 5.20 (d, J=11.2 Hz, 1H), 5.08 (d, J=11.6 Hz, 1H), 4.68 (d, J=4.6 Hz, 1H), 4.58 (dd, J=4.6, 4.6 Hz, 1H), 4.30 (dd, J=8.3, 8.3 Hz, 1H), 3.83 (s, 3H), 3.67 (dd, J=7.6, 7.6 Hz, 1H), 2.26-2.12 (m, 2H), 2.06-1.96 (m, 1H), 1.72-1.61 (m, 1H), 1.39-1.30 (m, 2H), 1.09 (d, J=6.8 Hz, 3H), 0.99 (m, 9H), 0.91 (d, J=6.9 Hz, 3H), 0.86 (d, J=6.8 Hz, 3H); $^{13}$C NMR (100 MHz, CDCl$_3$): δ 171.5, 170.0, 168.8, 168.1, 159.8, 130.3, 127.2, 113.9, 70.5, 67.0, 62.9, 58.7, 57.1, 55.3, 33.7, 31.1, 30.8, 26.7, 19.1, 18.9, 18.1, 17.5, 16.3, 11.0; HRMS (ESI+) m/z: [M+H]$^+$ Calc'd for C$_{26}$H$_{39}$N$_2$O$_7$ 491.2752; Found 491.2758. FIG. 55 shows the $^1$H NMR and $^{13}$C NMR spectra of compound 11f.

But-3-en-1-yl((2R,3S)-3-((S)-sec-butyl)-4-oxooxetane-2-carbonyl)-L-valyl-L-valinate (11g)

Figure 56:
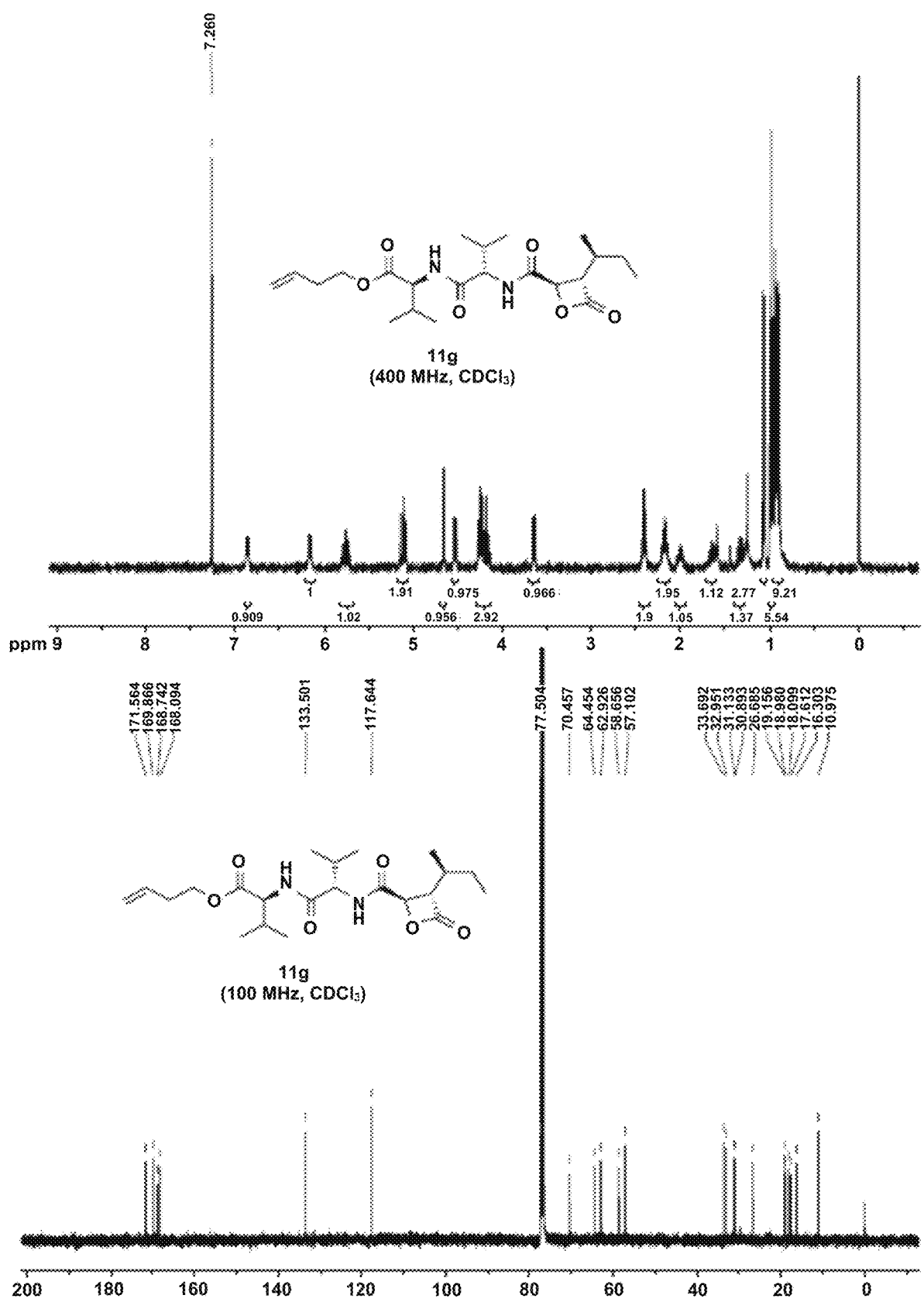
FIG. 56 shows the $^1$H NMR and $^{13}$C NMR spectra of compound 11g.

Colorless solid; Yield: 44%; $R_f$: 0.5 (Hexanes:EtOAc=4:1); $[α]_D^{25}$=−5.8 (c 0.1, CHCl$_3$); IR (γ, cm$^{-1}$): 3284, 2966, 1842, 1732, 1638, 1556, 1540; $^1$H NMR (400 MHz, CDCl$_3$): δ 6.87 (d, J=8.4 Hz, 1H), 6.17 (d, J=8.9 Hz, 1H), 5.81-5.71 (m, 1H), 5.14-5.08 (m, 2H), 4.66 (d, J=4.7 Hz, 1H), 4.55 (dd, J=8.8, 4.5 Hz, 1H), 4.27-4.22 (m, 2H), 4.21-4.14 (m, 1H), 3.66 (dd, J=7.5, 4.7 Hz, 1H), 2.43-2.38 (m, 2H), 2.23-2.14 (m, 2H), 2.04-1.96 (m, 1H), 1.70-1.62 (m, 1H), 1.38-1.27 (m, 1H), 1.08 (d, J=6.6 Hz, 3H), 1.0-0.95 (m, 6H), 0.94-0.88 (m, 9H); $^{13}$C NMR (100 MHz, CDCl$_3$): δ 171.6, 169.9, 168.8, 168.1, 133.5, 117.7, 70.5, 64.5, 62.9, 58.7, 57.1, 33.7, 33.0, 31.1, 30.9, 26.7, 19.2, 19.0, 18.1, 17.6, 16.3, 11.0; HRMS (ESI+) m/z: [M+H]$^+$ Calc'd for C$_{22}$H$_{37}$N$_2$O$_6$ 425.2646; Found 425.2670. FIG. 56 shows the $^1$H NMR and $^{13}$C NMR spectra of compound 11g.

Methyl ((2R,3S)-3-((S)-sec-butyl)-4-oxooxetane-2-carbonyl)-L-valyl-L-valinate (11h)

Figure 57:
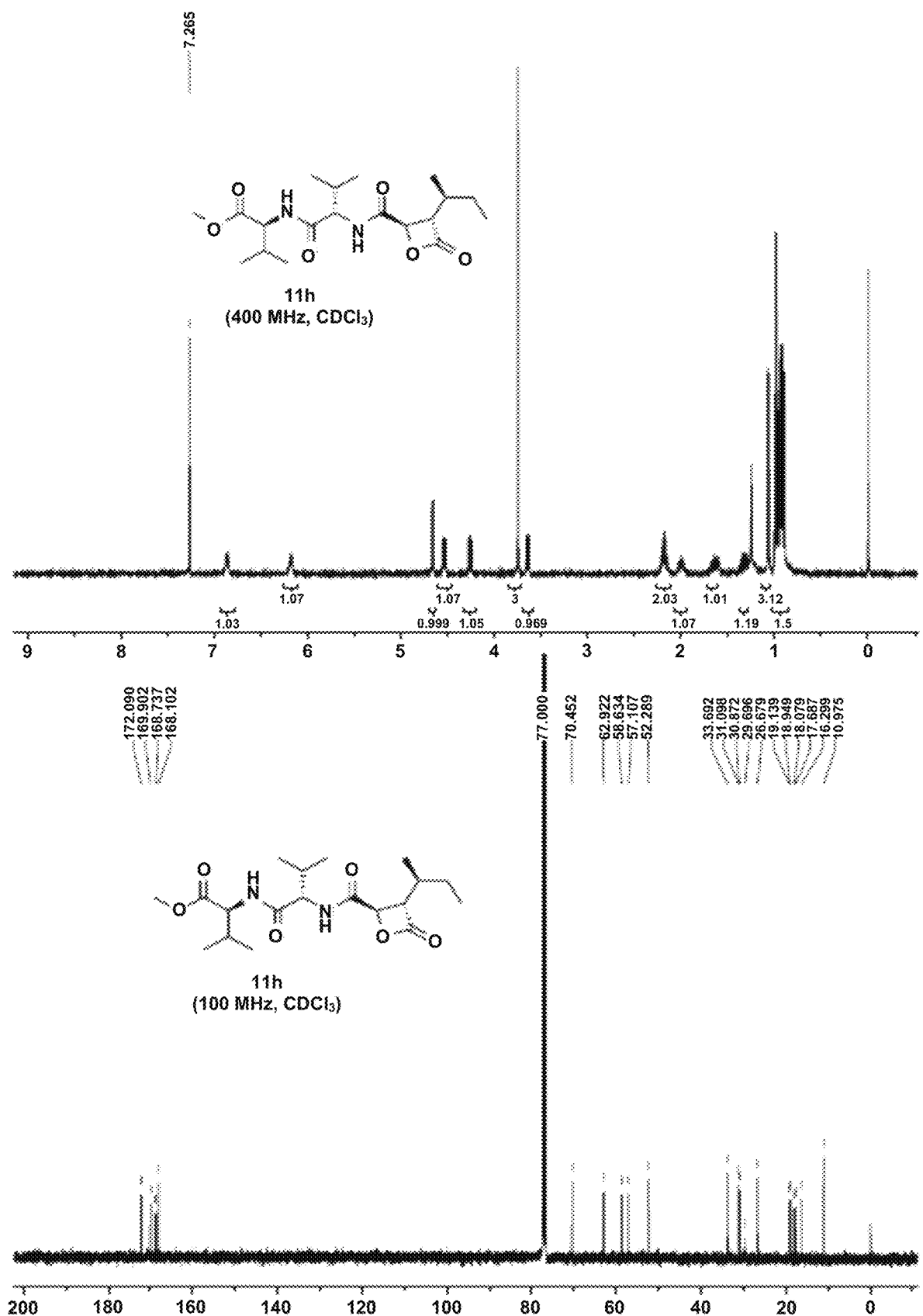
FIG. 57 shows the $^1$H NMR and $^{13}$C NMR spectra of compound 11h.

Colorless solid; Yield: 43%; $R_f$: 0.3 (Hexanes:EtOAc=4:1); $[α]_D^{23}$=−6.2 (c 0.003, CHCl$_3$); IR (γ, cm$^{-1}$): 2964, 1836, 1739, 1647, 1538, 1467; $^1$H NMR (400 MHz, CDCl$_3$): δ 6.87 (d, J=8.5 Hz, 1H), 6.18 (d, J=8.4 Hz, 1H), 4.86 (d, J=4.6 Hz, 1H), 4.55 (dd, J=8.8, 4.7 Hz, 1H), 4.28 (dd, J=8.4, 6.6 Hz, 1H), 3.75 (s, 3H), 3.66 (dd, J=7.7, 4.6 Hz, 1H), 2.23-2.13 (m, 2H), 2.05-1.96 (m, 1H), 1.69-1.60 (m, 1H), 1.37-1.27 (m, 1H), 1.08 (d, J=6.7 Hz, 3H), 1.00-0.89 (m, 15H); $^{13}$C NMR (100 MHz, CDCl$_3$): δ 172.1, 169.9, 168.7, 168.1, 70.5, 82.9, 58.6, 57.1, 52.3, 33.7, 31.1, 30.9, 26.7, 19.1, 18.9, 18.1, 17.7, 16.3, 11.0; HRMS (ESI+) m/z: [M+H]$^+$ Calc'd for C$_{19}$H$_{33}$N$_2$O$_6$ 385.2333; Found 385.2347. FIG. 57 shows the $^1$H NMR and $^{13}$C NMR spectra of compound 11h.

TABLE 1 shows the structures of the synthesized compounds.

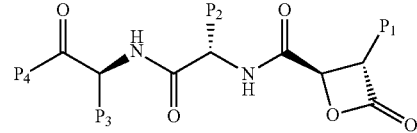

TABLE 1

| Compound | P4 | P3 | P2 | P1 |
|---|---|---|---|---|
| 8 | (benzyloxy) | (isopropyl) | (isopropyl) | (sec-butyl) |
| 9a | (benzyloxy) | (isopropyl) | (isopropyl) | (cyclopropyl) |
| 9b | (benzyloxy) | (isopropyl) | (isopropyl) | (cyclobutyl) |
| 9c | (benzyloxy) | (isopropyl) | (isopropyl) | (cyclopentyl) |

TABLE 1-continued

| Compound | P4 | P3 | P2 | P1 |
|---|---|---|---|---|
| 9d | BnO- | iPr | iPr | iBu |
| 10a | BnO- | iPr | H | sec-Bu |
| 10b | BnO- | iPr | CH2CH2Ph | sec-Bu |
| 10c | BnO- | CH2CH2Ph | iPr | sec-Bu |
| 10d | BnO- | CH2CH2Ph | CH2CH2Ph | sec-Bu |
| 10e | BnO- | iPr | tBu | sec-Bu |
| 10f | BnO- | tBu | iPr | sec-Bu |
| 10g | BnO- | tBu | tBu | sec-Bu |
| 10h | BnO- | iPr | iBu | sec-Bu |
| 10i | BnO- | iBu | iPr | sec-Bu |
| 10j | BnO- | iPr | CH2CH2OBn | sec-Bu |

TABLE 1-continued

| Compound | P4 | P3 | P2 | P1 |
|---|---|---|---|---|
| 10k | BnO- | -OBn | isopropyl | sec-butyl |
| 11a | allyl-O- | | isopropyl | sec-butyl |
| 11b | isobutyl-O- | | isopropyl | sec-butyl |
| 11c | 4-Cl-BnO- | | isopropyl | sec-butyl |
| 11d | cyclohexylmethyl-O- | | isopropyl | sec-butyl |
| 11e | BnNH- | | isopropyl | sec-butyl |
| 11f | 4-MeO-BnO- | | isopropyl | sec-butyl |
| 11g | homoallyl-O- | | isopropyl | sec-butyl |
| 11h | MeO- | | isopropyl | sec-butyl |
| 12a | BnNH- | -OBn | isopropyl | sec-butyl |

Example 13: Biological Assays

Cell Culture:

The human plasmacytoma cell line RPMI 8226 (ATCC: CCL-155), human T-cell leukemia cell line Jurkat (ATCC TIB-152, E6-1 clone), human mammary carcinoma MCF7 (ATCC® HTB-22™), and human breast adenocarcinoma cell line MDA-MB-231 (ATCC: HTB-26) were cultured using media composed of RPMI-1640 with glutamine supplemented with 10% FBS, 100 mg/L penicillin G, and 100 mg/L streptomycin. The cells were incubated at 37° C. in a humidified atmosphere with 5% $CO_2$.

Cell Lysate Preparation:

The human T-cell leukemia cell line, Jurkat (ATCC TIB-152, E6-1 clone), was cultured until the cell culture reached a density of approximately $2*10^6$ cells/mL. The cells were pelleted, washed twice with HEPES saline solution (pH 7.37), and lysed by resuspending the cells in Lysis Buffer (150 mM NaCl, 50 mM HEPES pH 7.6, 5 mM EDTA, and 1% Triton X-100) at a cell density of $2*10^6$ cells/mL. The lysate was then agitated on ice for 60 minutes. The final protein concentration of the lysed cells was ~0.5 mg/mL. The lysate was stored at −80° C. until the sample was used for the proteasome assay. The procedure was repeated for MCF7 cells at a final density of $5*10^5$ cells/mL.

Proteasome Assay:

Proteasome activity was determined by measuring the degree of peptide cleavage in Jurkat cell lysate, 8 µg/mL purified yeast proteasome, or 8 µg/mL purified immunoproteasomes (Enzo Life Sciences). Thawed cell lysate was centrifuged at ~10,000 G in order to remove precipitated proteins and remaining cell fragments. 90 µL of Jurkat lysate was added to each of the wells on a 96 well plate. 100 mM stock solutions of the compounds were prepared in DMSO, and 10 mM stock solutions of the fluorescent substrates were prepared in DMSO. The compounds were diluted with lysis buffer; 10 µL of the compound-containing solution was added to the test wells at ten times the final concentration. 10 µL of Lysis Buffer was added to the negative control samples, and 10 µL of 1 mM compound 8 was added to the remaining wells as an internal positive control. The plate was incubated at 37° C. for 30 minutes to allow binding. Following the incubation, 10 µL of fluorescent substrate (100 µM Suc-LLVY-AMC for Chymotrypsin-like activity and 100 µM SUC-RLR-AMC for Trypsin-like activity) was added to each well. The plate was incubated for 60 minutes at 37° C., and the proteasomal activity was determined by measuring the fluorescence of the cleaved substrate using a multilabel counter set at an excitation wavelength of 360 nM and emission wavelength of 480 nm. Each technical replicate was performed in biological quadruplicate, selecting the three best values at each concentration. The results are reported as the average of at least 3 technical replicates of $IC_{50}$ values for proteasome inhibition.

MTT Assay:

100 µL of cells were added to each well of a 96 well microtiter plate at a concentration of $4 \times 10^4$ cells/mL and incubated overnight to allow proper adhesion. (RPMI 8226 cells were plated at $4 \times 10^5$ cells/mL). The cells were treated with the panel of test compounds at a series of concentrations, along with vehicle control DMSO and untreated cells as controls. After 48 h incubation, 20 µL of MTT reagent (3-(4,5-dimethylthiazol-2-yl)-2,5-diphenyltetrazolium bromide) in PBS (5 mg/mL) was added to each well of the plates. The plate was incubated for 2 h at 37° C. For adherent cell lines, the media was removed from each well of the plate and the resulting formazan crystals dissolved in 100 µL of DMSO. For RPMI 8226 cells, 200 ul of DMF/SDS mix (50% DMF, 10% w/v SDS pH<4) was used to solubilize the formazan crystals. Optical density (OD) at 490 nm was measured using a microplate reader. Cells treated with 1 µM phenyl arsine oxide (PAO) served as a positive cell-killing control. Technical replicates of these assays were performed in biological quadruplicate, and the three best values were used for analysis in order to eliminate outliers. Data presented are the average $IC_{50}$ value calculated from at least 3 technical replicates with the corresponding standard deviation.

Cell Infiltration of PIs:

Cell infiltration was measured based on the amount of proteasome-inhibitory activity exhibited when whole cells were treated with proteasome inhibitors. 100 µL MCF7 cells at a concentration of 500,000 cells/mL were added to a 96 well microtiter plate and incubated overnight at 37° C. and 5% $CO_2$ to allow cells to adhere at 100% confluency. The cells were treated and then incubated for at 37° C. and 5% $CO_2$ for 1 hour as a standard time to allow for drug infiltration. Following incubation, wells were aspirated, washed 2 times with 100 µL of PBS, and then resuspended in 110 µL lysis buffer (150 mM NaCl, 50 mM HEPES pH 7.6, 5 mM EDTA, and 1% Triton X-100). The plate was rocked on ice for 1 hr and then 90 µL of cell lysate was transferred to a black 96 well microtiter plate. 10 µL of lysis buffer was added to the top of all wells containing treated cells and one set of control wells. 10 µL of 1 mM of compound 8 was added to the second set of control wells as a positive control for proteasome inhibition. The plate was then incubated at 37° C. for 15 minutes to allow for control drug binding. Chymotrypsin-like activity was then measured by adding 10 µL of 100 µM Suc-LLVY-AMC in lysis buffer to each well and then incubating for 1 h at 37° C. The change in fluorescence was measured using an excitation wavelength of 360 nM and emission wavelength of 480 nm. The three best values from biological quadruplicate at each concentration were used to determine the 1 h infiltration-dependent $IC_{50}$. Cellular infiltration was then represented as the ratio of $IC_{50}$ values for infiltration-dependent inhibition compared to direct inhibition of the proteasome in 0.5 mg/mL MCF7 lysate. Standard deviation for cell infiltration was calculated by propagating the error from the two $IC_{50}$ values.

Cell Cycle Assay:

Vybrant® DyeCycle™ Orange Stain was used for the cell cycle assay. The amount of fluorescence of DNA was used as a relative measure of a cell's stage in the cell cycle. 500,000 Jurkat cells were added to wells on a 24 well microtiter plate in 1 mL of supplemented RPMI media. The cells were then treated with Compound 1 (TABLE 2). Using the cells treated for 12 and 24 hours, stained DNA fluorescence was measured via flow cytometry. The cells were taken from each well, pelleted briefly, aspirated, resuspended in 300 µL of 2 µL/mL Vybrant® DyeCycle™ Orange Stain, incubated at 37° C. for 15 minutes, and analyzed by flow cytometry. Selecting whole cells based on forward and side scatter, stained DNA fluorescence was excited at 488 nm and measured at an emission wavelength of 585 nm, using amount of fluorescence as a means of distinguishing between populations of cells. Populations were identified as G1 for the peak associated with the lowest amount of fluorescence, S phase for increased fluorescence appearing as a shoulder off of the G1 peak, and G2/M for approximately 2 times the fluorescence as the G1 peak. Measurements were taken in biological triplicate and confirmed in technical triplicate.

Western Blot of Ubiquitinated Proteins:

In a 6 well plate, 1,000,000 MCF7 cells in 2 mL of RPMI media were treated with 1 µM compound 1, 10 µM compound 1, 1 µM compound 8, 10 µM compound 8, 0.1 µM carfilzomib as a positive control, and an untreated well as a negative control. The cells were incubated for 9.5 hrs at 37° C. and 5% $CO_2$. After washing with PBS twice, cells were scraped, pelleted and lysed with CytoBuster™ Protein Extraction Reagent \ containing 10 µM compound 8, 10 µM $Na_3VO_4$, 0.017 mg/mL Aprotinin, 1 mM PMSF, and 1% Protease Inhibitor Cocktail. Thereafter 30 µg of protein in sample buffer (50 mM Tris-HCl, 2% SDS, 10% Glycerol, 1% β-mercaptoethanol, 12.5 mM EDTA, 0.02% Bromophenol Blue, pH 6.8) that had been boiled at 90° C. for 5 min, was electrophoresed using 6/8% SDS-PAGE, and the protein transferred to a 0.2 µM PVDF membrane using a BioRad Trans-Blot® SD at 15 V for 17 minutes. The membrane was blocked with 1× casein buffer (Diluted 1:10 in water from casein blocking buffer 10×), and probed with either the polyclonal rabbit anti β-Actin (1:500) or the polyclonal rabbit anti-ubiquitin antibody (1:300), and stained with goat anti-rabbit IgG (H+L) HRP conjugate (1:3000) secondary antibodies. Antibody-recognized bands were visualized by a standard horseradish peroxidase chemiluminescent assay with an ECL kit.

Apoptosis assay: 1 mL of Jurkat cells, at a density of 500,000 cells per milliliter, was added to 12 wells of a 24 well microtiter plate. Cells were treated immediately using a serial dilution of the synthesized proteasome inhibitors, the benzyl ester of Cystargolide B and the belactosin-cystargolide hybrid molecule. 10 µM Paclitaxel and 0.2 µg/mL Doxorubicin hydrochloride were used as positive apoptosis controls and non-treated cells were used as a negative control. The cells were then incubated for 24 h at 37° C. and 5% $CO_2$. The following day, Annexin V-FITC conjugate was used to assay for the expression of phosphatidyl serine on the cytosolic leaflet of the cellular membrane. The cells were briefly pelleted, aspirated, and resuspended in 300 µL of a reaction mixture containing 0.2 µL/mL of the Annexin V FITC solution, 2 mM $CaCl_2$ to enable binding, and 2 µg/mL propidium iodide as an indicator of cell permeability. Each sample was incubated at 37° C. for 20 minutes, and then analyzed by flow cytometry. Single, whole cells were selected based on the forward and the side-scatter. With an excitation of 488 nm Annexin V-FITC binding was identified using FL1 533 nm emission. Propidium iodide staining was selected based on FL2 585 nm emission. Apoptotic populations were selected based on comparison to the positive controls of Doxorubicin hydrochloride and Paclitaxel which exhibited high levels of FITC fluorescence with minimal propidium iodide florescence. Measurements were taken in biological triplicate for each sample, and the results were confirmed in technical triplicate.

Statistical Analysis:

Statistical analysis was performed using nonparametric methods due to limited sample sizes. Pair-wise comparisons of two drug treatments were performed using the Mann-Whitney U test. One-way analysis of variance within groups of derivatives was performed using the Kruskal-Wallis test. ANOVA was not performed on any parameters where data were not measured in at least technical triplicate (n≥3) for each data point. For each analysis, the criterion used to determine statistical significance was $p<0.05$. All statistical analyses were performed using GraphPad Prism 6.0. $IC_{50}$ values were calculated using a non-linear regression, dose-response, variable slope model in GraphPad Prism 6.0. $IC_{50}$ values were only accepted when $R^2>0.95$ unless otherwise stated. Significance of statistical comparison is represented on the figures and table using the scheme: $^{ns}$ as $p>0.05$, * as $p<0.05$,  as $p<0.01$, * as $p<0.001$, and **** as $p<0.0001$.

Example 14: Biological Evaluation of $P_1$ Analogues

Figure 58:
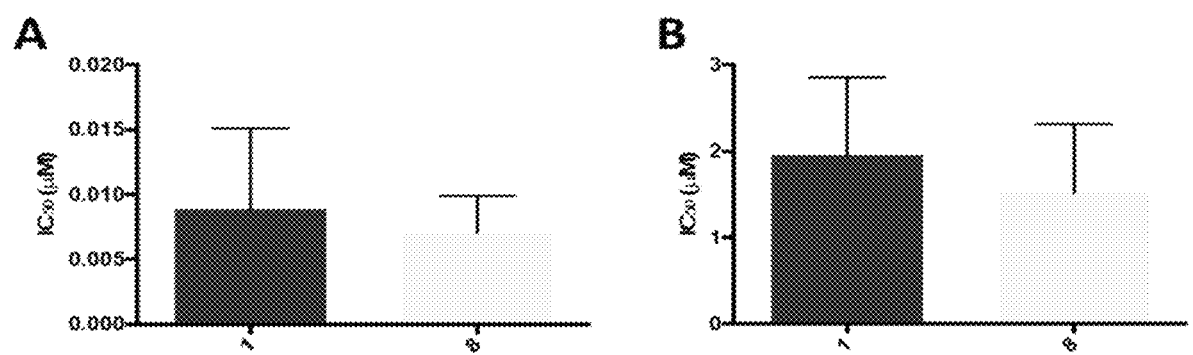
FIG. 58 PANEL A and PANEL B show $IC_{50}$ values associated with the inhibition of either chymotrypsin-like activity or trypsin-like activity of the 26S proteasome, respectively.

Compound 8, which incorporates a (1S)-methylpropyl (sec-butyl) moiety, was synthesized to increase the steric profile at $P_1$ and potentially induce a conformational change of Met45 in the active site of $β_5$ protease within the proteasome. This conformation change leads to changes in $β_5$ subunit selectivity from targeting the constitutive proteasome to targeting the immunoproteasome. The $IC_{50}$ values for ChT-L and T-L inhibition were not significantly different between compounds 8 and 1. FIG. 58 PANEL A and PANEL B show $IC_{50}$ values associated with the inhibition of either chymotrypsin-like activity or trypsin-like activity of the 26S proteasome, respectively. The average of at least three independent experiments performed in biological triplicate is reported with the corresponding standard deviation ($p>0.05$).

Figure 59:
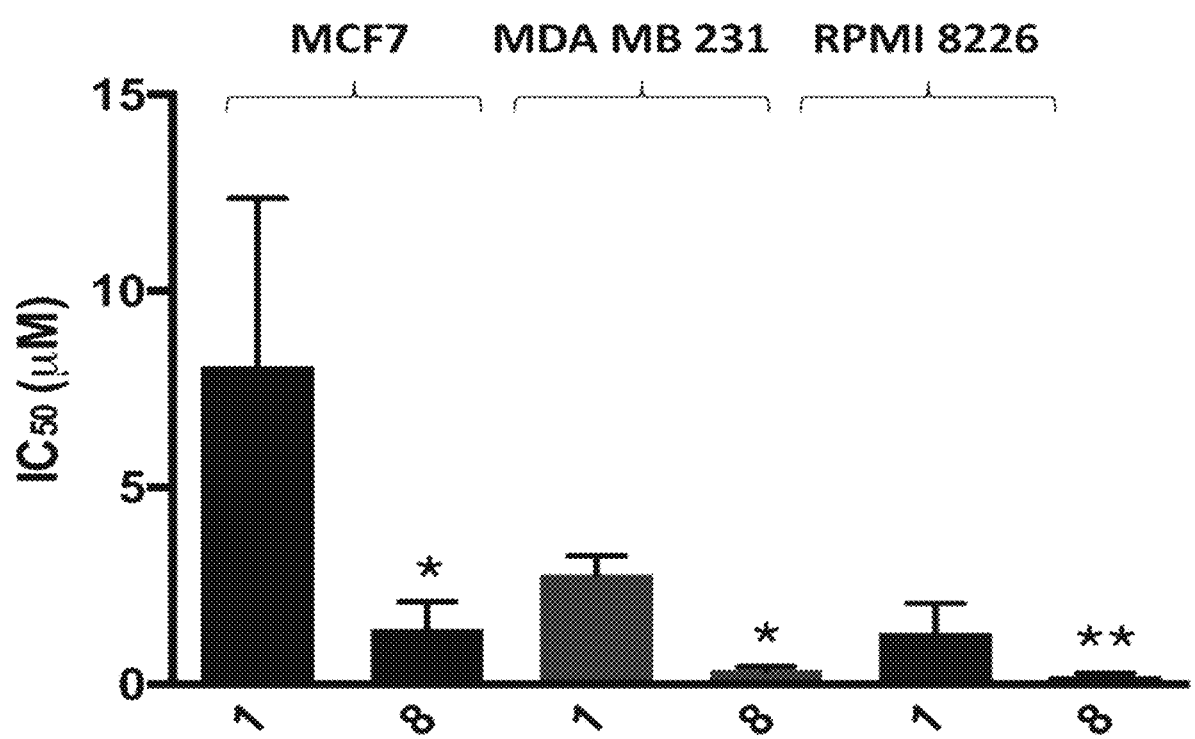
FIG. 59 shows the cytotoxicity profiles of compounds 1 and 8.

Compound 8 had a much improved cytotoxicity profile. FIG. 59 shows the cytotoxicity profiles of compounds 1 and 8. An average of at least three independent experiments performed in biological triplicate is reported with the corresponding standard deviation.

Western blot and flow cytometry assays confirmed that treatment of cancer cells with 1 and 8 led to an accumulation of ubiquitinated proteins, induction of apoptosis, and cell cycle arrest in the G2/M phase.

Example 15: Cell Infiltration of Proteasome Inhibitors

Figure 60:
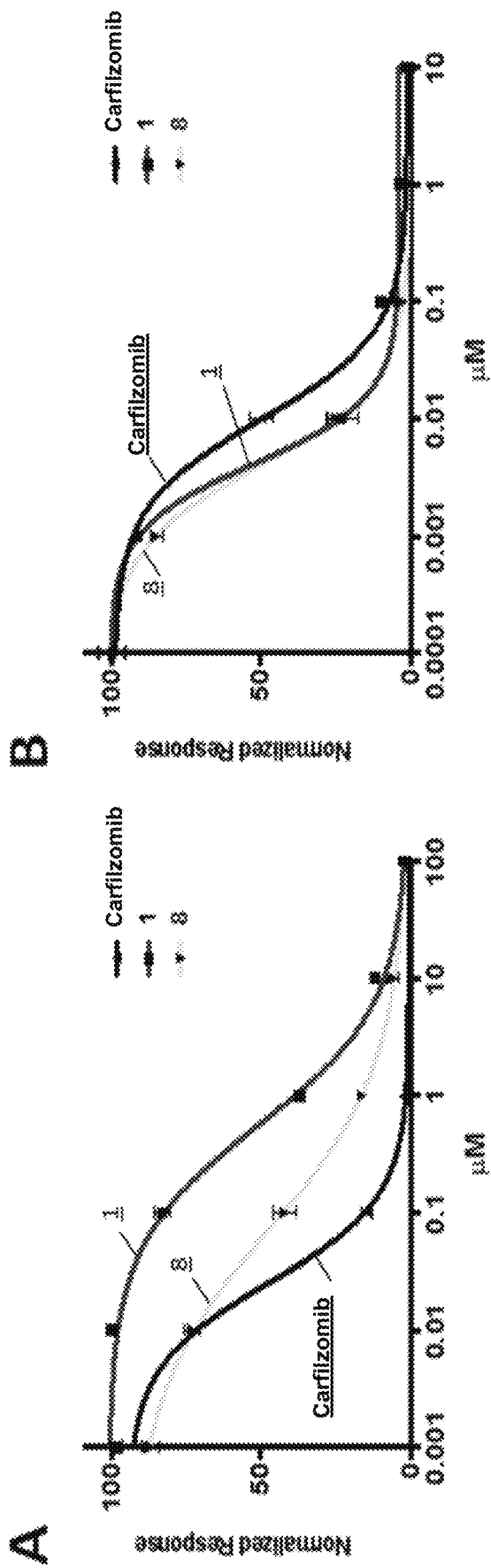
FIG. 60 PANEL A and PANEL B show dose response curves from the proteasome inhibition assay for the treatment of intact MCF-7 cells (PANEL A), and treatment of lysed MCF-7 cells (PANEL B).

The difference between proteasome inhibition within intact versus lysed cells was evaluated as a representative measure of PIs ability to infiltrate cells and access intracellular proteasomes. Treatment of intact MCF-7 cells with inhibitors 1 or 8, followed by cell washing, cell lysis, and evaluation of resulting proteasome activity showed that compound 8 was approximately 10 times more active than compound 1. FIG. 60 PANEL A and PANEL B shows dose response curves from the proteasome inhibition assay for the treatment of intact MCF-7 cells (PANEL A), and treatment of lysed MCF-7 cells (PANEL B). Assays were performed in biological triplicate, and the data points are reported with the corresponding standard deviations.

Modifications of compounds 9a-9d were selected to minimize the chain length and the rotational freedom of the P1 moieties, to improve $β_5$ selectivity via induced fit. TABLE 2 shows the cytotoxicity and inhibitory activity of the P1 analogues. The data show that increasing the size of the alicyclic side chains led to improved inhibitory selectivity of the proteasome ChT-L over T-L activity. The increased selectivity correlated with the total number of carbon atoms in the alicyclic chain at P1. Compound 9c exhibited the greatest selectivity. Each of the modifications led to a substantial decrease in cytotoxicity with respect to 8. $IC_{50}$ values were calculated as an average of at least three independent experiments performed in biological triplicate. Indicates that at least one value calculated from a non-linear dose-response model with $0.85<R^2<0.95$ in GraphPad Prism. Remaining values calculated with $R^2>0.95$ and are reported with the corresponding S.D. Superscript notation is used to represent the statistical results from a one-way ANOVA that compares compounds 8 and 9a-9d.

TABLE 2

| | | IC50 (μM) ± S.D. | | | | |
|---|---|---|---|---|---|---|
| | | Proteasome Inhibition | | Cytotoxicity | | |
| Comp | P1 | ChT-like[ns] | T-L-like** | MCF7 | MDA-MB-231 | RPMI 8226** |
| 1 | i-Pr | 0.0089 ± 0.0062 | 1.955 ± 0.901 | 8.089 ± 4.269 | 2.791 ± 0.464 | 1.309 ± 0.745 |
| 8 | sec-Bu | 0.0071 ± 0.0028 | 1.521 ± 0.788 | 1.412 ± 0.687 | 0.359 ± 0.072 | 0.201 ± 0.082 |
| 9a | cyc-Pr | 0.0122 ± 0.0056 | 2.475 ± 0.433 | >100 | >100 | 72.05 ± 13.85 |
| 9b | cyc-Bu | 0.0265 ± 0.0077 | 3.728 ± 0.775 | >50 | ~50 | 30.40 ± 4.75 |
| 9c | cyc-Pent | 0.0139 ± 0.0006 | 10.198 ± 3.388 | ~25 | 20.55 ± 3.94 | 1.980 ± 1.005 |
| 9d | i-Bu | 0.0160 ± 0.0047 | 6.668 ± 3.440 | ~40 | 25.30 ± 2.94 | 19.89 ± 8.06 |
| Carfilzomib | | 0.0106 ± 0.0026 | 0.176 ± 0.057 | 0.004 ± 0.001 | 0.004 ± 0.002 | 0.006 ± 0.002 |

Example 16: Cellular Infiltration of P1 Analogues

Figure 61:
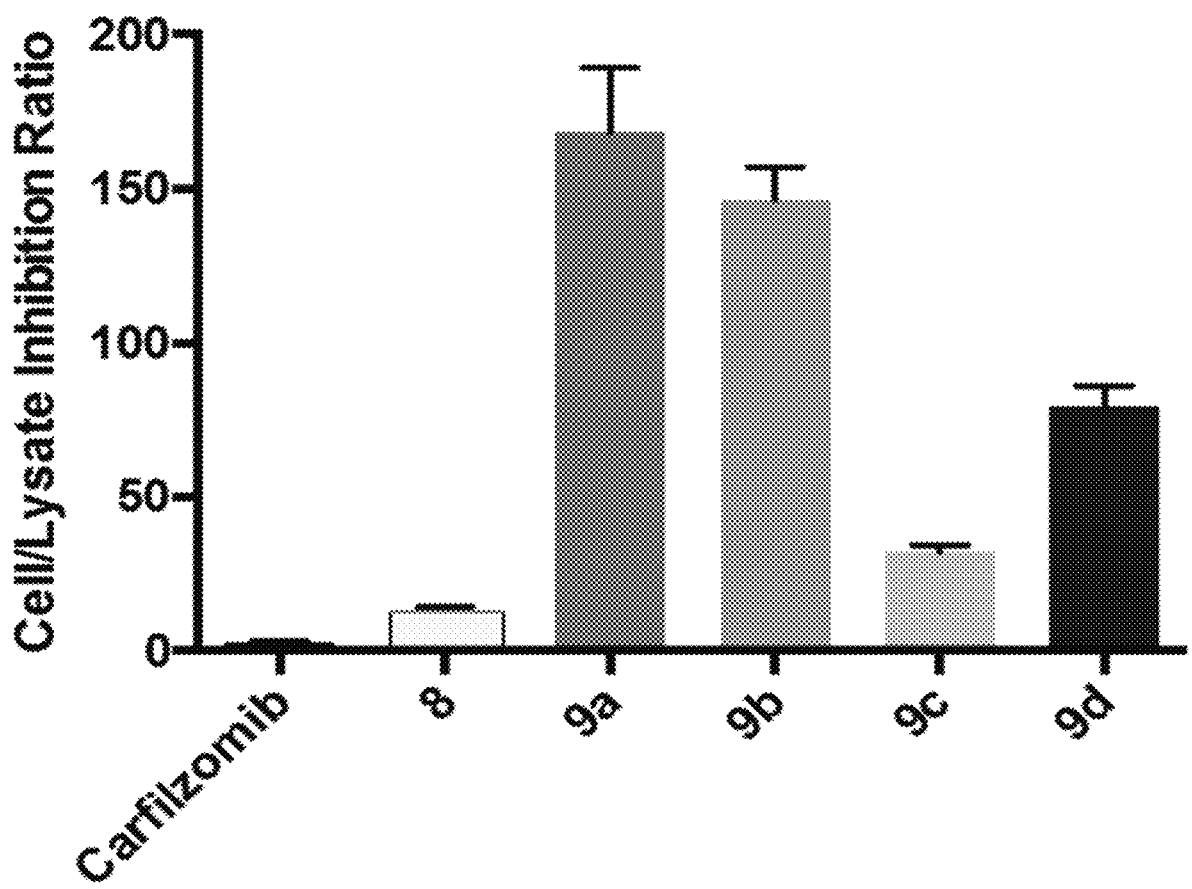
FIG. 61 shows the cellular infiltration of P1 analogues reported as the ratio of the $IC_{50}$ of proteasome inhibition when treating whole cells versus cell lysates.

Cellular infiltration as a compounding factor that would affect cytotoxicity was evaluated. Cellular infiltration was calculated as a ratio of $IC_{50}$ concentrations for proteasome inhibition within intact cells compared to lysed cells. Analogues 9a-9d exhibited moderate decreases in the ability to inhibit intracellular proteasomes. The decrease in cytotoxicity of compounds 9a-9d correlated with decreased cell infiltration. Compounds 9a-9c, which contain alicyclic side chains, decreased cell infiltration with the cyclopropyl P1 9a having the lowest performance. FIG. 61 shows the cellular infiltration of P1 analogues reported as the ratio of the $IC_{50}$ of proteasome inhibition when treating whole cells versus cell lysates. Each value is reported with the corresponding standard deviations determined from propagating the error of both of the $IC_{50}$ values that were determined from a serial dilution in biological triplicate.

Example 17: Biological Activity of P2/P3 Analogues

P2/P3 analogues were tested to assess the role of amino acid specificity with respect to (35 selectivity and cytotoxicity. Analogues 10a-10k were designed to assess the role of sterics at the P2 and P3 positions. P2 substitutions (i.e., 10a, 10b, 10e, 10h, and 10j) had the most noticeable impact on subunit selectivity. Analogues 10b and 10e, which have bulky hydrophobic P2 substituents, showed enhanced subunit selectivity. The glycine analogue, 10a, exhibited reduced selectivity. P3 substitutions (analogues 10c, 10f, 10i, and 10k) did not notably affect proteasome subunit selectivity, and the P3 substitutions did not have an effect on cytotoxicity. Analogues 10i and 10k exhibited midrange nanomolar $IC_{50}$ values for all three cell lines tested. Compound 10k displayed an exceptionally low $IC_{50}$ (2.8 nM) value for direct ChT-L proteasome inhibition.

TABLE 3 shows the cytotoxicity and inhibitory activity of P2/P3 analogues. $IC_{50}$ values were calculated as an average of at least three independent experiments performed in biological triplicate. ~Indicates that at least one value calculated from a non-linear dose-response model with $0.85 < R^2 < 0.95$ in GraphPad Prism. Remaining values calculated with $R^2 > 0.95$ and are reported with the corresponding S.D. Superscript notation is used to represent the statistical results from a one-way ANOVA that compares compounds 8 and 10a-10k.

TABLE 3

| | | | IC50 (μM) ± S.D. | | | | |
|---|---|---|---|---|---|---|---|
| | | | Proteasome Inhibition | | Cytotoxicity | | |
| Comp | P2 | P3 | ChT-like[ns] | T-L-like* | MCF7 | MDA-MB-231** | RPMI 8226** |
| 8 | i-Pr | i-Pr | 0.0071 ± 0.0049 | 1.521 ± 0.788 | 1.412 ± 0.687 | 0.359 ± 0.072 | 0.201 ± 0.082 |
| 10a | H | i-Pr | 0.0038 ± 0.0014 | 0.256 ± 0.072 | ~4 | 0.952 ± 0.262 | 0.840 ± 0.429 |
| 10b | Bn | i-Pr | 0.0077 ± 0.0017 | 3.818 ± 0.812 | ~5 | 3.437 ± 0.722 | 2.333 ± 0.610 |
| 10c | i-Pr | Bn | 0.0054 ± 0.0029 | 1.663 ± 0.204 | 2.302 ± 0.142 | 2.573 ± 0.705 | 1.035 ± 0.045 |
| 10d | Bn | Bn | 0.0126 ± 0.0057 | 3.050 ± 1.265 | 3.616 ± 2.496 | 4.655 ± 1.536 | 1.285 ± 0.527 |
| 10e | t-Bu | i-Pr | 0.0229 ± 0.0025 | 5.178 ± 1.491 | 2.138 ± 0.122 | 1.027 ± 0.644 | 1.052 ± 0.750 |
| 10f | i-Pr | t-Bu | 0.0159 ± 0.0010 | 3.712 ± 0.719 | 1.121 ± 0.332 | 1.111 ± 0.582 | 1.392 ± 0.131 |
| 10g | t-Bu | t-Bu | 0.0214 ± 0.0088 | 4.529 ± 2.184 | 1.694 ± 0.102 | 0.953 ± 0.484 | 0.866 ± 0.532 |
| 10h | i-Bu | i-Pr | 0.0047 ± 0.0018 | 2.563 ± 0.390 | 2.350 ± 0.458 | 2.083 ± 0.651 | 1.777 ± 1.021 |

TABLE 3-continued

[Structure: BnO-C(=O)-CH(P3)-NH-C(=O)-CH(P2)-NH-C(=O)-[β-lactone with i-Bu group]]

| | | | IC50 (μM) ± S.D. | | | | |
|---|---|---|---|---|---|---|---|
| | | | Proteasome Inhibition | | Cytotoxicity | | |
| Comp | P2 | P3 | ChT-like[ns] | T-L-like* | MCF7 | MDA-MB-231** | RPMI 8226** |
| 10i | i-Pr | i-Bu | 0.0078 ± 0.0016 | 1.353 ± 0.172 | 0.351 ± 0.031 | 0.287 ± 0.136 | 0.156 ± 0.096 |
| 10j | O-Bn | i-Pr | 0.0069 ± 0.0002 | 0.792 ± 0.240 | 2.765 ± 0.791 | 2.207 ± 0.764 | 1.428 ± 0.526 |
| 10k | i-Pr | O-Bn | 0.0028 ± 0.0004 | 1.335 ± 0.334 | 0.284 ± 0.132 | 0.090 ± 0.051 | 0.050 ± 0.028 |
| Carfilzomib | | | 0.0106 ± 0.0026 | 0.176 ± 0.057 | 0.004 ± 0.001 | 0.004 ± 0.002 | 0.006 ± 0.002 |

P2 analogues 10a, 10b, 10e, 10h, and 10j maintained or decreased the inhibition of intracellular proteasomes. The P2 glycine analogue 10a maintained cytotoxicity $IC_{50}$ values comparable to those of the other P2 analogues, but complete cytotoxicity was not achieved up to a concentration of >100 μM. Phenylarsine oxide was used as a positive cell-killing control. The abilities of P2 analogues 10d and 10j to inhibit intracellular proteasomes were drastically different, but 10d and 10j exhibited similar cytotoxicity. The only observed difference between 10d and 10j was subunit selectivity.

Figure 62:
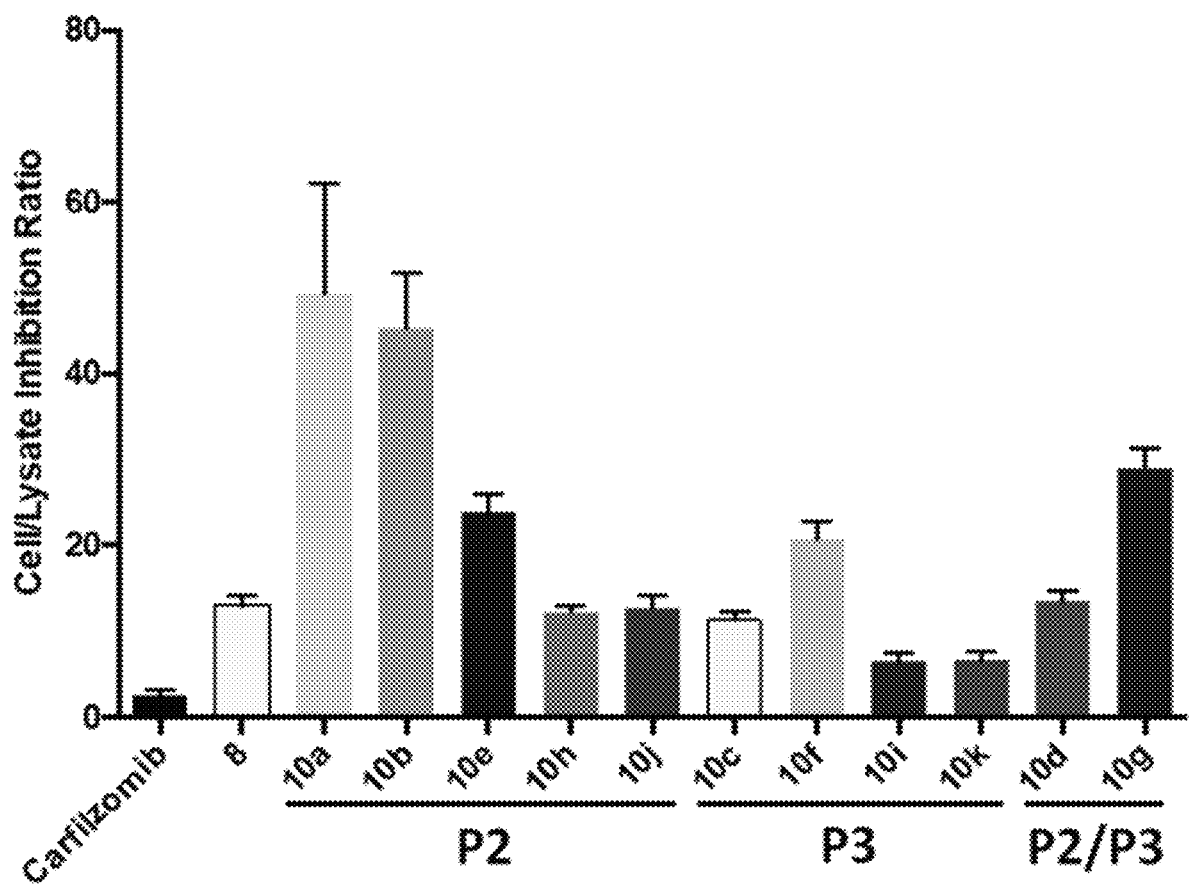
FIG. 62 shows the cellular infiltration of P2/P3 analogues reported as the ratio of the $IC_{50}$ of proteasome inhibition when treating whole cells versus cell lysates.

FIG. 62 shows the cellular infiltration of P2/P3 analogues reported as the ratio of the $IC_{50}$ of proteasome inhibition when treating whole cells versus cell lysates. Each value is reported with the corresponding standard deviations determined from propagating the error of both of the $IC_{50}$ values that were determined from a serial dilution in biological triplicate. Analogues are grouped based on the position of variation.

Analogues 10c, 10f, 10i, and 10k were used to evaluate the effects of substitution with larger steric profiles at the P3 position. Intracellular proteasomes tolerated increases in the steric profile at the P3 position better than the P2 analogues did. Increases in the steric profile close to the β-carbon atom of the amino acid correlated with a decreased infiltration of 10f and a decrease in cytotoxicity for 10c and 10f. Analogues 10i and 10k exhibited improved cellular infiltration and cytotoxicity in comparison to compounds 10c and 10f. Compound 10k exhibited cellular toxicity levels that were within ~1 magnitude of the observed $IC_{50}$ values of carfilzomib.

Example 18: Cytotoxicity and Inhibitory Activity of P4 Analogues

Systematic alteration of the steric and electronic characteristics of the P4 position was used to determine structure-activity relationships. Only the methyl ester compound 11h exhibited a significant change in direct proteasome activity (p<0.05) compared to compound 8, indicating that structural variation at this portion of the scaffold for proteasome inhibitory activity is acceptable. Analogue 11c, bearing an aliphatic cyclohexylmethyl ester group, preserved proteasome-inhibitory but showed decreased cytotoxicity compared to compounds 8, 11a, 11b, and 11d-11h. Allyl ester 11a displayed the best profile of cytotoxicity and proteasome inhibition. Compounds 11b, 11d, and 11f exhibited similar profiles for cytotoxicity and proteasome inhibition. Compounds 8, 11a, 11b, and 11f share an allylic π-system as a common feature. The π-system chemical structure is beneficial for promoting cytotoxicity. The results from this evaluation suggest that P4 tolerates structural variations for both proteasome inhibition and cytotoxicity.

TABLE 4 shows the cytotoxicity and inhibitory activity of P4 analogues. $IC_{50}$ values were calculated as an average of at least three independent experiments performed in biological triplicate and are reported with the corresponding S.D. Superscript notation is used to represent the statistical results from a one-way ANOVA that compares compounds 8 and 11a-11h.

TABLE 4

[Structure: P4-C(=O)-CH(i-Pr)-NH-C(=O)-CH(i-Pr)-NH-C(=O)-[β-lactone with i-Bu group]]

| | | IC50 (μM) ± S.D. | | | |
|---|---|---|---|---|---|
| | | Proteasome Inhibition | Cytotoxicity | | |
| Comp | P4 | ChT-like[ns] | MCF7**** | MDA-MB-231** | RPMI 8226** |
| 8 | BnO | 0.0071 ± 0.0049 | 1.412 ± 0.687 | 0.359 ± 0.072 | 0.201 ± 0.082 |
| 11a | allyl-O | 0.0116 ± 0.0028 | 0.311 ± 0.082 | 0.275 ± 0.112 | 0.094 ± 0.015 |
| 11b | p-Cl—BnO | 0.0102 ± 0.0070 | 0.954 ± 0.351 | 0.307 ± 0.166 | 0.088 ± 0.012 |

TABLE 4-continued

IC50 (µM) ± S.D.

| Comp | P4 | Proteasome Inhibition ChT-like[ns] | Cytotoxicity | | |
|---|---|---|---|---|---|
| | | | MCF7**** | MDA-MB-231** | RPMI 8226** |
| 11c | cyc-Hex-O | 0.0130 ± 0.0052 | 4.572 ± 1.646 | 1.925 ± 0.917 | 0.461 ± 0.194 |
| 11d | i-Bu | 0.0094 ± 0.0037 | 0.634 ± 0.072 | 0.355 ± 0.123 | 0.099 ± 0.007 |
| 11e | BnNH | 0.0045 ± 0.0029 | 0.814 ± 0.121 | 0.742 ± 0.212 | 0.387 ± 0.177 |
| 11f | p-MeO—BnO | 0.0090 ± 0.0042 | 0.574 ± 0.096 | 0.265 ± 0.114 | 0.117 ± 0.047 |
| 11g | homo-allyl-O | 0.0087 ± 0.0020 | 0.752 ± 0.384 | 0.361 ± 0.043 | 0.264 ± 0.048 |
| 11h | MeO | 0.0243 ± 0.0082 | 0.506 ± 0.207 | 0.316 ± 0.044 | 0.293 ± 0.071 |
| Carfilzomib | | 0.0106 ± 0.0026 | 0.004 ± 0.001 | 0.004 ± 0.002 | 0.006 ± 0.002 |

Example 19: Protein-Drug Co-Crystal Structure

The binding mode of compound 11a in the yeast proteasome was examined. The yeast proteasome (yCP) has high homology with mammalian proteasomes but is easier to crystallize. Compound 11a was incubated at a high concentration with active yCP, and the enzyme-inhibitor complex was analyzed using X-ray crystallography.

Figure 63:
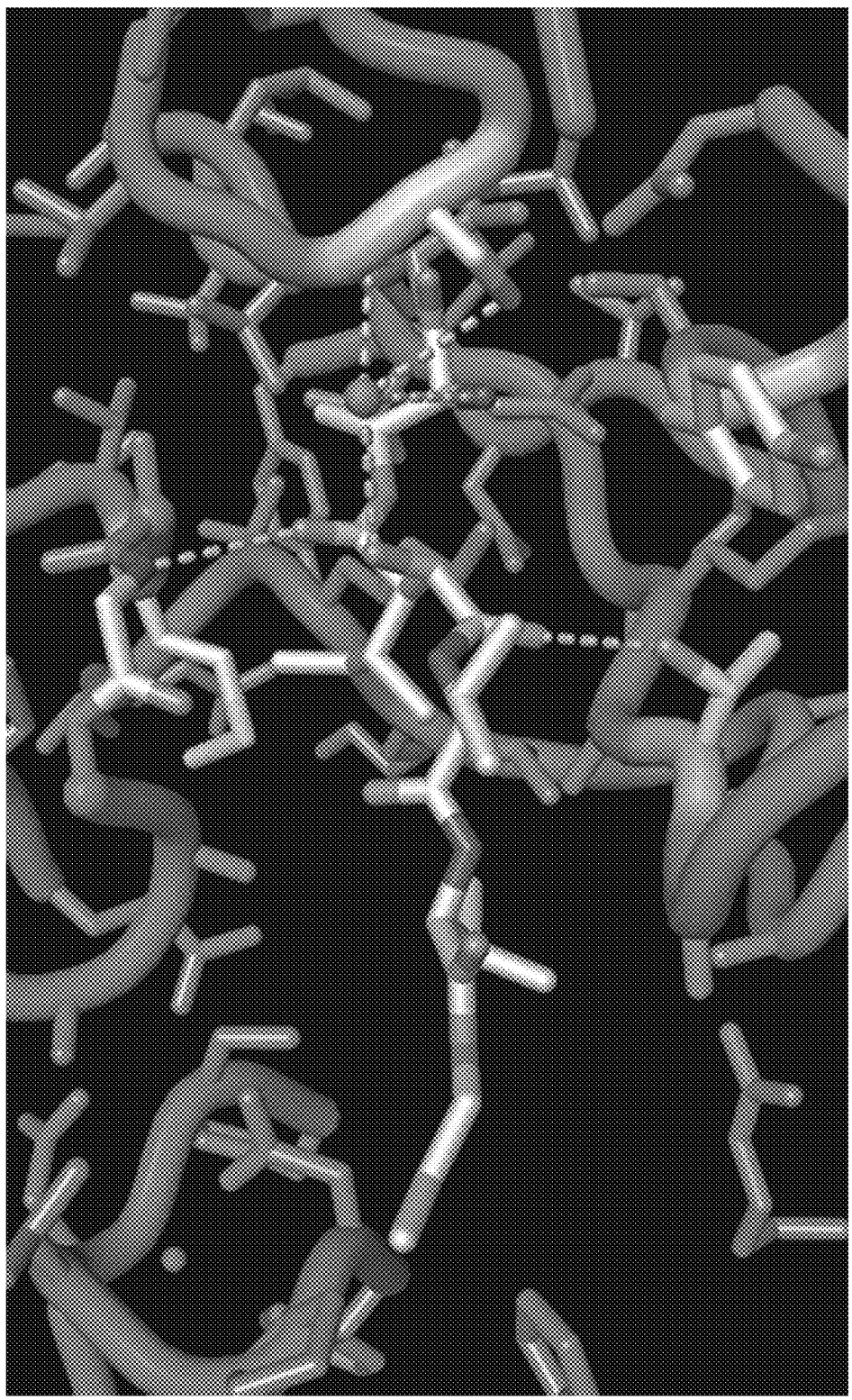
FIG. 63 shows PyMol rendering of compound 11a, crystallized in the $\beta_5$ subunit of the 26S yeast proteasome (yCP).

FIG. 63 shows PyMol rendering of compound 11a, crystallized in the $\beta_5$ subunit of the 26S yeast proteasome (yCP). Compound 11a binds covalently to Thr1Oγ at the active site of subunit $\beta_5$ of the yCP, positioning itself along the non-primed substrate-binding channel. Compound 11a does not cause a shift of Met45, in contrast to other, simpler β-lactone PIs that bear an isoleucine P1 side chain. Compound 11a is positioned in a kinked β-sheet-like conformation that is stabilized by hydrogen bonding with Thr21 and Gly47. The PI is further stabilized by the hydrophobic interaction of P3, whereas P2 and P4 lack any direct interactions within the binding pocket. The PI prevents the regeneration of the Thr1 catalytic site by complexing the water molecule generated by the hydrolysis of the β-lactone. The water molecule is stabilized in the binding pocket by residues Thr1, Ser131, and the hydroxyl group of the hydrolyzed lactone. The crystal structure reveals the importance of P1 and P3 substitution in PI stabilization, whereas P2 and P4 lack direct interaction with the protein. The biological effects of P2 and P4 can be attributed to the pharmacokinetics of the cystargolide scaffold instead of binding to the $\beta_5$ subunit of the proteasome.

Figure 64:
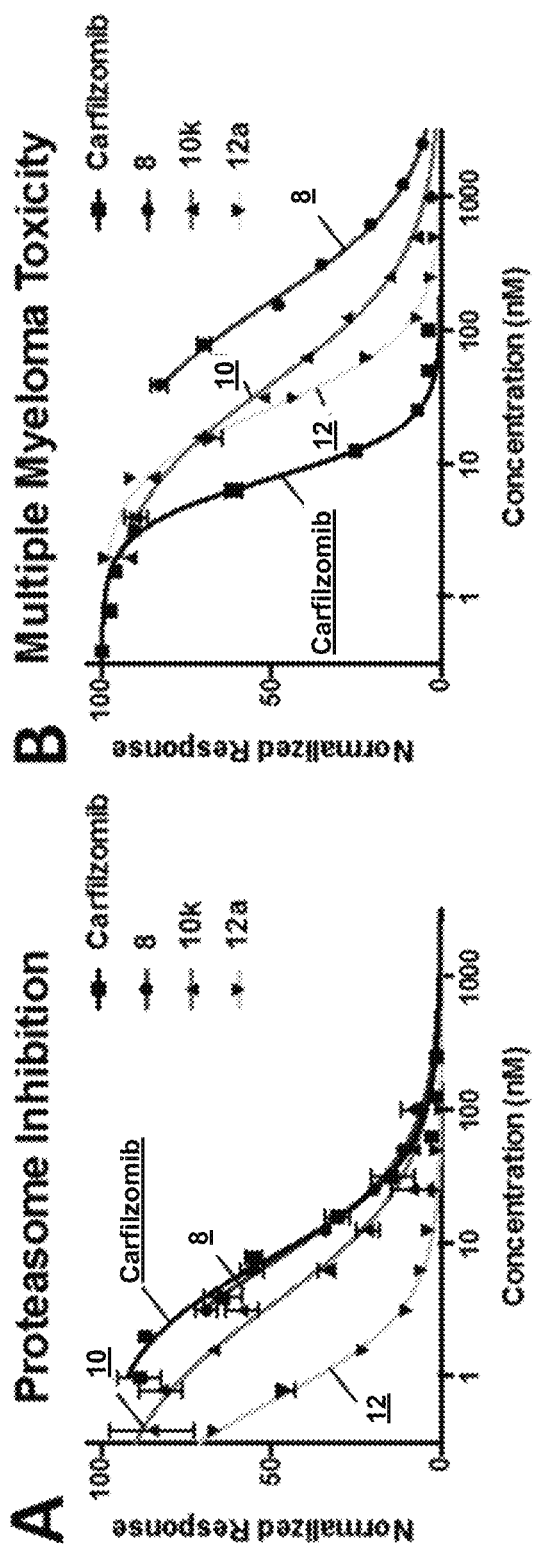

Example 20: Cytotoxicity and Proteasome Inhibition of Compounds 8, 10k, and 12a The ability of compounds 8, 10k, and 12a to inhibit the proteasome and to kill cancer cells is shown in FIG. 64 and TABLE 5. The biological activity of compounds 8, 10k, and 12a are compared to that of the commercially-available proteasome inhibitor carfilzomib. Compound 12a inhibited the proteasome and killed cancer cells completely. Compound 12a was 10 times more active as an inhibitor of the proteasome than carfilzomib was, but was slightly less active at killing cancer cells.

FIG. 64 PANEL A compares proteasome inhibitory effects of compounds 8, 10k, and 12a. FIG. 64 PANEL B compares the effects of compounds 8, 10k, and 12a on multiple myeloma toxicity. The complete toxicity (normalized response 0) of 12a helped prevent the development of chemical resistance since a surviving population was not left behind. The general scaffold exhibited full toxicity against multidrug resistant and taxol resistant cancer cells.

TABLE 5 shows the cytotoxicity and proteasome inhibition $IC_{50}$ values that were determined from associated dose-response curves. The values were calculated using a non-linear dose-response model within GraphPad Prism and are each reported with the corresponding standard deviation. Values were verified in at least technical duplicate.

TABLE 5

| | $IC_{50}$ (nM) ± S.D. | | | |
|---|---|---|---|---|
| | Proteasome Inhib. | Cytotoxicity | | |
| Compound | ChT-L | MCF7 | MDA-MB-231 | RPMI 8226 |
| Carfilzomib | 8.201 ± 0.662 | 4.075 ± 0.056 | 2.791 ± 0.464 | 6.763 ± 0.173 |
| 8 | 7.004 ± 0.311 | 1853 ± 261 | 379.9 ± 18.8 | 192.1 ± 32.3 |
| 10k | 3.803 ± 0.648 | 177.6 ± 23.4 | 75.60 ± 3.49 | 40.53 ± 1.66 |
| 12a | 0.647 ± 0.021 | 93.90 ± 2.94 | 56.34 ± 3.09 | 28.78 ± 1.09 |

Example 21: Ability of Compounds to Pass the Cell Membrane

Figure 65:
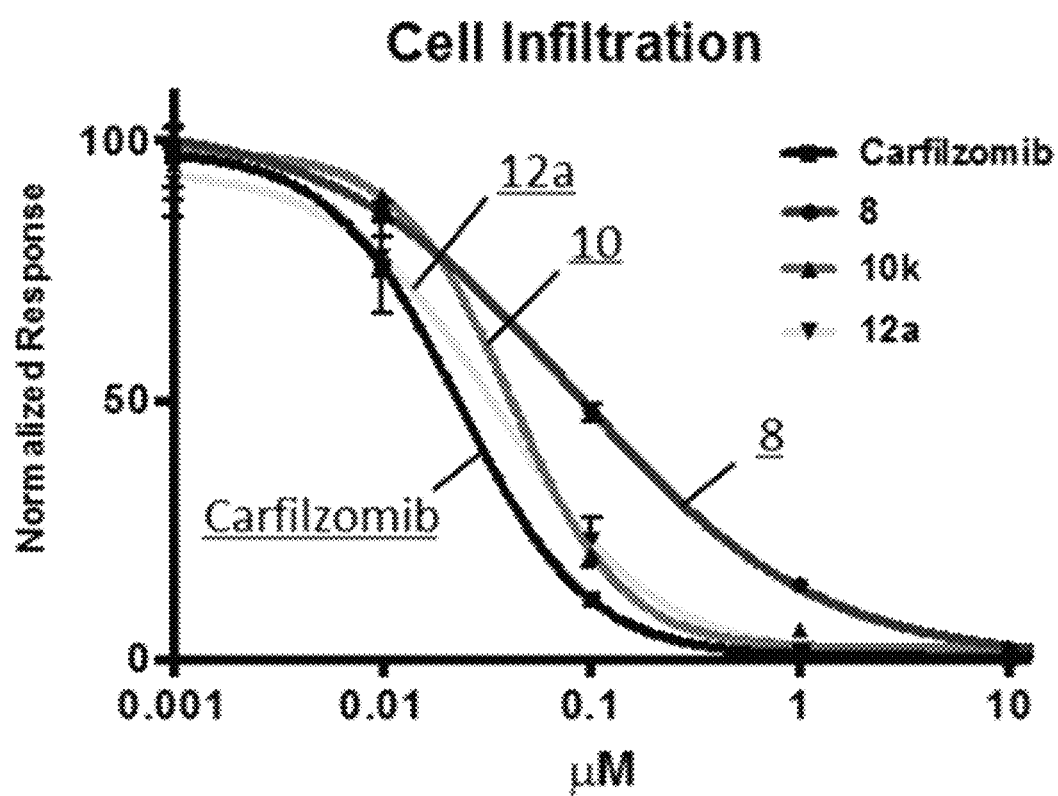
FIG. 65 shows the ability of compounds 8, 10k, and 12a to inhibit proteasomes within intact cells.

FIG. 65 shows the ability of compounds 8, 10k, and 12a to inhibit proteasomes within intact cells. Compound 12a exhibited the best ability to enter intact MCF-7 cells after one hour of treatment. Both 12a and 10k were about 10 times less cytotoxic than carfilzomib was but exhibited rates of infiltration that were not 10 times less than that of carfilzomib. The rate at which 12a and 10k infiltrated cells was limited by the deactivation of the compounds, which possibly occurred in the plasma cell surroundings.

FIG. 65 shows dose response curves for the inhibition of the ChT-L activity of 26S proteasomes in intact cells after one hour of treatment. The assays were performed in biological triplicate, and the data points are reported with the corresponding standard deviations.

Example 22: Drug Deactivation by Serum

The deactivation of compounds was evaluated by testing the toxicity of compounds 8 and 12a in three different types of serums (i.e., fetal bovine serum (FBS), newborn bovine serum (NBS), and human serum). FBS is taken during the development of a calf fetus, so the serum has less protein associated with the innate immune system, and less protein altogether compared to NBS and human serum. Compound 8 exhibited over a 100-fold decrease in activity when cells were supplemented with NBS or human serum instead of FBS. Compound 12a exhibited less than a 10-fold decrease in activity compared cells that were supplemented only with NBS or human serum and FBS. The structural optimization of compound 12a improved the serum stability of the drug: P3 was changed from isopropyl to $CH_2OBn$, and P4 was changed from OBn to NHBn. The OBn group of P4 was more sensitive to deactivation than NHBn.

Figure 66:
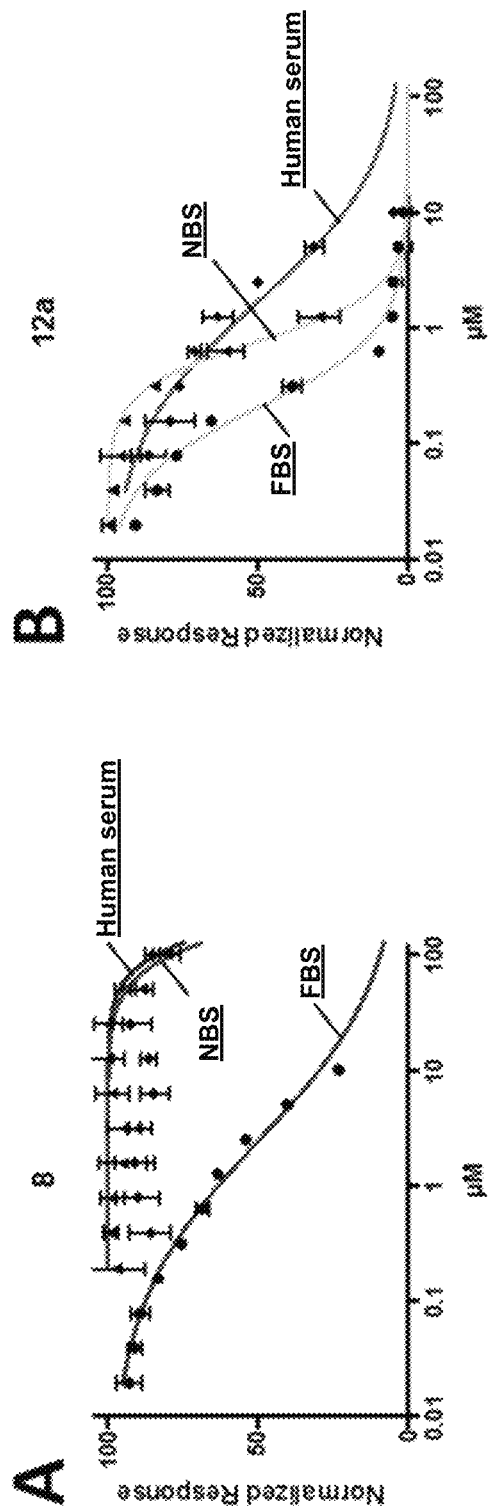
FIG. 66 PANEL A shows dose response curves for the cytotoxicity of compound 8 towards the MCF-7 breast cancer cell line.

FIG. 66 PANEL A shows dose response curves for the cytotoxicity of compound 8 towards the MCF-7 breast cancer cell line. FIG. 66 PANEL B shows dose response curves for the cytotoxicity of compound 12a towards the MCF-7 breast cancer cell line. The MCF-7 cells were cultured in three different types of serum. Assays were performed in biological triplicate, and the data points are reported with the corresponding standard deviation.

Example 23: Identification of Proteins Responsible for Drug Deactivation

Figure 67:
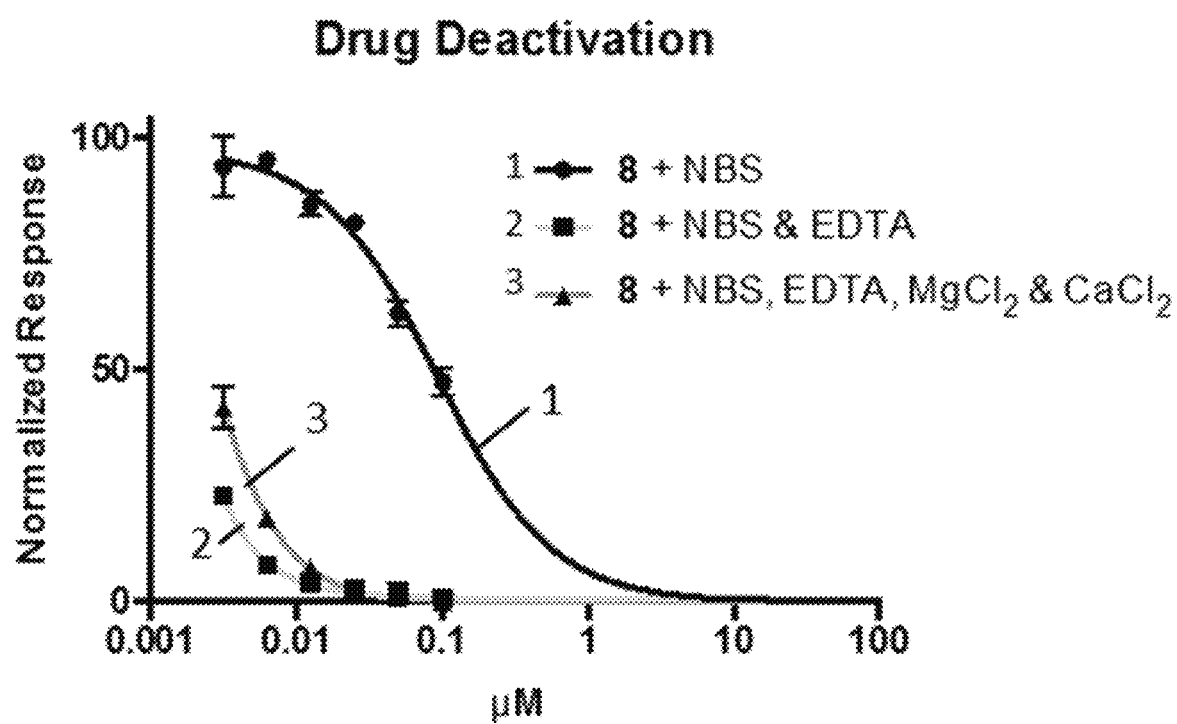
FIG. 67 shows the results of proteasome inhibition assays that were performed after pre-incubating compound 8 with newborn bovine serum.

FIG. 67 shows the results of proteasome inhibition assays that were performed after pre-incubating compound 8 with NBS, which deactivates compound 8. EDTA chelates divalent metal ions. By including EDTA during the pre-incubation step, EDTA protected compound 8 from being deactivated by NBS, shown by low proteasome activity below 5 nM of compound 8. The results show that the protein responsible for the deactivation of compound 8 is dependent on divalent metal ions. By systematically reintroducing divalent metal ions after EDTA treatment, the deactivating protein was shown to at least be partially dependent on $Ca^{2+}$ and $Mg^{2+}$.

FIG. 67 shows the dose response curves for the inhibition of ChT-L activity of the 26S proteasome by compound 8 after pre-incubating the compound for 1 hour at 37° C. using: 1) compound 8, NBS; 2) compound 8, NBS, EDTA; and 3) compound 8, NBS, EDTA, $MgCl_2$, $CaCl_2$. The assays were performed in biological triplicate, and the data points are reported with the corresponding standard deviations.

Figure 68:
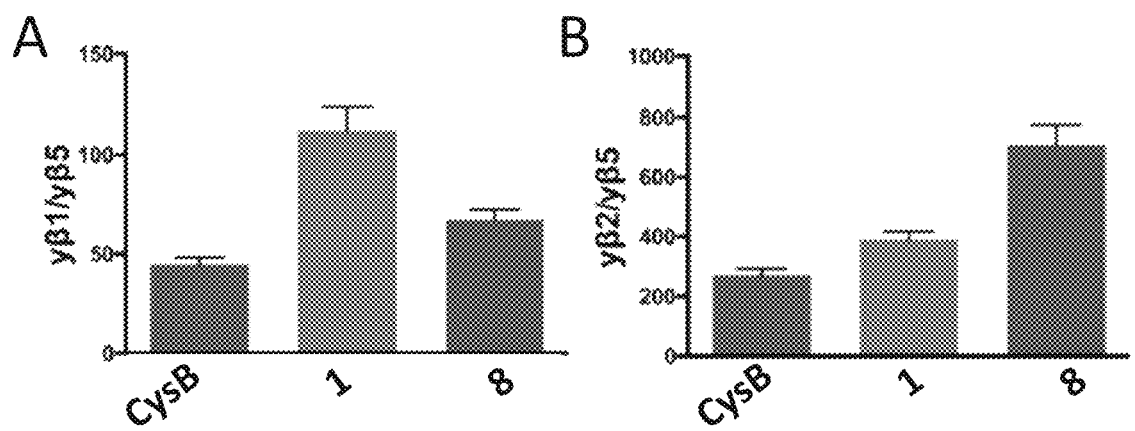
FIG. 68 shows selective inhibition of the $\beta5$ subunit of purified yeast proteasome reported as $IC_{50}$ values comparing either y$\beta$1:y$\beta$5 (left) or y$\beta$2:y$\beta$5 (right). CysB=Cystargolide B.

Example 24: Subunit Selectivity Between the Yeast Proteasome yβ1, yβ2, yβ5 Subunits and the Immunoproteasome i β5 Subunit Subunit selectivity $IC_{50}$ values were measured using 8 μg/mL of purified yCP or iCP, and probing the samples with subunit-specific fluorescent substrates. Values and standard deviations were calculated from an assay performed in biological triplicate. N.D. indicates that data were not determined. TABLE 6 shows the $IC_{50}$ values obtained for compounds 1, 8, 10k, 11a, 11e, and 12a against yeast proteasome yβ1, yβ2, yβ5 subunits and the immunoproteasome iβ5 subunit. Analysis of $IC_{50}$ values shows that compared to compound 1, the extra methyl group of the pseudo-isoleucine lactone for compound 8 did not improve the preference for yβ5 over yβ1 or yβ2. As can be seen in FIG. 68, the ratio of yβ1:yβ5 $IC_{50}$ values decreased 2 fold, whereas the yβ2:yβ5 $IC_{50}$ value ratio increased 2 fold.

TABLE 6

| | $IC_{50}$ (μM) ± SD | | | |
|---|---|---|---|---|
| Compound | yβ1 | yβ2 | yβ5 | iβ5 |
| CysB | 10.15 ± 0.78 | 61.56 ± 4.84 | 0.2263 ± 0.0147 | 0.6811 ± 0.1767 |
| 1 | 4.178 ± 0.438 | 14.61 ± 0.91 | 0.0372 ± 0.0045 | 0.0447 ± 0.0128 |
| 8 | 2.482 ± 0.184 | 26.08 ± 2.38 | 0.0368 ± 0.0035 | 0.0186 ± 0.0044 |
| 10k | 17.75 ± 2.07 | >50 | 0.0245 ± 0.0039 | 0.0091 ± 0.0027 |
| 11a | 0.779 ± 0.042 | >10 | 0.0195 ± 0.0008 | 0.0412 ± 0.0152 |
| 11e | 1.383 ± 0.106 | 2.92 ± 0.21 | 0.0054 ± 0.0005 | N.D. |
| 12a | 20.35 ± 12.90 | 13.60 ± 5.49 | 0.0082 ± 0.0014 | 0.0330 ± 0.0134 |
| Carfilzomib | >1 | >1 | 0.0059 ± 0.0008 | 0.0326 ± 0.0121 |

*CysB = Cystargolide B

EMBODIMENTS

The following non-limiting embodiments provide illustrative examples of the invention, but do not limit the scope of the invention.

Embodiment 1

A compound of the formula:

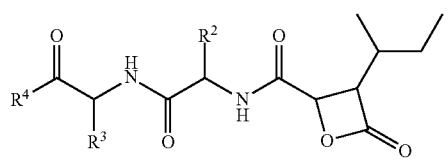

or a pharmaceutically-acceptable salt thereof, wherein:
$R^2$ is alkyl or branched alkyl, each of which is independently substituted or unsubstituted, or hydrogen;
$R^3$ is alkyl or branched alkyl, each of which is independently substituted or unsubstituted; and R[4] is alkoxy, which is substituted or unsubstituted, or NR[5]R[6], wherein each R[5] and R[6] is independently alkyl, which is substituted or unsubstituted, or hydrogen.

Embodiment 2

The compound of embodiment 1, wherein R[2] is branched alkyl.

Embodiment 3

The compound of embodiments 1 or 2, wherein R[2] is iso-propyl, tert-butyl, or sec-butyl.

Embodiment 4

The compound of embodiments 1 or 2, wherein R[2] is benzyl.

Embodiment 5

The compound of embodiment 1, wherein R[2] is hydrogen.

Embodiment 6

The compound of any one of embodiments 1-5, wherein R[3] is branched alkyl.

Embodiment 7

The compound of any one of embodiments 1-6, wherein R[3] is iso-propyl, tert-butyl, or sec-butyl.

Embodiment 8

The compound of any one of embodiments 1-6, wherein R[3] is benzyl.

Embodiment 9

The compound of any one of embodiments 1-8, wherein R[4] is alkoxy.

Embodiment 10

The compound of any one of embodiments 1-9, wherein R[4] is O-benzyl.

Embodiment 11

The compound of any one of embodiments 1-9, wherein R[4] is methoxy.

Embodiment 12

The compound of any one of embodiments 1-8, wherein R[4] is NR[5]R[6], wherein each R[5] and R[6] is independently substituted alkyl or hydrogen.

Embodiment 13

The compound of any one of embodiments 1-8 or 12, wherein R[5] is hydrogen, and R[6] is substituted alkyl.

Embodiment 14

The compound of any one of embodiments 1-8, 12, or 13, wherein R[6] is benzyl.

Embodiment 15

The compound of any one of embodiments 1-3, 6, 7, 9, or 10, wherein the compound is of the formula:

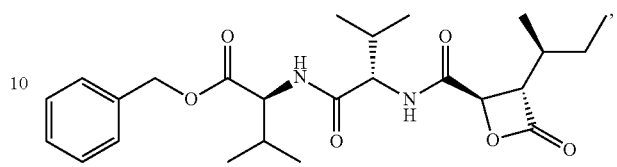

or a pharmaceutically-acceptable salt thereof.

Embodiment 16

The compound of any one of embodiments 1-3, 6, 8, or 12-14, wherein the compound is of the formula:

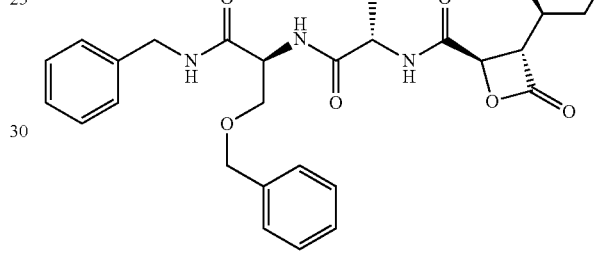

or a pharmaceutically-acceptable salt thereof.

Embodiment 17

A pharmaceutical composition comprising a compound of the formula:

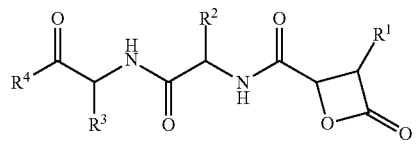

or a pharmaceutically-acceptable salt thereof, wherein:
R[1] is alkyl, which is substituted or unsubstituted.
R[2] is alkyl or branched alkyl, each of which is independently substituted or unsubstituted, or hydrogen;
R[3] is alkyl or branched alkyl, each of which is independently substituted or unsubstituted; and
R[4] is alkoxy, which is substituted or unsubstituted, or NR[5]R[6], wherein each R[5] and R[6] is independently alkyl, which is substituted or unsubstituted, or hydrogen.

Embodiment 18

The pharmaceutical composition of embodiment 17, wherein R[1] is cycloalkyl or branched alkyl.

Embodiment 19

The pharmaceutical composition of embodiments 17 or 18, wherein $R^1$ is cycloalkyl.

Embodiment 20

The pharmaceutical composition of any one of embodiments 17-19, wherein $R^1$ 15 cyclopropyl.

Embodiment 21

The pharmaceutical composition of any one of embodiments 17-19, wherein $R^1$ is cyclobutyl.

Embodiment 22

The pharmaceutical composition of any one of embodiments 17-19, wherein $R^1$ is cyclopentyl.

Embodiment 23

The pharmaceutical composition of embodiments 17 or 18, wherein $R^1$ is branched alkyl.

Embodiment 24

The pharmaceutical composition of any one of embodiments 17, 18, or 23, wherein $R^1$ is sec-butyl.

Embodiment 25

The pharmaceutical composition of any one of embodiments 17-24, wherein $R^2$ is branched alkyl.

Embodiment 26

The pharmaceutical composition of any one of embodiments 17-25, wherein $R^2$ is iso-propyl, tert-butyl, iso-butyl.

Embodiment 27

The pharmaceutical composition of any one of embodiments 17-25, wherein $R^2$ is benzyl.

Embodiment 28

The pharmaceutical composition of any one of embodiments 17-24, wherein $R^2$ is substituted alkyl.

Embodiment 29

The pharmaceutical composition of any one of embodiments 17-24 or 28, wherein $R^2$ is alkyl substituted with O-benzyl.

Embodiment 30

The pharmaceutical composition of any one of embodiments 17-24, wherein $R^2$ is hydrogen.

Embodiment 31

The pharmaceutical composition of any one of embodiments 17-30, wherein $R^3$ is branched alkyl.

Embodiment 32

The pharmaceutical composition of any one of embodiments 17-31, wherein $R^3$ is iso-propyl, tert-butyl, or iso-butyl.

Embodiment 33

The pharmaceutical composition of any one of embodiments 17-30, wherein $R^3$ is substituted alkyl.

Embodiment 34

The pharmaceutical composition of any one of embodiments 17-30 or 33, wherein $R^3$ is benzyl.

Embodiment 35

The pharmaceutical composition of any one of embodiments 17-30 or 33, wherein $R^3$ is alkyl substituted with O-benzyl.

Embodiment 36

The pharmaceutical composition of any one of embodiments 17-35, wherein $R^4$ is alkoxy.

Embodiment 37

The pharmaceutical composition of any one of embodiments 17-36, wherein $R^4$ is O-benzyl.

Embodiment 38

The pharmaceutical composition of any one of embodiments 17-36, wherein $R^4$ is methoxy.

Embodiment 39

The pharmaceutical composition of any one of embodiments 17-35, wherein $R^4$ is $NR^5R^6$, wherein each $R^5$ and $R^6$ is independently alkyl, which is substituted or unsubstituted.

Embodiment 40

The pharmaceutical composition of any one of embodiments 17-35, wherein $R^4$ is $NR^5R^6$, wherein each $R^5$ is hydrogen and $R^6$ is substituted alkyl.

Embodiment 41

The pharmaceutical composition of any one of embodiments 17-35 or 40, wherein $R^4$ is $NR^5R^6$, wherein each $R^5$ is hydrogen and $R^6$ is benzyl.

Embodiment 42

The pharmaceutical composition of any one of embodiments 17, 18, 23-26, 31, 32, 36, or 37, wherein the compound is of the formula:

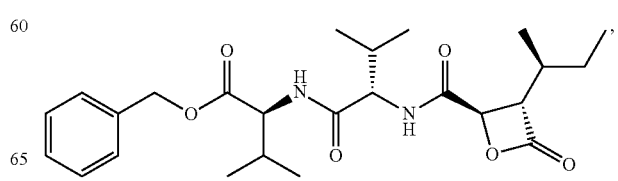

or a pharmaceutically-acceptable salt thereof.

Embodiment 43

The pharmaceutical composition of any one of embodiments 17, 18, 23-26, 33-35, 40, or 41, wherein the compound is of the formula:

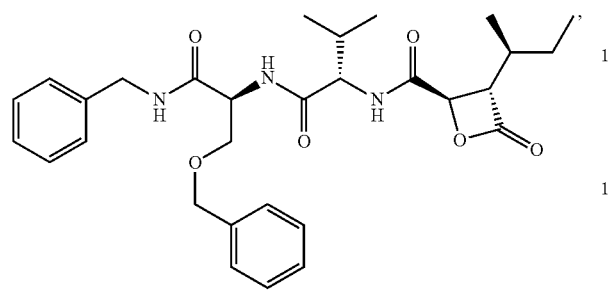

or a pharmaceutically-acceptable salt thereof.

Embodiment 44

The pharmaceutical composition of embodiment 17, further comprising an excipient.

Embodiment 45

A method of treating a condition, the method comprising administering to a subject in need thereof a therapeutically-effective amount of a compound of the formula:

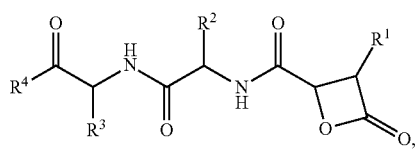

or a pharmaceutically-acceptable salt thereof.

Embodiment 46

The pharmaceutical composition of embodiment 45, wherein $R^1$ is cycloalkyl or branched alkyl.

Embodiment 47

The pharmaceutical composition of embodiments 45 or 46, wherein $R^1$ is cycloalkyl.

Embodiment 48

The pharmaceutical composition of any one of embodiments 45-47, wherein $R^1$ is cyclopropyl.

Embodiment 49

The pharmaceutical composition of any one of embodiments 45-47, wherein $R^1$ is cyclobutyl.

Embodiment 50

The pharmaceutical composition of any one of embodiments 45-47, wherein $R^1$ is cyclopentyl.

Embodiment 51

The pharmaceutical composition of embodiments 45 or 46, wherein $R^1$ is branched alkyl.

Embodiment 52

The pharmaceutical composition of any one of embodiments 45, 46 or 51, wherein $R^1$ is sec-butyl.

Embodiment 53

The pharmaceutical composition of any one of embodiments 45-52, wherein $R^2$ is branched alkyl.

Embodiment 54

The pharmaceutical composition of any one of embodiments 45-53, wherein $R^2$ is iso-propyl, tert-butyl, iso-butyl.

Embodiment 55

The pharmaceutical composition of any one of embodiments 45-52, wherein $R^2$ is benzyl.

Embodiment 56

The pharmaceutical composition of any one of embodiments 45-52, wherein $R^2$ is substituted alkyl.

Embodiment 57

The pharmaceutical composition of any one of embodiments 45-52 or 56, wherein $R^2$ is alkyl substituted with O-benzyl.

Embodiment 58

The pharmaceutical composition of any one of embodiments 45-52, wherein $R^2$ is hydrogen.

Embodiment 59

The pharmaceutical composition of any one of embodiments 45-58, wherein $R^3$ is branched alkyl.

Embodiment 60

The pharmaceutical composition of any one of embodiments 45-59, wherein $R^3$ is iso-propyl, tert-butyl, or iso-butyl.

Embodiment 61

The pharmaceutical composition of any one of embodiments 45-58, wherein $R^3$ is substituted alkyl.

Embodiment 62

The pharmaceutical composition of any one of embodiments 45-58 or 61, wherein $R^3$ is benzyl.

Embodiment 63

The pharmaceutical composition of any one of embodiments 45-58 or 61, wherein $R^3$ is alkyl substituted with O-benzyl.

Embodiment 64

The pharmaceutical composition of any one of embodiments 45-63, wherein $R^4$ is alkoxy.

Embodiment 65

The pharmaceutical composition of any one of embodiments 45-64, wherein $R^4$ is O-benzyl.

Embodiment 66

The pharmaceutical composition of any one of embodiments 45-64, wherein $R^4$ is methoxy.

Embodiment 67

The pharmaceutical composition of any one of embodiments 45-63, wherein $R^4$ is $NR^5R^6$, wherein each $R^5$ and $R^6$ is independently alkyl, which is substituted or unsubstituted.

Embodiment 68

The pharmaceutical composition of any one of embodiments 45-63 or 67, wherein $R^4$ is $NR^5R^6$, wherein each $R^5$ is hydrogen and $R^6$ is substituted alkyl.

Embodiment 69

The pharmaceutical composition of any one of embodiments 45-63, 67 or 68, wherein $R^4$ is $NR^5R^6$, wherein each $R^5$ is hydrogen and $R^6$ is benzyl.

Embodiment 70

The pharmaceutical composition of any one of embodiments 45, 46, 51-54, 59, 60, 64, or 65, wherein the compound is of the formula:

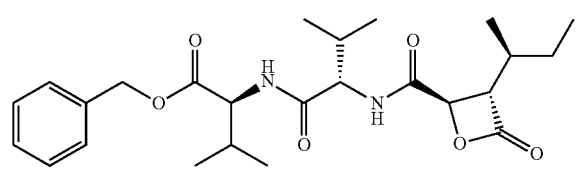

or a pharmaceutically-acceptable salt thereof.

Embodiment 71

The pharmaceutical composition of any one of embodiments 45, 46, 51-54, 61, 63, 68, or 69, wherein the compound is of the formula:

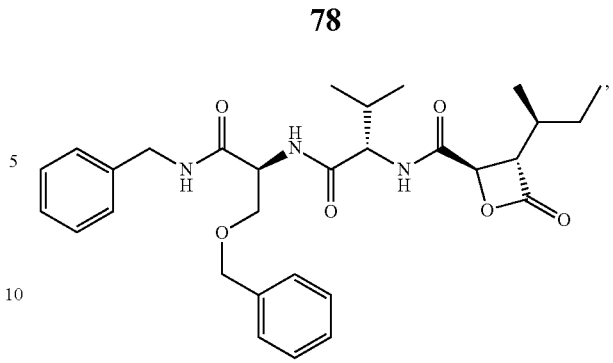

or a pharmaceutically-acceptable salt thereof.

Embodiment 72

The method of any one of embodiments 45-71, wherein the condition is cancer.

Embodiment 73

A method of inhibiting a proteasome, the method comprising administering to a subject in need thereof a therapeutically-effective amount of a compound of the formula:

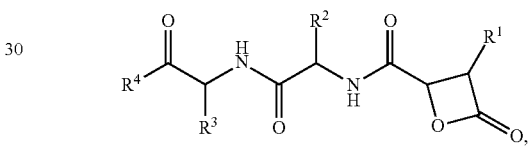

or a pharmaceutically-acceptable salt thereof.

Embodiment 74

The pharmaceutical composition of embodiment 73, wherein $R^1$ is cycloalkyl or branched alkyl.

Embodiment 75

The pharmaceutical composition of embodiments 73 or 74, wherein $R^1$ is cycloalkyl.

Embodiment 76

The pharmaceutical composition of any one of embodiments 73-75, wherein $R^1$ is cyclopropyl.

Embodiment 77

The pharmaceutical composition of any one of embodiments 73-75, wherein $R^1$ is cyclobutyl.

Embodiment 78

The pharmaceutical composition of any one of embodiments 73-75, wherein $R^1$ is cyclopentyl.

Embodiment 79

The pharmaceutical composition of embodiments 73 or 74, wherein $R^1$ is branched alkyl.

Embodiment 80

The pharmaceutical composition of any one of embodiments 73, 74, or 79, wherein $R^1$ is sec-butyl.

Embodiment 81

The pharmaceutical composition of any one of embodiments 73-80, wherein $R^2$ is branched alkyl.

Embodiment 82

The pharmaceutical composition of any one of embodiments 73-81, wherein $R^2$ is iso-propyl, tert-butyl, iso-butyl.

Embodiment 83

The pharmaceutical composition of any one of embodiments 73-81, wherein $R^2$ is benzyl.

Embodiment 84

The pharmaceutical composition of any one of embodiments 73-80, wherein $R^2$ is substituted alkyl.

Embodiment 85

The pharmaceutical composition of any one of embodiments 73-80 or 84, wherein $R^2$ is alkyl substituted with O-benzyl.

Embodiment 86

The pharmaceutical composition of any one of embodiments 73-80, wherein $R^2$ is hydrogen.

Embodiment 87

The pharmaceutical composition of any one of embodiments 73-86, wherein $R^3$ is branched alkyl.

Embodiment 88

The pharmaceutical composition of any one of embodiments 73-87, wherein $R^3$ is iso-propyl, tert-butyl, or iso-butyl.

Embodiment 89

The pharmaceutical composition of any one of embodiments 73-86, wherein $R^3$ is substituted alkyl.

Embodiment 90

The pharmaceutical composition of any one of embodiments 73-86 or 89, wherein $R^3$ is benzyl.

Embodiment 91

The pharmaceutical composition of any one of embodiments 73-86 or 89, wherein $R^3$ is alkyl substituted with O-benzyl.

Embodiment 92

The pharmaceutical composition of any one of embodiments 73-91, wherein $R^4$ is alkoxy.

Embodiment 93

The pharmaceutical composition of any one of embodiments 73-92, wherein $R^4$ is O-benzyl.

Embodiment 94

The pharmaceutical composition of any one of embodiments 73-92, wherein $R^4$ is methoxy.

Embodiment 95

The pharmaceutical composition of any one of embodiments 73-91, wherein $R^4$ is $NR^5R^6$, wherein each $R^5$ and $R^6$ is independently alkyl, which is substituted or unsubstituted.

Embodiment 96

The pharmaceutical composition of any one of embodiments 73-91, wherein $R^4$ is $NR^5R^6$, wherein each $R^5$ is hydrogen and $R^6$ is substituted alkyl.

Embodiment 97

The pharmaceutical composition of any one of embodiments 73-91 or 96, wherein $R^4$ is $NR^5R^6$, wherein each $R^5$ is hydrogen and $R^6$ is benzyl.

Embodiment 98

The pharmaceutical composition of any one of embodiments 73, 74, 79-82, 87, 88, 92, or 93, wherein the compound is of the formula:

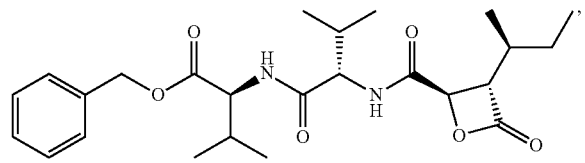 [SMILES: CC[C@H](C)[C@@H]1C(=O)O[C@H]1C(=O)N[C@H](C(=O)N[C@H](C(=O)OCc1ccccc1)C(C)C)C(C)C]

or a pharmaceutically-acceptable salt thereof.

Embodiment 99

The pharmaceutical composition of any one of embodiments 73, 74, 79-82, 89, 91, 96 or 97, wherein the compound is of the formula:

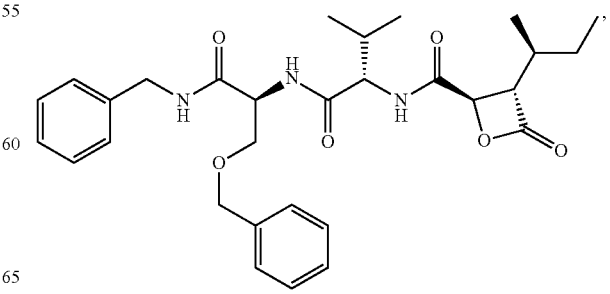

or a pharmaceutically-acceptable salt thereof.

Embodiment 100

The method of any one of embodiments 73-99, wherein the compound inhibits activity of a 26S proteasome.

Embodiment 101

The method of any one of embodiments 73-100, wherein the compound inhibits the ChT-L activity of the 26S proteasome.

Embodiment 102

The method of any one of embodiments 73-101, wherein the compound binds to the $\beta_5$ subunit of the proteasome.

Embodiment 103

The method of any one of embodiments 73-102, wherein the compound kills cancer cells.

Embodiment 104

The method of any one of embodiments 73-103, wherein the compound inhibits the proteasome after about one hour of administration.

Embodiment 105

The method of any one of embodiments 73-104, wherein the compound inhibits activity of a 20S proteasome.

What is claimed is:

1. A pharmaceutical composition comprising a compound of the formula:

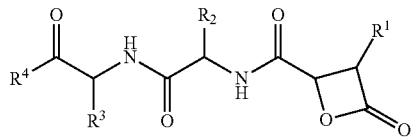

or a pharmaceutically-acceptable salt thereof, wherein:
R$^1$ is alkyl, which is substituted or unsubstituted,
R$^2$ is alkyl or branched alkyl, each of which is independently substituted or unsubstituted, or hydrogen;
R$^3$ is alkyl or branched alkyl, each of which is independently substituted or unsubstituted; and
R$^4$ is alkoxy, which is substituted or unsubstituted, or NR$^5$R$^6$, wherein each R$^5$ and R$^6$ is independently alkyl, which is substituted or unsubstituted, or hydrogen.

2. The pharmaceutical composition of claim 1, wherein R$^1$ is cycloalkyl or branched alkyl.

3. The pharmaceutical composition of claim 2, wherein R$^1$ is branched alkyl.

4. The pharmaceutical composition of claim 2, wherein R$^1$ is sec-butyl.

5. The pharmaceutical composition of claim 1, wherein R$^2$ is branched alkyl.

6. The pharmaceutical composition of claim 5, wherein R$^2$ is iso-propyl, tert-butyl, or iso-butyl.

7. The pharmaceutical composition of claim 1, wherein R$^2$ is substituted alkyl.

8. The pharmaceutical composition of claim 7, wherein R$^2$ is alkyl substituted with O-benzyl.

9. The pharmaceutical composition of claim 1, wherein R$^3$ is branched alkyl.

10. The pharmaceutical composition of claim 9, wherein R$^3$ is iso-propyl, tert-butyl, or iso-butyl.

11. The pharmaceutical composition of claim 1, wherein R$^3$ is substituted alkyl.

12. The pharmaceutical composition of claim 11, wherein R$^3$ is alkyl substituted with O-benzyl.

13. The pharmaceutical composition of claim 1, wherein R$^4$ is alkoxy.

14. The pharmaceutical composition of claim 1, wherein R$^4$ is O-benzyl.

15. The pharmaceutical composition of claim 1, wherein R$^4$ is NR$^5$R$^6$, wherein each R$^5$ and R$^6$ is independently alkyl, which is substituted or unsubstituted.

16. The pharmaceutical composition of claim 15, wherein R$^4$ is NR$^5$R$^6$, wherein each R$^5$ is hydrogen and R$^6$ is substituted alkyl.

17. The pharmaceutical composition of claim 15, wherein R$^4$ is NR$^5$R$^6$, wherein each R$^5$ is hydrogen and R$^6$ is benzyl.

18. The pharmaceutical composition of claim 1, wherein the compound is of the formula:

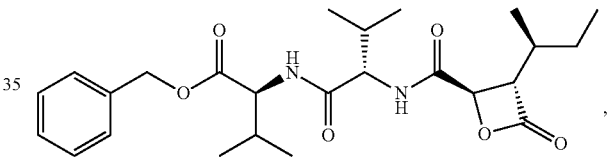

or a pharmaceutically-acceptable salt thereof.

19. The pharmaceutical composition of claim 1, wherein the compound is of the formula:

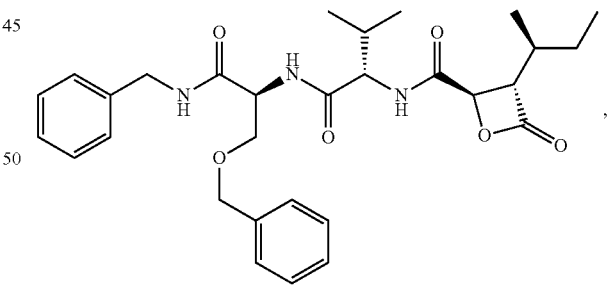

or a pharmaceutically-acceptable salt thereof.

20. The pharmaceutical composition of claim 1, further comprising an excipient.

* * * * *